US011207378B2

(12) United States Patent
Hewlett et al.

(10) Patent No.: US 11,207,378 B2
(45) Date of Patent: Dec. 28, 2021

(54) COMPOSITIONS FOR INHIBITING FORMATION OF AND/OR DISRUPTING BACTERIAL BIOFILMS AND METHODS OF USE THEREFOR

(71) Applicant: University of Virginia Patent Foundation, Charlottesville, VA (US)

(72) Inventors: Erik L. Hewlett, Charlottesville, VA (US); Casandra L. Hoffman, Portland, OR (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/091,046

(22) PCT Filed: Apr. 4, 2017

(86) PCT No.: PCT/US2017/026012
§ 371 (c)(1),
(2) Date: Oct. 3, 2018

(87) PCT Pub. No.: WO2017/176807
PCT Pub. Date: Oct. 12, 2017

(65) Prior Publication Data
US 2019/0111106 A1    Apr. 18, 2019

Related U.S. Application Data

(60) Provisional application No. 62/318,158, filed on Apr. 4, 2016.

(51) Int. Cl.
| | |
|---|---|
| *C07K 16/18* | (2006.01) |
| *A61K 38/16* | (2006.01) |
| *A01N 63/10* | (2020.01) |
| *C12P 21/00* | (2006.01) |
| *C12Q 1/02* | (2006.01) |
| *A61P 41/00* | (2006.01) |
| *A61P 31/04* | (2006.01) |
| *A01N 25/28* | (2006.01) |
| *A61K 39/00* | (2006.01) |

(52) U.S. Cl.
CPC ............ *A61K 38/164* (2013.01); *A01N 25/28* (2013.01); *A01N 63/10* (2020.01); *A61P 31/04* (2018.01); *A61P 41/00* (2018.01); *C12P 21/00* (2013.01); *C12Q 1/025* (2013.01); *A61K 39/00* (2013.01); *Y02A 50/30* (2018.01)

(58) Field of Classification Search
CPC combination set(s) only.
See application file for complete search history.

(56) References Cited

U.S. PATENT DOCUMENTS

| | | | |
|---|---|---|---|
| 4,057,626 A | 11/1977 | Metzgar et al. | |
| 5,183,745 A * | 2/1993 | Danchin | .............. C07K 14/235 435/232 |
| 6,559,176 B1 * | 5/2003 | Bassler | .................. A61K 31/34 514/408 |
| 6,726,898 B2 | 4/2004 | Jernberg | |
| 6,830,745 B1 | 12/2004 | Budny et al. | |
| 6,994,854 B1 | 2/2006 | Betsou et al. | |
| 7,393,924 B2 | 7/2008 | Vitaliano et al. | |
| 8,404,662 B2 | 3/2013 | Cheng et al. | |
| 8,444,992 B2 | 5/2013 | Borkowski | |
| 9,028,864 B2 | 5/2015 | Cipolla et al. | |
| 9,089,677 B2 | 7/2015 | Soo et al. | |
| 9,187,754 B2 | 11/2015 | Boonchird et al. | |
| 9,339,525 B2 | 5/2016 | O'Neil et al. | |
| 9,566,247 B2 | 2/2017 | Koo et al. | |
| 2002/0037260 A1 | 3/2002 | Budny et al. | |
| 2004/0009927 A1 | 1/2004 | Romeo et al. | |
| 2006/0105025 A1 | 5/2006 | Hill et al. | |
| 2010/0021391 A1 | 1/2010 | Douglas et al. | |
| 2010/0285068 A1 * | 11/2010 | Ostolaza Etxabe | .... A61K 35/74 424/234.1 |
| 2010/0322872 A1 | 12/2010 | Perraudin | |
| 2013/0110237 A1 | 5/2013 | Schaer et al. | |

FOREIGN PATENT DOCUMENTS

| | | |
|---|---|---|
| WO | WO 2009/004102 A1 | 1/2009 |
| WO | WO 2014/182172 A1 | 11/2014 |
| WO | WO 2016/008949 A1 | 1/2016 |

(Continued)

OTHER PUBLICATIONS

Altschul et al., "Basic local alignment search tool," J Mol Biol, vol. 215, pp. 403-410 (1990).
Altschul et al., "Gapped BLAST and PSI-BLAST: a new generation of protein database search programs," Nucleic Acids Res, vol. 25, pp. 3389-3402 (1997).
Altschul et al., "Protein database searches for multiple alignments," Proc Natl Acad Sci USA, vol. 87, pp. 5509-5513 (1990).
Arnal et al., "Bordetella pertussis isolates from argentinean whooping cough patients display enhanced biofilm formation capacity compared to Tohama I reference strain," Front Microbiol, vol. 6, p. 1352 (2015).
Basler et al., "Pore-forming and enzymatic activities of Bordetella pertussis adenylate cyclase toxin synergize in promoting lysis of monocytes," Infect Immun, vol. 74, pp. 2207-2214 (2006).
Birkebaek et al., "Bordetella pertussis and chronic cough in adults," Clin Infect Dis, vol. 29, pp. 1239-1242 (1999).

(Continued)

*Primary Examiner* — Thomas S Heard
(74) *Attorney, Agent, or Firm* — Jenkins, Wilson, Taylor & Hunt, P.A.

(57) ABSTRACT

Provided are compositions that include an effective amount of a peptide or polypeptide derived from a *Bordetella* ACT AC domain, optionally wherein the peptide or polypeptide is 80-100% identical to an amino acid sequence as set forth in SEQ ID NOs: 1-5 and 44-53. Also provided are methods of using the same for preventing and/or treating a diseases, disorders, and conditions associated with the presence and/or development of biofilm; and for reducing the incidence of nosocomial infections; for inhibiting biofilm development and/or for reducing or eliminating biofilm present on medical, dental, and industrial surfaces.

19 Claims, 40 Drawing Sheets
Specification includes a Sequence Listing.

(56) References Cited

FOREIGN PATENT DOCUMENTS

WO   WO 2017/176807 A2   10/2017

OTHER PUBLICATIONS

Borlee et al., "Pseudomonas aeruginosa uses a cyclic-di-GMP-regulated adhesin to reinforce the biofilm extracellular matrix," Mol Microbiol, vol. 75, pp. 827-842 (2010).
Bumba et al. "Bordetella adenylate cyclase toxin mobilizes its beta2 integrin receptor into lipid rafts to accomplish translocation across target cell membrane in two steps," PLoS Pathog, vol. 6, p. 1000901 (2010).
Bumba et al., "Calcium-Driven folding of RTX domain beta-rolls ratchets translocation of RTX proteins through type I secretion ducts," Mol Cell, vol. 62, pp. 47-62 (2016).
Cattelan et al., "Bordetella biofilms: a lifestyle leading to persistent infections," FEMS Pathogens and Disease, vol. 74, No. 1 pp. 1-8 (2015).
Conover et al., "BpsR modulates Bordetella biofilm formation by negatively regulating the expression of the Bps polysaccharide," J Bacteriol, vol. 194, pp. 233-242 (2012).
Conover et al., "Extracellular DNA is essential for maintaining Bordetella biofilm integrity on abiotic surfaces and in the upper respiratory tract of mice," PLoS One, vol. 6, p. e16861 (2011).
Conover et al., "The Bps polysaccharide of Bordetella pertussis promotes colonization and biofilm formation in the nose by functioning as an adhesin," Mol Microbiol, vol. 77, pp. 1439-1455 (2010).
De Gouw et al., "The vaccine potential of Bordetella pertussis biofilm-derived membrane proteins," Emerg Microbes Infect, vol. 3, p. e58 (2014).
Eby et al., "Role of CD11b/CD18 in the process of intoxication by the adenylate cyclase toxin of Bordetella pertussis," Infect Immun, vol. 80, pp. 850-859 (2012).
Eby et al., "Cyclic AMPmediated suppression of neutrophil extracellular trap formation and apoptosis by the Bordetella pertussis adenylate cyclase toxin," Infect Immun, vol. 82, pp. 5256-5269 (2014).
Eby et al., "Quantification of the adenylate cyclase toxin of Bordetella pertussis in vitro and during respiratory infection," Infect Immun, vol. 81, pp. 1390-1398 (2013).
Eby et al., "Selective translocation of the Bordetella pertussis adenylate cyclase toxin across the basolateral membranes of polarized epithelial cells," J Biol Chem, vol. 285, p. 10662-10670 (2010).
El-Azami-El-Idrissi et al., "Interaction of Bordetella pertussis adenylate cyclase with CD11b/CD18: Role of toxin acylation and identification of the main integrin interaction domain," J Biol Chem, vol. 278, p. 38514-38521 (2003).
Fiser et al., "Calcium influx rescues adenylate cyclase-hemolysin from rapid cell membrane removal and enables phagocyte permeabilization by toxin pores," PLoS Pathog, vol. 8, p. e1002580 (2012).
GENBANK® Accession No. NP_879578.1.
GENBANK® Accession No. NP_879839.1.
GENBANK® Accession No. NP_879898.1.
GENBANK® Accession No. NP_880302.1.
GENBANK® Accession No. NP 880571.1.
GENBANK® Accession No. NP_882282.1.
GENBANK® Accession No. NP_882283.1.
GENBANK® Accession No. NP_882284.1.
GENBANK® Accession No. NP_882285.1.
GENBANK® Accession No. NP_882286.1.
GENBANK® Accession No. WP_010927405.1.
GENBANK® Accession No. WP_010929490.1.
GENBANK® Accession No. WP 033446920.1.
GENBANK® Accession No. WP_033452809.1.
GENBANK® Accession No. WP_033452812.1.
GENBANK® Accession No. WP_033839724.1.
GENBANK® Accession No. WP_080702041.1.
GENBANK® Accession No. WP_015064783.1.
GENBANK® Accession No. WP_033468323.1.
GENBANK® Accession No. YP_006895400.1.
GENBANK® Accession No. YP 006895663.1.
GENBANK® Accession No. YP_006896577.1.
GENBANK® Accession No. YP 006898153.1.
GENBANK® Accession No. YP_006898154.1.
GENBANK® Accession No. YP_006898155.1.
GENBANK® Accession No. YP_006898156.1.
GENBANK® Accession No. YP_006967303.1.
GENBANK® Accession No. YP_006967865.1.
GENBANK® Accession No. YP_006897297.1.
GENBANK® Accession No. YP_006966876.1.
Gray et al., "Newly secreted adenylate cyclase toxin is responsible for intoxication of target cells by Bordetella pertussis," Mol Microbiol, vol. 53, pp. 1709-1719 (2004).
Gray et al., "Translocation-specific conformation of adenylate cyclase toxin from Bordetella pertussis inhibits toxin-mediated hemolysis," J Bacteriol, vol. 183, pp. 5904-5910 (2001).
Guermonprez et al., "The adenylate cyclase toxin of Bordetella pertussis binds to target cells via the alpha(M)beta(2) integrin (CD11b/CD18)," J Exp Med, vol. 193, pp. 1035-1044 (2001).
Guiso et al., "Protective activity of Bordetella adenylate cyclase-hemolysin against bacterial colonization," Microbial Pathogenesis, vol. 11, No. 6, pp. 423-431 (1991).
Guo et al., "Structural basis for the interaction of Bordetella pertussis adenylyl cyclase toxin with calmodulin," EMBO J, vol. 24, pp. 3190-3201 (2005).
Harlow & Lane, "Antibodies: A Laboratory Manual," Cold Spring Harbor Laboratory Press, Cold Spring Harbor, New York, United States of America. (1988).
Hewlett et al., "Macrophage cytotoxicity produced by adenylate cyclase toxin from Bordetella pertussis: more than just making cyclic AMP!," Mol Microbiol, vol. 59, pp. 447-459 (2006).
Hoffman et al., "Bordetella adenylate cyclase toxin interacts with filamentous haemagglutinin to inhibit biofilm formation in virtro," Molecular Microbiology, vol. 103, No. 2, pp. 214-228 (2016).
Inatsuka et al., "Pertactin Is Required for Bordetella Species To Resist Neutrophil-Mediated Clearance," Infect Immun, vol. 7, pp. 2901-2909 (2010).
International Preliminary Report on Patentability corresponding to International Application No. PCT/US17/26012 dated Oct. 9, 2018.
International Search Report corresponding to International Application No. PCT/US17/26012 dated Apr. 11, 2018.
Irie et al., "The Bvg virulence control system regulates biofilm formation in Bordetella bronchiseptica," J Bacteriol, vol. 186, pp. 5692-5698 (2004).
Jeffery, "An introduction to protein moonlighting," Biochem Soc Trans, vol. 42, pp. 1679-1683 (2014).
Jeffery, "Moonlighting proteins-an update," Mol Biosyst, vol. 5, pp. 345-350 (2009).
Jeffery, "Why study moonlighting proteins?" Front Genet, vol. 6, p. 211 (2015).-HAVE.
Kajava et al., "Beta-helix model for the filamentous haemagglutinin adhesin of Bordetella pertussis and related bacterial secretory proteins," Mol Microbiol, vol. 42,pp. 279-292 (2001). HAVE.
Karlin & Altschul, "Applications and statistics for multiple high-scoring segments in molecular sequences," Proc Natl Acad Sci USA, vol. 90, pp. 5873-5877 (1993). HAVE.
Karlin & Altschul, "Methods for assessing the statistical significance of molecular sequence features by using general scoring schemes," Proc Natl Acad Sci USA, vol. 87, pp. 2264-2268 (1990). HAVE.
Kragh et al., "Role of Multicellular Aggregates in Biofilm Formation," MBio, vol. 7, pp. e00237-e00216 (2016). HAVE.
Lee et al., "Epitope mapping of monoclonal antibodies against Bordetella pertussis adenylate cyclase toxin," Infect Immun, vol. 67, pp. 2090-2095 (1999). HAVE.
Mani et al., "MoonProt: a database for proteins that are known to moonlight," Nucleic Acids Res, vol. 43, pp. D277-D282 (2015).

(56) References Cited

OTHER PUBLICATIONS

Martin et al., "Bordetella adenylate cyclase toxin promotes calcium entry into both CD11b1 and CD11b- cells through cAMPdependent L-type-like calcium channels," J Biol Chem, vol. 285, pp. 357-364 (2010).
Mattoo & Cherry, "Molecular pathogenesis, epidemiology, and clinical manifestations of respiratory infections due to Bordetella pertussis and other Bordetella subspecies," Clin Microbiol Rev, vol. 18, pp. 326-382 (2005).
Mazar & Cotter, "Topology and maturation of filamentous haemagglutinin suggest a new model for two-parnter secretion," Mol. Microbiol, vol. 62, pp. 641-654 (2006).
Mishra et al., "The BvgAS signal transduction system regulates biofilm development in Bordetella," J Bacteriol, vol. 187, pp. 1474-1484 (2005).
Mouallem et al., "Bordetella pertussis adenylate cyclase toxin: intoxication of host cells by bacterial invasion," Infect Immun, vol. 58, pp. 3759-3764 (1990).
Noel et al., "The prodomain of the Bordetella two-partner secretion pathway protein FhaB remains intracellular yet affects the conformation of the mature C-terminal domain," Mol Microbiol, vol. 86, pp. 988-1006 (2012).
O'Toole, "Microtiter dish biofilm formation assay," J Vis Exp, vol. pii, p. 2437 (2011).
Osička et al., "Bordetella adenylate cyclase toxin is a unique ligand of the integrin complement receptors," eLife, vol. 4, p. e10766 (2015).
Osička et al., "Delivery of CD8+ T-Cell Epitopes into Major Histocompatibility Complex Class I Antigen Presentation Pathway by Bordetella pertussis Adenylate Cyclase: Delineation of Cell Invasive Structures and Permissive Insertion Sites," Infect Immun, vol. 68, pp. 247-256 (2000).
Osickova et al., "Adenylate cyclase toxin translocates across target cell membrane without forming a pore," Mol Microbiol, vol. 75, pp. 1550-1562 (2010).
Park et al., "Comparative genomics of the classical Bordetella subspecies: the evolution and exchange of virulence-associated diversity amongst closely related pathogens," BMC Genomics, vol. 13, p. 545 (2012).
Perez Vidakovics et al., "Adenylate cyclase influences filamentous haemagglutinin-mediated attachment of Bordetella pertussis to epithelial alveolar cells," FEMS Immunol Med Microbiol, vol. 48, pp. 140-147 (2006).
Perkins et al., "Bordetella pertussis adenylate cyclase toxin (ACT) induces cyclooxygenase-2 (COX-2) in murine macrophages and is facilitated by ACT interaction with CD11b/CD18 (Mac-1)," Mol Microbiol, vol. 66, pp. 1003-1015 (2007).
Quinn & McIntyre, "The impact of adolescent pertussis immunization, 2004-2009: lessons from Australia," Bull World Health Organ, vol. 89, pp. 666-674 (2011).
Sadilkova et al., "Single-step affinity purification of recombinant proteins using a self-excising module from Neisseria meningitidis FrpC," Protein Sci, vol. 17, pp. 1834-1843 (2008).
Sakamoto et al., "Bordetella pertussis adenylate cyclase toxin. Structural and functional independence of the catalytic and hemolytic activities," J Biol Chem, vol. 267, p. 13598-13602 (1992).
Serra et al., "Continuous nondestructive monitoring of Bordetella pertussis biofilms by Fourier transform infrared spectroscopy and other corroborative techniques," Anal Bioanal Chem vol. 387, pp. 1759-1767 (2007).
Serra et al., "FHA-mediated cell-substrate and cell-cell adhesions are critical for Bordetella pertussis biofilm formation on abiotic surfaces and in the mouse nose and the trachea," PLoS One, vol. 6, p. 28811 (2011).
Sisti et al., "Cyclic-di-GMP signalling regulates motility and biofilm formation in Bordetella bronchiseptica," Microbiology, vol. 159, pp. 869-879 (2013).
Sloan et al., "The Bordetella Bps polysaccharide is critical for biofilm development in the mouse respiratory tract," J Bacteriol vol. 189, pp. 8270-8276 (2007).
Sorroche et al., "A positive correlation between bacterial autoaggregation and biofilm formation in native Sinorhizobium meliloti isolates from Argentina," Appl Environ Microbiol, vol. 78, pp. 4092-4101 (2012).
Strebel et al., "Population-based incidence of pertussis among adolescents and adults," Minnesota, 1995-1996. J Infect Dis, vol. 183, pp. 1353-1359 (2001).
Strickley, "Solubilizing excipients in oral and injectable formulations," Pharm Res, vol. 21, pp. 201-230 (2004).
Sugisaki et al., "Role of (p)ppGpp in biofilm formation and expression of filamentous structures in Bordetella pertussis," Microbiology, vol. 159, pp. 1379-1389 (2013).
Thorstensson et al. "A phase I clinical study of a live attenuated Bordetella pertussis vaccine-BPZE1; a single centre, double-blind, placebocontrolled, dose-escalating study of BPZE1 given intranasally to healthy adult male volunteers," PLoS One, vol. 9, p. 83449 (2014).
Uribe et al.,"Ca21 influx and tyrosine kinases trigger Bordetella adenylate cyclase toxin (ACT) endocytosis. Cell physiology and expression of the CD11b/CD18 integrin major determinants of the entry route," PLoS One vol. 8, p. 74248 (2013).
Vergara-Lrigaray et al. "Evaluation of the role of the Bvg intermediate phase in Bordetella pertussis during experimental respiratory infection," Infect Immun, vol. 73, pp. 748-760 (2005).
Weiss et al. "Tn5-induced mutations affecting virulence factors of Bordetella pertussis," Infect Immun, vol. 42, pp. 33-41 (1983).
Wendelboe et al. "Transmission of Bordetella pertussis to young infants," Pediatr Infect Dis J, vol. 26, pp. 293-299 (2007).
Written Opinion of International Search Report corresponding to International Application No. PCT/US17/26012 dated Mar. 5, 2018.
Bisgard et al., "Infant pertussis: who was the source?" Pediatr Infect Dis J, vol. 23, pp. 985-989 (2004).
Costache et al. "Adenylate cyclases involvement in pathogenicity, a minireview," Roum Arch Microbiol Immunol, vol. 72, pp. 63-86 (2013).
Cotter & Miller, "A mutation in the *Bordetella bronchiseptica* bvgS gene results in reduced virulence and increased resistance to starvation, and identifies a new class of Bvg-regulated antigens," Mol Microbiol, vol. 24, pp. 671-685 (1997).
Fan et al., "Two-partner secretion of gram-negative bacteria: a single beta barrel protein enables transport across the outer membrane," J Biol Chem, vol. 287, pp. 2591-2599 (2012).
Fedele et al., "The virulence factors of Bordetella pertussis: talented modulators of host immune response," Arch Immunol Ther Exp (Warsz), vol. 61, pp. 445-457 (2013).
Jeffery, "Moonlighting proteins old proteins learning new tricks," Trends Genet, vol. 19, pp. 415-417 (2003).
Jeffery, "Moonlighting proteins," Trends Biochem Sci, vol. 24, pp. 8-11 (1999).
Rowe et al., (eds.) "Handbook of Pharmaceutical Excipients," 5th Ed., Pharmaceutical Press, London, United Kingdom (2006).
Sebo & Ladant, "Repeat sequences in the Bordetella pertussis adenylate cyclase toxin can be recognized as alternative carboxyproximal secretion signals by the *Escherichia coli* alphahaemolysin translocator," Mol Microbiol vol. 9, pp. 999-1009 (1993).
Vojtova et al. "Bordetella adenylate cyclase toxin induces a cascade of morphological changes of sheep erythrocytes and localizes into clusters in erythrocyte membranes," Microsc Res Tech, vol. 69, pp. 119-129 (2006).
Zaretzky et al., "Mechanism of association of adenylate cyclase toxin with the surface of Bordetella pertussis: a role for toxinfilamentous haemagglutinin interaction," Mol Microbiol, vol. 45, pp. 1589-1598 (2002).

* cited by examiner

**Biofilm Time Course
WT *B. pertussis* Strains**

- BP338
- BPSM

OD$_{595}$ vs Time (hours): 0, 24, 48, 72, 96

SEQUENCE LISTING

```
<160> NUMBER OF SEQ ID NOS: 62

<210> SEQ ID NO 1
<211> LENGTH: 1706
<212> TYPE: PRT
<213> ORGANISM: Bordetella pertussis

<400> SEQUENCE: 1

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
```

```
            115                 120                 125
Val Thr Gly Met Ala Asp Gly Val Ala Ser Asn His Ala Gly Tyr
        130                 135                 140
Glu Gln Phe Glu Phe Arg Val Lys Glu Thr Ser Asp Gly Arg Tyr Ala
145                 150                 155                 160
Val Gln Tyr Arg Arg Lys Gly Asp Asp Phe Glu Ala Val Lys Val
            165                 170                 175
Ile Gly Asn Ala Ala Gly Ile Pro Leu Thr Ala Asp Ile Asp Met Phe
            180                 185                 190
Ala Ile Met Pro His Leu Ser Asn Phe Arg Asp Ser Ala Arg Ser Ser
            195                 200                 205
Val Thr Ser Gly Asp Ser Val Thr Asp Tyr Leu Ala Arg Thr Arg Arg
            210                 215                 220
Ala Ala Ser Glu Ala Thr Gly Gly Leu Asp Arg Glu Arg Ile Asp Leu
225                 230                 235                 240
Leu Trp Lys Ile Ala Arg Ala Gly Ala Arg Ser Ala Val Gly Thr Glu
            245                 250                 255
Ala Arg Arg Gln Phe Arg Tyr Asp Gly Asp Met Asn Ile Gly Val Ile
            260                 265                 270
Thr Asp Phe Glu Leu Glu Val Arg Asn Ala Leu Asn Arg Arg Ala His
            275                 280                 285
Ala Val Gly Ala Gln Asp Val Val Gln His Gly Thr Glu Gln Asn Asn
            290                 295                 300
Pro Phe Pro Glu Ala Asp Glu Lys Ile Phe Val Val Ser Ala Thr Gly
305                 310                 315                 320
Glu Ser Gln Met Leu Thr Arg Gly Gln Leu Lys Glu Tyr Ile Gly Gln
            325                 330                 335
Gln Arg Gly Glu Gly Tyr Val Phe Tyr Glu Asn Arg Ala Tyr Gly Val
            340                 345                 350
Ala Gly Lys Ser Leu Phe Asp Asp Gly Leu Gly Ala Ala Pro Gly Val
            355                 360                 365
Pro Ser Gly Arg Ser Lys Phe Ser Pro Asp Val Leu Glu Thr Val Pro
370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
            405                 410                 415
Leu Gly Glu Val Ser Asp Met Ala Ala Val Glu Ala Ala Glu Leu Glu
            420                 425                 430
Met Thr Arg Gln Val Leu His Ala Gly Ala Arg Gln Asp Asp Ala Glu
            435                 440                 445
Pro Gly Val Ser Gly Ala Ser Ala His Trp Gly Gln Arg Ala Leu Gln
            450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
            485                 490                 495
Ala Ala Ser Leu Ser Ala Ala Val Phe Gly Leu Gly Glu Ala Ser Ser
            500                 505                 510
Ala Val Ala Glu Thr Val Ser Gly Phe Phe Arg Gly Ser Ser Arg Trp
            515                 520                 525
Ala Gly Gly Phe Gly Val Ala Gly Gly Ala Met Ala Leu Gly Gly Gly
            530                 535                 540
```

```
Ile Ala Ala Ala Val Gly Ala Gly Met Ser Leu Thr Asp Ala Pro
545                 550                 555                 560

Ala Gly Gln Lys Ala Ala Gly Ala Glu Ile Ala Leu Gln Leu Thr
            565                 570                 575

Gly Gly Thr Val Glu Leu Ala Ser Ser Ile Ala Leu Ala Leu Ala Ala
                580                 585                 590

Ala Arg Gly Val Thr Ser Gly Leu Gln Val Ala Gly Ala Ser Ala Gly
            595                 600                 605

Ala Ala Ala Gly Ala Leu Ala Ala Leu Ser Pro Met Glu Ile Tyr
            610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
            675                 680                 685

Ser Val Val Gly Ala Pro Val Ala Val Val Thr Ser Leu Leu Thr Gly
            690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
            755                 760                 765

Ala Ser Ser Val Ile Gly Val Gln Thr Thr Glu Ile Ser Lys Ser Ala
            770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Val Leu Asp Val Ala Ala Gly Gly Ile Asp Ile Ala Ser Arg
            820                 825                 830

Lys Gly Glu Arg Pro Ala Leu Thr Phe Ile Thr Pro Leu Ala Ala Pro
            835                 840                 845

Gly Glu Glu Gln Arg Arg Thr Lys Thr Gly Lys Ser Glu Phe Thr
850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
            885                 890                 895

Val Asp Ala Asn Gly Val Leu Lys His Ser Ile Lys Leu Asp Val Ile
            900                 905                 910

Gly Gly Asp Gly Asp Val Val Leu Ala Asn Ala Ser Arg Ile His
            915                 920                 925

Tyr Asp Gly Gly Ala Gly Thr Asn Thr Val Ser Tyr Ala Ala Leu Gly
            930                 935                 940

Arg Gln Asp Ser Ile Thr Val Ser Ala Asp Gly Glu Arg Phe Asn Val
945                 950                 955                 960
```

```
Arg Lys Gln Leu Asn Asn Ala Asn Val Tyr Arg Glu Gly Val Ala Thr
            965                 970                 975

Gln Thr Thr Ala Tyr Gly Lys Arg Thr Glu Asn Val Gln Tyr Arg His
        980                 985                 990

Val Glu Leu Ala Arg Val Gly Gln Leu Val Glu Val Asp Thr Leu Glu
    995                1000                1005

His Val Gln His Ile Ile Gly Gly Ala Gly Asn Asp Ser Ile Thr
1010                1015                1020

Gly Asn Ala His Asp Asn Phe Leu Ala Gly Ser Gly Asp Asp
1025                1030                1035

Arg Leu Asp Gly Gly Ala Gly Asn Asp Thr Leu Val Gly Gly Glu
1040                1045                1050

Gly Gln Asn Thr Val Ile Gly Gly Ala Gly Asp Asp Val Phe Leu
1055                1060                1065

Gln Asp Leu Gly Val Trp Ser Asn Gln Leu Asp Gly Gly Ala Gly
1070                1075                1080

Val Asp Thr Val Lys Tyr Asn Val His Gln Pro Ser Glu Glu Arg
1085                1090                1095

Leu Glu Arg Met Gly Asp Thr Gly Ile His Ala Asp Leu Gln Lys
1100                1105                1110

Gly Thr Val Glu Lys Trp Pro Ala Leu Asn Leu Phe Ser Val Asp
1115                1120                1125

His Val Lys Asn Ile Glu Asn Leu His Gly Ser Arg Leu Asn Asp
1130                1135                1140

Arg Ile Ala Gly Asp Asp Gln Asp Asn Glu Leu Trp Gly His Asp
1145                1150                1155

Gly Asn Asp Thr Ile Arg Gly Arg Gly Gly Asp Asp Ile Leu Arg
1160                1165                1170

Gly Gly Leu Gly Leu Asp Thr Leu Tyr Gly Glu Asp Gly Asn Asp
1175                1180                1185

Ile Phe Leu Gln Asp Asp Glu Thr Val Ser Asp Asp Ile Asp Gly
1190                1195                1200

Gly Ala Gly Leu Asp Thr Val Asp Tyr Ser Ala Met Ile His Pro
1205                1210                1215

Gly Arg Ile Val Ala Pro His Glu Tyr Gly Phe Gly Ile Glu Ala
1220                1225                1230

Asp Leu Ser Arg Glu Trp Val Arg Lys Ala Ser Ala Leu Gly Val
1235                1240                1245

Asp Tyr Tyr Asp Asn Val Arg Asn Val Glu Asn Val Ile Gly Thr
1250                1255                1260

Ser Met Lys Asp Val Leu Ile Gly Asp Ala Gln Ala Asn Thr Leu
1265                1270                1275

Met Gly Gln Gly Gly Asp Asp Thr Val Arg Gly Gly Asp Gly Asp
1280                1285                1290

Asp Leu Leu Phe Gly Gly Asp Gly Asn Asp Met Leu Tyr Gly Asp
1295                1300                1305

Ala Gly Asn Asp Thr Leu Tyr Gly Gly Leu Gly Asp Asp Thr Leu
1310                1315                1320

Glu Gly Gly Ala Gly Asn Asp Trp Phe Gly Gln Thr Gln Ala Arg
1325                1330                1335

Glu His Asp Val Leu Arg Gly Gly Asp Gly Val Asp Thr Val Asp
1340                1345                1350

Tyr Ser Gln Thr Gly Ala His Ala Gly Ile Ala Ala Gly Arg Ile
```

Gly Leu Gly Ile Leu Ala Asp Leu Gly Ala Gly Arg Val Asp Lys
         1370                1375                1380

Leu Gly Glu Ala Gly Ser Ser Ala Tyr Asp Thr Val Ser Gly Ile
         1385                1390                1395

Glu Asn Val Val Gly Thr Glu Leu Ala Asp Arg Ile Thr Gly Asp
         1400                1405                1410

Ala Gln Ala Asn Val Leu Arg Gly Ala Gly Ala Asp Val Leu
         1415                1420                1425

Ala Gly Gly Glu Gly Asp Asp Val Leu Leu Gly Asp Gly Asp
         1430                1435                1440

Asp Gln Leu Ser Gly Asp Ala Gly Arg Asp Arg Leu Tyr Gly Glu
         1445                1450                1455

Ala Gly Asp Asp Trp Phe Phe Gln Asp Ala Ala Asn Ala Gly Asn
         1460                1465                1470

Leu Leu Asp Gly Gly Asp Gly Arg Asp Thr Val Asp Phe Ser Gly
         1475                1480                1485

Pro Gly Arg Gly Leu Asp Ala Gly Ala Lys Gly Val Phe Leu Ser
         1490                1495                1500

Leu Gly Lys Gly Phe Ala Ser Leu Met Asp Glu Pro Glu Thr Ser
         1505                1510                1515

Asn Val Leu Arg Asn Ile Glu Asn Ala Val Gly Ser Ala Arg Asp
         1520                1525                1530

Asp Val Leu Ile Gly Asp Ala Gly Ala Asn Val Leu Asn Gly Leu
         1535                1540                1545

Ala Gly Asn Asp Val Leu Ser Gly Gly Ala Gly Asp Asp Val Leu
         1550                1555                1560

Leu Gly Asp Glu Gly Ser Asp Leu Leu Ser Gly Asp Ala Gly Asn
         1565                1570                1575

Asp Asp Leu Phe Gly Gly Gln Gly Asp Asp Thr Tyr Leu Phe Gly
         1580                1585                1590

Val Gly Tyr Gly His Asp Thr Ile Tyr Glu Ser Gly Gly Gly His
         1595                1600                1605

Asp Thr Ile Arg Ile Asn Ala Gly Ala Asp Gln Leu Trp Phe Ala
         1610                1615                1620

Arg Gln Gly Asn Asp Leu Glu Ile Arg Ile Leu Gly Thr Asp Asp
         1625                1630                1635

Ala Leu Thr Val His Asp Trp Tyr Arg Asp Ala Asp His Arg Val
         1640                1645                1650

Glu Ile Ile His Ala Ala Asn Gln Ala Val Asp Gln Ala Gly Ile
         1655                1660                1665

Glu Lys Leu Val Glu Ala Met Ala Gln Tyr Pro Asp Pro Gly Ala
         1670                1675                1680

Ala Ala Ala Ala Pro Pro Ala Ala Arg Val Pro Asp Thr Leu Met
         1685                1690                1695

Gln Ser Leu Ala Val Asn Trp Arg
         1700                1705

<210> SEQ ID NO 2
<211> LENGTH: 400
<212> TYPE: PRT
<213> ORGANISM: Bordetella pertussis

<400> SEQUENCE: 2

```
Met Gln Gln Ser His Gln Ala Gly Tyr Ala Asn Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Ser
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

<210> SEQ ID NO 3
<211> LENGTH: 225
<212> TYPE: PRT
```

<213> ORGANISM: Bordetella pertussis

<400> SEQUENCE: 3

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala
225

<210> SEQ ID NO 4
<211> LENGTH: 175
<212> TYPE: PRT
<213> ORGANISM: Bordetella pertussis

<400> SEQUENCE: 4

Ala Ser Glu Ala Thr Gly Gly Leu Asp Arg Glu Arg Ile Asp Leu Leu
1               5                   10                  15

Trp Lys Ile Ala Arg Ala Gly Ala Arg Ser Ala Val Gly Thr Glu Ala
            20                  25                  30

Arg Arg Gln Phe Arg Tyr Asp Gly Asp Met Asn Ile Gly Val Ile Thr
        35                  40                  45

Asp Phe Glu Leu Glu Val Arg Asn Ala Leu Asn Arg Arg Ala His Ala
    50                  55                  60

Val Gly Ala Gln Asp Val Val Gln His Gly Thr Glu Gln Asn Ser Pro
65                  70                  75                  80

Phe Pro Glu Ala Asp Glu Lys Ile Phe Val Val Ser Ala Thr Gly Glu
                85                  90                  95

Ser Gln Met Leu Thr Arg Gly Gln Leu Lys Glu Tyr Ile Gly Gln Gln
            100                 105                 110

Arg Gly Glu Gly Tyr Val Phe Tyr Glu Asn Arg Ala Tyr Gly Val Ala

```
            115                 120                 125
Gly Lys Ser Leu Phe Asp Asp Gly Leu Gly Ala Ala Pro Gly Val Pro
    130                 135                 140

Ser Gly Arg Ser Lys Phe Ser Pro Asp Val Leu Glu Thr Val Pro Ala
145                 150                 155                 160

Ser Pro Gly Leu Arg Arg Pro Ser Leu Gly Ala Val Glu Arg Gln
                165                 170                 175

<210> SEQ ID NO 5
<211> LENGTH: 400
<212> TYPE: PRT
<213> ORGANISM: Artificial Sequence
<220> FEATURE:
<223> OTHER INFORMATION: Bordetella AC domain with inactivating
      substitutions at amino acids 188 and 189

<400> SEQUENCE: 5

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Cys Thr Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Ser
    290                 295                 300
```

```
Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
            325                 330                 335

Gln Arg Gly Glu Gly Tyr Val Phe Tyr Glu Asn Arg Ala Tyr Gly Val
        340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

<210> SEQ ID NO 6
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 6
gctgggaccc gaggaaat                                              18

<210> SEQ ID NO 7
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 7
cgccaatgta gacgatgcc                                             19

<210> SEQ ID NO 8
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 8
cgaggcggtc aaggtgat                                              18

<210> SEQ ID NO 9
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 9
gcggaagttg gacagatgc                                             19

<210> SEQ ID NO 10
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 10
aggtcatcaa tgccgcca                                              18
```

```
<210> SEQ ID NO 11
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 11
gcaggacggt cagttcgc                                                 18

<210> SEQ ID NO 12
<211> LENGTH: 17
<212> TYPE: DNA
<213> ORGANISM: Artificial Sequence
<220> FEATURE:
<223> OTHER INFORMATION: Artificially synthesized oligonucleotide primer

<400> SEQUENCE: 12
caagggcggc aaggtga                                                  17

<210> SEQ ID NO 13
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 13
acaggatggc gaacaggct                                                19

<210> SEQ ID NO 14
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 14
ccagaacgga ttcacggc                                                 18

<210> SEQ ID NO 15
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 15
ctgctgctgg tggagacga                                                19

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 16
tcatgctggc tcgctatcac                                               20

<210> SEQ ID NO 17
<211> LENGTH: 20
<212> TYPE: DNA
<213> ORGANISM: Artificial Sequence
<220> FEATURE:
<223> OTHER INFORMATION: Artificially synthesized oligonucleotide primer
```

```
<400> SEQUENCE: 17
tcgctacaga atgcctgctc                                               20

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 18
agcaaggaca tcggctttgt                                               20

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 19
ttcgagcgtt ccgtacttcg                                               20

<210> SEQ ID NO 20
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 20
cgccctatta tcccagcgtc                                               20

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 21
taccgccatc acattgttgc                                               20

<210> SEQ ID NO 22
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 22
ccgatgtctt gcgcctgtat                                               20

<210> SEQ ID NO 23
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 23
gcgcatacga cacataggga                                               20

<210> SEQ ID NO 24
<211> LENGTH: 20
```

```
<212> TYPE: DNA
<213> ORGANISM: Artificial Sequence
<220> FEATURE:
<223> OTHER INFORMATION: Artificially synthesized oligonucleotide primer

<400> SEQUENCE: 24
atgaactctc ccatgcaccg                                                    20

<210> SEQ ID NO 25
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 25
tatgcaaccg gcacgtcatt                                                    20

<210> SEQ ID NO 26
<211> LENGTH: 269
<212> TYPE: PRT
<213> ORGANISM: Bordetella pertussis

<400> SEQUENCE: 26
```

Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Arg Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
            260                 265

<210> SEQ ID NO 27
<211> LENGTH: 226
<212> TYPE: PRT
<213> ORGANISM: Bordetella pertussis

<400> SEQUENCE: 27

Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Gly Pro Tyr Gly
        35                  40                  45

Arg Cys Ala Asn Lys Thr Arg Ala Leu Thr Val Ala Glu Leu Arg Gly
50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225

<210> SEQ ID NO 28
<211> LENGTH: 227
<212> TYPE: PRT
<213> ORGANISM: Bordetella pertussis

<400> SEQUENCE: 28

Met Leu Ile Asn Asn Lys Lys Leu Leu His His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

```
Gly Ile Ile Lys Asp Ala Pro Pro Gly Ala Gly Phe Ile Tyr Arg Glu
                100                 105                 110

Thr Phe Cys Ile Thr Thr Ile Tyr Lys Thr Gly Gln Pro Ala Ala Asp
            115                 120                 125

His Tyr Tyr Ser Lys Val Thr Ala Thr Arg Leu Leu Ala Ser Thr Asn
        130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225

<210> SEQ ID NO 29
<211> LENGTH: 152
<212> TYPE: PRT
<213> ORGANISM: Bordetella pertussis

<400> SEQUENCE: 29

Met Leu Arg Arg Phe Pro Thr Arg Thr Thr Ala Pro Gly Gln Gly Gly
1               5                   10                  15

Ala Arg Arg Ser Arg Val Arg Ala Leu Ala Trp Leu Leu Ala Ser Gly
                20                  25                  30

Ala Met Thr His Leu Ser Pro Ala Leu Ala Asp Val Pro Tyr Val Leu
            35                  40                  45

Val Lys Thr Asn Met Val Val Thr Ser Val Ala Met Lys Pro Tyr Glu
    50                  55                  60

Val Thr Pro Thr Arg Met Leu Val Cys Gly Ile Ala Ala Lys Leu Gly
65                  70                  75                  80

Ala Ala Ala Ser Ser Pro Asp Ala His Val Pro Phe Cys Phe Gly Lys
                85                  90                  95

Asp Leu Lys Arg Pro Gly Ser Ser Pro Met Glu Val Met Leu Arg Ala
                100                 105                 110

Val Phe Met Gln Gln Arg Pro Leu Arg Met Phe Leu Gly Pro Lys Gln
            115                 120                 125

Leu Thr Phe Glu Gly Lys Pro Ala Leu Glu Leu Ile Arg Met Val Glu
        130                 135                 140

Cys Ser Gly Lys Gln Asp Cys Pro
145                 150

<210> SEQ ID NO 30
<211> LENGTH: 133
<212> TYPE: PRT
<213> ORGANISM: Bordetella pertussis

<400> SEQUENCE: 30

Met Gln Arg Gln Ala Gly Leu Pro Leu Lys Ala Asn Pro Met His Thr
1               5                   10                  15

Ile Ala Ser Ile Leu Leu Ser Val Leu Gly Ile Tyr Ser Pro Ala Asp
                20                  25                  30
```

```
Val Ala Gly Leu Pro Thr His Leu Tyr Lys Asn Phe Thr Val Gln Glu
            35                  40                  45

Leu Ala Leu Lys Leu Lys Gly Lys Asn Gln Glu Phe Cys Leu Thr Ala
 50                  55                  60

Phe Met Ser Gly Arg Ser Leu Val Arg Ala Cys Leu Ser Asp Ala Gly
 65                  70                  75                  80

His Glu His Asp Thr Trp Phe Asp Thr Met Leu Gly Phe Ala Ile Ser
                 85                  90                  95

Ala Tyr Ala Leu Lys Ser Arg Ile Ala Leu Thr Val Glu Asp Ser Pro
            100                 105                 110

Tyr Pro Gly Thr Pro Gly Asp Leu Leu Glu Leu Gln Ile Cys Pro Leu
            115                 120                 125

Asn Gly Tyr Cys Glu
            130

<210> SEQ ID NO 31
<211> LENGTH: 269
<212> TYPE: PRT
<213> ORGANISM: Bordetella bronchiseptica

<400> SEQUENCE: 31

Met Arg Cys Thr Arg Ala Ile Arg Gln Thr Ala Arg Thr Gly Trp Leu
 1               5                  10                  15

Thr Trp Leu Ala Ile Leu Ala Val Thr Ala Pro Met Thr Ser Pro Ala
             20                  25                  30

Trp Ala Asp Asp Pro Pro Ala Thr Val Tyr Arg Tyr Asp Ser Arg Pro
         35                  40                  45

Pro Glu Asp Val Phe Leu Asn Gly Phe Thr Ala Trp Gly Asn Asn Asp
 50                  55                  60

Asn Val Leu Glu His Leu Thr Gly Arg Ser Cys Gln Val Gly Ser Ser
 65                  70                  75                  80

Asn Ser Ala Phe Val Ser Thr Ser Ser Arg Arg Tyr Thr Glu Val
                 85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Ile Arg Ala Asp
            115                 120                 125

Asn Asn Phe Tyr Gly Ala Ala Ser Ser Tyr Phe Glu Tyr Val Asp Thr
130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Pro Asn Leu Arg Tyr Val Ser Gln Gln Thr Arg Ala Asn
            195                 200                 205

Pro Asn Pro Tyr Thr Ser Arg Arg Ser Thr Ala Ser Ile Val Gly Thr
    210                 215                 220

Leu Val Arg Met Ala Pro Val Thr Gly Ala Cys Met Ala Arg Gln Ala
225                 230                 235                 240

Glu Ser Pro Glu Ala Met Ala Ala Trp Ser Glu Arg Ala Gly Glu Ala
                245                 250                 255

Met Val Leu Val Tyr Tyr Glu Ser Ile Ala Tyr Ser Phe
```

260 265

<210> SEQ ID NO 32
<211> LENGTH: 226
<212> TYPE: PRT
<213> ORGANISM: Bordetella bronchiseptica

<400> SEQUENCE: 32

Met Pro Ile Ser Arg Lys Thr Leu Ser His Leu Leu Ser Val Leu Pro
1               5                   10                  15

Leu Ala Phe Leu Gly Cys His Val Ala Arg Ala Ser Thr Pro Gly Ile
            20                  25                  30

Val Ile Pro Pro Gln Glu Gln Ile Thr Gln His Gly Gly Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225

<210> SEQ ID NO 33
<211> LENGTH: 227
<212> TYPE: PRT
<213> ORGANISM: Bordetella bronchiseptica

<400> SEQUENCE: 33

Met Leu Thr Asn Asn Lys Lys Leu Leu His His Ile Leu Pro Ile Leu
1               5                   10                  15

Leu Leu Ala Leu Leu Gly Met Arg Thr Ala Gln Ala Val Ala Pro Gly
20 25 30

Ile Val Ile Pro Pro Lys Ala Leu Leu Thr Lys Gln Gly Gly Ala Tyr
35 40 45

Gly Arg Cys Pro Asn Gly Thr Arg Ala Leu Thr Ala Ala Glu Leu Arg
50 55 60

Gly Ser Ala Glu Leu Gln Thr Tyr Leu Arg Gln Ile Thr Pro Gly Trp
65 70 75 80

Ser Ile Tyr Gly Leu Tyr Asp Gly Thr Tyr Leu Gly Gln Ser Tyr Gly

Gly Ile Ile Lys Asp Ala Pro Pro Gly Gly Phe Ile Tyr His Glu
                100                 105                 110

Thr Phe Cys Ile Thr Thr Ile Tyr Tyr Thr Gly Gln Pro Asp Thr Asp
            115                 120                 125

His Tyr Tyr Ser Lys Val Thr Ala Thr Arg Leu Leu Ala Ser Thr Asn
        130                 135                 140

Ser Gly Leu Cys Ala Val Phe Ala Arg Asp Gly Lys Pro Leu Ile Gly
145                 150                 155                 160

Ala Cys Thr Arg Pro Tyr Gln Ser Ser Tyr Gly Asp Met Tyr Asp Val
                165                 170                 175

Leu Arg Arg Leu Leu Tyr Met Val Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Glu Thr Tyr Ala Leu Thr Gly Ile Ser Leu Cys Asn Pro Ala Ala
210                 215                 220

Ser Ile Cys
225

<210> SEQ ID NO 34
<211> LENGTH: 152
<212> TYPE: PRT
<213> ORGANISM: Bordetella bronchiseptica

<400> SEQUENCE: 34

Met Leu Arg Arg Phe Pro Thr Arg Thr Thr Ala Pro Gly Gln Gly Gly
1               5                   10                  15

Ala Arg Arg Ser Arg Val Arg Ala Leu Ala Trp Leu Leu Thr Ser Gly
            20                  25                  30

Ala Met Thr His Leu Ser Pro Ala Leu Ala Asp Val Pro Tyr Val Leu
        35                  40                  45

Val Lys Thr Asn Met Val Val Thr Ser Val Ala Met Lys Pro Tyr Glu
    50                  55                  60

Val Thr Pro Thr Arg Met Leu Val Cys Gly Ile Ala Ala Lys Leu Gly
65                  70                  75                  80

Ala Ala Ala Ser Ser Pro Asp Ala His Val Pro Phe Cys Phe Gly Lys
                85                  90                  95

Asp Leu Lys Arg Ser Gly Ser Ser Pro Met Glu Val Met Leu Arg Ala
            100                 105                 110

Val Phe Met Gln Gln Arg Pro Leu Arg Met Phe Leu Gly Pro Lys Gln
        115                 120                 125

Leu Thr Phe Glu Gly Lys Pro Ala Leu Glu Leu Ile Arg Met Val Glu
    130                 135                 140

Cys Ser Gly Lys Gln Asp Cys Pro
145                 150

<210> SEQ ID NO 35
<211> LENGTH: 133
<212> TYPE: PRT
<213> ORGANISM: Bordetella bronchiseptica

<400> SEQUENCE: 35

Met Gln Arg Gln Ala Gly Leu Pro Leu Lys Ala Asn Thr Met His Thr
1               5                   10                  15

Ile Ala Ser Ile Leu Leu Ser Val Leu Gly Ile Tyr Ser Pro Ala Asp

```
            20                  25                  30
Val Ala Gly Leu Pro Thr His Leu Tyr Lys Asn Phe Thr Val Gln Glu
         35                  40                  45

Leu Ala Leu Lys Leu Lys Gly Lys Asn Gln Glu Phe Cys Leu Thr Ala
 50                  55                  60

Phe Met Pro Gly Arg Ser Leu Val Arg Ala Cys Leu Ser Asp Ala Gly
 65                  70                  75                  80

His Glu His Asp Thr Trp Phe Asp Thr Met Leu Gly Phe Ala Ile Ser
                 85                  90                  95

Ala Tyr Ala Leu Lys Ser Arg Ile Ala Leu Thr Val Glu Asp Ser Pro
             100                 105                 110

Tyr Pro Gly Thr Pro Gly Asp Leu Leu Glu Leu Gln Ile Cys Pro Leu
         115                 120                 125

Asn Gly Tyr Cys Glu
         130

<210> SEQ ID NO 36
<211> LENGTH: 3590
<212> TYPE: PRT
<213> ORGANISM: Bordetella pertussis

<400> SEQUENCE: 36

Met Asn Thr Asn Leu Tyr Arg Leu Val Phe Ser His Val Arg Gly Met
 1               5                  10                  15

Leu Val Pro Val Ser Glu His Cys Thr Val Gly Asn Thr Phe Cys Gly
             20                  25                  30

Arg Thr Arg Gly Gln Ala Arg Ser Gly Ala Arg Ala Thr Ser Leu Ser
         35                  40                  45

Val Ala Pro Asn Ala Leu Ala Trp Ala Leu Met Leu Ala Cys Thr Gly
 50                  55                  60

Leu Pro Leu Val Thr His Ala Gln Gly Leu Val Pro Gln Gly Gln Thr
 65                  70                  75                  80

Gln Val Leu Gln Gly Gly Asn Lys Val Pro Val Asn Ile Ala Asp
             85                  90                  95

Pro Asn Ser Gly Gly Val Ser His Asn Lys Phe Gln Gln Phe Asn Val
             100                 105                 110

Ala Asn Pro Gly Val Val Phe Asn Asn Gly Leu Thr Asp Gly Val Ser
         115                 120                 125

Arg Ile Gly Gly Ala Leu Thr Lys Asn Pro Asn Leu Thr Arg Gln Ala
 130                 135                 140

Ser Ala Ile Leu Ala Glu Val Thr Asp Thr Ser Pro Ser Arg Leu Ala
145                 150                 155                 160

Gly Thr Leu Glu Val Tyr Gly Lys Gly Ala Asp Leu Ile Ile Ala Asn
                 165                 170                 175

Pro Asn Gly Ile Ser Val Asn Gly Leu Ser Thr Leu Asn Ala Ser Asn
             180                 185                 190

Leu Thr Leu Thr Thr Gly Arg Pro Ser Val Asn Gly Arg Ile Gly
         195                 200                 205

Leu Asp Val Gln Gln Gly Thr Val Thr Ile Glu Arg Gly Gly Val Asn
 210                 215                 220

Ala Thr Gly Leu Gly Tyr Phe Asp Val Val Ala Arg Leu Val Lys Leu
225                 230                 235                 240

Gln Gly Ala Val Ser Ser Lys Gln Gly Lys Pro Leu Ala Asp Ile Ala
                 245                 250                 255
```

Val Val Ala Gly Ala Asn Arg Tyr Asp His Ala Thr Arg Ala Thr
            260                 265                 270

Pro Ile Ala Ala Gly Ala Arg Gly Ala Ala Gly Ala Tyr Ala Ile
            275                 280                 285

Asp Gly Thr Ala Ala Gly Ala Met Tyr Gly Lys His Ile Thr Leu Val
            290                 295                 300

Ser Ser Asp Ser Gly Leu Gly Val Arg Gln Leu Gly Ser Leu Ser Ser
305                 310                 315                 320

Pro Ser Ala Ile Thr Val Ser Ser Gln Gly Glu Ile Ala Leu Gly Asp
            325                 330                 335

Ala Thr Val Gln Arg Gly Pro Leu Ser Leu Lys Gly Ala Gly Val Val
            340                 345                 350

Ser Ala Gly Lys Leu Ala Ser Gly Gly Ala Val Asn Val Ala Gly
            355                 360                 365

Gly Gly Ala Val Lys Ile Ala Ser Ala Ser Ser Val Gly Asn Leu Ala
            370                 375                 380

Val Gln Gly Gly Lys Val Gln Ala Thr Leu Leu Asn Ala Gly Gly
385                 390                 395                 400

Thr Leu Leu Val Ser Gly Arg Gln Ala Val Gln Leu Gly Ala Ala Ser
            405                 410                 415

Ser Arg Gln Ala Leu Ser Val Asn Ala Gly Gly Ala Leu Lys Ala Asp
            420                 425                 430

Lys Leu Ser Ala Thr Arg Arg Val Asp Val Asp Gly Lys Gln Ala Val
            435                 440                 445

Ala Leu Gly Ser Ala Ser Ser Asn Ala Leu Ser Val Arg Ala Gly Gly
            450                 455                 460

Ala Leu Lys Ala Gly Lys Leu Ser Ala Thr Gly Arg Leu Asp Val Asp
465                 470                 475                 480

Gly Lys Gln Ala Val Thr Leu Gly Ser Val Ala Ser Asp Gly Ala Leu
            485                 490                 495

Ser Val Ser Ala Gly Gly Asn Leu Arg Ala Lys Gln Leu Val Ser Ser
            500                 505                 510

Ala Gln Leu Glu Val Arg Gly Gln Arg Glu Val Ala Leu Asp Asp Ala
            515                 520                 525

Ser Ser Ala Arg Gly Met Thr Val Val Ala Ala Gly Ala Leu Ala Ala
            530                 535                 540

Arg Asn Leu Gln Ser Lys Gly Ala Ile Gly Val Gln Gly Gly Glu Ala
545                 550                 555                 560

Val Ser Val Ala Asn Ala Asn Ser Asp Ala Glu Leu Arg Val Arg Gly
            565                 570                 575

Arg Gly Gln Val Asp Leu His Asp Leu Ser Ala Ala Arg Gly Ala Asp
            580                 585                 590

Ile Ser Gly Glu Gly Arg Val Asn Ile Gly Arg Ala Arg Ser Asp Ser
            595                 600                 605

Asp Val Lys Val Ser Ala His Gly Ala Leu Ser Ile Asp Ser Met Thr
            610                 615                 620

Ala Leu Gly Ala Ile Gly Val Gln Ala Gly Gly Ser Val Ser Ala Lys
625                 630                 635                 640

Asp Met Arg Ser Arg Gly Ala Val Thr Val Ser Gly Gly Ala Val
            645                 650                 655

Asn Leu Gly Asp Val Gln Ser Asp Gly Gln Val Arg Ala Thr Ser Ala
            660                 665                 670

Gly Ala Met Thr Val Arg Asp Val Ala Ala Ala Ala Asp Leu Ala Leu

```
            675                 680                 685
Gln Ala Gly Asp Ala Leu Gln Ala Gly Phe Leu Lys Ser Ala Gly Ala
        690                 695                 700
Met Thr Val Asn Gly Arg Asp Ala Val Arg Leu Asp Gly Ala His Ala
705                 710                 715                 720
Gly Gly Gln Leu Arg Val Ser Ser Asp Gly Gln Ala Ala Leu Gly Ser
                725                 730                 735
Leu Ala Ala Lys Gly Glu Leu Thr Val Ser Ala Arg Ala Ala Thr
        740                 745                 750
Val Ala Glu Leu Lys Ser Leu Asp Asn Ile Ser Val Thr Gly Gly Glu
            755                 760                 765
Arg Val Ser Val Gln Ser Val Asn Ser Ala Ser Arg Val Ala Ile Ser
        770                 775                 780
Ala His Gly Ala Leu Asp Val Gly Lys Val Ser Ala Lys Ser Gly Ile
785                 790                 795                 800
Gly Leu Glu Gly Trp Gly Ala Val Gly Ala Asp Ser Leu Gly Ser Asp
                805                 810                 815
Gly Ala Ile Ser Val Ser Gly Arg Asp Ala Val Arg Val Asp Gln Ala
            820                 825                 830
Arg Ser Leu Ala Asp Ile Ser Leu Gly Ala Glu Gly Ala Thr Leu
        835                 840                 845
Gly Ala Val Glu Ala Ala Gly Ser Ile Asp Val Arg Gly Gly Ser Thr
        850                 855                 860
Val Ala Ala Asn Ser Leu His Ala Asn Arg Asp Val Arg Val Ser Gly
865                 870                 875                 880
Lys Asp Ala Val Arg Val Thr Ala Ala Thr Ser Gly Gly Leu His
                885                 890                 895
Val Ser Ser Gly Arg Gln Leu Asp Leu Gly Ala Val Gln Ala Arg Gly
            900                 905                 910
Ala Leu Ala Leu Asp Gly Gly Ala Gly Val Ala Leu Gln Ser Ala Lys
        915                 920                 925
Ala Ser Gly Thr Leu His Val Gln Gly Gly Glu His Leu Asp Leu Gly
        930                 935                 940
Thr Leu Ala Ala Val Gly Ala Val Asp Val Asn Gly Thr Gly Asp Val
945                 950                 955                 960
Arg Val Ala Lys Leu Val Ser Asp Ala Gly Ala Asp Leu Gln Ala Gly
                965                 970                 975
Arg Ser Met Thr Leu Gly Ile Val Asp Thr Thr Gly Asp Leu Gln Ala
            980                 985                 990
Arg Ala Gln Gln Lys Leu Glu Leu Gly Ser Val Lys Ser Asp Gly Gly
        995                 1000                1005
Leu Gln Ala Ala Ala Gly Gly Ala Leu Ser Leu Ala Ala Ala Glu
        1010                1015                1020
Val Ala Gly Ala Leu Glu Leu Ser Gly Gln Gly Val Thr Val Asp
        1025                1030                1035
Arg Ala Ser Ala Ser Arg Ala Arg Ile Asp Ser Thr Gly Ser Val
        1040                1045                1050
Gly Ile Gly Ala Leu Lys Ala Gly Ala Val Glu Ala Ala Ser Pro
        1055                1060                1065
Arg Arg Ala Arg Arg Ala Leu Arg Gln Asp Phe Phe Thr Pro Gly
        1070                1075                1080
Ser Val Val Val Arg Ala Gln Gly Asn Val Thr Val Gly Arg Gly
        1085                1090                1095
```

-continued

```
Asp Pro His Gln Gly Val Leu Ala Gln Gly Asp Ile Ile Met Asp
    1100                1105                1110
Ala Lys Gly Gly Thr Leu Leu Leu Arg Asn Asp Ala Leu Thr Glu
    1115                1120                1125
Asn Gly Thr Val Thr Ile Ser Ala Asp Ser Ala Val Leu Glu His
    1130                1135                1140
Ser Thr Ile Glu Ser Lys Ile Ser Gln Ser Val Leu Ala Ala Lys
    1145                1150                1155
Gly Asp Lys Gly Lys Pro Ala Val Ser Val Lys Val Ala Lys Lys
    1160                1165                1170
Leu Phe Leu Asn Gly Thr Leu Arg Ala Val Asn Asp Asn Asn Glu
    1175                1180                1185
Thr Met Ser Gly Arg Gln Ile Asp Val Val Asp Gly Arg Pro Gln
    1190                1195                1200
Ile Thr Asp Ala Val Thr Gly Glu Ala Arg Lys Asp Glu Ser Val
    1205                1210                1215
Val Ser Asp Ala Ala Leu Val Ala Asp Gly Gly Pro Ile Val Val
    1220                1225                1230
Glu Ala Gly Glu Leu Val Ser His Ala Gly Gly Ile Gly Asn Gly
    1235                1240                1245
Arg Asn Lys Glu Asn Gly Ala Ser Val Thr Val Arg Thr Thr Gly
    1250                1255                1260
Asn Leu Val Asn Lys Gly Tyr Ile Ser Ala Gly Lys Gln Gly Val
    1265                1270                1275
Leu Glu Val Gly Gly Ala Leu Thr Asn Glu Phe Leu Val Gly Ser
    1280                1285                1290
Asp Gly Thr Gln Arg Ile Glu Ala Gln Arg Ile Glu Asn Arg Gly
    1295                1300                1305
Thr Phe Gln Ser Gln Ala Pro Ala Gly Thr Ala Gly Ala Leu Val
    1310                1315                1320
Val Lys Ala Ala Glu Ala Ile Val His Asp Gly Val Met Ala Thr
    1325                1330                1335
Lys Gly Glu Met Gln Ile Ala Gly Lys Gly Gly Gly Ser Pro Thr
    1340                1345                1350
Val Thr Ala Gly Ala Lys Ala Thr Thr Ser Ala Asn Lys Leu Ser
    1355                1360                1365
Val Asp Val Ala Ser Trp Asp Asn Ala Gly Ser Leu Asp Ile Lys
    1370                1375                1380
Lys Gly Gly Ala Gln Val Thr Val Ala Gly Arg Tyr Ala Glu His
    1385                1390                1395
Gly Glu Val Ser Ile Gln Gly Asp Tyr Thr Val Ser Ala Asp Ala
    1400                1405                1410
Ile Ala Leu Ala Ala Gln Val Thr Gln Arg Gly Gly Ala Ala Asn
    1415                1420                1425
Leu Thr Ser Arg His Asp Thr Arg Phe Ser Asn Lys Ile Arg Leu
    1430                1435                1440
Met Gly Pro Leu Gln Val Asn Ala Gly Gly Ala Val Ser Asn Thr
    1445                1450                1455
Gly Asn Leu Lys Val Arg Glu Gly Val Thr Val Thr Ala Ala Ser
    1460                1465                1470
Phe Asp Asn Glu Thr Gly Ala Glu Val Met Ala Lys Ser Ala Thr
    1475                1480                1485
```

```
Leu Thr Thr Ser Gly Ala Ala Arg Asn Ala Gly Lys Met Gln Val
    1490            1495                1500

Lys Glu Ala Ala Thr Ile Val Ala Ala Ser Val Ser Asn Pro Gly
1505                1510                1515

Thr Phe Thr Ala Gly Lys Asp Ile Thr Val Thr Ser Arg Gly Gly
1520                1525                1530

Phe Asp Asn Glu Gly Lys Met Glu Ser Asn Lys Asp Ile Val Ile
1535                1540                1545

Lys Thr Glu Gln Phe Ser Asn Gly Arg Val Leu Asp Ala Lys His
1550                1555                1560

Asp Leu Thr Val Thr Ala Ser Gly Gln Ala Asp Asn Arg Gly Ser
1565                1570                1575

Leu Lys Ala Gly His Asp Phe Thr Val Gln Ala Gln Arg Ile Asp
1580                1585                1590

Asn Ser Gly Thr Met Ala Ala Gly His Asp Ala Thr Leu Lys Ala
1595                1600                1605

Pro His Leu Arg Asn Thr Gly Gln Val Val Ala Gly His Asp Ile
1610                1615                1620

His Ile Ile Asn Ser Ala Lys Leu Glu Asn Thr Gly Arg Val Asp
1625                1630                1635

Ala Arg Asn Asp Ile Ala Leu Asp Val Ala Asp Phe Thr Asn Thr
1640                1645                1650

Gly Ser Leu Tyr Ala Glu His Asp Ala Thr Leu Thr Leu Ala Gln
1655                1660                1665

Gly Thr Gln Arg Asp Leu Val Val Asp Gln Asp His Ile Leu Pro
1670                1675                1680

Val Ala Glu Gly Thr Leu Arg Val Lys Ala Lys Ser Leu Thr Thr
1685                1690                1695

Glu Ile Glu Thr Gly Asn Pro Gly Ser Leu Ile Ala Glu Val Gln
1700                1705                1710

Glu Asn Ile Asp Asn Lys Gln Ala Ile Val Val Gly Lys Asp Leu
1715                1720                1725

Thr Leu Ser Ser Ala His Gly Asn Val Ala Asn Glu Ala Asn Ala
1730                1735                1740

Leu Leu Trp Ala Ala Gly Glu Leu Thr Val Lys Ala Gln Asn Ile
1745                1750                1755

Thr Asn Lys Arg Ala Ala Leu Ile Glu Ala Gly Gly Asn Ala Arg
1760                1765                1770

Leu Thr Ala Ala Val Ala Leu Leu Asn Lys Leu Gly Arg Ile Arg
1775                1780                1785

Ala Gly Glu Asp Met His Leu Asp Ala Pro Arg Ile Glu Asn Thr
1790                1795                1800

Ala Lys Leu Ser Gly Glu Val Gln Arg Lys Gly Val Gln Asp Val
1805                1810                1815

Gly Gly Gly Glu His Gly Arg Trp Ser Gly Ile Gly Tyr Val Asn
1820                1825                1830

Tyr Trp Leu Arg Ala Gly Asn Gly Lys Lys Ala Gly Thr Ile Ala
1835                1840                1845

Ala Pro Trp Tyr Gly Gly Asp Leu Thr Ala Glu Gln Ser Leu Ile
1850                1855                1860

Glu Val Gly Lys Asp Leu Tyr Leu Asn Ala Gly Ala Arg Lys Asp
1865                1870                1875

Glu His Arg His Leu Leu Asn Glu Gly Val Ile Gln Ala Gly Gly
```

-continued

```
            1880                1885                1890
His Gly His Ile Gly Gly Asp Val Asp Asn Arg Ser Val Val Arg
        1895                1900                1905
Thr Val Ser Ala Met Glu Tyr Phe Lys Thr Pro Leu Pro Val Ser
        1910                1915                1920
Leu Thr Ala Leu Asp Asn Arg Ala Gly Leu Ser Pro Ala Thr Trp
        1925                1930                1935
Asn Phe Gln Ser Thr Tyr Glu Leu Leu Asp Tyr Leu Leu Asp Gln
        1940                1945                1950
Asn Arg Tyr Glu Tyr Ile Trp Gly Leu Tyr Pro Thr Tyr Thr Glu
        1955                1960                1965
Trp Ser Val Asn Thr Leu Lys Asn Leu Asp Leu Gly Tyr Gln Ala
        1970                1975                1980
Lys Pro Ala Pro Thr Ala Pro Pro Met Pro Lys Ala Pro Glu Leu
        1985                1990                1995
Asp Leu Arg Gly His Thr Leu Glu Ser Ala Glu Gly Arg Lys Ile
        2000                2005                2010
Phe Gly Glu Tyr Lys Lys Leu Gln Gly Glu Tyr Glu Lys Ala Lys
        2015                2020                2025
Met Ala Val Gln Ala Val Glu Ala Tyr Gly Glu Ala Thr Arg Arg
        2030                2035                2040
Val His Asp Gln Leu Gly Gln Arg Tyr Gly Lys Ala Leu Gly Gly
        2045                2050                2055
Met Asp Ala Glu Thr Lys Glu Val Asp Gly Ile Ile Gln Glu Phe
        2060                2065                2070
Ala Ala Asp Leu Arg Thr Val Tyr Ala Lys Gln Ala Asp Gln Ala
        2075                2080                2085
Thr Ile Asp Ala Glu Thr Asp Lys Val Ala Gln Arg Tyr Lys Ser
        2090                2095                2100
Gln Ile Asp Ala Val Arg Leu Gln Ala Ile Gln Pro Gly Arg Val
        2105                2110                2115
Thr Leu Ala Lys Ala Leu Ser Ala Ala Leu Gly Ala Asp Trp Arg
        2120                2125                2130
Ala Leu Gly His Ser Gln Leu Met Gln Arg Trp Lys Asp Phe Lys
        2135                2140                2145
Ala Gly Lys Arg Gly Ala Glu Ile Ala Phe Tyr Pro Lys Glu Gln
        2150                2155                2160
Thr Val Leu Ala Ala Gly Ala Gly Leu Thr Leu Ser Asn Gly Ala
        2165                2170                2175
Ile His Asn Gly Glu Asn Ala Ala Gln Asn Arg Gly Arg Pro Glu
        2180                2185                2190
Gly Leu Lys Ile Gly Ala His Ser Ala Thr Ser Val Ser Gly Ser
        2195                2200                2205
Phe Asp Ala Leu Arg Asp Val Gly Leu Glu Lys Arg Leu Asp Ile
        2210                2215                2220
Asp Asp Ala Leu Ala Ala Val Leu Val Asn Pro His Ile Phe Thr
        2225                2230                2235
Arg Ile Gly Ala Ala Gln Thr Ser Leu Ala Asp Gly Ala Ala Gly
        2240                2245                2250
Pro Ala Leu Ala Arg Gln Ala Arg Gln Ala Pro Glu Thr Asp Gly
        2255                2260                2265
Met Val Asp Ala Arg Gly Leu Gly Ser Ala Asp Ala Leu Ala Ser
        2270                2275                2280
```

```
Leu Ala Ser Leu Asp Ala Ala Gln Gly Leu Glu Val Ser Gly Arg
    2285            2290                2295
Arg Asn Ala Gln Val Ala Asp Ala Gly Leu Ala Gly Pro Ser Ala
    2300            2305                2310
Val Ala Ala Pro Ala Val Gly Ala Ala Asp Val Gly Val Glu Pro
    2315            2320                2325
Val Thr Gly Asp Gln Val Asp Gln Pro Val Val Ala Val Gly Leu
    2330            2335                2340
Glu Gln Pro Val Ala Thr Val Arg Val Ala Pro Ala Val Ala
    2345            2350                2355
Leu Pro Arg Pro Leu Phe Glu Thr Arg Ile Lys Phe Ile Asp Gln
    2360            2365                2370
Ser Lys Phe Tyr Gly Ser Arg Tyr Phe Phe Glu Gln Ile Gly Tyr
    2375            2380                2385
Lys Pro Asp Arg Ala Ala Arg Val Ala Gly Asp Asn Tyr Phe Asp
    2390            2395                2400
Thr Thr Leu Val Arg Glu Gln Val Arg Arg Ala Leu Gly Gly Tyr
    2405            2410                2415
Glu Ser Arg Leu Pro Val Arg Gly Val Ala Leu Val Ala Lys Leu
    2420            2425                2430
Met Asp Ser Ala Gly Thr Val Gly Lys Ala Leu Gly Leu Lys Val
    2435            2440                2445
Gly Val Ala Pro Thr Ala Gln Gln Leu Lys Gln Ala Asp Arg Asp
    2450            2455                2460
Phe Val Trp Tyr Val Asp Thr Val Ile Asp Gly Gln Lys Val Leu
    2465            2470                2475
Ala Pro Arg Leu Tyr Leu Thr Glu Ala Thr Arg Gln Gly Ile Thr
    2480            2485                2490
Asp Gln Tyr Ala Gly Gly Gly Ala Leu Ile Ala Ser Gly Gly Asp
    2495            2500                2505
Val Thr Val Asn Thr Asp Gly His Asp Val Ser Ser Val Asn Gly
    2510            2515                2520
Leu Ile Gln Gly Arg Ser Val Lys Val Asp Ala Gly Lys Gly Lys
    2525            2530                2535
Val Val Val Ala Asp Ser Lys Gly Ala Gly Gly Gly Ile Glu Ala
    2540            2545                2550
Asp Asp Glu Val Asp Val Ser Gly Arg Asp Ile Gly Ile Glu Gly
    2555            2560                2565
Gly Lys Leu Arg Gly Lys Asp Val Arg Leu Lys Ala Asp Thr Val
    2570            2575                2580
Lys Val Ala Thr Ser Met Arg Tyr Asp Asp Lys Gly Arg Leu Ala
    2585            2590                2595
Ala Arg Gly Asp Gly Ala Leu Asp Ala Gln Gly Gly Gln Leu His
    2600            2605                2610
Ile Glu Ala Lys Arg Leu Glu Thr Ala Gly Ala Thr Leu Lys Gly
    2615            2620                2625
Gly Lys Val Lys Leu Asp Val Asp Asp Val Lys Leu Gly Gly Val
    2630            2635                2640
Tyr Glu Ala Gly Ser Ser Tyr Glu Asn Lys Ser Ser Thr Pro Leu
    2645            2650                2655
Gly Ser Leu Phe Ala Ile Leu Ser Ser Thr Thr Glu Thr Asn Gln
    2660            2665                2670
```

```
Ser Ala His Ala Asn His Tyr Gly Thr Arg Ile Glu Ala Gly Thr
2675                2680                2685

Leu Glu Gly Lys Met Gln Asn Leu Glu Ile Glu Gly Gly Ser Val
2690                2695                2700

Asp Ala Ala His Thr Asp Leu Ser Val Ala Arg Asp Ala Arg Phe
2705                2710                2715

Lys Ala Ala Ala Asp Phe Ala His Ala Glu His Glu Lys Asp Val
2720                2725                2730

Arg Gln Leu Ser Leu Gly Ala Lys Val Gly Ala Gly Gly Tyr Glu
2735                2740                2745

Ala Gly Phe Ser Leu Gly Ser Glu Ser Gly Leu Glu Ala His Ala
2750                2755                2760

Gly Arg Gly Met Thr Ala Gly Ala Glu Val Lys Val Gly Tyr Arg
2765                2770                2775

Ala Ser His Glu Gln Ser Ser Glu Thr Glu Lys Ser Tyr Arg Asn
2780                2785                2790

Ala Asn Leu Asn Phe Gly Gly Gly Ser Val Glu Ala Gly Asn Val
2795                2800                2805

Leu Asp Ile Gly Gly Ala Asp Ile Asn Arg Asn Arg Tyr Gly Gly
2810                2815                2820

Ala Ala Lys Gly Asn Ala Gly Thr Glu Glu Ala Leu Arg Met Arg
2825                2830                2835

Ala Lys Lys Val Glu Ser Thr Lys Tyr Val Ser Glu Gln Thr Ser
2840                2845                2850

Gln Ser Ser Gly Trp Ser Val Glu Val Ala Ser Thr Ala Ser Ala
2855                2860                2865

Arg Ser Ser Leu Leu Thr Ala Ala Thr Arg Leu Gly Asp Ser Val
2870                2875                2880

Ala Gln Asn Val Glu Asp Gly Arg Glu Ile Arg Gly Glu Leu Met
2885                2890                2895

Ala Ala Gln Val Ala Ala Glu Ala Thr Gln Leu Val Thr Ala Asp
2900                2905                2910

Thr Ala Ala Val Ala Leu Ser Ala Gly Ile Ser Ala Asp Phe Asp
2915                2920                2925

Ser Ser His Ser Arg Ser Thr Ser Gln Asn Thr Gln Tyr Leu Gly
2930                2935                2940

Gly Asn Leu Ser Ile Glu Ala Thr Glu Gly Asp Ala Thr Leu Val
2945                2950                2955

Gly Ala Lys Phe Gly Gly Gly Asp Gln Val Ser Leu Lys Ala Ala
2960                2965                2970

Lys Ser Val Asn Leu Met Ala Ala Glu Ser Thr Phe Glu Ser Tyr
2975                2980                2985

Ser Glu Ser His Asn Phe His Ala Ser Ala Asp Ala Asn Leu Gly
2990                2995                3000

Ala Asn Ala Val Gln Gly Ala Val Gly Leu Gly Leu Thr Ala Gly
3005                3010                3015

Met Gly Thr Ser His Gln Ile Thr Asn Glu Thr Gly Lys Thr Tyr
3020                3025                3030

Ala Gly Thr Ser Val Asp Ala Ala Asn Val Ser Ile Asp Ala Gly
3035                3040                3045

Lys Asp Leu Asn Leu Ser Gly Ser Arg Val Arg Gly Lys His Val
3050                3055                3060

Val Leu Asp Val Glu Gly Asp Ile Asn Ala Thr Ser Lys Gln Asp
```

```
                3065                3070                3075
Glu Arg Asn Tyr Asn Ser Ser Gly Gly Gly Trp Asp Ala Ser Ala
        3080            3085            3090
Gly Val Ala Ile Gln Asn Arg Thr Leu Val Ala Pro Val Gly Ser
        3095            3100            3105
Ala Gly Phe Asn Phe Asn Thr Glu His Asp Asn Ser Arg Leu Thr
        3110            3115            3120
Asn Asp Gly Ala Ala Gly Val Val Ala Ser Asp Gly Leu Thr Gly
        3125            3130            3135
His Val Lys Gly Asp Ala Asn Leu Thr Gly Ala Thr Ile Ala Asp
        3140            3145            3150
Leu Ser Gly Lys Gly Asn Leu Lys Val Asp Gly Ala Val Asn Ala
        3155            3160            3165
Gln Asn Leu Lys Asp Tyr Arg Asp Lys Asp Gly Ser Gly Gly
        3170            3175            3180
Leu Asn Val Gly Ile Ser Ser Thr Thr Leu Ala Pro Thr Val Gly
        3185            3190            3195
Val Ala Phe Gly Arg Val Ala Gly Glu Asp Tyr Gln Ala Glu Gln
        3200            3205            3210
Arg Ala Thr Ile Asp Val Gly Gln Thr Lys Asp Pro Ala Arg Leu
        3215            3220            3225
Gln Val Gly Gly Gly Val Lys Gly Thr Leu Asn Gln Asp Ala Ala
        3230            3235            3240
Gln Ala Thr Val Val Gln Arg Asn Lys His Trp Ala Gly Gly Gly
        3245            3250            3255
Ser Glu Phe Ser Val Ala Gly Lys Ser Leu Lys Lys Lys Asn Gln
        3260            3265            3270
Val Arg Pro Val Glu Thr Pro Thr Pro Asp Val Val Asp Gly Pro
        3275            3280            3285
Pro Ser Arg Pro Thr Thr Pro Pro Ala Ser Pro Gln Pro Ile Arg
        3290            3295            3300
Ala Thr Val Glu Val Ser Ser Pro Pro Val Ser Val Ala Thr
        3305            3310            3315
Val Glu Val Val Pro Arg Pro Lys Val Glu Thr Ala Gln Pro Leu
        3320            3325            3330
Pro Pro Arg Pro Val Ala Ala Gln Val Val Pro Val Thr Pro Pro
        3335            3340            3345
Lys Val Glu Val Ala Lys Val Glu Val Val Pro Arg Pro Lys Val
        3350            3355            3360
Glu Thr Ala Gln Pro Leu Pro Pro Arg Pro Val Val Ala Glu Lys
        3365            3370            3375
Val Thr Thr Pro Ala Val Gln Pro Gln Leu Ala Lys Val Glu Thr
        3380            3385            3390
Val Gln Pro Val Lys Pro Glu Thr Thr Lys Pro Leu Pro Lys Pro
        3395            3400            3405
Leu Pro Val Ala Lys Val Thr Lys Ala Pro Pro Val Val Glu
        3410            3415            3420
Thr Ala Gln Pro Leu Pro Pro Val Lys Pro Gln Lys Ala Thr Pro
        3425            3430            3435
Gly Pro Val Ala Glu Val Gly Lys Ala Thr Val Thr Thr Val Gln
        3440            3445            3450
Val Gln Ser Ala Pro Pro Lys Pro Ala Pro Val Ala Lys Gln Pro
        3455            3460            3465
```

```
Ala Pro  Ala Pro Lys Pro Lys Pro Lys Pro  Lys Ala Glu
    3470         3475             3480

Arg Pro  Lys Pro Gly Lys Thr  Thr Pro Leu  Ser Gly Arg His Val
    3485         3490              3495

Val Gln  Gln Gln Val Gln  Val Leu Gln Arg  Gln Ala Ser Asp Ile
    3500         3505              3510

Asn Asn  Thr Lys Ser Leu Pro  Gly Gly Lys Leu Pro  Lys Pro Val
    3515         3520             3525

Thr Val  Lys Leu Thr Asp Glu  Asn Gly Lys Pro Gln  Thr Tyr Thr
    3530         3535             3540

Ile Asn  Arg Arg Glu Asp Leu  Met Lys Leu Asn Gly  Lys Val Leu
    3545         3550             3555

Ser Thr  Lys Thr Thr Leu Gly  Leu Glu Gln Thr Phe  Arg Leu Arg
    3560         3565             3570

Val Glu  Asp Ile Gly Gly Lys  Asn Tyr Arg Val Phe  Tyr Glu Thr
    3575         3580             3585

Asn Lys
    3590

<210> SEQ ID NO 37
<211> LENGTH: 3640
<212> TYPE: PRT
<213> ORGANISM: Bordetella bronchiseptica

<400> SEQUENCE: 37

Met Leu Ala Cys Ala Gly Leu Pro Leu Val Thr His Ala Gln Gly Leu
1               5                   10                  15

Val Pro Gln Gly Gln Thr Gln Val Leu Gln Gly Gly Asn Lys Val Pro
            20                  25                  30

Val Val Asn Ile Ala Asn Pro Asn Ser Gly Gly Val Ser His Asn Lys
        35                  40                  45

Phe Gln Gln Phe Asn Val Ala Asn Pro Gly Val Val Phe Asn Asn Gly
    50                  55                  60

Leu Thr Asp Gly Val Ser Arg Ile Gly Gly Ala Leu Thr Lys Asn Pro
65                  70                  75                  80

Asn Leu Thr Arg Gln Ala Ser Ala Ile Leu Ala Glu Val Thr Gly Thr
                85                  90                  95

Ser Pro Ser Arg Leu Ala Gly Thr Leu Glu Val Tyr Gly Lys Gly Ala
            100                 105                 110

Asp Leu Ile Ile Ala Asn Pro Asn Gly Ile Ser Val Asn Gly Leu Ser
        115                 120                 125

Thr Leu Asn Ala Ser Asn Leu Thr Leu Thr Thr Gly Arg Pro Ser Val
    130                 135                 140

Asn Gly Gly Arg Ile Gly Leu Asp Val Gln Gln Gly Thr Val Thr Ile
145                 150                 155                 160

Glu Arg Gly Gly Val Asn Val Thr Gly Leu Gly Tyr Phe Asp Val Val
                165                 170                 175

Ala Arg Leu Val Lys Leu Gln Gly Ala Val Ser Ser Glu Gln Gly Lys
            180                 185                 190

Pro Leu Ala Asp Ile Ala Val Val Ala Gly Ala Asn Arg Tyr Asp His
        195                 200                 205

Ala Thr Arg Arg Ala Thr Pro Ile Ala Ala Gly Ala Arg Gly Ala Ala
    210                 215                 220

Ala Gly Ala Tyr Ala Ile Asp Gly Thr Ala Ala Gly Ala Met Tyr Gly
```

-continued

```
                225                 230                 235                 240
Lys His Ile Thr Leu Val Ser Ser Asp Ser Gly Leu Gly Val Arg Gln
                    245                 250                 255

Leu Gly Ser Leu Ser Ser Pro Ser Ala Ile Thr Val Ser Ser Gln Gly
                260                 265                 270

Glu Ile Ala Leu Gly Asp Ala Thr Val Gln Arg Gly Pro Leu Ser Leu
                275                 280                 285

Lys Gly Ala Gly Ala Val Ser Ala Gly Lys Leu Ala Ser Gly Gly Ala
        290                 295                 300

Val Arg Val Ala Gly Gly Ala Val Lys Ile Ala Ser Ala Ser Ser
305                 310                 315                 320

Val Gly Asn Leu Ala Val Gln Gly Gly Lys Val Gln Ala Thr Leu
                325                 330                 335

Leu Asn Ala Gly Gly Thr Leu Gln Val Ser Gly Arg Gln Ala Val Gln
                340                 345                 350

Leu Gly Thr Ala Ser Ser Arg Gln Val Leu Ser Val Asn Ala Gly Gly
                355                 360                 365

Ala Leu Lys Ala Asp Gln Leu Ser Ala Thr Gly Arg Leu Glu Val Asp
        370                 375                 380

Gly Lys Gln Ala Val Thr Leu Gly Ser Ala Ala Ser Arg Asn Ala Leu
385                 390                 395                 400

Ser Val Arg Ala Gly Gly Ala Leu Lys Ala Asp Lys Leu Ser Ala Thr
                405                 410                 415

Gly Arg Leu Glu Val Asp Gly Gln Gln Ala Val Thr Leu Gly Ser Ala
                420                 425                 430

Ala Ser Gly Asp Ala Leu Ser Val Ser Ala Gly Ala Ala Leu Arg Ala
        435                 440                 445

Asp Lys Leu Ser Ala Thr Gly Arg Leu Asp Val Asp Gly Lys Gln Ala
        450                 455                 460

Val Thr Leu Gly Ser Ala Ala Ser Gly Asp Ala Leu Ser Val Ser Ala
465                 470                 475                 480

Gly Ala Ala Leu Arg Ala Asp Lys Leu Ser Ala Thr Arg Arg Leu Gly
                485                 490                 495

Val Asp Gly Lys Gln Ala Val Thr Leu Gly Ser Val Ala Ser Asp Gly
                500                 505                 510

Ala Leu Ser Val Ser Ala Gly Gly Asn Leu Gln Ala Lys Gln Leu Val
                515                 520                 525

Ser Asn Ala Gly Leu Asp Val Arg Gly Gln Arg Glu Val Ser Leu Glu
        530                 535                 540

Ala Ala Ser Ser Val Arg Gly Met Thr Val Ala Ala Ala Gly Thr Leu
545                 550                 555                 560

Ala Ala Arg Asn Leu Gln Ser Lys Gly Ala Ile Arg Val Gln Gly Gly
                565                 570                 575

Glu Ala Val Ser Val Ala Asn Ala Asn Ser Asp Ala Glu Leu His Val
                580                 585                 590

Ser Gly Arg Gly Gln Val Asp Leu Gly Asp Leu Ser Ala Ala Arg Gly
                595                 600                 605

Ala Asp Ile Thr Gly Glu Gln Arg Val Ser Ile Gly Arg Ala His Ser
        610                 615                 620

Asp Gly Asp Val Lys Val Ala Ala Arg Gly Ala Leu Ser Ile Asp Ser
625                 630                 635                 640

Met Thr Ala Leu Gly Ala Ile Gly Val Gln Ala Gly Asp Ser Val Ser
                645                 650                 655
```

```
Ala Lys Asp Met Arg Ser Arg Gly Ala Val Thr Val Ser Gly Gly Gly
            660                 665                 670

Ser Val Asn Leu Gly Asp Val Gln Ser Asp Gly Gln Val Arg Ala Thr
            675                 680                 685

Ser Ala Gly Ala Met Thr Val Arg Asp Ala Ala Ala Ala Asp Leu
690                 695                 700

Ala Leu Gln Ala Gly Ala Leu Gln Ala Gly Phe Leu Lys Ser Ala
705                 710                 715                 720

Gly Ala Met Thr Val Asn Gly Arg Asp Ala Val Arg Leu Asp Gly Ala
                725                 730                 735

Gln Ala Gly Gly Gln Leu Arg Val Ser Ser Asp Gly Gln Ala Ala Leu
            740                 745                 750

Gly Ser Leu Ala Ala Lys Gly Ala Leu Thr Val Ser Ala Ala Arg Ala
            755                 760                 765

Ala Thr Val Ala Glu Leu Lys Ser Leu Asp Ser Ile Ser Val Thr Gly
            770                 775                 780

Gly Glu Arg Val Ser Val Gln Ser Val Asn Ser Ala Ser Arg Val Ala
785                 790                 795                 800

Ile Ser Ala His Gly Ala Leu Glu Val Gly Lys Val Ser Ala Lys Ser
                805                 810                 815

Gly Ile Gly Ile Glu Gly Trp Gly Ala Val Ala Val Asp Ser Leu Gly
            820                 825                 830

Ser Asp Gly Ala Ile Ser Val Ser Gly Arg Asp Ala Val Arg Val Asp
            835                 840                 845

His Ala Arg Ser Leu Ala Asp Ile Ser Leu Gly Ala Glu Gly Gly Ala
            850                 855                 860

Thr Leu Gly Ala Val Glu Ala Ala Gly Ser Ile Asp Val Arg Gly Gly
865                 870                 875                 880

Ser Thr Val Ala Ala Asn Ser Leu Arg Ala Asn Arg Asp Val Arg Val
                885                 890                 895

Ser Gly Lys Asp Ala Val Arg Val Thr Ala Ala Thr Ser Gly Gly Gly
            900                 905                 910

Leu His Val Ser Ser Gly Arg Gln Leu Asp Leu Gly Ala Val Gln Ala
            915                 920                 925

Arg Gly Ala Leu Ala Leu Asp Gly Gly Ala Gly Val Ala Leu Gln Ser
930                 935                 940

Ala Lys Ala Gly Gly Thr Leu His Val Gln Gly Gly Glu His Leu Asp
945                 950                 955                 960

Leu Gly Thr Leu Ala Ala Val Gly Ala Val Asp Val Asn Gly Thr Gly
                965                 970                 975

Asp Val Arg Val Ala Lys Leu Val Ser Asp Ala Gly Ala Asp Leu Gln
            980                 985                 990

Ala Gly Arg Ser Met Thr Leu Gly Thr Val Asp Thr Thr Gly Asp Leu
            995                 1000                1005

Gln Ala  Arg Ala Gln Gln Ala  Leu Glu Leu Gly Ser  Val Lys Thr
    1010                1015                 1020

Glu Gly  Gly Leu Gln Ala Ala  Ala Gly Gly Ala Leu  Ser Leu Ala
    1025                1030                 1035

Ala Ala  Glu Val Ala Gly Ala  Leu Glu Leu Ser Gly  His Gly Val
    1040                1045                 1050

Thr Val  Asp Arg Ala Ser Ala  Gly Arg Ala Arg Ile  Asp Ser Thr
    1055                1060                 1065
```

```
Gly Ser Val Gly Ile Gly Ala Leu Lys Ala Gly Ala Val Glu Ala
    1070                1075                1080

Ala Ser Pro Arg Arg Ala Arg Arg Ala Leu Arg Gln Asp Phe Phe
    1085                1090                1095

Thr Pro Gly Ser Val Val Val Arg Ala Gln Gly Asn Val Thr Val
    1100                1105                1110

Gly Arg Gly Asp Pro His Gln Gly Val Leu Ala Gln Gly Asp Ile
    1115                1120                1125

Val Met Asp Ala Lys Gly Gly Thr Leu Leu Leu Arg Asn Asp Val
    1130                1135                1140

Leu Thr Glu Asn Gly Thr Val Thr Ile Ser Ala Asp Ser Ala Val
    1145                1150                1155

Leu Glu His Ser Thr Ile Glu Ser Lys Ile Ser Gln Ser Ala Leu
    1160                1165                1170

Ala Ala Lys Gly Asp Lys Gly Lys Pro Ala Val Ser Val Lys Val
    1175                1180                1185

Ala Lys Lys Leu Phe Leu Asn Gly Thr Leu Arg Ala Val Asn Asp
    1190                1195                1200

Asn Glu Glu Thr Met Pro Gly Arg Gln Ile Asp Val Val Asp Gly
    1205                1210                1215

Arg Pro Gln Ile Thr Asp Ala Val Thr Gly Glu Glu Arg Lys Asp
    1220                1225                1230

Glu Ser Val Val Ser Asp Ala Ala Leu Val Ala Asp Gly Gly Pro
    1235                1240                1245

Ile Val Val Glu Ala Gly Glu Leu Val Ser His Ala Gly Gly Ile
    1250                1255                1260

Gly Asn Gly Arg Asn Lys Gly Asp Gly Ala Asp Val Thr Val Arg
    1265                1270                1275

Thr Thr Gly Asn Val Met Asn Lys Gly Tyr Ile Ser Ala Gly Lys
    1280                1285                1290

Gln Gly Val Leu Glu Val Gly Gly Thr Leu Thr Asn Glu Phe Leu
    1295                1300                1305

Val Gly Ser Asp Gly Thr Gln Arg Val Glu Ala Gln Arg Ile Glu
    1310                1315                1320

Asn Arg Gly Thr Phe Gln Ser Gln Ala Pro Ala Gly Thr Ala Gly
    1325                1330                1335

Ala Leu Val Val Lys Ala Ala Glu Ala Ile Val His Asp Gly Val
    1340                1345                1350

Met Ala Thr Glu Gly Glu Met Gln Ile Ala Gly Lys Gly Gly Gly
    1355                1360                1365

Ser Pro Ala Val Thr Ala Gly Ala Lys Ala Thr Ser Ala Asn
    1370                1375                1380

Lys Leu Ser Val Asp Val Ala Ser Trp Asp Asn Ala Gly Ser Leu
    1385                1390                1395

Asp Ile Lys Lys Gly Gly Ala Gln Val Thr Val Ala Gly Arg Tyr
    1400                1405                1410

Ala Glu His Gly Lys Val Ser Ile Gln Gly Asp Tyr Thr Val Ser
    1415                1420                1425

Ala Asp Ala Ile Ala Leu Ala Ala Gln Val Thr Gln Arg Gly Gly
    1430                1435                1440

Ala Ala Asn Leu Thr Ser Arg His Asp Thr Arg Phe Ser Asn Asn
    1445                1450                1455

Ile Arg Leu Met Gly Pro Leu Gln Val Asn Ala Gly Gly Ala Val
```

-continued

```
           1460               1465               1470
Ser Asn Thr Gly Asn Leu Lys Val Arg Glu Gly Val Ser Val Thr
    1475               1480               1485
Ala Ala Ser Phe Asp Asn Glu Ala Gly Ala Glu Val Met Ala Lys
    1490               1495               1500
Ser Ala Ala Leu Thr Thr Ser Gly Ala Val Arg Asn Ala Gly Lys
    1505               1510               1515
Met Gln Val Lys Glu Ala Ala Thr Ile Val Ala Ala Ser Val Ser
    1520               1525               1530
Asn Pro Gly Thr Phe Thr Ala Gly Lys Asp Leu Thr Val Thr Ser
    1535               1540               1545
Arg Gly Gly Phe Asp Asn Asn Gly Lys Met Glu Ser Asn Lys Asp
    1550               1555               1560
Ile Val Ile Lys Ala Glu Gln Phe Ser Asn Ala Gly Val Leu Asp
    1565               1570               1575
Ala Lys His Asp Leu Thr Val Thr Ala Ser Gly Gln Ala Asp Asn
    1580               1585               1590
Arg Gly Ser Leu Lys Ala Gly His Asp Phe Thr Val Gln Ala Gln
    1595               1600               1605
Arg Ile Asp Asn Ser Gly Thr Met Ala Ala Gly His Asp Ala Thr
    1610               1615               1620
Leu Lys Ala Pro His Leu Arg Asn Thr Gly Gln Ile Val Ala Gly
    1625               1630               1635
His Asp Ile His Ile Ile Asn Ser Ala Lys Leu Glu Asn Thr Gly
    1640               1645               1650
Arg Val Asp Ala Arg Asn Asp Ile Ala Leu Asp Val Ala Asp Phe
    1655               1660               1665
Thr Asn Thr Gly Ser Leu Tyr Ala Glu His Asp Ala Thr Leu Thr
    1670               1675               1680
Leu Ala Gln Gly Thr Gln Arg Asp Leu Val Val Asp Gln Asp His
    1685               1690               1695
Ile Leu Pro Val Ala Glu Gly Thr Leu Arg Val Lys Ala Lys Ser
    1700               1705               1710
Leu Thr Thr Glu Ile Glu Thr Gly Asn Pro Gly Ser Leu Ile Ala
    1715               1720               1725
Glu Val Gln Glu Asn Ile Asp Asn Lys Gln Ala Ile Val Val Gly
    1730               1735               1740
Lys Asp Leu Thr Leu Ser Ser Ala His Gly Asn Val Ala Asn Glu
    1745               1750               1755
Ala Asn Ala Leu Leu Trp Ala Ala Gly Asp Leu Thr Val Lys Ala
    1760               1765               1770
Gln Asn Ile Thr Asn Glu Arg Ala Ala Leu Ile Glu Ala Gly Gly
    1775               1780               1785
Asn Ala Arg Leu Thr Ala Ala Val Ala Leu Leu Asn Lys Leu Gly
    1790               1795               1800
Arg Ile Arg Ala Gly Glu Asp Met His Leu Asp Ala Pro Arg Ile
    1805               1810               1815
Glu Asn Thr Ala Lys Leu Ser Gly Glu Val Gln Arg Lys Gly Val
    1820               1825               1830
Gln Asp Val Gly Gly Gly Glu Tyr Gly Arg Trp Ser Gly Ile Gly
    1835               1840               1845
Tyr Val Asn Tyr Trp Leu Arg Ala Gly Asn Gly Lys Lys Ala Gly
    1850               1855               1860
```

-continued

Thr Ile Ala Ala Pro Trp Tyr Gly Gly Asp Leu Thr Ala Glu Gln
1865             1870                1875

Ser Leu Ile Glu Val Gly Lys Asp Leu Tyr Leu Asn Ala Gly Ala
1880             1885                1890

Arg Lys Asp Glu His Arg His Leu Leu Asn Glu Gly Val Ile Gln
1895             1900                1905

Ala Gly Gly His Gly His Ile Gly Gly Asp Val Asp Asn Arg Ser
1910             1915                1920

Val Val Arg Thr Val Ser Ala Met Glu Tyr Phe Lys Thr Pro Leu
1925             1930                1935

Pro Val Ser Leu Thr Ala Leu Asp Asn Arg Ala Gly Leu Ser Pro
1940             1945                1950

Ala Thr Trp Asn Phe Asn Ser Thr Tyr Glu Leu Leu Asp Tyr Leu
1955             1960                1965

Leu Asp Gln Asn Arg Tyr Glu Tyr Ile Trp Gly Val Tyr Pro Thr
1970             1975                1980

Tyr Thr Glu Trp Ser Val Asn Thr Leu Lys Asn Leu Asn Leu Gly
1985             1990                1995

Tyr Gln Ala Lys Pro Ala Pro Thr Ala Pro Pro Met Pro Lys Ala
2000             2005                2010

Pro Glu Leu Asp Leu Arg Gly His Thr Leu Glu Ser Ala Glu Gly
2015             2020                2025

Arg Lys Ile Phe Ala Glu Tyr Lys Lys Gln Gln Gly Glu Tyr Glu
2030             2035                2040

Lys Ala Lys Thr Ala Val Gln Ala Val Glu Ala Tyr Gly Glu Ala
2045             2050                2055

Thr Arg Arg Val His Asp Gln Leu Gly Gln Arg Tyr Gly Lys Ala
2060             2065                2070

Leu Gly Gly Met Asp Ala Glu Thr Lys Glu Val Asp Gly Ile Ile
2075             2080                2085

Gln Ala Phe Ala Ala Asp Leu Arg Thr Val Tyr Ala Lys Gln Ala
2090             2095                2100

Asp Gln Ala Ser Ile Asp Ala Glu Thr Asp Lys Val Ala Gln Arg
2105             2110                2115

Tyr Lys Ser Gln Ile Asp Ala Val Arg Leu Glu Ala Ile Gln Pro
2120             2125                2130

Gly Arg Val Met Leu Ala Lys Ala Leu Ser Ala Ala Leu Gly Ala
2135             2140                2145

Asp Trp Arg Ala Leu Gly His Ala Glu Leu Met Gln Arg Trp Lys
2150             2155                2160

Asp Phe Lys Ala Gly Lys Arg Gly Ala Asn Ile Ala Phe Tyr Pro
2165             2170                2175

Lys Glu Gln Thr Val Leu Ala Ala Gly Ala Gly Leu Thr Leu Ser
2180             2185                2190

Asn Gly Ala Val His Asn Gly Glu Asn Ala Ala Gln Asn Arg Gly
2195             2200                2205

Arg Pro Glu Asn Leu Lys Ile Gly Ala His Ser Ala Thr Ser Val
2210             2215                2220

Gly Gly Ser Phe Asp Ala Leu Arg Asp Val Gly Leu Glu Lys Arg
2225             2230                2235

Leu Asp Ile Asp Asp Ala Leu Ala Ala Val Leu Val Asn Pro His
2240             2245                2250

```
Ile Phe Thr Arg Ile Gly Ala Ala Gln Ala Ser Leu Ala Asp Gly
    2255                2260                2265

Ala Ala Gly Pro Ala Leu Ala Arg Gln Ala Arg Gln Ala Pro Gly
    2270                2275                2280

Thr Asp Gly Met Val Asp Ala Arg Gly Leu Gly Ser Ala Asp Ala
    2285                2290                2295

Leu Ala Ser Leu Ala Ser Leu Asp Ala Ala Gln Gly Leu Glu Val
    2300                2305                2310

Ser Gly Arg Arg Asn Ala Gln Val Ala Asp Ala Arg Leu Ala Gly
    2315                2320                2325

Pro Ser Ala Val Ala Ala Pro Ala Val Gly Ala Ala Asp Val Gly
    2330                2335                2340

Val Glu Pro Val Ala Gly Asp Gln Val Asp Gln Pro Val Val Ala
    2345                2350                2355

Val Gly Phe Glu Gln Pro Ala Ala Val Arg Val Ala Pro Pro
    2360                2365                2370

Ala Val Ala Leu Pro Arg Pro Leu Phe Glu Thr Arg Ile Lys Phe
    2375                2380                2385

Ile Asp Gln Ser Lys Phe Tyr Gly Ser Arg Tyr Phe Phe Glu Gln
    2390                2395                2400

Ile Gly Tyr Lys Pro Asp Arg Ala Ala Arg Val Ala Gly Asp Asn
    2405                2410                2415

Tyr Phe Asp Thr Thr Leu Val Arg Glu Gln Val Arg Arg Ala Leu
    2420                2425                2430

Gly Gly Tyr Glu Ser Arg Leu Pro Val Arg Gly Val Ala Leu Val
    2435                2440                2445

Ala Lys Leu Met Asp Ser Ala Gly Thr Val Gly Lys Ala Leu Gly
    2450                2455                2460

Leu Lys Val Gly Val Ala Pro Thr Ala Gln Gln Leu Lys Gln Ala
    2465                2470                2475

Asp Arg Asp Phe Val Trp Tyr Val Asp Thr Val Ile Asp Gly Gln
    2480                2485                2490

Lys Val Leu Ala Pro Arg Leu Tyr Leu Thr Glu Ala Thr Arg Gln
    2495                2500                2505

Gly Ile Thr Asp Gln Tyr Ala Gly Gly Ala Leu Ile Ala Ser
    2510                2515                2520

Gly Gly Asp Val Asn Val Asp Thr Asn Gly His Asp Val Ser Ser
    2525                2530                2535

Val Asn Gly Leu Ile Gln Gly Lys Arg Val Lys Val Asp Ala Gly
    2540                2545                2550

Lys Gly Arg Val Leu Val Ala Asp Ser Lys Gly Thr Gly Gly Gly
    2555                2560                2565

Ile Glu Ala Asp Asp Glu Val Asp Val Ser Ala Gln Asp Ile Asp
    2570                2575                2580

Ile Glu Gly Gly Lys Leu Arg Gly Lys Asp Val Lys Leu Lys Ala
    2585                2590                2595

Asp Thr Val Lys Val Ala Thr Ser Met Arg Tyr Asp Asp Lys Gly
    2600                2605                2610

Arg Leu Ala Ala Arg Gly Asp Gly Ala Leu Asp Ala Gln Gly Gly
    2615                2620                2625

Gln Leu His Ile Glu Ala Lys Arg Leu Glu Thr Ala Gly Ala Thr
    2630                2635                2640

Leu Lys Gly Ser Lys Val Lys Leu Asp Val Asp Asp Val Lys Leu
```

-continued

|  |  | 2645 |  |  |  | 2650 |  |  |  | 2655 |  |
| Gly | Gly | Val | Tyr | Glu | Ala | Gly | Ser | Ser | Tyr | Glu | Asn | Lys | Ser | Ser |
|  |  | 2660 |  |  |  | 2665 |  |  |  | 2670 |  |
| Thr | Pro | Leu | Gly | Ser | Leu | Phe | Ala | Ile | Leu | Ser | Ser | Thr | Thr | Glu |
|  |  | 2675 |  |  |  | 2680 |  |  |  | 2685 |  |
| Thr | Asn | Gln | Ser | Ala | Arg | Ala | Asn | His | Tyr | Gly | Thr | Arg | Ile | Ala |
|  |  | 2690 |  |  |  | 2695 |  |  |  | 2700 |  |
| Ala | Gly | Thr | Leu | Glu | Gly | Lys | Met | Gln | Asn | Leu | Glu | Ile | Glu | Gly |
|  |  | 2705 |  |  |  | 2710 |  |  |  | 2715 |  |
| Gly | Ser | Val | Glu | Ala | Ala | His | Thr | Asp | Leu | Ser | Val | Ala | Arg | Asp |
|  |  | 2720 |  |  |  | 2725 |  |  |  | 2730 |  |
| Ala | Ser | Phe | Lys | Ala | Ala | Ala | Asp | Phe | Ala | His | Thr | Glu | His | Glu |
|  |  | 2735 |  |  |  | 2740 |  |  |  | 2745 |  |
| Lys | Asp | Val | Arg | Gln | Leu | Ser | Leu | Gly | Ala | Lys | Val | Gly | Ala | Gly |
|  |  | 2750 |  |  |  | 2755 |  |  |  | 2760 |  |
| Gly | Tyr | Glu | Ala | Gly | Phe | Ser | Leu | Gly | Ser | Glu | Ser | Gly | Leu | Glu |
|  |  | 2765 |  |  |  | 2770 |  |  |  | 2775 |  |
| Ala | His | Ala | Gly | Arg | Gly | Met | Thr | Ala | Gly | Ala | Glu | Val | Lys | Val |
|  |  | 2780 |  |  |  | 2785 |  |  |  | 2790 |  |
| Gly | Tyr | Gln | Ala | Ser | His | Glu | Gln | Ser | Ser | Glu | Thr | Glu | Lys | Ser |
|  |  | 2795 |  |  |  | 2800 |  |  |  | 2805 |  |
| Tyr | Arg | Asn | Ala | Asn | Leu | Asn | Phe | Gly | Gly | Gly | Ser | Val | Glu | Val |
|  |  | 2810 |  |  |  | 2815 |  |  |  | 2820 |  |
| Gly | Asn | Val | Leu | Asp | Ile | Gly | Gly | Ala | Asp | Ile | Asn | Arg | Asn | Arg |
|  |  | 2825 |  |  |  | 2830 |  |  |  | 2835 |  |
| Tyr | Gly | Gly | Ala | Ala | Lys | Gly | Lys | Ala | Gly | Ala | Glu | Glu | Ala | Leu |
|  |  | 2840 |  |  |  | 2845 |  |  |  | 2850 |  |
| Arg | Met | Arg | Ala | Lys | Lys | Val | Glu | Ser | Thr | Lys | Tyr | Val | Ser | Glu |
|  |  | 2855 |  |  |  | 2860 |  |  |  | 2865 |  |
| Gln | Thr | Ser | Gln | Ser | Ser | Gly | Trp | Ser | Val | Glu | Val | Ala | Ala | Thr |
|  |  | 2870 |  |  |  | 2875 |  |  |  | 2880 |  |
| Ala | Ser | Ala | Arg | Ser | Ser | Val | Leu | Thr | Ala | Ala | Thr | Arg | Leu | Gly |
|  |  | 2885 |  |  |  | 2890 |  |  |  | 2895 |  |
| Asp | Ser | Val | Ala | Gln | Asn | Val | Glu | Asp | Gly | Arg | Glu | Ile | Arg | Gly |
|  |  | 2900 |  |  |  | 2905 |  |  |  | 2910 |  |
| Glu | Leu | Met | Ala | Ala | Gln | Val | Ala | Ala | Glu | Ala | Thr | Gln | Leu | Val |
|  |  | 2915 |  |  |  | 2920 |  |  |  | 2925 |  |
| Thr | Ala | Asp | Thr | Ala | Ala | Val | Ala | Leu | Ser | Ala | Gly | Ile | Ser | Ala |
|  |  | 2930 |  |  |  | 2935 |  |  |  | 2940 |  |
| Asp | Phe | Asp | Ser | Ser | His | Ser | Arg | Ser | Thr | Ser | Gln | Asn | Thr | Gln |
|  |  | 2945 |  |  |  | 2950 |  |  |  | 2955 |  |
| Tyr | Leu | Gly | Gly | Asn | Leu | Ser | Ile | Glu | Ala | Thr | Glu | Gly | Asp | Ala |
|  |  | 2960 |  |  |  | 2965 |  |  |  | 2970 |  |
| Thr | Leu | Val | Gly | Ala | Lys | Phe | Gly | Gly | Asp | Gln | Val | Ser | Leu |
|  |  | 2975 |  |  |  | 2980 |  |  |  | 2985 |  |
| Lys | Ala | Ala | Lys | Asn | Val | Asn | Leu | Met | Ala | Ala | Glu | Ser | Thr | Phe |
|  |  | 2990 |  |  |  | 2995 |  |  |  | 3000 |  |
| Glu | Ser | His | Ser | Glu | Ser | His | Asn | Phe | His | Ala | Ser | Ala | Asp | Ala |
|  |  | 3005 |  |  |  | 3010 |  |  |  | 3015 |  |
| Asn | Leu | Gly | Ala | Asn | Ala | Val | Gln | Gly | Ala | Val | Gly | Leu | Gly | Leu |
|  |  | 3020 |  |  |  | 3025 |  |  |  | 3030 |  |
| Thr | Ala | Gly | Met | Gly | Thr | Ser | His | Gln | Ile | Thr | Asn | Glu | Thr | Gly |
|  |  | 3035 |  |  |  | 3040 |  |  |  | 3045 |  |

```
Lys Thr Tyr Ala Gly Thr Ser Val Asp Ala Ala Asn Val Ser Ile
    3050                3055                3060

Asp Ala Gly Lys Asp Leu Asn Leu Ser Gly Ser Arg Val Arg Gly
    3065                3070                3075

Lys His Val Val Leu Asp Val Glu Gly Asp Ile Asn Ala Thr Ser
    3080                3085                3090

Lys Gln Asp Glu Arg Asn Tyr Asn Ser Ser Gly Gly Gly Trp Asp
    3095                3100                3105

Val Ser Ala Gly Val Ala Ile Gln Asn Arg Thr Leu Val Ala Pro
    3110                3115                3120

Val Gly Ser Ala Gly Phe Asn Phe Asn Thr Glu His Asp Asn Ser
    3125                3130                3135

Arg Leu Thr Asn Asp Gly Ala Ala Gly Val Val Ala Ser Asp Gly
    3140                3145                3150

Leu Thr Gly His Val Lys Gly Asp Ala Asn Leu Thr Gly Ala Thr
    3155                3160                3165

Ile Ala Asp Leu Ser Asp Lys Gly Asn Leu Lys Val Asp Gly Ala
    3170                3175                3180

Val Asn Ala Gln Asn Leu Lys Asp Tyr Arg Asp Lys Asp Gly Gly
    3185                3190                3195

Ser Gly Gly Leu Asn Val Gly Ile Ser Ser Thr Leu Ala Pro
    3200                3205                3210

Thr Val Gly Val Ala Phe Gly Arg Val Ala Gly Glu Asp Tyr Gln
    3215                3220                3225

Ala Glu Gln Arg Ala Thr Ile Asp Val Gly Gln Ala Lys Asp Pro
    3230                3235                3240

Ser Arg Leu Gln Val Gly Gly Val Lys Gly Thr Leu Asn Gln
    3245                3250                3255

Asp Ala Ala Lys Ala Thr Val Val Gln Arg Asn Lys His Trp Ala
    3260                3265                3270

Gly Gly Gly Ser Glu Phe Ser Val Ala Gly Lys Ser Leu Lys Lys
    3275                3280                3285

Lys Asn Gln Val Arg Pro Val Glu Thr Pro Thr Pro Asp Ala Val
    3290                3295                3300

Asp Gly Pro Pro Ser Arg Pro Thr Thr Pro Pro Ala Ser Pro Gln
    3305                3310                3315

Pro Ile Arg Ala Thr Val Glu Val Ser Ser Pro Pro Val Ser
    3320                3325                3330

Val Ala Thr Val Glu Val Val Pro Arg Pro Lys Val Glu Thr Ala
    3335                3340                3345

Gln Pro Leu Pro Pro Arg Pro Val Pro Ala Lys Ala Val Pro Met
    3350                3355                3360

Val Pro Pro Lys Val Glu Val Ala Lys Val Glu Val Val Pro Arg
    3365                3370                3375

Pro Lys Val Glu Thr Ala Gln Pro Leu Pro Pro Arg Pro Val Pro
    3380                3385                3390

Ala Lys Ala Val Pro Met Val Pro Pro Lys Val Glu Val Ala Lys
    3395                3400                3405

Val Glu Val Val Pro Arg Pro Lys Val Glu Thr Ala Gln Pro Leu
    3410                3415                3420

Pro Pro Arg Pro Val Val Ala Glu Lys Val Thr Thr Pro Ala Val
    3425                3430                3435
```

```
Gln Pro Gln Leu Ala Lys Val Glu Thr Val Gln Pro Val Lys Pro
    3440                3445                3450

Glu Thr Ala Lys Pro Leu Pro Lys Pro Leu Pro Val Ala Lys Val
    3455                3460                3465

Thr Glu Ala Pro Pro Val Met Glu Thr Ala Gln Pro Leu Pro
    3470                3475                3480

Pro Val Lys Pro Gln Lys Ala Thr Pro Gly Pro Val Ala Glu Val
    3485                3490                3495

Gly Lys Ala Thr Val Thr Val Gln Val Gln Ser Ala Pro Pro
    3500                3505                3510

Lys Pro Ala Pro Val Ala Lys Gln Pro Ala Pro Ala Pro Lys Pro
    3515                3520                3525

Lys Pro Lys Ala Glu Arg Pro Lys Pro Gly Lys Thr Thr Pro Leu
    3530                3535                3540

Ser Gly Arg His Val Val Gln Gln Val Gln Val Leu Gln Arg
    3545                3550                3555

Gln Ala Ser Asp Ile Asn Asn Thr Lys Ser Leu Pro Gly Gly Lys
    3560                3565                3570

Leu Pro Lys Pro Val Thr Val Lys Leu Thr Asp Glu Asn Gly Lys
    3575                3580                3585

Pro Gln Thr Tyr Thr Ile Asn Arg Arg Glu Asp Leu Met Lys Leu
    3590                3595                3600

Asn Gly Lys Val Leu Ser Thr Lys Thr Leu Gly Leu Glu Gln
    3605                3610                3615

Thr Phe Arg Leu Arg Val Glu Asp Ile Gly Gly Lys Asn Tyr Arg
    3620                3625                3630

Val Phe Tyr Glu Thr Asn Lys
    3635                3640

<210> SEQ ID NO 38
<211> LENGTH: 210
<212> TYPE: PRT
<213> ORGANISM: Bordetella pertussis

<400> SEQUENCE: 38

Met Leu Pro Met Gln Ile Pro Phe Gln Arg Ala Leu Arg Leu Cys Leu
1               5                   10                  15

Arg Ala Leu Ala Ala Ile Ala Ser Ala Ala His Ala Asp Asp Gly
            20                  25                  30

Thr Ile Val Ile Thr Gly Thr Ile Thr Asp Thr Thr Cys Val Ile Glu
            35                  40                  45

Asp Pro Ser Gly Pro Asn His Thr Lys Val Val Gln Leu Pro Lys Ile
50                  55                  60

Ser Lys Asn Ala Leu Lys Ala Asn Gly Asp Gln Ala Gly Arg Thr Pro
65                  70                  75                  80

Phe Ile Ile Lys Leu Lys Asp Cys Pro Ser Ser Leu Gly Asn Gly Val
                85                  90                  95

Lys Ala Tyr Phe Glu Pro Gly Pro Thr Thr Asp Tyr Ser Thr Gly Asp
                100                 105                 110

Leu Arg Ala Tyr Lys Met Val Tyr Ala Thr Asn Pro Gln Thr Gln Leu
            115                 120                 125

Ser Asn Ile Thr Ala Ala Thr Glu Ala Gln Gly Val Gln Val Arg Ile
            130                 135                 140

Ser Asn Leu Asn Asp Ser Lys Ile Thr Met Gly Ala Asn Glu Ala Thr
145                 150                 155                 160
```

Gln Gln Ala Ala Gly Phe Asp Pro Glu Val Gln Thr Gly Gly Thr Ser
                165                 170                 175

Arg Thr Val Thr Met Arg Tyr Leu Ala Ser Tyr Val Lys Lys Asn Gly
            180                 185                 190

Asp Val Glu Ala Ser Ala Ile Thr Thr Tyr Val Gly Phe Ser Val Val
        195                 200                 205

Tyr Pro
    210

<210> SEQ ID NO 39
<211> LENGTH: 204
<212> TYPE: PRT
<213> ORGANISM: Bordetella pertussis

<400> SEQUENCE: 39

Met Ser Lys Phe Ser Tyr Pro Ala Leu Arg Ala Ala Leu Ile Leu Ala
1               5                   10                  15

Ala Ser Pro Val Leu Pro Ala Leu Ala Asn Asp Gly Thr Ile Val Ile
            20                  25                  30

Thr Gly Ser Ile Ser Asp Gln Thr Cys Val Ile Glu Glu Pro Ser Thr
        35                  40                  45

Leu Asn His Ile Lys Val Val Gln Leu Pro Lys Ile Ser Lys Asn Ala
    50                  55                  60

Leu Arg Asn Asp Gly Asp Thr Ala Gly Ala Thr Pro Phe Asp Ile Lys
65                  70                  75                  80

Leu Lys Glu Cys Pro Gln Ala Leu Gly Ala Leu Lys Leu Tyr Phe Glu
                85                  90                  95

Pro Gly Ile Thr Thr Asn Tyr Asp Thr Gly Asp Leu Ile Ala Tyr Lys
            100                 105                 110

Gln Thr Tyr Asn Ala Ser Gly Asn Gly Asn Leu Ser Thr Val Ser Ser
        115                 120                 125

Ala Thr Lys Ala Lys Gly Val Glu Phe Arg Leu Ala Asn Leu Asn Gly
    130                 135                 140

Gln His Ile Arg Met Gly Thr Asp Lys Thr Thr Gln Ala Ala Gln Thr
145                 150                 155                 160

Phe Thr Gly Lys Val Thr Asn Gly Ser Lys Ser Tyr Thr Leu Arg Tyr
                165                 170                 175

Leu Ala Ser Tyr Val Lys Lys Pro Lys Glu Asp Val Asp Ala Ala Gln
            180                 185                 190

Ile Thr Ser Tyr Val Gly Phe Ser Val Val Tyr Pro
        195                 200

<210> SEQ ID NO 40
<211> LENGTH: 209
<212> TYPE: PRT
<213> ORGANISM: Bordetella bronchiseptica

<400> SEQUENCE: 40

Met His Val Pro Ala Pro Arg Arg Ala Val Leu Ala Ala Leu Leu Thr
1               5                   10                  15

Pro Ala Leu Phe Ala Pro Ala Ala His Ala Asn Asp Gly Thr Ile
            20                  25                  30

Val Val Thr Gly Ala Ile Thr Asp Thr Cys Val Val Glu Asp Pro
        35                  40                  45

Gly Gly Pro Thr His Thr Lys Val Val Gln Leu Pro Lys Ile Ser Lys
    50                  55                  60

```
Ser Ala Leu Ala Lys Asp Gly Asp Glu Ala Gly Arg Thr Pro Phe Leu
 65                  70                  75                  80

Ile Thr Leu Lys Asp Cys Pro Thr Ser Leu Asn Asn Gly Val Lys Ala
                 85                  90                  95

Tyr Phe Glu Pro Gly Pro Thr Thr Asp Tyr Val Thr Gly Asp Leu Lys
            100                 105                 110

Ala Tyr Ser Ile Ala Tyr Asn Asn Pro Ala Thr Thr Gln Ser Ala
        115                 120                 125

Ile Val Ala Ala Ala Glu Ala Gln Gly Val Gln Ile Arg Ile Ser Asn
130                 135                 140

Gln Asn Gly Thr Lys Ile Pro Met Gly Ala Asp Ala Ala Ala Gln Asn
145                 150                 155                 160

Ala Gln Ala Phe Asp Pro Val Thr Asp Thr Ala Asn Asn Asn Lys Lys
                165                 170                 175

Lys Val Thr Leu Arg Tyr Leu Ala Ser Tyr Val Lys Lys Ala Gly Asn
            180                 185                 190

Ile Thr Ala Gly Gln Val Thr Thr Tyr Val Gly Phe Ser Met Val Tyr
        195                 200                 205

Pro

<210> SEQ ID NO 41
<211> LENGTH: 208
<212> TYPE: PRT
<213> ORGANISM: Bordetella bronchiseptica

<400> SEQUENCE: 41

Met Ser Lys Phe Ser Tyr Pro Ala Leu Arg Thr Ala Leu Ile Leu Ala
  1               5                  10                  15

Ala Ser Pro Val Leu Pro Ala Leu Ala Asn Asp Gly Thr Ile Val Ile
                 20                  25                  30

Thr Gly Ser Ile Ser Asp Gln Thr Cys Val Ile Glu Glu Pro Ser Ala
            35                  40                  45

Pro Asn His Ile Lys Val Val Gln Leu Pro Lys Ile Ser Lys Ser Ala
        50                  55                  60

Leu Arg Asn Asp Gly Asp Thr Ala Gly Ala Thr Pro Phe Asp Ile Arg
 65                  70                  75                  80

Leu Lys Glu Cys Pro Gln Ala Leu Gly Ala Leu Lys Leu Tyr Phe Glu
                 85                  90                  95

Pro Gly Ile Thr Thr Asn Tyr Asp Thr Gly Asp Leu Ile Ala Tyr Lys
            100                 105                 110

Gln Ala Tyr Asn Pro Ala Gly Asn Gly Asn Leu Ser Thr Val Ser Ser
        115                 120                 125

Ala Thr Lys Ala Lys Gly Val Glu Phe Arg Leu Ala Asn Leu Asn Gly
130                 135                 140

Gln His Ile Arg Met Gly Thr Asp Glu Thr Thr Gln Ala Ala Gln Thr
145                 150                 155                 160

Phe Thr Gly Thr Glu Val Thr Asn Gly Asn Thr Thr Lys Ser Tyr
                165                 170                 175

Thr Leu Arg Tyr Leu Ala Ser Tyr Val Lys Lys Pro Asn Glu Asp Val
            180                 185                 190

Asp Ala Ala Gln Ile Thr Ser Tyr Val Gly Phe Ser Val Val Tyr Pro
        195                 200                 205

<210> SEQ ID NO 42
```

```
<211> LENGTH: 910
<212> TYPE: PRT
<213> ORGANISM: Bordetella pertussis

<400> SEQUENCE: 42

Met Asn Met Ser Leu Ser Arg Ile Val Lys Ala Ala Pro Leu Arg Arg
1               5                   10                  15

Thr Thr Leu Ala Met Ala Leu Gly Ala Leu Gly Ala Ala Pro Ala Ala
                20                  25                  30

His Ala Asp Trp Asn Asn Gln Ser Ile Val Lys Thr Gly Glu Arg Gln
            35                  40                  45

His Gly Ile His Ile Gln Gly Ser Asp Pro Gly Gly Val Arg Thr Ala
        50                  55                  60

Ser Gly Thr Thr Ile Lys Val Ser Gly Arg Gln Ala Gln Gly Ile Leu
65                  70                  75                  80

Leu Glu Asn Pro Ala Ala Glu Leu Gln Phe Arg Asn Gly Ser Val Thr
                85                  90                  95

Ser Ser Gly Gln Leu Ser Asp Asp Gly Ile Arg Arg Phe Leu Gly Thr
            100                 105                 110

Val Thr Val Lys Ala Gly Lys Leu Val Ala Asp His Ala Thr Leu Ala
        115                 120                 125

Asn Val Gly Asp Thr Trp Asp Asp Gly Ile Ala Leu Tyr Val Ala
    130                 135                 140

Gly Glu Gln Ala Gln Ala Ser Ile Ala Asp Ser Thr Leu Gln Gly Ala
145                 150                 155                 160

Gly Gly Val Gln Ile Glu Arg Gly Ala Asn Val Thr Val Gln Arg Ser
                165                 170                 175

Ala Ile Val Asp Gly Gly Leu His Ile Gly Ala Leu Gln Ser Leu Gln
            180                 185                 190

Pro Glu Asp Leu Pro Pro Ser Arg Val Val Leu Arg Asp Thr Asn Val
        195                 200                 205

Thr Ala Val Pro Ala Ser Gly Ala Pro Ala Ala Val Ser Val Leu Gly
    210                 215                 220

Ala Ser Glu Leu Thr Leu Asp Gly Gly His Ile Thr Gly Gly Arg Ala
225                 230                 235                 240

Ala Gly Val Ala Ala Met Gln Gly Ala Val Val His Leu Gln Arg Ala
                245                 250                 255

Thr Ile Arg Arg Gly Asp Ala Pro Gly Gly Ala Val Pro Gly Gly
            260                 265                 270

Ala Val Pro Gly Gly Ala Val Pro Gly Gly Phe Gly Pro Gly Gly Phe
        275                 280                 285

Gly Pro Val Leu Asp Gly Trp Tyr Gly Val Asp Val Ser Gly Ser Ser
    290                 295                 300

Val Glu Leu Ala Gln Ser Ile Val Glu Ala Pro Glu Leu Gly Ala Ala
305                 310                 315                 320

Ile Arg Val Gly Arg Gly Ala Arg Val Thr Val Ser Gly Gly Ser Leu
                325                 330                 335

Ser Ala Pro His Gly Asn Val Ile Glu Thr Gly Gly Ala Arg Arg Phe
            340                 345                 350

Ala Pro Gln Ala Ala Pro Leu Ser Ile Thr Leu Gln Ala Gly Ala His
        355                 360                 365

Ala Gln Gly Lys Ala Leu Leu Tyr Arg Val Leu Pro Glu Pro Val Lys
    370                 375                 380

Leu Thr Leu Thr Gly Gly Ala Asp Ala Gln Gly Asp Ile Val Ala Thr
```

-continued

```
            385                 390                 395                 400
        Glu Leu Pro Ser Ile Pro Gly Thr Ser Ile Gly Pro Leu Asp Val Ala
                        405                 410                 415

Leu Ala Ser Gln Ala Arg Trp Thr Gly Ala Thr Arg Ala Val Asp Ser
                        420                 425                 430

Leu Ser Ile Asp Asn Ala Thr Trp Val Met Thr Asp Asn Ser Asn Val
                        435                 440                 445

Gly Ala Leu Arg Leu Ala Ser Asp Gly Ser Val Asp Phe Gln Gln Pro
                        450                 455                 460

Ala Glu Ala Gly Arg Phe Lys Val Leu Thr Val Asn Thr Leu Ala Gly
        465                 470                 475                 480

Ser Gly Leu Phe Arg Met Asn Val Phe Ala Asp Leu Gly Leu Ser Asp
                        485                 490                 495

Lys Leu Val Val Met Gln Asp Ala Ser Gly Gln His Arg Leu Trp Val
                        500                 505                 510

Arg Asn Ser Gly Ser Glu Pro Ala Ser Ala Asn Thr Leu Leu Leu Val
                        515                 520                 525

Gln Thr Pro Leu Gly Ser Ala Ala Thr Phe Thr Leu Ala Asn Lys Asp
                        530                 535                 540

Gly Lys Val Asp Ile Gly Thr Tyr Arg Tyr Arg Leu Ala Ala Asn Gly
        545                 550                 555                 560

Asn Gly Gln Trp Ser Leu Val Gly Ala Lys Ala Pro Pro Ala Pro Lys
                        565                 570                 575

Pro Ala Pro Gln Pro Gly Pro Gln Pro Pro Gln Pro Pro Gln Pro Gln
                        580                 585                 590

Pro Glu Ala Pro Ala Pro Gln Pro Pro Ala Gly Arg Glu Leu Ser Ala
                        595                 600                 605

Ala Ala Asn Ala Ala Val Asn Thr Gly Gly Val Gly Leu Ala Ser Thr
                        610                 615                 620

Leu Trp Tyr Ala Glu Ser Asn Ala Leu Ser Lys Arg Leu Gly Glu Leu
        625                 630                 635                 640

Arg Leu Asn Pro Asp Ala Gly Gly Ala Trp Gly Arg Gly Phe Ala Gln
                        645                 650                 655

Arg Gln Gln Leu Asp Asn Arg Ala Gly Arg Arg Phe Asp Gln Lys Val
                        660                 665                 670

Ala Gly Phe Glu Leu Gly Ala Asp His Ala Val Ala Val Ala Gly Gly
                        675                 680                 685

Arg Trp His Leu Gly Gly Leu Ala Gly Tyr Thr Arg Gly Asp Arg Gly
                        690                 695                 700

Phe Thr Gly Asp Gly Gly His Thr Asp Ser Val His Val Gly Gly
        705                 710                 715                 720

Tyr Ala Thr Tyr Ile Ala Asp Ser Gly Phe Tyr Leu Asp Ala Thr Leu
                        725                 730                 735

Arg Ala Ser Arg Leu Glu Asn Asp Phe Lys Val Ala Gly Ser Asp Gly
                        740                 745                 750

Tyr Ala Val Lys Gly Lys Tyr Arg Thr His Gly Val Gly Ala Ser Leu
                        755                 760                 765

Glu Ala Gly Arg Arg Phe Thr His Ala Asp Gly Trp Phe Leu Glu Pro
                        770                 775                 780

Gln Ala Glu Leu Ala Val Phe Arg Ala Gly Gly Ala Tyr Arg Ala
        785                 790                 795                 800

Ala Asn Gly Leu Arg Val Arg Asp Glu Gly Gly Ser Ser Val Leu Gly
                        805                 810                 815
```

```
Arg Leu Gly Leu Glu Val Gly Lys Arg Ile Glu Leu Ala Gly Gly Arg
            820                 825                 830

Gln Val Gln Pro Tyr Ile Lys Ala Ser Val Leu Gln Glu Phe Asp Gly
            835                 840                 845

Ala Gly Thr Val His Thr Asn Gly Ile Ala His Arg Thr Glu Leu Arg
850                 855                 860

Gly Thr Arg Ala Glu Leu Gly Leu Gly Met Ala Ala Leu Gly Arg
865                 870                 875                 880

Gly His Ser Leu Tyr Ala Ser Tyr Glu Tyr Ser Lys Gly Pro Lys Leu
                885                 890                 895

Ala Met Pro Trp Thr Phe His Ala Gly Tyr Arg Tyr Ser Trp
            900                 905                 910

<210> SEQ ID NO 43
<211> LENGTH: 907
<212> TYPE: PRT
<213> ORGANISM: Bordetella bronchiseptica

<400> SEQUENCE: 43

Met Asn Met Ser Leu Ser Arg Ile Val Lys Ala Ala Pro Leu Arg Arg
1               5                   10                  15

Thr Thr Leu Ala Met Ala Leu Gly Ala Leu Gly Ala Ala Pro Ala Ala
            20                  25                  30

His Ala Asp Trp Asn Asn Gln Ser Ile Val Lys Thr Gly Glu Arg Gln
            35                  40                  45

His Gly Ile His Ile Gln Gly Ser Asp Pro Gly Gly Val Arg Thr Ala
        50                  55                  60

Ser Gly Thr Thr Ile Lys Val Ser Gly Arg Gln Ala Gln Gly Ile Leu
65                  70                  75                  80

Leu Glu Asn Pro Ala Ala Glu Leu Gln Phe Arg Asn Gly Ser Val Thr
                85                  90                  95

Ser Ser Gly Gln Leu Phe Asp Asp Gly Ile Arg Arg Phe Leu Gly Thr
            100                 105                 110

Val Thr Val Lys Ala Gly Lys Leu Val Ala Asp His Ala Thr Leu Ala
            115                 120                 125

Asn Val Gly Asp Thr Trp Asp Asp Gly Ile Ala Leu Tyr Val Ala
        130                 135                 140

Gly Glu Gln Ala Gln Ala Ser Ile Ala Asp Ser Thr Leu Gln Gly Ala
145                 150                 155                 160

Gly Gly Val Gln Val Glu Arg Gly Ala Asn Val Thr Val Gln Arg Ser
                165                 170                 175

Ala Ile Val Asp Gly Gly Leu His Ile Gly Ala Leu Gln Ser Leu Gln
            180                 185                 190

Pro Glu Asp Leu Pro Pro Ser Arg Val Val Leu Arg Asp Thr Asn Val
            195                 200                 205

Thr Ala Val Pro Ala Ser Gly Ala Pro Ala Ala Val Ser Val Leu Gly
        210                 215                 220

Ala Ser Glu Leu Thr Leu Asp Gly Gly His Ile Thr Gly Gly Arg Ala
225                 230                 235                 240

Ala Gly Val Ala Ala Met Gln Gly Ala Val Val His Leu Gln Arg Ala
                245                 250                 255

Thr Ile Arg Arg Gly Asp Ala Pro Ala Gly Gly Val Pro Gly Gly
            260                 265                 270

Ala Val Pro Gly Gly Phe Gly Pro Gly Gly Phe Gly Pro Val Leu Asp
```

```
              275                 280                 285
Gly Trp Tyr Gly Val Asp Val Ser Gly Ser Val Glu Leu Ala Gln
290                 295                 300
Ser Ile Val Glu Ala Pro Glu Leu Gly Ala Ala Ile Arg Val Gly Arg
305                 310                 315                 320
Gly Ala Arg Val Thr Val Ser Gly Gly Ser Leu Ser Ala Pro His Gly
                    325                 330                 335
Asn Val Ile Glu Thr Gly Gly Ala Arg Arg Phe Ala Pro Gln Ala Ala
                340                 345                 350
Pro Leu Ser Ile Thr Leu Gln Ala Gly Ala His Ala Gln Gly Lys Ala
                355                 360                 365
Leu Leu Tyr Arg Val Leu Pro Glu Pro Val Lys Leu Thr Leu Thr Gly
370                 375                 380
Gly Ala Asp Ala Gln Gly Asp Ile Val Ala Thr Glu Leu Pro Pro Ile
385                 390                 395                 400
Pro Gly Thr Ser Ser Gly Pro Leu Asp Val Ala Leu Ala Ser Gln Ala
                    405                 410                 415
Arg Trp Thr Gly Ala Thr Arg Ala Val Asp Ala Leu Ser Ile Asp Asn
                420                 425                 430
Ala Thr Trp Val Met Thr Asp Asn Ser Asn Val Gly Ala Leu Arg Leu
                435                 440                 445
Ala Ser Asp Gly Ser Val Asp Phe Gln Gln Pro Ala Glu Ala Gly Arg
450                 455                 460
Phe Lys Val Leu Thr Val Asn Thr Leu Ala Gly Ser Gly Leu Phe Arg
465                 470                 475                 480
Met Asn Val Phe Ala Asp Leu Gly Leu Ser Asp Lys Leu Val Val Met
                    485                 490                 495
Gln Asp Ala Ser Gly Gln His Arg Leu Trp Val Arg Asn Ser Gly Ser
                500                 505                 510
Glu Pro Ala Ser Ala Asn Thr Leu Leu Val Gln Thr Pro Arg Gly
                515                 520                 525
Ser Ala Ala Thr Phe Thr Leu Ala Asn Lys Asp Gly Lys Val Asp Ile
530                 535                 540
Gly Thr Tyr Arg Tyr Arg Leu Ala Ala Asn Gly Asn Gly Gln Trp Ser
545                 550                 555                 560
Leu Val Gly Ala Lys Ala Pro Ala Pro Lys Pro Ala Pro Gln Pro
                    565                 570                 575
Gly Pro Gln Pro Pro Gln Pro Gln Pro Gln Pro Gln Pro Glu Ala
                580                 585                 590
Pro Ala Pro Gln Pro Pro Ala Gly Arg Glu Leu Ser Ala Ala Ala Asn
                595                 600                 605
Ala Ala Val Asn Thr Gly Gly Val Gly Leu Ala Ser Thr Leu Trp Tyr
                610                 615                 620
Ala Glu Ser Asn Ala Leu Ser Lys Arg Leu Gly Glu Leu Arg Leu Asn
625                 630                 635                 640
Pro Asp Ala Gly Gly Ala Trp Gly Arg Gly Phe Ala Gln Arg Gln Gln
                    645                 650                 655
Leu Asp Asn Arg Ala Gly Arg Arg Phe Asp Lys Val Ala Gly Phe
                660                 665                 670
Glu Leu Gly Ala Asp His Ala Val Ala Val Ala Gly Arg Trp His
                675                 680                 685
Leu Gly Gly Leu Ala Gly Tyr Thr Arg Gly Asp Arg Gly Phe Thr Gly
690                 695                 700
```

```
Asp Gly Gly Gly His Thr Asp Ser Val His Val Gly Tyr Ala Thr
705                 710                 715                 720

Tyr Ile Ala Asn Ser Gly Phe Tyr Leu Asp Ala Thr Leu Arg Ala Ser
            725                 730                 735

Arg Leu Glu Asn Asp Phe Lys Val Ala Gly Ser Asp Gly Tyr Ala Val
            740                 745                 750

Lys Gly Lys Tyr Arg Thr His Gly Val Gly Ala Ser Leu Glu Ala Gly
        755                 760                 765

Arg Arg Phe Ser His Ala Asp Gly Trp Phe Leu Glu Pro Gln Ala Glu
770                 775                 780

Leu Ala Val Phe Arg Ala Gly Gly Ala Tyr Arg Ala Ala Asn Gly
785                 790                 795                 800

Leu Arg Val Arg Asp Glu Gly Gly Asn Ser Val Leu Gly Arg Leu Gly
                805                 810                 815

Leu Glu Val Gly Lys Arg Ile Glu Leu Ala Gly Gly Arg Gln Val Gln
                820                 825                 830

Pro Tyr Ile Lys Ala Ser Val Leu Gln Glu Phe Asp Gly Ala Gly Thr
            835                 840                 845

Val Arg Thr Asn Gly Ile Ala His Arg Thr Glu Leu Arg Gly Thr Arg
850                 855                 860

Ala Glu Leu Gly Leu Gly Met Ala Ala Ala Leu Gly Arg Gly His Ser
865                 870                 875                 880

Leu Tyr Ala Ser Tyr Glu Tyr Ser Lys Gly Pro Lys Leu Ala Met Pro
                885                 890                 895

Trp Thr Phe His Ala Gly Tyr Arg Tyr Ser Trp
                900                 905

<210> SEQ ID NO 44
<211> LENGTH: 1706
<212> TYPE: PRT
<213> ORGANISM: Bordetella bronchiseptica

<400> SEQUENCE: 44

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asn Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Asp Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
```

-continued

```
                165                 170                 175
Ile Gly Asn Ala Ala Gly Ile Pro Leu Thr Ala Asp Ile Asp Met Phe
                180                 185                 190
Ala Ile Met Pro His Leu Ser Asn Phe Arg Asp Ser Ala Arg Ser Ser
                195                 200                 205
Val Thr Ser Gly Asp Ser Val Thr Asp Tyr Leu Ala Arg Thr Arg Arg
                210                 215                 220
Ala Ala Ser Glu Ala Thr Gly Leu Asp Arg Glu Arg Ile Asp Leu
225                 230                 235                 240
Leu Trp Lys Ile Ala Arg Ala Gly Ala Arg Ser Ala Val Gly Thr Glu
                245                 250                 255
Ala Arg Arg Gln Phe Arg Tyr Asp Gly Glu Met Asn Ile Gly Val Ile
                260                 265                 270
Thr Asp Phe Glu Leu Glu Val Arg Asn Ala Leu Asn Arg Arg Ala His
                275                 280                 285
Ala Val Gly Ala Gln Asp Val Val Gln His Gly Thr Glu Gln Asn Asn
                290                 295                 300
Pro Phe Pro Glu Ala Asp Glu Lys Ile Phe Val Val Ser Ala Thr Gly
305                 310                 315                 320
Glu Ser Gln Met Leu Thr Arg Gly Gln Leu Lys Glu Tyr Ile Gly Gln
                325                 330                 335
Gln Arg Gly Glu Gly Tyr Val Phe Tyr Glu Asn Arg Ala Tyr Gly Val
                340                 345                 350
Ala Gly Lys Ser Leu Phe Asp Asp Gly Leu Gly Thr Ala Pro Gly Val
                355                 360                 365
Pro Ser Gly Arg Ser Lys Ser Ser Pro Asp Val Leu Glu Thr Val Pro
370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
                405                 410                 415
Leu Gly Glu Val Ser Asp Met Ala Ala Val Glu Ala Val Glu Leu Glu
                420                 425                 430
Met Thr Arg Gln Val Leu His Ala Gly Ala Pro Gln Asp Asp Ala Glu
                435                 440                 445
Pro Gly Val Ser Gly Ala Ser Ala Leu Trp Gly Gln Arg Ser Leu Lys
                450                 455                 460
Gly Val Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                485                 490                 495
Ala Ala Ser Leu Ser Ala Val Phe Gly Leu Gly Glu Ala Ser Ser
                500                 505                 510
Ala Val Ala Glu Thr Val Ser Gly Phe Phe Arg Gly Ser Ser Arg Trp
                515                 520                 525
Ala Gly Gly Phe Gly Val Ala Gly Ala Met Ala Leu Gly Gly Gly
                530                 535                 540
Ile Ala Ala Ala Val Gly Ala Gly Met Ser Leu Thr Asp Asp Ala Pro
545                 550                 555                 560
Ala Gly Gln Lys Ala Ala Ala Gly Ala Glu Ile Ala Leu Gln Leu Thr
                565                 570                 575
Gly Gly Thr Val Glu Leu Ala Ser Ser Ile Ala Leu Ala Leu Ala Ala
                580                 585                 590
```

```
Ala Arg Gly Val Thr Ser Gly Leu Gln Val Ala Gly Ala Ser Ala Gly
            595                 600                 605

Ala Ala Ala Gly Ala Leu Ala Ala Ala Leu Ser Pro Met Glu Ile Tyr
            610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Gly Asp Ala Leu Leu Ala Gln
                645                 650                 655

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
            675                 680                 685

Ser Val Val Gly Ala Pro Val Ala Val Val Thr Ser Leu Leu Thr Gly
            690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
            755                 760                 765

Ala Ser Ser Val Ile Gly Val Gln Thr Thr Glu Ile Ser Lys Ser Ala
770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Val Leu Asp Val Ala Ala Gly Gly Ile Asp Ile Ala Ser Arg
            820                 825                 830

Lys Gly Glu Arg Pro Ala Leu Thr Phe Ile Thr Pro Leu Ala Ala Pro
            835                 840                 845

Gly Glu Glu Gln Arg Arg Thr Lys Thr Gly Lys Ser Glu Phe Thr
850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
            900                 905                 910

Gly Gly Asp Gly Asp Val Val Leu Ala Asn Ala Ser Arg Ile His
            915                 920                 925

Tyr Asp Gly Gly Ala Gly Thr Asn Thr Val Ser Tyr Ala Ala Leu Gly
            930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
            980                 985                 990

Val Glu Leu Ala Arg Val Gly Gln  Leu Val Glu Val Asp  Thr Leu Glu
            995                 1000                1005
```

His Val Gln His Ile Ile Gly Gly Ala Gly Asn Asp Ser Ile Thr
1010                1015                1020

Gly Asn Ala His Asp Asn Phe Leu Ala Gly Gly Ser Gly Asp Asp
1025                1030                1035

Arg Leu Asp Gly Gly Ala Gly Asn Asp Thr Leu Val Gly Gly Glu
1040                1045                1050

Gly Gln Asn Thr Val Ile Gly Gly Ala Gly Asp Asp Val Phe Leu
1055                1060                1065

Gln Asp Leu Gly Val Trp Ser Asn Gln Leu Asp Gly Gly Ala Gly
1070                1075                1080

Val Asp Thr Val Lys Tyr Asn Val His Gln Pro Ser Glu Glu Arg
1085                1090                1095

Leu Glu Arg Met Gly Asp Thr Gly Ile His Ala Asp Leu Gln Lys
1100                1105                1110

Gly Thr Val Glu Lys Trp Pro Ala Leu Asn Leu Phe Ser Val Asp
1115                1120                1125

His Val Lys Asn Ile Glu Asn Leu His Gly Ser Arg Leu Asn Asp
1130                1135                1140

Arg Ile Ala Gly Asp Asp Arg Asp Asn Glu Leu Trp Gly His Asp
1145                1150                1155

Gly Asn Asp Thr Ile Arg Gly Arg Gly Gly Asp Asp Ile Leu Arg
1160                1165                1170

Gly Gly Leu Gly Leu Asp Thr Leu Tyr Gly Glu Asp Gly Asn Asp
1175                1180                1185

Ile Phe Leu Gln Asp Asp Glu Thr Val Ser Asp Asp Ile Asp Gly
1190                1195                1200

Gly Ala Gly Leu Asp Thr Val Asp Tyr Ser Ala Met Ile His Pro
1205                1210                1215

Gly Arg Ile Val Ala Pro His Glu Tyr Gly Phe Gly Ile Glu Ala
1220                1225                1230

Asp Leu Ser Arg Glu Trp Val Arg Lys Ala Ser Ala Leu Gly Val
1235                1240                1245

Asp Tyr Tyr Asp Asn Val Arg Asn Val Glu Asn Val Ile Gly Thr
1250                1255                1260

Ser Met Lys Asp Val Leu Ile Gly Asp Ala Gln Ala Asn Thr Leu
1265                1270                1275

Met Gly Gln Gly Gly Asp Asp Thr Val Arg Gly Gly Asp Gly Asp
1280                1285                1290

Asp Leu Leu Phe Gly Gly Asp Gly Asn Asp Met Leu Tyr Gly Asp
1295                1300                1305

Ala Gly Asn Asp Thr Leu Tyr Gly Gly Leu Gly Asp Asp Thr Leu
1310                1315                1320

Glu Gly Gly Ala Gly Asn Asp Trp Phe Gly Gln Thr Gln Ala Arg
1325                1330                1335

Glu His Asp Val Leu Arg Gly Gly Asp Gly Val Asp Thr Val Asp
1340                1345                1350

Tyr Ser Gln Thr Gly Ala His Ala Gly Ile Ala Ala Gly Arg Ile
1355                1360                1365

Gly Leu Gly Ile Leu Ala Asp Leu Gly Ala Gly Arg Val Asp Lys
1370                1375                1380

Leu Gly Glu Ala Gly Ser Ser Ala Tyr Asp Thr Val Ser Gly Ile
1385                1390                1395

Glu Asn Val Val Gly Thr Glu Leu Ala Asp Arg Ile Thr Gly Asp

```
                1400                1405                1410

Ala Gln Ala Asn Val Leu Arg Gly Ala Gly Gly Ala Asp Val Leu
    1415                1420                1425

Ala Gly Gly Glu Gly Asp Val Leu Leu Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg His Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
    1640                1645                1650

Glu Ala Ile His Ala Ala Asn Gln Ala Val Asp Pro Ala Gly Ile
    1655                1660                1665

Glu Lys Leu Val Glu Ala Met Ala Gln Tyr Pro Asp Pro Gly Ala
    1670                1675                1680

Ala Ala Ala Ala Pro Pro Ala Ala Arg Val Pro Asp Thr Leu Met
    1685                1690                1695

Gln Ser Leu Ala Val Asn Trp Arg
    1700                1705

<210> SEQ ID NO 45
<211> LENGTH: 400
<212> TYPE: PRT
<213> ORGANISM: Bordetella bronchiseptica

<400> SEQUENCE: 45

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
        35                  40                  45
```

Ser Leu Ile Ala Glu Gly Val Ala Thr Lys Gly Leu Gly Val His Ala
 50                  55                  60

Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asn Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Val Val Ala Ser Asn His Ala Gly Tyr
130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Glu Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Thr Ala Pro Gly Val
        355                 360                 365

Pro Ser Gly Arg Ser Lys Ser Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

<210> SEQ ID NO 46
<211> LENGTH: 225
<212> TYPE: PRT
<213> ORGANISM: Bordetella bronchiseptica

<400> SEQUENCE: 46

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

-continued

```
Glu Lys Asn Ala Thr Leu Met Phe Arg Leu Val Asn Pro His Ser Thr
         35                  40                  45

Ser Leu Ile Ala Glu Gly Val Ala Thr Lys Gly Leu Gly Val His Ala
 50                  55                  60

Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asn Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala
225

<210> SEQ ID NO 47
<211> LENGTH: 175
<212> TYPE: PRT
<213> ORGANISM: Bordetella bronchiseptica

<400> SEQUENCE: 47

Ala Ser Glu Ala Thr Gly Gly Leu Asp Arg Glu Arg Ile Asp Leu Leu
 1               5                  10                  15

Trp Lys Ile Ala Arg Ala Gly Ala Arg Ser Ala Val Gly Thr Glu Ala
                20                  25                  30

Arg Arg Gln Phe Arg Tyr Asp Gly Glu Met Asn Ile Gly Val Ile Thr
        35                  40                  45

Asp Phe Glu Leu Glu Val Arg Asn Ala Leu Asn Arg Arg Ala His Ala
 50                  55                  60

Val Gly Ala Gln Asp Val Val Gln His Gly Thr Glu Gln Asn Asn Pro
 65                  70                  75                  80

Phe Pro Glu Ala Asp Glu Lys Ile Phe Val Val Ser Ala Thr Gly Glu
                 85                  90                  95

Ser Gln Met Leu Thr Arg Gly Gln Leu Lys Tyr Ile Gly Gln Gln
            100                 105                 110

Arg Gly Glu Gly Tyr Val Phe Tyr Glu Asn Arg Ala Tyr Gly Val Ala
        115                 120                 125

Gly Lys Ser Leu Phe Asp Asp Gly Leu Gly Thr Ala Pro Gly Val Pro
    130                 135                 140

Ser Gly Arg Ser Lys Ser Ser Pro Asp Val Leu Glu Thr Val Pro Ala
145                 150                 155                 160

Ser Pro Gly Leu Arg Arg Pro Ser Leu Gly Ala Val Glu Arg Gln
                165                 170                 175
```

<210> SEQ ID NO 48
<211> LENGTH: 400
<212> TYPE: PRT
<213> ORGANISM: Bordetella bronchiseptica

<400> SEQUENCE: 48

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asn Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Asp Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Cys Thr Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Glu Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Thr Ala Pro Gly Val
        355                 360                 365
```

-continued

Pro Ser Gly Arg Ser Lys Ser Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

<210> SEQ ID NO 49
<211> LENGTH: 1740
<212> TYPE: PRT
<213> ORGANISM: Bordetella parapertussis

<400> SEQUENCE: 49

Met Leu Asp Val Trp Phe Leu Gln Lys Asp Glu Val Leu Ser Ala Thr
1               5                   10                  15

His Arg Leu Arg Arg Cys Glu Ser Val Gln Ser Thr Thr Tyr Arg Gln
            20                  25                  30

Ile His Met Gln Gln Ser His Gln Ala Gly Tyr Ala Asn Ala Ala Asp
        35                  40                  45

Arg Glu Ser Gly Ile Pro Ala Ala Val Leu Asp Gly Ile Lys Ala Val
    50                  55                  60

Ala Lys Glu Lys Asn Ala Thr Leu Met Phe Arg Leu Val Asn Pro His
65                  70                  75                  80

Ser Thr Ser Leu Ile Ala Glu Gly Val Ala Thr Lys Gly Leu Gly Val
                85                  90                  95

His Ala Lys Ser Ser Asp Trp Gly Leu Gln Ala Gly Tyr Ile Pro Val
            100                 105                 110

Asn Pro Asn Leu Ser Lys Leu Phe Gly Arg Ala Pro Glu Val Ile Ala
        115                 120                 125

Arg Ala Asp Asn Asp Val Asn Ser Ser Leu Ala His Gly His Thr Ala
    130                 135                 140

Val Asp Leu Thr Leu Ser Lys Glu Arg Leu Asp Tyr Leu Arg Gln Ala
145                 150                 155                 160

Gly Leu Val Thr Gly Met Ala Asp Gly Val Val Ala Ser Asn His Ala
                165                 170                 175

Gly Tyr Glu Gln Phe Glu Phe Arg Val Lys Glu Thr Ser Asp Gly Arg
            180                 185                 190

Tyr Ala Val Gln Tyr Arg Arg Lys Gly Gly Asp Asp Phe Glu Ala Val
        195                 200                 205

Lys Val Ile Gly Asn Ala Ala Gly Ile Pro Leu Thr Ala Asp Ile Asp
    210                 215                 220

Met Phe Ala Ile Met Pro His Leu Ser Asn Phe Arg Asp Ser Ala Arg
225                 230                 235                 240

Ser Ser Val Thr Ser Gly Asp Ser Val Thr Asp Tyr Leu Ala Arg Thr
                245                 250                 255

Arg Arg Ala Ala Ser Glu Ala Thr Gly Gly Leu Asp Arg Glu Arg Ile
            260                 265                 270

Asp Leu Leu Trp Lys Ile Ala Arg Ala Gly Ala Arg Ser Ala Val Gly
        275                 280                 285

Thr Glu Ala Arg Arg Gln Phe Arg Tyr Asp Gly Asp Met Asn Ile Gly
    290                 295                 300

Val Ile Thr Asp Phe Glu Leu Glu Val Arg Asn Ala Leu Asn Arg Arg
305                 310                 315                 320

Ala His Ala Val Gly Ala Gln Asp Val Val Gln His Gly Thr Glu Gln
                325                 330                 335

Asn Asn Pro Phe Pro Glu Ala Asp Glu Lys Ile Phe Val Val Ser Ala
            340                 345                 350

```
Thr Gly Glu Ser Gln Met Leu Thr Arg Gly Gln Leu Lys Glu Tyr Ile
            355                 360                 365
Gly Gln Gln Arg Gly Glu Gly Tyr Val Phe Tyr Glu Asn Arg Ala Tyr
        370                 375                 380
Gly Val Ala Gly Lys Ser Leu Phe Asp Asp Gly Leu Gly Ala Ala Pro
385                 390                 395                 400
Gly Val Pro Gly Gly Arg Ser Lys Ser Ser Pro Asp Val Leu Glu Thr
                405                 410                 415
Val Pro Ala Ser Pro Gly Leu Arg Arg Pro Ser Leu Gly Ala Val Glu
            420                 425                 430
Arg Gln Asp Ser Gly Tyr Asp Ser Leu Asp Gly Val Gly Ser Arg Ser
        435                 440                 445
Phe Ser Leu Gly Glu Val Ser Asp Met Ala Ala Val Glu Ala Ala Glu
    450                 455                 460
Leu Glu Met Thr Arg Gln Val Leu His Ala Ala Arg Gln Asp Asp
465                 470                 475                 480
Ala Glu Pro Gly Val Ser Gly Ala Ser Ala His Trp Gly Gln Arg Ala
                485                 490                 495
Leu Gln Gly Ala Gln Ala Val Ala Ala Gln Arg Leu Val His Ala
        500                 505                 510
Ile Ala Leu Met Thr Gln Phe Gly Arg Ala Gly Ser Thr Asn Thr Pro
    515                 520                 525
Gln Glu Ala Ala Ser Leu Ser Ala Ala Val Phe Gly Leu Gly Glu Ala
    530                 535                 540
Ser Ser Ala Val Ala Glu Thr Val Ser Gly Phe Phe Arg Gly Ser Ser
545                 550                 555                 560
Arg Trp Ala Gly Gly Phe Gly Val Ala Gly Ala Met Ala Leu Gly
                565                 570                 575
Gly Gly Ile Ala Ala Ala Val Gly Ala Gly Met Ser Leu Thr Asp Asp
            580                 585                 590
Ala Pro Ala Gly Gln Lys Ala Ala Val Gly Ala Glu Ile Ala Leu Gln
        595                 600                 605
Leu Thr Gly Gly Thr Val Glu Leu Ala Ser Ser Ile Ala Leu Ala Leu
    610                 615                 620
Ala Ala Ala Arg Gly Val Thr Ser Gly Leu Gln Val Ala Gly Ala Ser
625                 630                 635                 640
Ala Gly Ala Ala Ala Gly Ala Leu Ala Ala Leu Ser Pro Met Glu
                645                 650                 655
Ile Tyr Gly Leu Val Gln Ser His Tyr Ala Asp Gln Leu Asp Lys
            660                 665                 670
Leu Ala Gln Glu Ser Ser Ala Tyr Gly Tyr Glu Gly Asp Ala Leu Leu
        675                 680                 685
Ala Gln Leu Tyr Arg Asp Lys Thr Ala Glu Gly Ala Val Ala Gly
    690                 695                 700
Val Ser Ala Val Leu Ser Thr Val Gly Ala Val Ser Ile Ala Ala
705                 710                 715                 720
Ala Ala Ser Val Val Gly Ala Pro Val Ala Val Thr Ser Leu Leu
                725                 730                 735
Thr Gly Ala Leu Asn Gly Ile Leu Arg Gly Val Gln Gln Pro Ile Ile
            740                 745                 750
Glu Lys Leu Ala Asn Asp Tyr Ala Arg Lys Ile Asp Glu Leu Gly Gly
        755                 760                 765
```

```
Pro Gln Ala Tyr Phe Glu Lys Asn Leu Gln Ala Arg His Glu Gln Leu
770                 775                 780

Ala Asn Ser Asp Gly Leu Arg Lys Met Leu Ala Asp Leu Gln Ala Gly
785                 790                 795                 800

Trp Asn Ala Ser Ser Val Ile Gly Val Gln Thr Thr Glu Ile Ser Lys
                805                 810                 815

Ser Ala Leu Glu Leu Ala Ala Ile Thr Gly Asn Ala Asp Asn Leu Lys
                820                 825                 830

Ser Ala Asp Val Phe Val Asp Arg Phe Ile Gln Gly Glu Arg Val Ala
                835                 840                 845

Gly Gln Pro Val Val Leu Asp Val Ala Ala Gly Gly Ile Asp Ile Ala
850                 855                 860

Ser Arg Lys Gly Glu Arg Pro Ala Leu Thr Phe Ile Thr Pro Leu Ala
865                 870                 875                 880

Ala Pro Gly Glu Glu Gln Arg Arg Arg Thr Lys Thr Gly Lys Ser Glu
                885                 890                 895

Phe Thr Thr Phe Val Glu Ile Val Gly Lys Gln Asp Arg Trp Arg Ile
                900                 905                 910

Arg Asp Gly Ala Ala Asp Thr Thr Ile Asp Leu Ala Lys Val Val Ser
                915                 920                 925

Gln Leu Val Asp Ala Asn Gly Val Leu Lys His Ser Ile Lys Leu Glu
930                 935                 940

Val Ile Gly Gly Asp Gly Asp Asp Val Val Leu Ala Asn Ala Ser Arg
945                 950                 955                 960

Ile His Tyr Asp Gly Gly Ala Gly Thr Asn Thr Val Ser Tyr Ala Ala
                965                 970                 975

Leu Gly Arg Gln Asp Ser Ile Thr Val Ser Ala Asp Gly Glu Arg Phe
                980                 985                 990

Asn Val Arg Lys Gln Leu Asn Asn  Ala Asn Val Tyr Arg Glu Gly Val
                995                 1000                1005

Ala Thr  Gln Lys Thr Ala Tyr  Gly Lys Arg Thr Glu  Asn Val Gln
1010                1015                1020

Tyr Arg  His Val Glu Leu Ala  Arg Val Gly Gln Leu  Val Glu Val
1025                1030                1035

Asp Thr  Leu Glu His Val Gln  His Ile Ile Gly Gly  Ala Gly Asn
1040                1045                1050

Asp Ser  Ile Thr Gly Asn Ala  His Asp Asn Phe Leu  Ala Gly Gly
1055                1060                1065

Ala Gly  Asp Asp Arg Leu Asp  Gly Gly Ala Gly Asn  Asp Thr Leu
1070                1075                1080

Val Gly  Gly Glu Gly His Asn  Thr Val Val Gly Gly  Ala Gly Asp
1085                1090                1095

Asp Val  Phe Leu Gln Asp Leu  Gly Val Trp Ser Asn  Gln Leu Asp
1100                1105                1110

Gly Gly  Ala Gly Val Asp Thr  Val Lys Tyr Asn Val  His Gln Pro
1115                1120                1125

Ser Glu  Glu Arg Leu Glu Arg  Met Gly Asp Thr Gly  Ile His Ala
1130                1135                1140

Asp Leu  Gln Lys Gly Thr Val  Glu Lys Trp Pro Ala  Leu Asn Leu
1145                1150                1155

Phe Ser  Val Asp His Val Lys  Asn Ile Glu Asn Leu  His Gly Ser
1160                1165                1170

Ser Leu  Asn Asp Ser Ile Ala  Gly Asp Asp Arg Asp  Asn Glu Leu
```

-continued

```
            1175                1180                1185
Trp Gly Asp Asp Gly Asn Asp Thr Ile His Gly Arg Gly Gly Asp
    1190                1195                1200

Asp Ile Leu Arg Gly Gly Leu Gly Leu Asp Thr Leu Tyr Gly Glu
    1205                1210                1215

Asp Gly Asn Asp Ile Phe Leu Gln Asp Asp Glu Thr Val Ser Asp
    1220                1225                1230

Asp Ile Asp Gly Gly Ala Gly Leu Asp Thr Val Asp Tyr Ser Ala
    1235                1240                1245

Met Ile His Ala Gly Lys Ile Val Ala Pro His Glu Tyr Gly Phe
    1250                1255                1260

Gly Ile Glu Ala Asp Leu Ser Glu Gly Trp Val Arg Lys Ala Ala
    1265                1270                1275

Arg Arg Gly Met Gly Tyr Tyr Asp Ser Val Arg Ser Val Glu Asn
    1280                1285                1290

Val Ile Gly Thr Ser Met Lys Asp Val Leu Ile Gly Asp Ala Gln
    1295                1300                1305

Ala Asn Thr Leu Met Gly Gln Gly Gly Asp Asp Thr Val Arg Gly
    1310                1315                1320

Gly Asp Gly Asp Asp Leu Leu Phe Gly Gly Asp Gly Asn Asp Met
    1325                1330                1335

Leu Tyr Gly Asp Ala Gly Asn Asp Thr Leu Tyr Gly Gly Leu Gly
    1340                1345                1350

Asp Asp Thr Leu Glu Gly Gly Ala Gly Asn Asp Trp Phe Gly Gln
    1355                1360                1365

Thr Pro Ala Arg Glu His Asp Val Leu Arg Gly Gly Ala Gly Val
    1370                1375                1380

Asp Thr Val Asp Tyr Ser Gln Ala Gly Ala His Ala Gly Val Ala
    1385                1390                1395

Thr Gly Arg Ile Gly Leu Gly Ile Leu Ala Asp Leu Gly Ala Gly
    1400                1405                1410

Arg Val Asp Lys Leu Gly Glu Ala Gly Ser Ser Ala Tyr Asp Thr
    1415                1420                1425

Val Ser Gly Ile Glu Asn Val Val Gly Thr Glu Leu Ala Asp Arg
    1430                1435                1440

Ile Thr Gly Asp Ala Gln Ala Asn Val Leu Arg Gly Ala Gly Gly
    1445                1450                1455

Ala Asp Val Leu Ala Gly Gly Glu Gly Asp Asp Val Leu Leu Gly
    1460                1465                1470

Gly Glu Gly Asp Asp Gln Leu Ser Gly Asp Ala Gly Arg Asp Arg
    1475                1480                1485

Leu Tyr Gly Glu Ala Gly Asp Asp Trp Phe Phe Gln Asp Ala Ala
    1490                1495                1500

Asn Ala Gly Asn Leu Leu Asp Gly Gly Asp Gly Asn Asp Thr Val
    1505                1510                1515

Asp Phe Ser Gly Pro Gly Arg Gly Leu Asp Ala Gly Ala Lys Gly
    1520                1525                1530

Val Phe Leu Ser Leu Gly Lys Gly Phe Ala Ser Leu Met Asp Glu
    1535                1540                1545

Pro Glu Thr Ser Asn Val Leu Arg His Ile Glu Asn Ala Val Gly
    1550                1555                1560

Ser Val Arg Asp Asp Val Leu Ile Gly Asp Ala Gly Ala Asn Val
    1565                1570                1575
```

```
Leu Asn Gly Leu Ala Gly Asn Asp Val Leu Ser Gly Gly Ala Gly
        1580                1585                1590

Asp Asp Val Leu Leu Gly Asp Glu Gly Ser Asp Leu Leu Ser Gly
        1595                1600                1605

Asp Ala Gly Asn Asp Asp Leu Phe Gly Gly Gln Gly Asp Asp Thr
        1610                1615                1620

Tyr Leu Phe Gly Ala Gly Tyr Gly His Asp Thr Ile Tyr Glu Ser
        1625                1630                1635

Gly Gly Gly His Asp Thr Ile Arg Ile Asn Ala Gly Ala Asp Gln
        1640                1645                1650

Leu Trp Phe Ala Arg Gln Gly Asn Asp Leu Glu Ile Arg Ile Leu
        1655                1660                1665

Gly Thr Asp Asp Ala Leu Thr Val His Asp Trp Tyr Arg Asp Ala
        1670                1675                1680

Asp His Arg Val Glu Ala Ile His Ala Ala Asn Gln Ala Ile Asp
        1685                1690                1695

Pro Ala Gly Ile Glu Lys Leu Val Glu Ala Met Ala Gln Tyr Pro
        1700                1705                1710

Asp Pro Gly Ala Ala Ala Ala Pro Pro Ala Ala Arg Val Pro
        1715                1720                1725

Asp Thr Leu Met Gln Ser Leu Ala Val Asn Trp Arg
        1730                1735                1740

<210> SEQ ID NO 50
<211> LENGTH: 400
<212> TYPE: PRT
<213> ORGANISM: Bordetella parapertussis

<400> SEQUENCE: 50

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
```

```
                195                 200                 205
Val Thr Ser Gly Asp Ser Val Thr Asp Tyr Leu Ala Arg Thr Arg Arg
210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
                260                 265                 270

Thr Asp Phe Glu Leu Glu Val Arg Asn Ala Leu Asn Arg Arg Ala His
                275                 280                 285

Ala Val Gly Ala Gln Asp Val Val Gln His Gly Thr Glu Gln Asn Asn
290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
                340                 345                 350

Ala Gly Lys Ser Leu Phe Asp Asp Gly Leu Gly Ala Ala Pro Gly Val
                355                 360                 365

Pro Gly Gly Arg Ser Lys Ser Ser Pro Asp Val Leu Glu Thr Val Pro
370                 375                 380

Ala Ser Pro Gly Leu Arg Arg Pro Ser Leu Gly Ala Val Glu Arg Gln
385                 390                 395                 400

<210> SEQ ID NO 51
<211> LENGTH: 225
<212> TYPE: PRT
<213> ORGANISM: Bordetella parapertussis

<400> SEQUENCE: 51

Val Gln Ser Thr Thr Tyr Arg Gln Ile His Met Gln Gln Ser His Gln
1               5                   10                  15

Ala Gly Tyr Ala Asn Ala Ala Asp Arg Glu Ser Gly Ile Pro Ala Ala
                20                  25                  30

Val Leu Asp Gly Ile Lys Ala Val Ala Lys Glu Lys Asn Ala Thr Leu
                35                  40                  45

Met Phe Arg Leu Val Asn Pro His Ser Thr Ser Leu Ile Ala Glu Gly
                50                  55                  60

Val Ala Thr Lys Gly Leu Gly Val His Ala Lys Ser Ser Asp Trp Gly
65                  70                  75                  80

Leu Gln Ala Gly Tyr Ile Pro Val Asn Pro Asn Leu Ser Lys Leu Phe
                85                  90                  95

Gly Arg Ala Pro Glu Val Ile Ala Arg Ala Asp Asn Asp Val Asn Ser
                100                 105                 110

Ser Leu Ala His Gly His Thr Ala Val Asp Leu Thr Leu Ser Lys Glu
                115                 120                 125

Arg Leu Asp Tyr Leu Arg Gln Ala Gly Leu Val Thr Gly Met Ala Asp
                130                 135                 140

Gly Val Val Ala Ser Asn His Ala Gly Tyr Glu Gln Phe Glu Phe Arg
145                 150                 155                 160

Val Lys Glu Thr Ser Asp Gly Arg Tyr Ala Val Gln Tyr Arg Arg Lys
                165                 170                 175
```

```
Gly Gly Asp Asp Phe Glu Ala Val Lys Val Ile Gly Asn Ala Ala Gly
            180                 185                 190

Ile Pro Leu Thr Ala Asp Ile Asp Met Phe Ala Ile Met Pro His Leu
        195                 200                 205

Ser Asn Phe Arg Asp Ser Ala Arg Ser Ser Val Thr Ser Gly Asp Ser
    210                 215                 220

Val
225

<210> SEQ ID NO 52
<211> LENGTH: 175
<212> TYPE: PRT
<213> ORGANISM: Bordetella parapertussis

<400> SEQUENCE: 52

Ala Ser Glu Ala Thr Gly Gly Leu Asp Arg Glu Arg Ile Asp Leu Leu
1               5                   10                  15

Trp Lys Ile Ala Arg Ala Gly Ala Arg Ser Ala Val Gly Thr Glu Ala
            20                  25                  30

Arg Arg Gln Phe Arg Tyr Asp Gly Asp Met Asn Ile Gly Val Ile Thr
        35                  40                  45

Asp Phe Glu Leu Glu Val Arg Asn Ala Leu Asn Arg Arg Ala His Ala
    50                  55                  60

Val Gly Ala Gln Asp Val Val Gln His Gly Thr Glu Gln Asn Asn Pro
65                  70                  75                  80

Phe Pro Glu Ala Asp Glu Lys Ile Phe Val Val Ser Ala Thr Gly Glu
                85                  90                  95

Ser Gln Met Leu Thr Arg Gly Gln Leu Lys Glu Tyr Ile Gly Gln Gln
            100                 105                 110

Arg Gly Glu Gly Tyr Val Phe Tyr Glu Asn Arg Ala Tyr Gly Val Ala
        115                 120                 125

Gly Lys Ser Leu Phe Asp Asp Gly Leu Gly Ala Ala Pro Gly Val Pro
    130                 135                 140

Gly Gly Arg Ser Lys Ser Ser Pro Asp Val Leu Glu Thr Val Pro Ala
145                 150                 155                 160

Ser Pro Gly Leu Arg Arg Pro Ser Leu Gly Ala Val Glu Arg Gln
                165                 170                 175

<210> SEQ ID NO 53
<211> LENGTH: 400
<212> TYPE: PRT
<213> ORGANISM: Bordetella parapertussis

<400> SEQUENCE: 53

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95
```

-continued

```
Asp Asn Asp Val Asn Ser Ser Leu Ala His Gly His Thr Ala Val Asp
             100                 105                 110

Leu Thr Leu Ser Lys Glu Arg Leu Asp Tyr Leu Arg Gln Ala Gly Leu
         115                 120                 125

Val Thr Gly Met Ala Asp Gly Val Val Ala Ser Asn His Ala Gly Tyr
     130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                 165                 170                 175

Ile Gly Asn Ala Ala Gly Ile Pro Leu Thr Ala Cys Thr Asp Met Phe
             180                 185                 190

Ala Ile Met Pro His Leu Ser Asn Phe Arg Asp Ser Ala Arg Ser Ser
         195                 200                 205

Val Thr Ser Gly Asp Ser Val Thr Asp Tyr Leu Ala Arg Thr Arg Arg
     210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                 245                 250                 255

Ala Arg Arg Gln Phe Arg Tyr Asp Gly Asp Met Asn Ile Gly Val Ile
             260                 265                 270

Thr Asp Phe Glu Leu Glu Val Arg Asn Ala Leu Asn Arg Arg Ala His
         275                 280                 285

Ala Val Gly Ala Gln Asp Val Val Gln His Gly Thr Glu Gln Asn Asn
     290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                 325                 330                 335

Gln Arg Gly Glu Gly Tyr Val Phe Tyr Glu Asn Arg Ala Tyr Gly Val
             340                 345                 350

Ala Gly Lys Ser Leu Phe Asp Asp Gly Leu Gly Ala Ala Pro Gly Val
         355                 360                 365

Pro Gly Gly Arg Ser Lys Ser Ser Pro Asp Val Leu Glu Thr Val Pro
     370                 375                 380

Ala Ser Pro Gly Leu Arg Arg Pro Ser Leu Gly Ala Val Glu Arg Gln
385                 390                 395                 400
```

<210> SEQ ID NO 54
<211> LENGTH: 269
<212> TYPE: PRT
<213> ORGANISM: Bordetella parapertussis

<400> SEQUENCE: 54

```
Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Met Thr Ser Pro Ala
             20                  25                  30

Trp Ala Asp Asp Pro Pro Ala Thr Val Tyr Arg Tyr Ser Arg Pro
         35                  40                  45

Pro Glu Asp Val Phe Gln Asn Gly Phe Thr Ala Trp Gly Asn Asn Asp
     50                  55                  60

Asn Val Leu Glu His Leu Thr Gly Arg Ser Cys Gln Val Gly Ser Ser
65                  70                  75                  80
```

```
Asn Ser Ala Phe Val Ser Thr Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Ile Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Thr Val Thr Arg Val Tyr His Asn Gly Ile Thr Gly Glu Thr Thr Thr
            180                 185                 190

Thr Glu Tyr Pro Asn Leu Arg Tyr Val Ser Gln Gln Thr Arg Ala Asn
        195                 200                 205

Thr Asn Pro Tyr Thr Ser Arg Arg Ser Thr Ala Ser Ile Val Gly Thr
    210                 215                 220

Leu Val Arg Met Ala Pro Val Thr Gly Ala Cys Met Ala Arg Gln Ala
225                 230                 235                 240

Glu Ser Pro Glu Ala Met Ala Ala Trp Ser Glu Arg Thr Gly Glu Ala
                245                 250                 255

Met Val Leu Val Tyr Tyr Glu Ser Ile Ala Tyr Ser Phe
            260                 265

<210> SEQ ID NO 55
<211> LENGTH: 226
<212> TYPE: PRT
<213> ORGANISM: Bordetella parapertussis

<400> SEQUENCE: 55

Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Gly Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asn Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
```

```
                 180                 185                 190
His Val Ser Lys Glu Glu Gln Tyr Tyr Asp Tyr Glu Asp Ala Thr Phe
            195                 200                 205

Glu Thr Tyr Ala Leu Thr Gly Ile Ser Ile Cys Asn Pro Gly Ser Ser
        210                 215                 220

Leu Cys
225
```

```
<210> SEQ ID NO 56
<211> LENGTH: 227
<212> TYPE: PRT
<213> ORGANISM: Bordetella parapertussis

<400> SEQUENCE: 56

Met Leu Ile Asn Asn Lys Lys Leu Leu His His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
    50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

Gly Ile Ile Lys Asp Ala Pro Pro Gly Ala Gly Phe Ile Tyr Arg Glu
            100                 105                 110

Thr Phe Cys Ile Thr Thr Met Tyr Lys Thr Gly Gln Pro Ala Ala Asp
        115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Val
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225
```

```
<210> SEQ ID NO 57
<211> LENGTH: 152
<212> TYPE: PRT
<213> ORGANISM: Bordetella parapertussis

<400> SEQUENCE: 57

Met Leu Arg Arg Phe Leu Thr Arg Thr Thr Ala Pro Gly Gln Gly Gly
1               5                   10                  15

Ala Arg Arg Pro Arg Val Arg Ala Leu Ala Trp Leu Leu Ala Ser Gly
            20                  25                  30

Thr Met Met His Leu His Pro Ala Gln Ala Asp Val Pro Tyr Val Leu
```

```
                35                  40                  45
Val Lys Thr Asn Met Val Val Thr Ser Val Ala Met Lys Pro Tyr Glu
 50                  55                  60

Val Asn Pro Thr Arg Met Leu Val Cys Gly Ile Ala Ala Lys Leu Gly
 65                  70                  75                  80

Ala Thr Ala Ser Ser Pro Asp Ala His Val Pro Phe Cys Phe Gly Lys
                 85                  90                  95

Asp Leu Lys Arg Ser Gly Ser Ser Pro Met Glu Val Met Leu Arg Ala
                100                 105                 110

Val Phe Met Gln Gln Arg Pro Leu Arg Met Phe Leu Gly Pro Lys Gln
            115                 120                 125

Leu Thr Phe Glu Gly Lys Pro Ala Leu Glu Leu Ile Arg Met Val Glu
        130                 135                 140

Cys Ser Gly Lys Gln Asp Cys Pro
145                 150
```

<210> SEQ ID NO 58
<211> LENGTH: 120
<212> TYPE: PRT
<213> ORGANISM: Bordetella parapertussis

<400> SEQUENCE: 58

```
Met His Thr Ile Ala Ser Ile Leu Leu Ser Val Leu Gly Ile Tyr Ser
 1               5                  10                  15

Pro Ala Asp Val Ala Gly Leu Pro Thr His Leu Tyr Lys Asn Phe Thr
                20                  25                  30

Val Gln Glu Leu Ala Leu Lys Leu Gly Lys Asn Gln Glu Phe Cys
            35                  40                  45

Leu Thr Ala Phe Met Pro Gly Arg Ser Leu Val Arg Ala Cys Leu Ser
 50                  55                  60

Asp Ala Gly His Glu His Asp Thr Trp Phe Asp Thr Met Leu Gly Phe
 65                  70                  75                  80

Ala Ile Ser Ala Tyr Ala Leu Lys Ser Arg Ile Ala Leu Thr Val Glu
                 85                  90                  95

Asp Ser Pro Tyr Pro Gly Thr Pro Gly Asp Leu Leu Glu Leu Gln Ile
                100                 105                 110

Cys Pro Leu Asn Gly Tyr Cys Glu
            115                 120
```

<210> SEQ ID NO 59
<211> LENGTH: 3831
<212> TYPE: PRT
<213> ORGANISM: Bordetella parapertussis

<400> SEQUENCE: 59

```
Met Leu Ala Cys Ala Gly Leu Pro Leu Val Thr His Ala Gln Gly Leu
 1               5                  10                  15

Val Pro Gln Gly Gln Thr Gln Val Leu Gln Gly Gly Asn Lys Val Pro
                20                  25                  30

Val Val Asn Ile Ala Asn Pro Asn Ser Gly Gly Val Ser His Asn Lys
            35                  40                  45

Phe Gln Gln Phe Asn Val Ala Asn Pro Gly Val Val Phe Asn Asn Gly
 50                  55                  60

Leu Thr Asp Gly Val Ser Arg Ile Gly Gly Ala Leu Thr Lys Asn Pro
 65                  70                  75                  80

Asn Leu Thr Arg Gln Ala Ser Ala Ile Leu Ala Glu Val Thr Gly Thr
```

```
                   85                  90                  95
Ser Pro Ser Arg Leu Ala Gly Thr Leu Glu Val Tyr Gly Lys Gly Ala
                100                 105                 110
Asp Leu Ile Ile Ala Asn Pro Asn Gly Ile Ser Val Asn Gly Leu Ser
                115                 120                 125
Thr Leu Asn Ala Ser Asn Leu Thr Leu Thr Thr Gly Arg Pro Ser Val
                130                 135             140
Asn Gly Gly Arg Ile Gly Leu Asp Val Gln Gln Gly Thr Val Thr Ile
145                 150                 155                 160
Glu Arg Gly Gly Val Asn Ala Thr Gly Leu Gly Tyr Phe Asp Val Val
                165                 170                 175
Ala Arg Leu Val Lys Leu Gln Gly Ala Val Ser Thr Glu Gln Gly Lys
                180                 185                 190
Pro Leu Ala Asp Ile Ala Val Val Ala Gly Ala Asn Arg Tyr Asp His
                195                 200                 205
Ala Thr Arg Arg Ala Thr Pro Ile Ala Ala Gly Ala Arg Gly Ala Ala
                210                 215                 220
Ala Gly Ala Tyr Ala Ile Asp Gly Thr Ala Ala Gly Ala Met Tyr Gly
225                 230                 235                 240
Lys His Ile Thr Leu Val Ser Ser Asp Ser Gly Leu Gly Val Arg Gln
                245                 250                 255
Leu Gly Ser Leu Ser Ser Pro Leu Ala Ile Thr Val Ser Ser Gln Gly
                260                 265                 270
Glu Ile Ala Leu Gly Asp Ala Thr Val Gln Arg Gly Pro Leu Ser Leu
                275                 280                 285
Lys Gly Ala Gly Ala Val Ser Ala Gly Lys Leu Ala Ser Gly Gly Ala
                290                 295                 300
Val Ser Val Ala Gly Gly Ala Val Thr Val Ala Ser Ala Ser Ser
305                 310                 315                 320
Val Gly Asn Leu Ala Val Gln Gly Gly Thr Val Gln Ala Thr Leu
                325                 330                 335
Leu Asn Ala Gly Gly Thr Leu Gln Val Ser Gly Arg Gln Ala Val Gln
                340                 345                 350
Leu Gly Thr Ala Ser Ser Arg Gln Val Leu Ser Val Asn Ala Gly Gly
                355                 360                 365
Ala Leu Lys Ala Asp Gln Leu Ser Ala Thr Gly Arg Leu Glu Val Asp
                370                 375             380
Gly Lys Gln Ala Val Thr Leu Gly Ser Ala Ala Ser Gly Asp Ala Leu
385                 390                 395                 400
Ser Val Ser Ala Gly Ala Ala Leu Arg Ala Asp Gln Leu Ser Ala Thr
                405                 410                 415
Gly Arg Leu Asp Val Asp Gly Lys Gln Ala Val Thr Leu Gly Ser Ala
                420                 425                 430
Ala Ser Gly Asp Ala Leu Ser Val Ser Ala Gly Ser Ala Leu Arg Ala
                435                 440                 445
Asp Gln Leu Ser Ala Thr Arg Arg Leu Gly Val Asp Gly Lys Gln Ala
                450                 455                 460
Val Thr Leu Gly Ser Ala Ala Ser Arg Asn Ala Leu Ser Val Arg Ala
465                 470                 475                 480
Gly Gly Ala Leu Lys Ala Asp Lys Leu Ser Ala Thr Gly Arg Leu Asp
                485                 490                 495
Val Asp Gly Lys Gln Ala Val Thr Leu Gly Ser Ala Ala Ser Gly Asp
                500                 505                 510
```

```
Ala Leu Ser Val Ser Ala Gly Ala Ala Leu Arg Ala Asp Gln Leu Ser
            515                 520                 525

Ala Thr Arg Arg Leu Gly Val Asp Gly Lys Gln Ala Val Thr Leu Gly
    530                 535                 540

Ser Val Ala Ser Asp Gly Ala Leu Ser Val Ser Ala Gly Gly Asn Leu
545                 550                 555                 560

Gln Ala Lys Gln Leu Val Ser Asn Ala Gly Leu Asp Val Arg Gly Gln
                565                 570                 575

Arg Glu Val Ser Leu Glu Ala Ala Ser Ser Gly Asp Ala Leu Ser Val
            580                 585                 590

Ser Ala Gly Ala Ala Leu Arg Ala Asp Gln Leu Ser Ala Thr Gly Arg
        595                 600                 605

Leu Asp Val Asp Gly Lys Gln Ala Val Thr Leu Gly Ser Ala Ala Ser
        610                 615                 620

Gly Asp Ala Leu Ser Val Ser Ala Gly Ala Ala Leu Arg Ala Asp Gln
625                 630                 635                 640

Leu Ser Ala Thr Gly Arg Leu Asp Val Asp Gly Lys Gln Ala Val Thr
                645                 650                 655

Leu Gly Ser Ala Ala Ser Gly Asp Ala Leu Ser Val Ser Ala Gly Ala
            660                 665                 670

Ala Leu Arg Ala Asp Gln Leu Ser Ala Thr Gly Arg Leu Asp Val Asp
        675                 680                 685

Gly Lys Gln Ala Val Thr Leu Gly Ser Ala Ala Ser Gly Asp Ala Leu
        690                 695                 700

Ser Val Ser Ala Gly Ala Ala Leu Arg Ala Asp Gln Leu Ser Ala Thr
705                 710                 715                 720

Gly Arg Leu Asp Val Asp Gly Lys Gln Ala Val Thr Leu Gly Ser Ala
                725                 730                 735

Ala Ser Asp Gly Ala Leu Ser Val Ser Ala Gly Gly Asn Leu Gln Ala
            740                 745                 750

Lys Gln Leu Val Ser Asn Ala Gly Leu Asp Val Arg Gly Gln Arg Glu
        755                 760                 765

Val Ser Leu Glu Ala Ala Ser Ser Val Arg Gly Met Thr Val Ala Ala
        770                 775                 780

Ala Gly Thr Leu Ala Ala Arg Asn Leu Gln Ser Gln Gly Ala Ile Arg
785                 790                 795                 800

Ile Gln Gly Gly Gln Ala Val Ser Val Ala Asn Ala Asn Ser Asp Ala
                805                 810                 815

Glu Leu His Val Ser Gly Arg Gly Gln Val Asp Leu Gly Asp Leu Ser
            820                 825                 830

Ala Ala Arg Gly Ala Asp Ile Thr Gly Glu Gln Arg Val Ser Ile Gly
        835                 840                 845

Arg Ala His Ser Asp Gly Asp Val Asn Val Ala Ala Arg Gly Ala Leu
        850                 855                 860

Ser Ile Asp Ser Met Thr Ala Leu Gly Ala Ile Gly Val Gln Ala Gly
865                 870                 875                 880

Asp Ser Val Ser Ala Lys Asp Met Arg Ser Arg Gly Ala Val Thr Val
                885                 890                 895

Ser Gly Gly Gly Ser Val Asn Leu Gly Asp Val Gln Ser Asp Gly Gln
            900                 905                 910

Val Arg Ala Thr Ser Ala Gly Ala Met Thr Val Arg Asp Ala Ala Ala
        915                 920                 925
```

```
Ala Ala Asp Leu Ala Leu Gln Ala Gly Gly Ala Leu Gln Ala Gly Phe
930                 935                 940

Leu Lys Ser Ala Gly Ala Met Thr Val Asn Gly Arg Asp Ala Val Arg
945                 950                 955                 960

Leu Asp Gly Ala Gln Ala Gly Gly Gln Leu Arg Val Ser Ser Asp Gly
                965                 970                 975

Gln Ala Ala Leu Gly Ser Leu Ala Ala Lys Gly Ala Leu Thr Val Ser
            980                 985                 990

Ala Ala Arg Ala Ala Thr Val Ala Glu Leu Lys Ser Leu Asp Ser Ile
        995                 1000                1005

Ser Val Thr Gly Gly Glu Arg Val Ser Val Gln Ser Val Asn Ser
    1010                1015                1020

Ala Ser Arg Val Ala Ile Ser Ala His Gly Ala Leu Glu Val Gly
    1025                1030                1035

Lys Val Ser Ala Lys Ser Gly Ile Gly Ile Glu Gly Trp Gly Ala
    1040                1045                1050

Val Ala Ala Asp Ser Leu Gly Ser Asp Gly Ala Ile Ser Val Ser
    1055                1060                1065

Gly Arg Asp Ala Val Arg Val Asp His Ala Arg Ser Leu Ala Asp
    1070                1075                1080

Ile Ser Leu Gly Ala Glu Gly Gly Ala Thr Leu Gly Ala Val Glu
    1085                1090                1095

Ala Ala Gly Ser Ile Asp Val Arg Gly Gly Ser Thr Val Ala Ala
    1100                1105                1110

Asn Ser Leu Arg Ala Asn Arg Asp Val Arg Val Ser Gly Lys Asp
    1115                1120                1125

Ala Val Arg Val Thr Ala Ala Thr Ser Gly Gly Gly Leu His Val
    1130                1135                1140

Ser Ser Gly Arg Gln Leu Asp Leu Gly Ala Val Gln Ala Arg Gly
    1145                1150                1155

Ala Leu Ala Leu Asp Gly Gly Ala Gly Val Ala Leu Gln Ser Ala
    1160                1165                1170

Lys Ala Gly Gly Thr Leu His Val Gln Gly Gly Glu His Leu Asp
    1175                1180                1185

Leu Gly Thr Leu Ala Ala Val Gly Ala Val Asp Val Asn Gly Ala
    1190                1195                1200

Gly Asp Val Arg Val Ala Lys Leu Val Ser Asp Ala Gly Ala Asp
    1205                1210                1215

Leu Gln Ala Gly Arg Ser Met Thr Leu Gly Thr Val Asp Thr Thr
    1220                1225                1230

Gly Asp Leu Gln Ala Arg Ala Gln Gln Ala Leu Glu Leu Gly Ser
    1235                1240                1245

Val Lys Thr Glu Gly Gly Leu Gln Ala Ala Gly Gly Ala Phe
    1250                1255                1260

Ser Leu Ala Ala Ala Glu Val Ala Gly Ala Leu Glu Leu Ser Gly
    1265                1270                1275

His Gly Val Thr Val Asp Arg Ala Ser Ala Gly Arg Ala Arg Ile
    1280                1285                1290

Asp Ser Thr Gly Ser Val Gly Ile Gly Ala Leu Lys Ala Gly Ala
    1295                1300                1305

Val Glu Ala Ala Ser Pro Arg Arg Ala Arg Arg Ala Leu Arg Gln
    1310                1315                1320

Asp Phe Phe Thr Pro Gly Ser Val Val Val Arg Ala Gln Gly Asn
```

```
              1325                1330                1335
Val Thr Val Gly Arg Gly Asp Pro His Gln Gly Val Leu Ala Gln
    1340                1345                1350
Gly Asp Ile Val Met Asp Ala Lys Gly Gly Thr Leu Leu Leu Arg
    1355                1360                1365
Asn Asp Val Leu Thr Glu Asn Gly Thr Val Thr Ile Ser Ala Asp
    1370                1375                1380
Ser Ala Val Leu Glu His Ser Thr Ile Glu Ser Lys Ile Ser Gln
    1385                1390                1395
Ser Ala Leu Ala Ala Lys Gly Asp Lys Gly Lys Pro Ala Val Ser
    1400                1405                1410
Val Lys Val Ala Lys Lys Leu Phe Leu Asn Gly Thr Leu Arg Ala
    1415                1420                1425
Val Asn Asp Asn Glu Glu Thr Met Pro Gly Arg Gln Ile Asp Val
    1430                1435                1440
Val Asp Gly Arg Pro Gln Ile Thr Asp Ala Val Thr Gly Glu Glu
    1445                1450                1455
Arg Lys Asp Glu Ser Val Val Ser Asp Ala Ala Leu Val Ala Asp
    1460                1465                1470
Gly Gly Pro Ile Val Val Glu Ala Gly Glu Leu Val Ser His Ala
    1475                1480                1485
Gly Gly Ile Gly Asn Gly Arg Asn Lys Gly Asp Gly Ala Asp Val
    1490                1495                1500
Thr Val Arg Thr Thr Gly Asn Val Met Asn Lys Gly Tyr Ile Ser
    1505                1510                1515
Ala Gly Lys Gln Gly Val Leu Glu Val Gly Gly Thr Leu Thr Asn
    1520                1525                1530
Glu Phe Leu Val Ser Ser Asp Gly Thr Gln Arg Ile Glu Ala Gln
    1535                1540                1545
Arg Ile Glu Asn Arg Gly Thr Phe Gln Ser Gln Ala Pro Ala Gly
    1550                1555                1560
Thr Ala Gly Ala Leu Val Val Lys Ala Ala Glu Ala Ile Val His
    1565                1570                1575
Asp Gly Val Met Ala Thr Glu Gly Glu Met Gln Ile Ala Gly Lys
    1580                1585                1590
Gly Gly Arg Ser Pro Ala Val Thr Ala Gly Ala Lys Ala Thr Thr
    1595                1600                1605
Ser Ala Asn Lys Leu Ser Ala Asp Val Ala Ser Trp Asp Asn Ala
    1610                1615                1620
Gly Ser Leu Asp Ile Lys Lys Gly Gly Ala Arg Val Thr Ala Thr
    1625                1630                1635
Gly Arg Tyr Ala Glu His Gly Lys Val Ser Ile Gln Gly Asp Tyr
    1640                1645                1650
Thr Val Ser Ala Asp Ala Ile Ala Leu Ala Ala Gln Ile Thr Gln
    1655                1660                1665
Arg Gly Gly Ala Ala Asp Leu Thr Ser Gly His Asp Thr Arg Phe
    1670                1675                1680
Ser Asn Asn Ile Arg Leu Met Gly Pro Leu Gln Val Ser Ala Gly
    1685                1690                1695
Gly Ala Val Ser Asn Thr Gly Asn Leu Lys Val Arg Glu Gly Val
    1700                1705                1710
Arg Val Thr Ala Ala Ser Phe Asp Asn Glu Ala Gly Ala Glu Val
    1715                1720                1725
```

Met Ala Lys Ser Ala Ala Leu Thr Thr Ser Gly Ala Val Arg Asn
1730                1735                1740

Ala Gly Lys Met Gln Val Lys Glu Ala Thr Ile Val Ala Ala
1745                1750                1755

Ser Val Ser Asn Pro Gly Thr Phe Thr Ala Gly Lys Asp Leu Thr
1760                1765                1770

Val Thr Ser Arg Gly Gly Phe Asp Asn Asp Gly Lys Met Glu Ser
1775                1780                1785

Asn Lys Asp Ile Val Ile Lys Thr Glu Gln Phe Ser Asn Ala Gly
1790                1795                1800

Ile Leu Asp Ala Lys His Asp Leu Thr Val Thr Ala Ser Gly Gln
1805                1810                1815

Ala Asp Asn Arg Gly Ser Leu Lys Ala Gly His Asp Phe Thr Val
1820                1825                1830

Gln Ala Gln Arg Ile Asp Asn Ser Gly Thr Met Ala Ala Gly Tyr
1835                1840                1845

Asp Ala Thr Leu Lys Ala Pro His Leu Arg Asn Thr Gly Gln Ile
1850                1855                1860

Val Ala Gly His Asp Ile His Ile Ile Asn Ser Ala Lys Leu Glu
1865                1870                1875

Asn Thr Gly Arg Val Asp Ala Arg Asn Asp Leu Val Leu Asp Val
1880                1885                1890

Glu Asp Phe Thr Asn Thr Gly Ser Leu Tyr Ala Glu His Asp Ala
1895                1900                1905

Thr Leu Thr Leu Ala Gln Gly Thr Gln Arg Asp Leu Val Val Asp
1910                1915                1920

Gln Asp His Ile Leu Pro Val Ala Glu Gly Thr Leu Arg Val Lys
1925                1930                1935

Ala Lys Ser Leu Thr Thr Glu Ile Glu Thr Gly Asn Ser Gly Ser
1940                1945                1950

Leu Ile Ala Glu Val Gln Glu Asn Ile Asp Asn Lys Gln Ala Ile
1955                1960                1965

Val Val Gly Lys Asp Leu Thr Leu Ser Ser Ala His Gly Asn Val
1970                1975                1980

Ala Asn Glu Ala Asn Ala Leu Leu Trp Ala Ala Gly Asp Leu Thr
1985                1990                1995

Val Lys Ala Gln Asn Ile Thr Asn Glu Arg Ala Ala Leu Ile Glu
2000                2005                2010

Ala Gly Gly Asn Ala Arg Leu Thr Ala Ala Val Ala Leu Leu Asn
2015                2020                2025

Lys Leu Gly Arg Ile Arg Ala Gly Glu Asp Met His Leu Asp Ala
2030                2035                2040

Pro Arg Ile Glu Asn Thr Ala Lys Leu Ser Gly Glu Val Gln Arg
2045                2050                2055

Lys Gly Val Gln Tyr Val Gly Gly Thr Tyr Gly Arg Trp Ser
2060                2065                2070

Gly Ile Gly Tyr Val Asn Tyr His Leu Ser Ser Gly Ser Gly Ala
2075                2080                2085

Ile Ala Ala Pro Trp Tyr Gly Ser Asp Leu Thr Ala Glu Gln Ser
2090                2095                2100

Leu Ile Glu Val Gly Lys Asp Leu Tyr Leu Asn Ala Gly Ala Arg
2105                2110                2115

-continued

```
Lys Asp Glu His Arg His Leu Leu Asn Glu Gly Val Ile Gln Ala
2120                2125                2130

Gly Gly His Gly Tyr Ile Gly Gly Asp Val Asp Asn Arg Ser Val
2135                2140                2145

Val Arg Thr Val Ser Ala Met Glu Tyr Phe Lys Thr Pro Leu Pro
2150                2155                2160

Val Ser Leu Thr Ala Leu Asp Asn Arg Ala Gly Leu Ser Pro Ala
2165                2170                2175

Thr Trp Asn Phe Gln Ser Thr Tyr Glu Leu Leu Asp Tyr Leu Leu
2180                2185                2190

Asp Gln Asn Arg Tyr Glu Tyr Ile Trp Gly Leu Tyr Pro Thr Tyr
2195                2200                2205

Thr Glu Trp Ser Val Asn Thr Leu Lys Asn Leu Asp Leu Gly Tyr
2210                2215                2220

Gln Ala Lys Pro Ala Pro Thr Ala Pro Pro Met Pro Lys Ala Pro
2225                2230                2235

Glu Leu Asp Leu Arg Gly His Thr Leu Glu Ser Ala Glu Gly Arg
2240                2245                2250

Lys Ile Phe Gly Glu Tyr Lys Lys Leu Gln Gly Glu Tyr Glu Lys
2255                2260                2265

Ala Lys Thr Ala Val Gln Ala Val Glu Ala Tyr Gly Glu Ala Thr
2270                2275                2280

Arg Arg Val His Asp Gln Leu Gly Gln Arg Tyr Gly Lys Ala Leu
2285                2290                2295

Gly Gly Met Asp Ala Glu Thr Lys Glu Val Asp Gly Ile Ile Gln
2300                2305                2310

Ala Phe Ala Ala Asp Leu Arg Thr Val Tyr Ala Lys Gln Ala Asp
2315                2320                2325

Gln Ala Thr Ile Asp Ala Glu Thr Asp Lys Val Ala Gln Arg Tyr
2330                2335                2340

Lys Ser Gln Ile Asp Ala Val Arg Leu Gln Ala Ile Gln Pro Gly
2345                2350                2355

Arg Val Thr Leu Ala Lys Ala Leu Ser Ala Ala Leu Gly Ala Asp
2360                2365                2370

Trp Arg Ala Leu Gly His Ser Gln Leu Met Gln Arg Trp Lys Asp
2375                2380                2385

Phe Lys Ala Gly Lys Arg Gly Ala Glu Ile Ala Phe Tyr Pro Lys
2390                2395                2400

Glu Gln Thr Val Leu Ala Ala Gly Ala Gly Leu Thr Leu Ser Asn
2405                2410                2415

Gly Ala Val His Asn Gly Glu Asn Ala Ala Gln Asn Arg Gly Arg
2420                2425                2430

Pro Glu Asn Leu Lys Ile Gly Ala His Ser Ala Thr Ser Val Gly
2435                2440                2445

Gly Ser Phe Asp Ala Leu Arg Asp Val Gly Leu Glu Lys Arg Leu
2450                2455                2460

Asp Ile Asp Asp Ala Leu Ala Ala Val Leu Val Asn Pro His Ile
2465                2470                2475

Phe Thr Arg Ile Gly Ala Val Gln Ala Ser Leu Ser Asp Ala Ala
2480                2485                2490

Ala Gly Pro Ala Leu Ala Arg Gln Ala Arg Gln Ala Pro Gly Thr
2495                2500                2505

Asp Gly Met Val Asp Ala Arg Gly Leu Gly Ser Ala Asp Ala Leu
```

-continued

```
               2510                2515               2520
Ala Ser Leu Ala Ser Leu Asp Ala Ala Gln Gly Leu Glu Val Ser
               2525                2530               2535
Gly Arg Arg Asn Ala Gln Val Ala Asp Ala Arg Leu Ala Gly Pro
               2540                2545               2550
Ser Ala Val Ala Ala Pro Ala Val Gly Ala Val Asp Val Gly Val
               2555                2560               2565
Glu Pro Val Thr Gly Asp Gln Val Asp Gln Pro Val Val Ala Val
               2570                2575               2580
Gly Leu Glu Gln Pro Val Ala Ala Val Arg Val Ala Pro Pro Ala
               2585                2590               2595
Val Ala Leu Pro Arg Pro Leu Phe Glu Thr Arg Ile Lys Phe Ile
               2600                2605               2610
Asp Gln Ser Lys Phe Tyr Gly Ser Arg Tyr Phe Phe Glu Gln Ile
               2615                2620               2625
Gly Tyr Lys Pro Asp Arg Ala Ala Arg Val Ala Gly Asp Asn Tyr
               2630                2635               2640
Phe Asp Thr Thr Leu Val Arg Glu Gln Val Arg Arg Ala Leu Gly
               2645                2650               2655
Gly Tyr Glu Ser Arg Leu Pro Val Arg Gly Val Ala Leu Val Ala
               2660                2665               2670
Lys Leu Met Asp Ser Ala Gly Thr Val Gly Lys Ala Leu Gly Leu
               2675                2680               2685
Lys Val Gly Val Ala Pro Thr Glu Gln Gln Leu Lys Gln Ala Asp
               2690                2695               2700
Arg Asp Phe Val Trp Tyr Val Asp Thr Val Ile Asp Gly Gln Lys
               2705                2710               2715
Val Leu Ala Pro Arg Leu Tyr Leu Thr Glu Ala Thr Arg Gln Gly
               2720                2725               2730
Ile Thr Asp Gln Tyr Ala Gly Gly Gly Ala Leu Ile Ala Ser Gly
               2735                2740               2745
Gly Asp Val Thr Val Asn Thr Asp Gly His Asp Val Ser Ser Val
               2750                2755               2760
Asn Gly Leu Ile Gln Gly Lys Gly Val Lys Val Asp Ala Gly Lys
               2765                2770               2775
Gly Lys Val Leu Val Ala Asp Asn Lys Gly Met Gly Ser Gly Ile
               2780                2785               2790
Glu Ala Asp Asp Glu Val Asp Val Ser Ala Gln Asp Ile Asp Ile
               2795                2800               2805
Glu Gly Gly Lys Leu Arg Gly Lys Asp Val Lys Leu Lys Ala Asp
               2810                2815               2820
Thr Val Lys Val Ala Thr Ser Met Arg Tyr Asp Asp Lys Gly Arg
               2825                2830               2835
Leu Ala Ala Arg Gly Asp Gly Ala Leu Asp Ala Gln Gly Gly Gln
               2840                2845               2850
Leu His Ile Glu Ala Lys Arg Leu Glu Thr Ala Gly Ala Thr Leu
               2855                2860               2865
Lys Gly Ser Lys Val Lys Leu Asp Val Asp Asp Val Lys Leu Gly
               2870                2875               2880
Gly Val Tyr Glu Ala Gly Ser Ser Tyr Glu Asn Lys Ser Ser Thr
               2885                2890               2895
Pro Leu Gly Ser Leu Phe Ala Ile Leu Ser Ser Thr Thr Glu Thr
               2900                2905               2910
```

-continued

```
Asn Gln Ser Ala Arg Ala Asn His Tyr Gly Thr Arg Ile Glu Ala
2915                2920                2925

Gly Thr Leu Glu Gly Lys Met Gln Asn Leu Glu Ile Glu Gly Gly
2930                2935                2940

Ser Val Glu Ala Ala His Thr Asp Leu Ser Val Ala Arg Asp Ala
2945                2950                2955

Arg Phe Lys Ala Ala Ala Asp Phe Ser His Ala Glu His Glu Lys
2960                2965                2970

Asp Val Arg Gln Leu Phe Val Ser Ala Lys Val Gly Ala Gly Gly
2975                2980                2985

Tyr Glu Ala Gly Phe Ser Leu Gly Ser Glu Lys Gly Leu Glu Ala
2990                2995                3000

His Ala Gly Arg Gly Lys Thr Ala Gly Ala Glu Val Arg Val Gly
3005                3010                3015

Tyr Gln Ala Ser His Glu Gln Ser Ser Glu Thr Glu Lys Ser Tyr
3020                3025                3030

Arg Asn Ala Asn Leu Asn Phe Gly Gly Gly Ser Val Glu Ala Gly
3035                3040                3045

Asn Val Leu Asp Ile Gly Gly Ala Asp Ile Asn Arg Asn Arg Tyr
3050                3055                3060

Gly Gly Ala Ala Glu Gly Lys Ala Gly Ala Glu Glu Ala Leu Arg
3065                3070                3075

Met Arg Ala Lys Lys Val Glu Ser Thr Lys Tyr Val Ser Glu Gln
3080                3085                3090

Thr Ser Gln Ser Ser Gly Trp Ser Val Glu Val Gly Ala Thr Gly
3095                3100                3105

Ser Ala Arg Ser Ser Val Leu Thr Ala Ala Thr Arg Leu Gly Asp
3110                3115                3120

Ser Val Ala Gln Asn Val Glu Asp Gly Arg Glu Ile Arg Gly Glu
3125                3130                3135

Leu Met Ala Ala Gln Ala Ala Ala Glu Ala Thr Gln Leu Val Thr
3140                3145                3150

Ala Asp Thr Ala Ala Leu Ala Val Ser Leu Gly Ile Ser Ala Asp
3155                3160                3165

Phe Asp Ser Ser Gln Ser Arg Ser Thr Ser Gln Asn Thr Gln Tyr
3170                3175                3180

Leu Gly Gly Asn Leu Ser Ile Glu Ala Thr Glu Gly Asp Ala Thr
3185                3190                3195

Leu Val Gly Ala Lys Phe Gly Gly Asp Gln Val Ser Leu Lys
3200                3205                3210

Ala Ala Lys Asn Val Asn Leu Met Ala Ala Glu Ser Thr Phe Glu
3215                3220                3225

Ser His Ser Glu Ser His Asn Phe His Ala Ser Ala Asp Ala Asn
3230                3235                3240

Leu Gly Ala Asn Ala Val Gln Gly Ala Val Gly Leu Gly Leu Thr
3245                3250                3255

Ala Gly Met Gly Thr Ser His Gln Ile Thr Asn Glu Thr Gly Lys
3260                3265                3270

Thr Tyr Ala Gly Thr Ser Val Asp Ala Ala Asn Val Ser Ile Asp
3275                3280                3285

Ala Gly Lys Asp Leu Asn Leu Ser Gly Ser Arg Val Arg Gly Gln
3290                3295                3300
```

```
Arg  Val  Val  Leu  Gly  Val  Glu  Gly  Asp  Ile  Asn  Ala  Thr  Ser  Lys
3305                3310                     3315

Gln  Asp  Glu  Arg  Asn  Tyr  Asn  Ser  Ser  Gly  Gly  Gly  Trp  Asp  Ala
3320                3325                     3330

Ser  Ala  Gly  Val  Ala  Ile  Gln  Asn  Arg  Thr  Leu  Val  Ala  Pro  Val
3335                3340                     3345

Gly  Ser  Ala  Gly  Phe  Asn  Phe  Asn  Thr  Glu  His  Asp  Asn  Ser  Arg
3350                3355                     3360

Leu  Thr  Asn  Asp  Gly  Ala  Ala  Gly  Val  Val  Ala  Ser  Asp  Gly  Leu
3365                3370                     3375

Thr  Gly  His  Val  Lys  Gly  Asp  Ala  Asn  Leu  Thr  Gly  Ala  Thr  Ile
3380                3385                     3390

Ala  Asp  Leu  Ser  Gly  Lys  Gly  Asn  Leu  Lys  Val  Asp  Gly  Ala  Val
3395                3400                     3405

Asn  Ala  Gln  Asn  Leu  Lys  Asp  Tyr  Arg  Asp  Lys  Asp  Gly  Gly  Ser
3410                3415                     3420

Gly  Gly  Leu  Asn  Val  Gly  Ile  Ser  Ser  Thr  Thr  Leu  Ala  Pro  Thr
3425                3430                     3435

Val  Gly  Val  Ala  Phe  Gly  Arg  Val  Ala  Gly  Glu  Asp  Tyr  Gln  Ala
3440                3445                     3450

Glu  Gln  Arg  Ala  Thr  Ile  Asp  Val  Gly  Gln  Ile  Lys  Asp  Pro  Ala
3455                3460                     3465

Arg  Leu  Gln  Val  Gly  Gly  Gly  Val  Lys  Gly  Thr  Leu  Asn  Gln  Asp
3470                3475                     3480

Ala  Ala  Gln  Ala  Thr  Val  Val  Gln  Arg  Asn  Lys  His  Trp  Ala  Gly
3485                3490                     3495

Gly  Gly  Ser  Glu  Phe  Ser  Val  Ala  Gly  Lys  Ser  Leu  Lys  Lys  Asn
3500                3505                     3510

Gln  Val  Arg  Pro  Val  Glu  Thr  Pro  Thr  Pro  Asp  Val  Val  Asp  Gly
3515                3520                     3525

Pro  Pro  Ser  Arg  Pro  Thr  Thr  Pro  Pro  Ala  Ser  Pro  Gln  Pro  Ile
3530                3535                     3540

Arg  Ala  Thr  Val  Glu  Val  Ser  Ser  Pro  Pro  Val  Ser  Val  Ala
3545                3550                     3555

Thr  Val  Glu  Val  Val  Pro  Arg  Pro  Lys  Val  Glu  Thr  Ala  Gln  Pro
3560                3565                     3570

Ile  Pro  Pro  Arg  Pro  Val  Ala  Ala  Gln  Val  Val  Pro  Val  Thr  Pro
3575                3580                     3585

Pro  Lys  Val  Glu  Val  Ala  Lys  Val  Glu  Val  Val  Pro  Arg  Pro  Lys
3590                3595                     3600

Val  Glu  Thr  Ala  Gln  Pro  Leu  Pro  Pro  Arg  Pro  Val  Val  Ala  Glu
3605                3610                     3615

Arg  Val  Thr  Thr  Pro  Ala  Val  Gln  Pro  Gln  Leu  Ala  Lys  Val  Glu
3620                3625                     3630

Thr  Val  Gln  Pro  Val  Lys  Pro  Glu  Thr  Ala  Lys  Pro  Leu  Pro  Lys
3635                3640                     3645

Pro  Leu  Pro  Val  Ala  Lys  Val  Thr  Glu  Ala  Pro  Pro  Val  Val
3650                3655                     3660

Glu  Thr  Ala  Gln  Pro  Leu  Pro  Pro  Val  Lys  Pro  Gln  Lys  Ala  Thr
3665                3670                     3675

Pro  Gly  Pro  Val  Ala  Glu  Val  Gly  Lys  Ala  Thr  Val  Thr  Thr  Val
3680                3685                     3690

Gln  Val  Gln  Ser  Ala  Pro  Pro  Lys  Pro  Ala  Pro  Val  Ala  Lys  Gln
```

```
              3695           3700           3705
Pro Ala Pro Ala Pro Lys Pro Lys Pro Lys Pro Lys Ala
    3710           3715           3720

Glu Arg Pro Lys Pro Gly Lys Thr Thr Pro Leu Ser Gly Arg His
    3725           3730               3735

Val Val Gln Gln Gln Val Gln Val Leu Gln Arg Gln Ala Ser Asp
    3740           3745               3750

Ile Asn Asn Thr Lys Ser Leu Pro Gly Gly Lys Leu Pro Lys Pro
    3755           3760               3765

Val Thr Val Lys Leu Thr Asp Glu Asn Gly Lys Pro Gln Thr Tyr
    3770           3775               3780

Thr Ile Asn Arg Arg Glu Asp Leu Met Lys Leu Asn Gly Lys Val
    3785           3790               3795

Leu Ser Thr Lys Thr Thr Leu Gly Leu Glu Gln Thr Phe Arg Leu
    3800           3805               3810

Arg Val Glu Asp Ile Gly Gly Lys Asn Tyr Arg Val Phe Tyr Glu
    3815           3820               3825

Thr Asn Lys
    3830

<210> SEQ ID NO 60
<211> LENGTH: 209
<212> TYPE: PRT
<213> ORGANISM: Bordetella parapertussis

<400> SEQUENCE: 60

Met Lys Gln Val Pro Pro His Phe Leu Leu Ala Pro Ala Val Leu Ala
1               5                   10                  15

Gly Val Leu Ala Trp His Ile Pro Ala Arg Ala Asn Asp Gly Thr Ile
            20                  25                  30

Val Ile Thr Gly Thr Ile Thr Asp Thr Thr Cys Met Val Glu Asp Pro
        35                  40                  45

Ala Gly Pro Ser His Thr Lys Val Val Thr Leu Pro Lys Ile Ala Lys
    50                  55                  60

Thr Ala Leu Lys Asn Val Gly Asp Gln Ala Gly Arg Thr Pro Phe Ile
65                  70                  75                  80

Ile Lys Leu Lys Asp Cys Pro Ser Ser Leu Gly Asn Gly Val Lys Ala
                85                  90                  95

Tyr Phe Glu Pro Gly Pro Thr Thr Asp Tyr Ser Thr Gly Asp Leu Arg
            100                 105                 110

Ala Tyr Lys Met Val Tyr Ala Thr Asn Pro Gln Thr Gln Leu Ser Asn
        115                 120                 125

Ile Thr Ala Ala Thr Glu Ala Gln Gly Val Gln Val Arg Ile Ser Asn
    130                 135                 140

Leu Asn Asp Ser Lys Ile Thr Met Gly Ala Asp Glu Ala Thr Gln Gln
145                 150                 155                 160

Ala Ala Gly Phe Asp Pro Glu Val Gln Thr Gly Glu Ala Ser Lys Arg
                165                 170                 175

Thr Val Thr Met Arg Tyr Leu Ala Ser Tyr Val Lys Lys Asn Gly Asn
            180                 185                 190

Val Glu Ala Ser Ala Ile Thr Thr Tyr Val Gly Phe Ser Val Val Tyr
        195                 200                 205

Pro
```

-continued

```
<210> SEQ ID NO 61
<211> LENGTH: 209
<212> TYPE: PRT
<213> ORGANISM: Bordetella parapertussis

<400> SEQUENCE: 61
```

Met Ser Lys Phe Ser Tyr Pro Ala Leu Arg Thr Ala Leu Ile Leu Ala
1               5                   10                  15

Ala Ser Pro Val Leu Pro Ala Leu Ala Asn Asp Gly Thr Ile Val Ile
            20                  25                  30

Thr Gly Ser Ile Ser Asp Gln Thr Cys Val Ile Glu Glu Pro Ser Ala
        35                  40                  45

Pro Asn His Ile Lys Val Val Gln Leu Pro Lys Ile Ser Lys Asn Ala
    50                  55                  60

Leu Arg Asn Asp Gly Asp Thr Ala Gly Ala Thr Pro Phe Asp Ile Arg
65                  70                  75                  80

Leu Lys Glu Cys Pro Gln Ala Leu Gly Ala Leu Lys Leu Tyr Phe Glu
                85                  90                  95

Pro Gly Ile Thr Thr Asn Tyr Asp Thr Gly Asp Leu Ile Ala Tyr Lys
            100                 105                 110

Gln Ala Tyr Asn Ala Ser Gly Asn Gly Asn Leu Ser Thr Val Ser Ser
        115                 120                 125

Ala Thr Lys Ala Lys Gly Val Glu Phe Arg Leu Ala Asn Leu Asn Gly
130                 135                 140

Gln His Ile Arg Met Gly Thr Asp Glu Thr Thr Gln Ala Ala Gln Thr
145                 150                 155                 160

Phe Thr Gly Thr Asp Val Thr Asn Gly Ser Gly Lys Thr Thr Lys Ser
                165                 170                 175

Tyr Thr Leu Arg Tyr Leu Ala Ser Tyr Val Lys Lys Pro Lys Glu Asp
            180                 185                 190

Val Asp Ala Ala Gln Ile Thr Ser Tyr Val Gly Phe Ser Val Val Tyr
        195                 200                 205

Pro

```
<210> SEQ ID NO 62
<211> LENGTH: 921
<212> TYPE: PRT
<213> ORGANISM: Bordetella parapertussis

<400> SEQUENCE: 62
```

Met Asn Met Ser Leu Ser Arg Ile Val Lys Ala Ala Pro Leu Arg Arg
1               5                   10                  15

Thr Thr Leu Ala Met Ala Leu Gly Ala Leu Gly Ala Leu Gly Ala Ala
            20                  25                  30

Pro Ala Ala Tyr Ala Asp Trp Asn Asn Gln Ser Ile Ile Lys Ala Gly
        35                  40                  45

Glu Arg Gln His Gly Ile His Ile Lys Gln Ser Asp Gly Ala Gly Val
    50                  55                  60

Arg Thr Ala Thr Gly Thr Thr Ile Lys Val Ser Gly Arg Gln Ala Gln
65                  70                  75                  80

Gly Val Leu Leu Glu Asn Pro Ala Ala Glu Leu Arg Phe Gln Asn Gly
                85                  90                  95

Ser Val Thr Ser Ser Gly Gln Leu Phe Asp Glu Gly Val Arg Arg Phe
            100                 105                 110

Leu Gly Thr Val Thr Val Lys Ala Gly Lys Leu Val Ala Asp His Ala
        115                 120                 125

```
Thr Leu Ala Asn Val Ser Asp Thr Arg Asp Asp Gly Ile Ala Leu
    130                 135                 140

Tyr Val Ala Gly Glu Gln Ala Gln Ala Ser Ile Ala Asp Ser Thr Leu
145                 150                 155                 160

Gln Gly Ala Gly Gly Val Arg Val Glu Arg Gly Ala Asn Val Thr Val
                165                 170                 175

Gln Arg Ser Thr Ile Val Asp Gly Gly Leu His Ile Gly Thr Leu Gln
                180                 185                 190

Pro Leu Gln Pro Glu Asp Leu Pro Pro Ser Arg Val Val Leu Gly Asp
            195                 200                 205

Thr Ser Val Thr Ala Val Pro Ala Ser Gly Ala Pro Ala Ala Val Ser
    210                 215                 220

Val Phe Gly Ala Asn Glu Leu Thr Val Asp Gly Gly His Ile Thr Gly
225                 230                 235                 240

Gly Arg Ala Ala Gly Val Ala Ala Met Asp Gly Ala Ile Val His Leu
                245                 250                 255

Gln Arg Ala Thr Ile Arg Arg Gly Asp Ala Pro Ala Gly Gly Ala Val
                260                 265                 270

Pro Gly Gly Ala Val Pro Gly Gly Ala Val Pro Gly Gly Ala Val Pro
            275                 280                 285

Gly Gly Phe Gly Pro Leu Leu Asp Gly Trp Tyr Gly Val Asp Val Ser
    290                 295                 300

Asp Ser Thr Val Asp Leu Ala Gln Ser Ile Val Glu Ala Pro Gln Leu
305                 310                 315                 320

Gly Ala Ala Ile Arg Ala Gly Arg Gly Ala Arg Val Thr Val Ser Gly
                325                 330                 335

Gly Ser Leu Ser Ala Pro His Gly Asn Val Ile Glu Thr Gly Gly Gly
                340                 345                 350

Ala Arg Arg Phe Pro Pro Pro Ala Ser Pro Leu Ser Ile Thr Leu Gln
            355                 360                 365

Ala Gly Ala Arg Ala Gln Gly Arg Ala Leu Leu Tyr Arg Val Leu Pro
    370                 375                 380

Glu Pro Val Lys Leu Thr Leu Ala Gly Gly Ala Gln Gly Gln Gly Asp
385                 390                 395                 400

Ile Val Ala Thr Glu Leu Pro Pro Ile Pro Gly Ala Ser Ser Gly Pro
                405                 410                 415

Leu Asp Val Ala Leu Ala Ser Gln Ala Arg Trp Thr Gly Ala Thr Arg
                420                 425                 430

Ala Val Asp Ser Leu Ser Ile Asp Asn Ala Thr Trp Val Met Thr Asp
            435                 440                 445

Asn Ser Asn Val Gly Ala Leu Arg Leu Ala Ser Asp Gly Ser Val Asp
    450                 455                 460

Phe Gln Gln Pro Ala Glu Ala Gly Arg Phe Lys Val Leu Met Val Asp
465                 470                 475                 480

Thr Leu Ala Gly Ser Gly Leu Phe Arg Met Asn Val Phe Ala Asp Leu
                485                 490                 495

Gly Leu Ser Asp Lys Leu Val Val Met Arg Asp Ala Ser Gly Gln His
                500                 505                 510

Arg Leu Trp Val Arg Asn Ser Gly Ser Glu Pro Ala Ser Ala Asn Thr
            515                 520                 525

Met Leu Leu Val Gln Thr Pro Arg Gly Ser Ala Ala Thr Phe Thr Leu
    530                 535                 540
```

-continued

```
Ala Asn Lys Asp Gly Lys Val Asp Ile Gly Thr Tyr Arg Tyr Arg Leu
545                 550                 555                 560

Ala Ala Asn Gly Asn Gly Gln Trp Ser Leu Val Gly Ala Lys Ala Pro
                565                 570                 575

Ser Ala Pro Lys Pro Ala Pro Gln Pro Gly Pro Gln Pro Gly Pro Gln
            580                 585                 590

Pro Pro Gln Pro Pro Gln Pro Pro Gln Arg Gln Pro Glu Ala Pro Ala
        595                 600                 605

Pro Gln Pro Pro Ala Gly Arg Glu Leu Ser Ala Ala Ala Asn Ala Ala
    610                 615                 620

Val Asn Thr Gly Gly Val Gly Leu Ala Ser Thr Leu Trp Tyr Ala Glu
625                 630                 635                 640

Ser Asn Ala Leu Ser Lys Arg Leu Gly Glu Leu Arg Leu Asn Pro Asp
                645                 650                 655

Ala Gly Gly Ala Trp Gly Arg Gly Phe Ala Gln Arg Gln Gln Leu Asp
            660                 665                 670

Asn Arg Ala Gly Arg Arg Phe Asp Gln Lys Val Ala Gly Phe Glu Leu
        675                 680                 685

Gly Ala Asp His Ala Val Ala Val Ala Gly Gly Arg Trp His Leu Gly
    690                 695                 700

Gly Leu Ala Gly Tyr Thr Arg Gly Asp Arg Gly Phe Thr Gly Asp Gly
705                 710                 715                 720

Gly Gly His Thr Asp Ser Val His Val Gly Gly Tyr Ala Thr Tyr Ile
                725                 730                 735

Ala Asn Ser Gly Phe Tyr Leu Asp Ala Thr Leu Arg Ala Ser Arg Leu
            740                 745                 750

Glu Asn Asp Phe Lys Val Ala Gly Ser Asp Gly Tyr Ala Val Lys Gly
        755                 760                 765

Lys Tyr Arg Thr His Gly Val Gly Val Ser Leu Glu Ala Gly Arg Arg
    770                 775                 780

Phe Ala His Ala Asp Gly Trp Phe Leu Glu Pro Gln Ala Glu Leu Ala
785                 790                 795                 800

Val Phe Arg Val Gly Gly Gly Ala Tyr Arg Ala Ala Asn Gly Leu Arg
                805                 810                 815

Val Arg Asp Glu Gly Gly Ser Ser Val Leu Gly Arg Leu Gly Leu Glu
            820                 825                 830

Val Gly Lys Arg Ile Glu Leu Ala Gly Gly Arg Gln Val Gln Pro Tyr
        835                 840                 845

Ile Lys Ala Ser Val Leu Gln Glu Phe Asp Gly Ala Gly Thr Val Arg
    850                 855                 860

Thr Asn Gly Ile Ala His Arg Thr Glu Leu Arg Gly Thr Arg Ala Glu
865                 870                 875                 880

Leu Gly Leu Gly Met Ala Ala Ala Leu Gly Arg Gly His Ser Leu Tyr
                885                 890                 895

Ala Ser Tyr Glu Tyr Ser Lys Gly Pro Lys Leu Ala Met Pro Trp Thr
            900                 905                 910

Phe His Ala Gly Tyr Arg Tyr Ser Trp
        915                 920
```

COMPOSITIONS FOR INHIBITING FORMATION OF AND/OR DISRUPTING BACTERIAL BIOFILMS AND METHODS OF USE THEREFOR

CROSS-REFERENCE TO RELATED APPLICATION

This application is a national phase application of PCT International Patent Application PCT/US2017/026012, filed Apr. 4, 2017, which claims the benefit of U.S. Provisional Patent Application Ser. No. 62/318,158, filed Apr. 4, 2016, each of which is incorporated herein by reference in its entirety.

GRANT STATEMENT

This invention was made with government support under Grant Nos. AI018000 and AI007046 awarded by the National Institutes of Health. The government has certain rights in the invention.

TECHNICAL FIELD

The presently disclosed subject matter relates to compositions and methods for inhibiting the formation bacterial biofilms, disrupting bacterial biofilms, and methods of use therefor. In some embodiments, the compositions and methods described herein are used to prevent and/or treat diseases, disorders, and conditions associated with the formation and/or presence of bacterial biofilms, and in some embodiments the compositions and methods described herein are used to prevent the formation of and/or disrupt bacterial biofilms formed in various settings including but not limited to industrial settings and medical settings, thereby reducing or eliminating one or more detrimental effects associated with the presence of bacterial biofilms.

BACKGROUND

Biofilms are communities of surface-associated bacteria, encased in a matrix of polysaccharides, eDNA, and proteins. In nature, bacteria are more frequently found in biofilm structures than they are isolated as individual, free-floating organisms in settings other than the laboratory. These biofilms can lead to serious medical problems in humans, and it is estimated that more than two thirds of all infections of bacterial origin are associated with biofilm. In addition to its role in human infections, biofilm can cause substantial environmental and industrial problems, by clogging water pipelines, disrupting processes in sewage treatment plants, recycling plants, paper pulping plants, and even in oil pipelines. The removal of biofilm is a serious issue across many fields, and although treatments are available to remove biofilm, which include abrasive mechanical disruption coupled with harsh chemical treatments, these are not feasible for all types of biofilm. A major goal of medical and industrial biofilm research is to prevent biofilm formation from occurring in the first place, and for this, broad-spectrum biofilm inhibitors are needed.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments a composition for inhibiting bacterial biofilm development and/or for reducing or eliminating a bacterial biofilm present on a surface. In some embodiments, the composition comprises an effective amount of a peptide or polypeptide derived from Adenylate Cyclase Toxin (ACT) of Bordetella or a catalytic domain (AC domain) thereof, optionally wherein the peptide or polypeptide comprising an amino acid sequence that is at least 80%, 85%, 90%, 91%, 92%, 93%, 94%, 95%, 96%, 97%, 98%, or 99% identical to an amino acid sequence selected from the group consisting of SEQ ID NOs: 1-5 and 44-53, optionally wherein the percent identity exists over the full length of one of SEQ ID NOs: 1-5 and 44-53. In some embodiments, the peptide or polypeptide comprises, consists essentially of, or consists of an amino acid sequence selected from the group consisting of SEQ ID NOs: 1-5 and 44-53.

In some embodiments, the composition is a pharmaceutical composition comprising or consisting essentially of the peptide or polypeptide and one or more pharmaceutically acceptable excipients and/or carriers. In some embodiments, the composition comprises a delivery vehicle, optionally wherein the peptide or polypeptide is associated with, conjugated to, and/or encapsulated by a delivery vehicle. In some embodiments, the delivery vehicle comprises a liposome, a microparticle, or a nanoparticle, optionally wherein the liposome, microparticle, or nanoparticle is designed to be biodegradable in a subject. In some embodiments, the one or more pharmaceutically acceptable excipients and/or carriers are pharmaceutically acceptable for use in a human. In some embodiments, the pharmaceutical composition is formulated for oral administration, intravenous administration, intramuscular administration, intrathecal administration, cutaneous administration, topical administration, transdermal administration, systemic administration, subcutaneous administration, sublingual administration, buccal administration, ocular administration, otic administration, nasal administration, inhalation, nebulization, or any combination thereof.

In some embodiments, the bacterial biofilm comprises a strain of bacteria selected from the group consisting of Bordetella spp., optionally Bordetella pertussis or Bordetella bronchiseptica; Salmonella spp., optionally Salmonella typhimurium; Pseudomonas sp., optionally Pseudomonas aeruginosa; coliform bacterial including E. coli spp.; Listeria spp.; Neisseria spp.; Streptococcus spp.; Staphylococcus spp.; Yersinia spp.; Campylobacter spp.; Helicobacter spp.; Aeromonas spp.; atypical Mycobacteria; and Legionella spp.

The presently disclosed subject matter provides in some embodiments a method for preventing and/or treating a disease, disorder, or condition associated with the presence and/or development of bacterial biofilm in a subject. In some embodiments, the method comprises administering to the subject a composition of the presently disclosed subject matter in an effective amount and via a route sufficient for preventing and/or reducing the severity of at least one symptom of the disease, disorder, or condition. In some embodiments, the disease, disorder, or condition is selected from the group consisting of whooping cough, cystic fibrosis, bacterial vaginosis, urinary tract infections, infections associated with catheter use, middle ear infections, formation of dental plaque, gingivitis, eye infections associated with contact lens use, endocarditis, and infections resulting from use of medical and/or dental implants such as but not limited to joint prostheses and heart valves.

The presently disclosed subject matter provides in some embodiments a method for reducing the incidence of nosocomial infection. In some embodiments, the method comprises contacting a surface present in a medical and/or dental facility with a composition of the presently disclosed subject matter in an amount sufficient to inhibit bacterial biofilm development and/or reduce or eliminate bacterial biofilm present on the surface, wherein the bacterial biofilm is associated with the incidence of nosocomial infection. In some embodiments, the surface is a door surface, a door handle surface, a sink surface, a toilet surface, a faucet surface, a furniture surface, optionally a bed surface, and a window surface.

The presently disclosed subject matter provides in some embodiments a method of inhibiting bacterial biofilm development and/or for reducing or eliminating a bacterial biofilm present on a surface, the method comprising contacting the surface or the biofilm present thereon with an effective amount of a composition of the presently disclosed subject matter, whereby bacterial biofilm development on the surface is inhibited and/or existing bacterial biofilm on the on the surface is reduced or eliminated. In some embodiments, the bacterial biofilm comprises a strain of bacteria selected from the group consisting of Bordetella spp., optionally Bordetella pertussis or Bordetella bronchiseptica; Salmonella spp., optionally Salmonella typhimurium; Pseudomonas sp., optionally Pseudomonas aeruginosa; coliform bacterial including E. coli spp.; Listeria spp.; Neisseria spp.; Streptococcus spp.; Staphylococcus spp.; Yersinia spp.; Campylobacter spp.; Helicobacter spp.; Aeromonas spp.; atypical Mycobacteria; and Legionella spp.

In some embodiments, the surface is a part of a device selected from the group consisting of a medical device, a dental device, and an industrial device. In some embodiments, the medical device is selected from the group consisting of a surgical tool, an implant, a catheter, a stent, a ventilator tubing, and a bone or joint implant, optionally a hip, knee, ankle, wrist, elbow, or shoulder prosthesis. In some embodiments, the implant is a cardiac implant. In some embodiments, the industrial device is selected from the group consisting of a pipe, a tube, a valve, an air-cooled tower, a warm water system, a coolant circuit, a silo, a fermenter, a colander, a piece of furniture, and a sink. In some embodiments, the industrial device is part of device used for water treatment, sewage treatment, petroleum manufacturing and/or storage, or recycling.

In some embodiments, the surface is a cellular surface, a tissue surface, and/or an organ surface present within a subject. In some embodiments, the contacting comprises administering a pharmaceutical composition comprising the peptide or polypeptide to the subject in an amount and via a route of administration whereby the peptide or polypeptide contacts the surface or the biofilm present thereon and inhibits bacterial biofilm development on the surface and/or reduces or eliminates the existing bacterial biofilm present thereon. In some embodiments, the surface is a nasal surface and/or a lung surface and the pharmaceutical composition is configured for inhalation and/or insufflation by the subject. In some embodiments, the composition comprises a delivery vehicle, optionally wherein the peptide or polypeptide is associated with, conjugated to, and/or encapsulated by a delivery vehicle in the pharmaceutical composition. In some embodiments, the delivery vehicle comprises a liposome, a microparticle, or a nanoparticle, optionally wherein the liposome, microparticle, or nanoparticle is designed to be biodegradable in the subject. In some embodiments, the method further comprises contacting the surface with one or more additional compositions that inhibit bacterial biofilm development and/or reduces or eliminates bacterial biofilm present on the surface.

Various aspects and embodiments of the presently disclosed subject matter are described in further detail below.

These and other aspects and embodiments which will be apparent to those of skill in the art upon reading the specification provide the art with tools and agents useful for preventing and/or treating biofilms.

BRIEF DESCRIPTION OF THE DRAWINGS

In FIG. 4A, B. pertussis strains were grown in 5 mL cultures with increasing concentrations of urea added to ensure urea had no effect on bacterial growth. Data are expressed as the mean±two (2) standard deviations, compiled from 3 experiments run in triplicate. In FIG. 4B, B. pertussis strain BP338 was grown in static 100 μL cultures in the presence and absence of ACT or AC domain in 96 well plates. $OD_{600}$ measurements were recorded every 24 hours.

FIG. 12A is an image of wild-type BP338 *B. pertussis* (15,000 X); FIG. 12B is an image of Bvg(−) BP347 *B. pertussis* (5000 X); and FIG. 12C is an image of wild-type BP338+10 ng/ml AC domain (5000 X).

In FIG. 13A, *B. pertussis* strains were grown as 5 ml shaking cultures, in the presence or absence of 100 ng/ml AC domain. At 24 hours, samples were removed from the culture and the Aggregation Index was determined. Mean values are represented by bars, error bars represent standard deviations. Data expressed as the mean±two (2) standard deviations, compiled from 3 experiments run in triplicate. In FIG. 13B, BP338 biofilm formation (solid circles; black line) was measured every 24 hours via the crystal violet assay. AC domain was added at time zero (squares; gray line) or was added at 72 hours (open circles; dashed line) and biofilm was measured every 24 hours. Mean values represented by lines and error bars represent standard deviations. Data compiled from 5 experiments run in triplicate. **p<0.001 compared to BP338.

FIG. 16C shows that CaM blocked the AC domain—FHA interaction. The AC domain (10 μM) and the freshly-prepared complexes of the AC domain with CaM mixed in molar ratios of 10:1, 1:1, and 1:10 AC domain:CaM were injected in parallel over the SPR sensor chip coated with FHA at flow rate of 30 μl/min. Inhibition of binding of the AC/CaM 1:10 complex to FHA is represented by a decrease of SPR signal response. No binding of CaM alone was observed to FHA. Results are representative data from three independent experiments.

FIGS. 18A and 18B show growth of wild-type *B. pertussis* strains BP338 and BPSM over 96 hours in shakling culture and ACT and FHA protein expression in these strains at 24 hours. FIG. 18A is a time course of biofilm growth of the wild-type *B. pertussis* strains BP338 (squares) and BPSM (circles). FIG. 18B is an image of ACT and FHA protein expression of BP338 and BPSM at 24 hours in shaking culture. 20 μL of $OD_{600}$ normalized bacteria were run on SDS-PAGE gel and protein expression was determined by western blot analysis; polyclonal anti-ACT antibody was used to detect ACT and monoclonal anti-CRD antibody (Noel et al., 2012) was used to detect FHA.

FIGS. 19A and 19B are bar graphs showing the inhibitory effects of ACT and anti-MCD antibodies on biofilm production. FIG. 19A is a bar graph showing that the MCD of FHA must be present and properly folded for ACT inhibition of biofilm. FHA mutant proteins were generated in the wild-type *B. pertussis* BPSM parent strain. BPSM JS20 (ΔMCD) had the entire MCD sequence deleted. BPSM T-N had a transposon inserted into the prodomain sequence, precluding prodomain cleavage and processing of the MCD, leaving the MCD unfolded in the final FHA molecule. *B. pertussis* strains were allowed to form biofilm for 96 hours in the presence or absence of 100 ng/ml ACT. Biofilm was measured by crystal violet assay. Data expressed as the mean±two (2) standard deviations, compiled from 3 experiments run in triplicate. *p<0.05 and **p<0.01 compared to wild-type (BPSM). FIG. 19B is a bar graph showing that anti-MCD antibodies blocked biofilm production. Anti-MCD antibodies were added at 1:1000 and 1:100 dilutions to anti-MCD antibodies *B. pertussis* (BP338) cultures in 96-well microtiter plates to observe their effects on biofilm formation. Biofilm formation was measured at 96 hours using the crystal violet assay. All values were normalized to the control ($OD_{450}$ 0.284) using Graphpad Prism6 software (GraphPad Software, Inc., La Jolla, Calif., United States of America). Data are expressed as the mean±two (2) standard deviations, compiled from three (3) experiments run in triplicate **p<0.01 compared to anti-MCD antibodies alone. n.s.: not significant.

FIG. 21 is a model of biofilm inhibition by ACT. In the model, the AC domain of ACT binds FHA via the MCD at the distal tip of the FHA molecule. This binding blocks FHA function in biofilm, either through FHA-FHA interactions within biofilm or FHA-surface interactions as previously suggested, or possibly through some signaling event due to conformation change in the FHA protein.

FIGS. 22A and 22B are bar graphs of wild-type *P. aeruginosa* PA01 (FIG. 22A) and wild-type *P. aeruginosa* PA14 (FIG. 22B) biofilm formation in the presence of increasing concentrations of recombinant purified ACT (0.1, 1, and 10 μg/ml; bars 2, 3, and 4, respectively, in each of FIGS. 22A and 22B) and AC domain ACT (0.1, 1, and 10 μg/ml; bars 5, 6, and 7, respectively, in each of FIGS. 22A and 22B) was assessed at 12 hours. Biofilm formation was measured by crystal violet assay. Data expressed as the mean±two (2) standard deviations, compiled from four (4) experiments run in triplicate. * p<0.05;  p<0.01; * p<0.001; **** p<0.0001 compared to wild-type *P. aeruginosa* PA01 (bar 1 in FIG. 22A) and PA14 (bar 1 in FIG. 22B) without ACT or AC domain added. FIG. 22C is a graph of the growth of wild-type *P. aeruginosa* PA01 and wild-type *P. aeruginosa* PA14 over 12 hours in the presence or absence of 10 μg/ml recombinant purified ACT or 10 μg/ml AC Domain. Inverted triangle: PA01 alone; diamond: PA01+10 μg/ml AC Domain; solid black circle: PA01+10 μg/ml recombinant purified ACT; solid gray circle: PA14 alone; square: PA14+10 μg/ml AC Domain; triangle: PA14+10 μg/ml recombinant purified ACT.

FIG. 25A shows a lack of inhibition with respect to wild-type *E. coli* MC4100, FIG. 25B shows inhibition of wild-type *E. coli* 87-23 and FIG. 25C shows inhibition of wild-type *S. typhimurium* S1344 biofilm formation in the presence (gray bars in FIGS. 25A-25C) or the absence (black bars in FIGS. 25A-25C) of 10 μg/ml AC domain assessed at 12 hours. Biofilm formation was measured by crystal violet assay. Data expressed as the mean±two (2) standard deviations, compiled from four (4) experiments run in triplicate. p values are indicated on graphs. n.s.: not significant.

FIG. 26A is a schematic depiction of the ACT holoenzyme, showing the locations of the AC domain, the T18 peptide, and the T25 peptide. FIG. 26B is a bar graph of wild-type *B. pertussis* BP338 biofilm formation in the presence of increasing concentrations of recombinant purified T18 (0.1, 1, and 10 µg/ml; bars 2, 3, and 4, respeectively) and T25 peptides (0.1, 1, and 10 µg/ml; bars 5, 6, and 7, repetively) was assessed at 12 hours. Biofilm formation was measured by crystal violet assay. Data expressed as the mean±two (2) standard deviations, compiled from two (2) experiments run in triplicate. **** $p<0.0001$ compared to wild-type *P. aeruginosa* grown without peptides added.

BRIEF DESCRIPTION OF THE SEQUENCE LISTING

Figure 1:
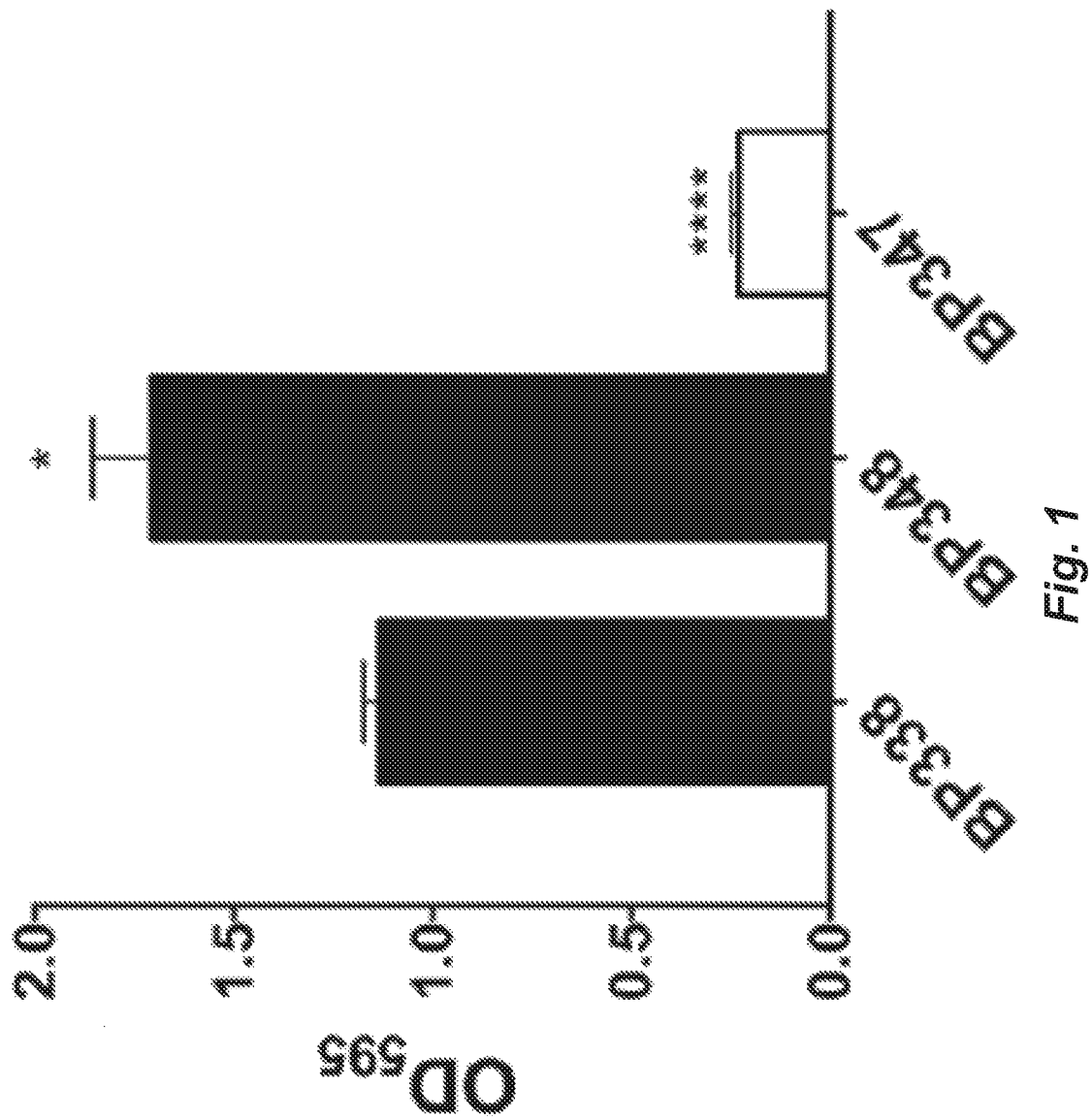
FIG. 1 is bar graph showing that BP348, a B. pertussis strain lacking ACT, made more biofilm than wild-type (WT) BP338 B. pertussis. Strains were grown in 96-well microtiter plates and biofilm formation was assessed using the crystal violet assay at 96 hours. Bvg(−) BP347 serves as a negative control. Data expressed as the mean±two (2) standard deviations, compiled from 3 experiments run in triplicate. *$p<0.05$ and ****$p<0.0001$ compared to wild-type BP338.
Figure 2A:
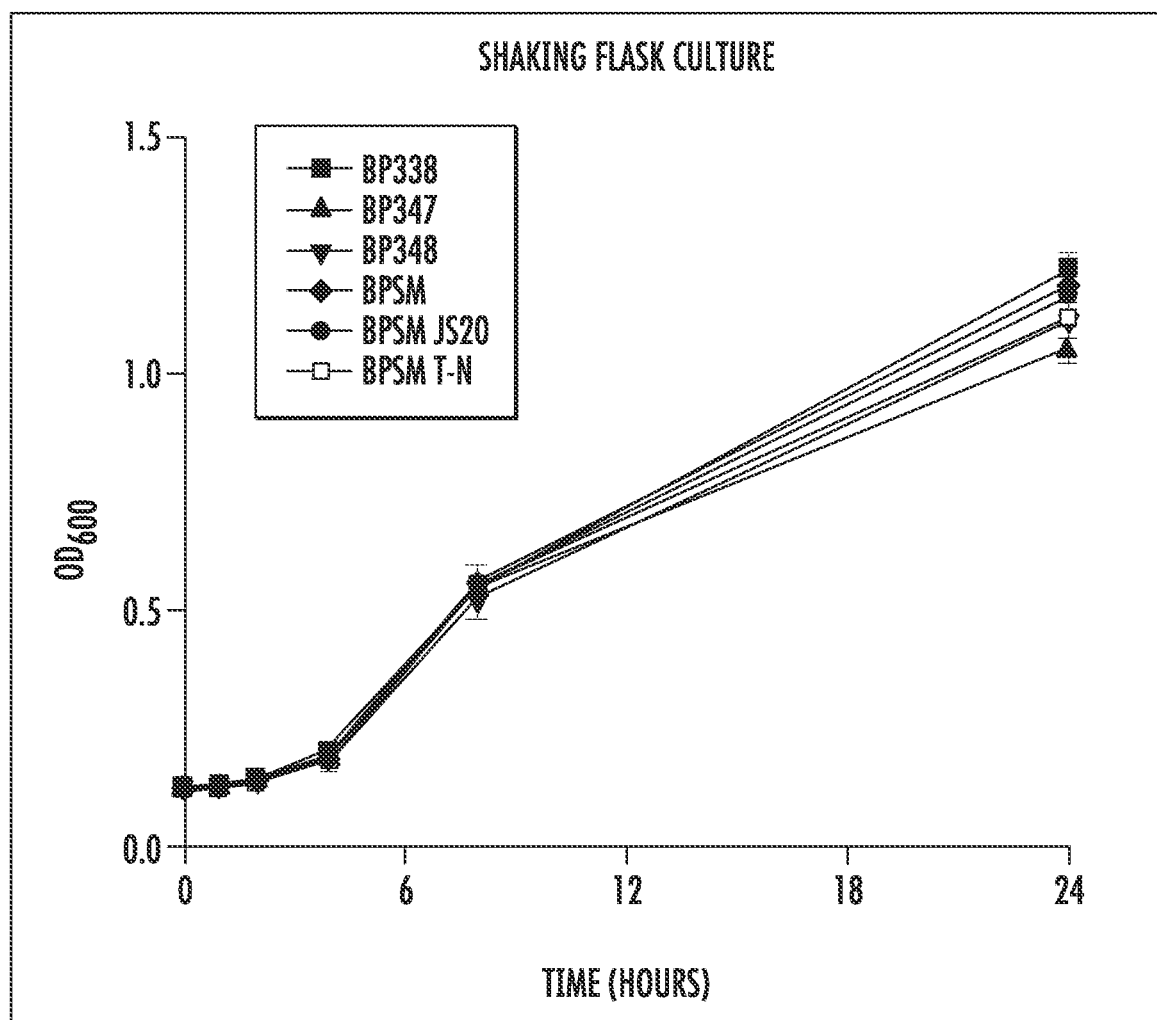
FIGS. 2A and 2B are growth curves of bacterial strains grown in SSM shaking 10 mL culture (FIG. 2A) and SSM static 100 μL culture in 96 well plates (FIG. 2B). $OD_{600}$ measurements were recorded over 24 hours for shaking cultures and 96 hours for static 100 μL cultures.
Figure 2B:
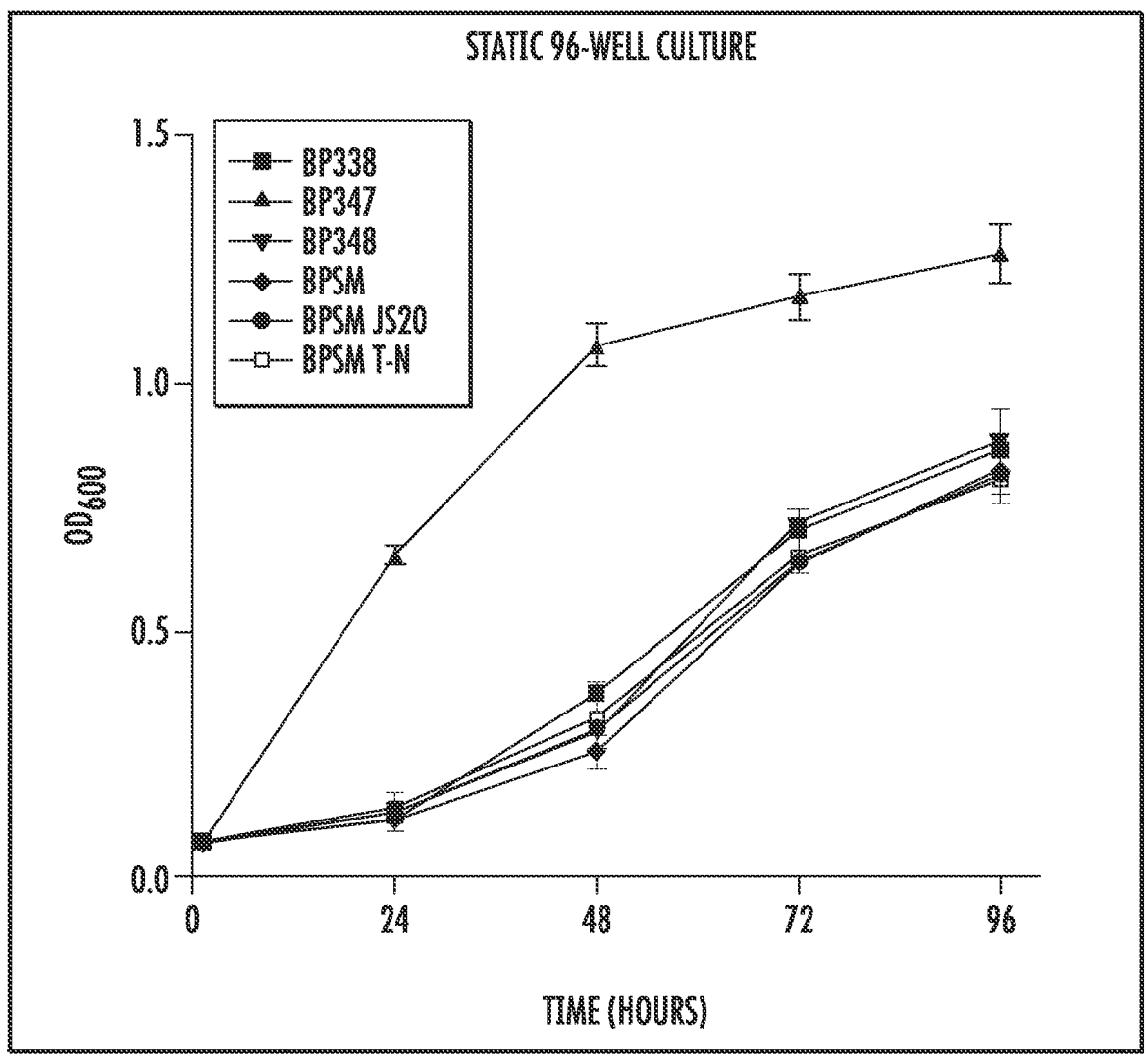
Figure 3:
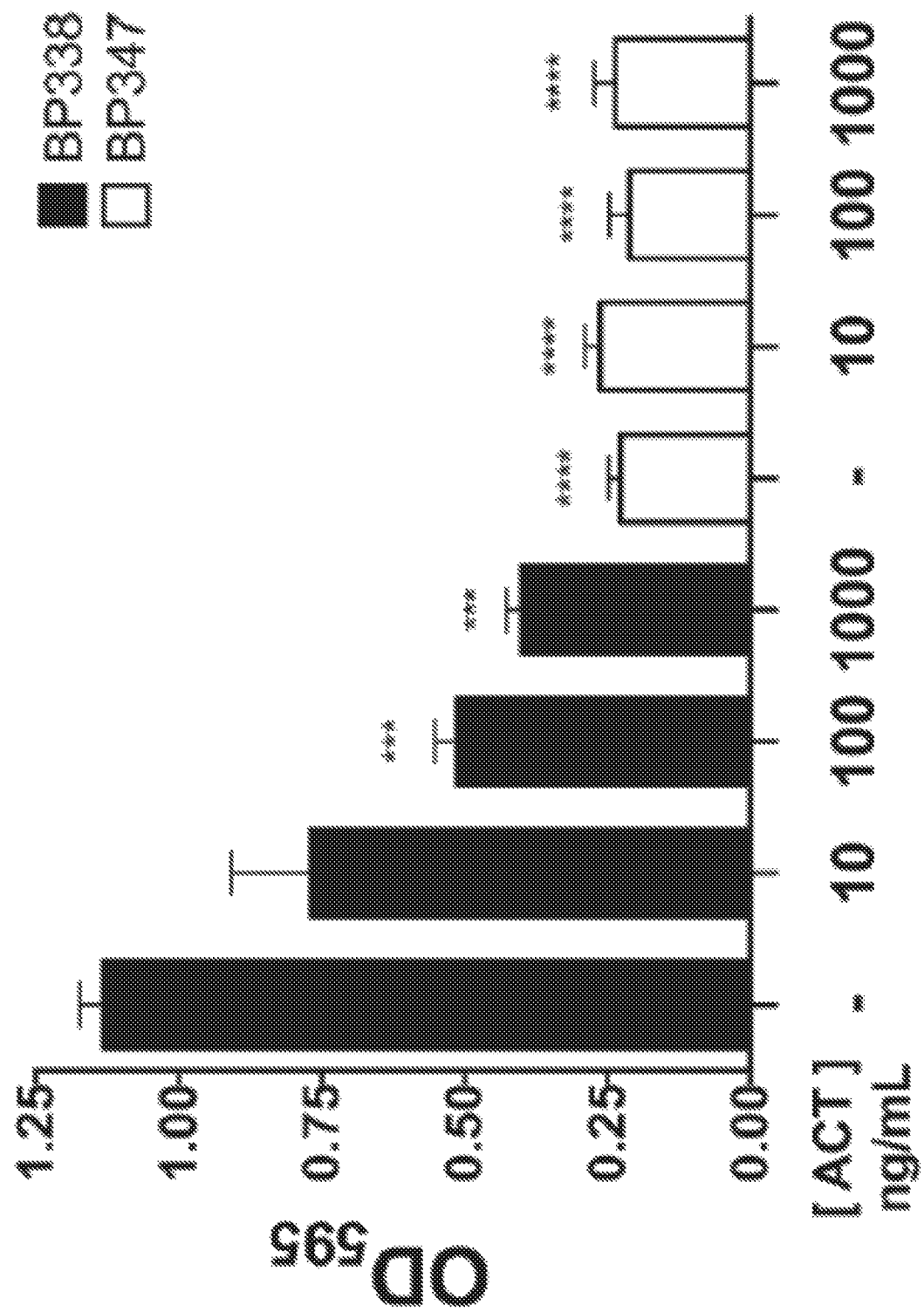
FIG. 3 is a bar graph showing that ACT inhibited biofilm in a concentration-dependent manner. wild-type BP338 biofilm formation in the presence of increasing concentrations of recombinant purified ACT (ng/ml) was assessed at 96 hours. Biofilm formation was measured by crystal violet assay. Bvg(−) BP347 served as negative control. Data expressed as the mean±two (2) standard deviations, compiled from 5 experiments run in triplicate. *$p<0.001$, **$p<0.0001$ compared to wild-type BP338 without ACT.

SEQ ID NO: 1 is an amino acid sequence of a *Bordetella pertussis* ACT holoenzyme polypeptide. It corresponds to Accession No. NP_879578.1 in the GENBANK® biosequence database.

SEQ ID NO: 2 is an amino acid sequence of a *Bordetella pertussis* AC Domain polypeptide. It corresponds to amino acids 1-400 of SEQ ID NO: 1.

SEQ ID NOs: 3 and 4 are amino acid sequences of the T25 and T18 peptides, respectively, derived from the *Bordetella pertussis* AC Domain polypeptide of SEQ ID NO: 1. They correspond to amino acids 1-225 and 226-400 of SEQ ID NO: 1, respectively.

SEQ ID NO: 5 is an amino acid sequence of an inactivated *Bordetella pertussis* AC Domain polypeptide. The polypeptide has been inactivated by substituting the aspartic acid at amino acid 188 of SEQ ID NO: 1 with a cysteine and the isoleucine at amino acid 189 of SEQ ID NO: 1 with a threonine.

SEQ ID NOs: 6-25 are the nucleotide sequences of the primers listed in Table 1.

SEQ ID NOs: 26-30 are the amino acid sequences of subunits 1-5, respectively, of a *Bordetella pertussis* PT polypeptide. SEQ ID NOs: 26-30 correspond to GENBANK® biosequence database Accession Nos. NP_882282.1, NP_882283.1, NP_882286.1, NP_882284.1, and NP_882285.1, respectively.

SEQ ID NOs: 31-35 are the amino acid sequences of subunits 1-5, respectively, of a *Bordetella bronchiseptica* PT polypeptide. SEQ ID NOs: 31-35 correspond to GENBANK® biosequence database Accession Nos. WP_033452809.1, WP_033452812.1, WP_015064783.1, WP_033468323.1, and WP_033446920.1, respectively.

SEQ ID NOs: 36 and 37 are the amino acid sequences of FHA polypeptides from *Bordetella pertussis* and *Bordetella bronchiseptica*, respectively. SEQ ID NOs: 36 and 37 correspond to GENBANK® biosequence database Accession Nos. NP_880571.1 and YP_006966876.1, respectively.

SEQ ID NOs: 38 and 39 are the amino acid sequences of Fim2 and Fim3 polypeptides, respectively, from *Bordetella pertussis*. SEQ ID NOs: 38 and 39 correspond to GENBANK® biosequence database Accession Nos. NP_879898.1 and NP_880302.1, respectively.

SEQ ID NOs: 40 and 41 are the amino acid sequences of Fim2 and Fim3 polypeptides, respectively, from *Bordetella bronchiseptica*. SEQ ID NOs: 40 and 41 correspond to GENBANK® biosequence database Accession Nos. YP_006967303.1 and YP_006967865.1, respectively.

SEQ ID NOs: 42 and 43 are the amino acid sequences of PRN polypeptides from *Bordetella pertussis* and *Bordetella bronchiseptica*, respectively. SEQ ID NOs: 42 and 43 correspond to GENBANK® biosequence database Accession Nos. NP_879839.1 and WP_033839724.1, respectively.

SEQ ID NO: 44 is an amino acid sequence of a *Bordetella bronchiseptica* ACT holoenzyme polypeptide. SEQ ID NO: 44 corresponds to Accession No. WP_080702041.1 in the GENBANK® biosequence database.

SEQ ID NO: 45 is an amino acid sequence of a *Bordetella bronchiseptica* AC Domain polypeptide. SEQ ID NO: 45 corresponds to amino acids 1-400 of SEQ ID NO: 44.

SEQ ID NOs: 46 and 47 are amino acid sequences of the T25 and T18 peptides, respectively, derived from the *Bordetella bronchiseptica* AC Domain polypeptide of SEQ ID NO: 1. SEQ ID NOs: 46 and 47 correspond to amino acids 1-225 and 226-400 of SEQ ID NO: 1, respectively.

SEQ ID NO: 48 is an amino acid sequence of an inactivated *Bordetella bronchiseptica* AC Domain polypeptide. The polypeptide has been inactivated by substituting the aspartic acid at amino acid 188 of SEQ ID NO: 44 with a cysteine and the isoleucine at amino acid 189 of SEQ ID NO: 44 with a threonine.

SEQ ID NO: 49 is an amino acid sequence of a *Bordetella parapertussis* ACT holoenzyme polypeptide (hemolysin). SEQ ID NO: 49 corresponds to Accession No. WP_010927405.1 in the GENBANK® biosequence database.

SEQ ID NO: 50 is an amino acid sequence of a *Bordetella parapertussis* AC Domain polypeptide. SEQ ID NO: 50 corresponds to amino acids 35-434 of SEQ ID NO: 49.

SEQ ID NOs: 51 and 52 are amino acid sequences of the T25 and T18 peptides, respectively, derived from the *Bordetella parapertussis* AC Domain polypeptide of SEQ ID NO: 49. SEQ ID NOs: 51 and 52 correspond to amino acids 35-249 and 250-434 of SEQ ID NO: 49, respectively.

SEQ ID NO: 53 is an amino acid sequence of an inactivated *Bordetella parapertussis* AC Domain polypeptide. The polypeptide has been inactivated by substituting the aspartic acid at amino acid 222 of SEQ ID NO: 49 with a cysteine and the isoleucine at amino acid 223 of SEQ ID NO: 49 with a threonine.

SEQ ID NOs: 54-58 are the amino acid sequences of subunits 1-5, respectively, of a *Bordetella parapertussis* PT polypeptide. SEQ ID NOs: 54-58 correspond to GENBANK® biosequence database Accession Nos. WP_010929490.1, YP_006898153.1, YP_006898156.1, YP_006898154.1, and YP_006898155.1, respectively.

SEQ ID NO: 59 is the amino acid sequence of an FHA polypeptide from *Bordetella parapertussis*. SEQ ID NO: 59 corresponds to GENBANK® biosequence database Accession No. YP_006896577.1.

SEQ ID NOs: 60 and 61 are the amino acid sequences of Fim2 and Fim3 polypeptides, respectively, from *Bordetella parapertussis*. SEQ ID NOs: 60 and 61 correspond to GENBANK® biosequence database Accession Nos. YP_006895663.1 and YP_006895400.1, respectively.

SEQ ID NO: 62 is the amino acid sequence of a PRN polypeptide from *Bordetella parapertussis*. SEQ ID NO: 62 corresponds to GENBANK® biosequence database Accession No. YP_006897297.1.

DETAILED DESCRIPTION

*Bordetella pertussis* is the causative agent of whooping cough (pertussis) and a reemerging health threat in the United States and globally, as illustrated by the increasing number of cases reported each year. Despite high vaccination rates of children and adolescents, there were approximately 33,000 cases in the United States reported to the United States Centers for Disease Control and Prevention (CDC) in 2014. The most striking shift in the age-specific incidence of pertussis has been in subjects aged 15 and older (Strebel et al., 2001), who are now more frequently infected with *B. pertussis*. In contrast to the potential fatality of pertussis in infants and young children, adolescents and adults develop a persistent cough with fewer systemic manifestations of the disease (Birkebaek et al., 1999; Wendelboe et al., 2007) and often serve as sources of pertussis transmission (Nelson, 1978; Cherry & Olin, 1999; Bisgard et al., 2004; Quinn & McIntyre, 2011).

*Bordetella pertussis* has been shown to form biofilm in vitro on abiotic surfaces and in vivo, primarily on nasal septum and the trachea (Sloan et al., 2007; Serra et al., 2007; Conover et al., 2010; Serra et al., 2011). Ongoing studies support the concept that *B. pertussis* forms biofilm during infection; recent clinical isolates form more biofilm compared to a lab-passaged isolate, BP338. The closely related animal pathogen, *B. bronchiseptica*, forms biofilm in vitro on abiotic surfaces and biofilm formation contributes to its chronic infection of dogs and other mammals (Fenwick, 2013). Although the specific role of biofilm in human infections with *B. pertussis* has not yet been established, the fact that these organisms produce biofilm both in vitro and in vivo provides a modality to investigate the production of biofilm as well as possible ways to interrupt biofilm formation.

Biofilms are complex structures controlled by a variety of bacterial signaling systems. They are comprised of aggregative bacteria surrounded by a matrix of polysaccharides, proteins, and extracellular DNA (eDNA). *Bordetella* biofilm has been shown to require eDNA (Conover et al., 2011), Bps (*Bordetella* polysaccharide) (Conover et al., 2010), which resembles *S. aureus* poly-N-acetyl-beta-(1-6)-glucosamine, and multiple proteins. Of significance to the presently disclosed subject matter is the observation that filamentous haemagglutinin (FHA) is an important component of *B. pertussis* and *B. bronchiseptica* biofilm formation. This surface displayed adhesin promotes the formation and maintenance of biofilm by mediating bacteria-substrate as well as bacteria-bacteria interactions. Serra et al. showed that anti-FHA antibodies blocked biofilm formation by *B. pertussis*, and a strain lacking FHA (ΔfhaB BPGR4) made less biofilm in vitro and in vivo on mouse trachea and nasal septum compared to wild-type BPSM (Serra et al., 2011).

Although less is known about the regulation of biofilm in Bordetellae compared to other medically relevant biofilm-forming bacterial species, several modes of regulation have been implicated. Nutrient limitation and oxidative stress activate (p)ppGpp signaling to enhance biofilm formation in *B. pertussis* (Sugisaki et al., 2013), while c-di-GMP signaling regulates motility and biofilm formation in *B. bronchiseptica* (Sisti et al., 2013). The machinery for synthesis of the Bps matrix component is encoded by the bpsABCD operon and is under control of the BpsR repressor, but the factor, process, or signal that relieves BpsR repression is unknown (Conover et al., 2012). Multiple signals, including those from the "master regulator" of virulence, *Bordetella* virulence gene two-component regulatory system, BvgAS, are integrated to control *Bordetella* biofilm. Biofilm formation occurs in the Bvg(+) phase and Bvg(i) phase, but biofilm is not observed in the Bvg(−) phase. Irie et al. showed biofilm formation was maximal in the Bvg(i) phase in *B. bronchiseptica* (Irie et al., 2004). In contrast, Mishra et al. found biofilm formation was equal in the Bvg(+) and Bvg(i) phases for *B. pertussis* (Mishra et al., 2005). Irie et al. also showed that a *B. bronchiseptica* strain lacking adenylate cyclase toxin (ACT; ΔcyaA RB58) made more biofilm than the parental wild-type RB50 strain and in light of the earlier observation demonstrating a direct interaction between ACT and FHA (Zaretzky et al., 2002), suggested that this protein-protein interaction could function to regulate biofilm production in *Bordetella*.

ACT is an important virulence factor of both *B. pertussis* and *B. bronchiseptica*. The 177 kDa protein toxin is secreted by a type I secretion system and remains surface-associated or is released as a function of free calcium concentration in the medium (Bumba et al., 2016). ACT that has been released from the bacterial surface is the active form of the toxin, which affects target cells (Gray et al., 2004). ACT uses complement receptor 3, the heterodimeric aMb2 integrin (CD11b/CD18 or Mac-1), as its receptor (Guermonprez et al., 2001; Osička et al., 2015), but can also intoxicate cells that lack this integrin heterodimer (Eby et al., 2010). Following binding to the host cell, the catalytic domain of the toxin is translocated across the plasma membrane and into the host cytoplasm, where calmodulin (CaM) binds the enzymatic (catalytic) domain, activating it to convert ATP to cAMP (Guermonprez et al., 2001; El-Azami-El-Idrissi et al., 2003; Perkins et al., 2007; Martin et al., 2010; Osickova et al., 2010; Eby et al., 2012; Uribe et al., 2013). This in turn leads to supraphysiological levels of cAMP and can cause a massive reduction in intracellular ATP (Basler et al., 2006; Hewlett et al., 2006; Bumba et al., 2010; Eby et al., 2012). Through these mechanisms, ACT inhibits phagocytosis, chemotaxis, and superoxide generation by neutrophils, is required for the establishment of infection in the mouse model and human infections with the attenuated strain, BPZE1 (Thorstensson et al., 2014; Lim et al., 2014) and serves as a protective antigen (Confer & Eaton, 1982; Weiss et al., 1983; Pearson et al., 1987; Cherry & Heinninger, 2004; Vojtova et al., 2006; Basler et al., 2006; Hewlett et al., 2006; Fiser et al., 2012; Costache et al., 2013; Fedele et al., 2013; Thorstensson et al., 2014; Bumba et al., 2016). In previous studies, the secretion, release, binding to host cells, interaction with host cells, functional effects of ACT on host cells, and its role in establishing an infection have been characterized. This host-directed protein bacterial toxin has not, however, been studied for effects on the bacterium itself.

The 177 kD Adenylate Cyclase Toxin (ACT) of *Bordetella* and fragments thereof, including but not limited to the 40 kD derived catalytic domain (AC domain) and peptides T18 and T25, are disclosed herein to be potent biofilm inhibitors in *B. pertussis* and *B. bronchiseptica*. While not wishing to be bound by any particular theory of operation, the inhibitors appear to function by directly binding the distal tip of the surface-displayed biofilm adhesin, Filamentous Hemagglutinin (FHA). Many bacterial species express FHA-like proteins that display high structural or sequence homology to *Bordetella* FHA, and some of these proteins are involved in biofilm formation. The ACT holoenzyme, the AC domain, and peptides derived from the AC domain were tested for their abilities to inhibit biofilm of *Bordetellae, Pseudomonas aeruginosa, Escherichia coli*, and *Salmonella typhimurium* in vitro. The AC domain demonstrated an inhibitory effect on biofilm formation for several bacteria tested. Using a *Pseudomonas aeruginosa* transposon mutant that lacks CdrA, the FHA-like protein of *Pseudomonas*, it has been demonstrated that the AC domain might inhibit biofilm of other bacteria via a similar mechanism, which involves the AC domain binding FHA-like proteins. These data, taken together, showed that the AC domain and derived peptides could serve as general biofilm inhibitors, specifically for bacteria that express FHA-like proteins.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter. Thus, unless defined otherwise, all technical and scientific terms and any acronyms used herein have the same meanings as commonly understood by one of ordinary skill in the art in the field of the presently disclosed subject matter. Although any compositions, methods, kits, and means for communicating information similar or equivalent to those described herein can be used to practice the presently disclosed subject matter, particular compositions, methods, kits, and means for communicating information are described herein. It is understood that the particular compositions, methods, kits, and means for communicating information described herein are exemplary only and the presently disclosed subject matter is not intended to be limited to just those embodiments.

The articles "a", "an", and "the" are used herein to refer to one or to more than one (i.e., to at least one) of the grammatical object of the article. By way of example, "an element" means one element or more than one element.

As used herein, the term "about" means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of in some embodiments ±20%, in some embodiments ±15%, in some embodiments ±10%, in some embodiments ±5%, in some embodiments ±1%, in some embodiments ±0.5%, in some embodiments ±0.1%, and in some embodiments less than ±0.1%.

As use herein, the terms "administration of" and or "administering" with respect to a compound, peptide, composition, etc. should be understood to mean providing a compound, peptide, composition, etc. of the presently disclosed subject matter or a prodrug of a compound, peptide, composition, etc. of the presently disclosed subject matter to a subject in need thereof, in some embodiments to ameliorate at least one symptom of a disease, disorder, or condition in the subject, to prevent the occurrence of at least one symptom of a disease, disorder, or condition in the subject, and/or to prevent the further development of at least one symptom of a disease, disorder, or condition in the subject.

As used herein, the term "aerosol" refers to suspension in the air. In particular, aerosol refers to the particlization or atomization of a formulation of the presently disclosed subject matter and its suspension in the air.

As used herein, an "agonist" is a composition of matter which, when administered to a mammal such as a human, enhances or extends a biological activity attributable to the level or presence of a target compound, peptide, composition, molecule of interest, etc. in the mammal.

An "antagonist" is a composition of matter which when administered to a mammal such as a human, inhibits a biological activity attributable to the level or presence of a target compound, peptide, composition, molecule of interest, etc. in the mammal.

As used herein, the phrase "alleviating a disease or disorder symptom" refers to reducing the severity of the symptom or the frequency with which such a symptom is experienced by a subject, or both. In some embodiments, "alleviating a disease or disorder symptom" refers to eliminating the symptom experienced by the subject.

As used herein, amino acids are represented by the full name thereof, by the three-letter code corresponding thereto, and/or by the one-letter code corresponding thereto, as indicated in the following:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The phrase "amino acid" is used interchangeably with "amino acid residue", and may refer to a free amino acid and/or to an amino acid residue of a peptide. It will be apparent from the context in which the term is used whether it refers to a free amino acid or a residue of a peptide.

Amino acids have the following general structure:

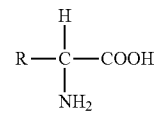

They may be classified into seven groups based on the side chain R: (1) aliphatic side chains; (2) side chains containing a hydroxylic (OH) group; (3) side chains containing sulfur atoms; (4) side chains containing an acidic or amide group;

(5) side chains containing a basic group; (6) side chains containing an aromatic ring; and (7) proline, an imino acid in which the side chain is fused to the amino group.

The nomenclature used to describe the peptide compounds of the presently disclosed subject matter follows the conventional practice wherein the amino group is presented to the left and the carboxy group to the right of each amino acid residue. In the formulae representing selected specific embodiments of the presently disclosed subject matter, the amino- and carboxy-terminal groups, although not specifically shown, will be understood to be in the form they would assume at physiologic pH values, unless otherwise specified.

The term "basic" and the phrase "positively charged" as they relate to amino acids refer herein to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antigen" as used herein refers to a molecule that provokes an immune response in vitro and/or in vivo. This immune response can involve antibody production, the activation of specific immunologically-competent cells, or both. An antigen can be derived from an organism, a subunit of a protein, a killed or inactivated whole cell or lysate, or any other source to which an organism's immune system or a component thereof (e.g., an immune cell) can react.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

As used herein, the phrase "binding partner" refers to a molecule capable of binding to another molecule. In some embodiments, binding partner bind to each other in vitro, ex vivo, in vivo, and/or under physiological conditions.

The term "biocompatible", as used herein, refers to a material that does not elicit a substantial detrimental response in the host.

As used herein, the phrases "biologically active fragment" and "bioactive fragment" of polypeptides encompass natural and synthetic portions of full-length polypeptides that have one or more desirable characteristics of the full-length polypeptides, including but not limited to specific binding to their natural ligand(s) and/or performing desirable functions of the polypeptides.

The phrase "biological sample", as used herein, refers to samples obtained and/or otherwise isolated from a subject, including, but not limited to, skin, hair, tissue, blood, plasma, cells, sweat, and urine.

A "coding region" of a gene includes the nucleotide residues of the coding strand of the gene and/or genetic locus and the nucleotides of the non-coding strand of the gene which are homologous with or complementary to, respectively, the coding region of an mRNA molecule which is produced by transcription of the gene. A "coding region" thus comprises the "open reading frame" of the genetic locus.

A "compound", as used herein, refers to any type of substance or agent that is commonly considered a drug, or a candidate for use as a drug, as well as combinations and mixtures of the above.

As used herein, the phrase "conservative amino acid substitution" is defined herein as an amino acid exchange within one of the following five groups:

A. Small aliphatic, nonpolar, or slightly polar residues: Ala, Ser, Thr, Pro, Gly;
B. Polar, negatively charged residues and their amides: Asp, Asn, Glu, Gln;
C. Polar, positively charged residues: His, Arg, Lys;
D. Large, aliphatic, nonpolar residues: Met, Leu, Ile, Val, Cys; and
E. Large, aromatic residues: Phe, Tyr, Trp.

Thus, a conservative amino acid substitution includes a substitution of in some embodiments any small aliphatic, nonpolar, or slightly polar residue for any other small aliphatic, nonpolar, or slightly polar residues; in some embodiments any polar, negatively charged residue and its amide for any other polar, negatively charged residue and its amide; in some embodiments any polar, positively charged residue for any other polar, positively charged residue; in some embodiments any large, aliphatic, nonpolar residue for any other large, aliphatic, nonpolar residue; and/or in some embodiments any large, aromatic residue for any other large, aromatic residue.

As used herein, a "derivative" of a compound refers to a chemical compound that may be produced from another compound of similar structure in one or more steps, as in replacement of H by an alkyl, acyl, or amino group.

A "disease" is a state of health of an animal wherein the animal cannot maintain homeostasis, and wherein if the disease is not ameliorated then the animal's health would be expected to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular, and helical domains, and/or properties such as ligand binding, signal transduction, cell penetration, and the like. Specific examples of binding domains include, but are not limited to, DNA binding domains and ATP binding domains.

As used herein, an "effective amount" or "therapeutically effective amount" means an amount sufficient to produce a desired effect, such as ameliorating or alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is ameliorated and/or alleviated to a greater extent by one treatment relative to a second treatment to which it is being compared.

The term "elixir", as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, and mRNA) or a defined sequence of amino acids and the biological properties resulting therefrom. Thus, a genetic locus encodes a protein if transcription and translation of mRNA corresponding to that genetic locus produces the protein in a cell or other biological system. Both the coding strand (i.e., the nucleotide sequence of which is identical to the mRNA sequence and is usually provided in sequence listings), and the non-coding strand, used as the template for transcription of a gene or cDNA, can be referred to as encoding the protein or other product of that genetic locus or cDNA.

The term "epitope" as used herein is defined as a small chemical group on an antigen molecule that can elicit and react with an antibody. An antigen can have one or more epitopes. Most antigens have many epitopes; i.e., they are multivalent. In general, epitopes are roughly five to eight amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein in some embodiments at least about 95%, in some embodiments at least about 97%, and in some embodiments at least about 99%, by weight, of the total protein or total peptide in the preparation is the particular protein or peptide of interest.

A "fragment" or "segment" is a portion of an amino acid sequence (i.e., a subsequence) comprising at least one amino acid or a portion of a nucleic acid sequence comprising at least one nucleotide. The terms "fragment" and "segment" are used interchangeably herein.

As used herein, a "functional" biological molecule is a biological molecule in a form in which it exhibits a desirable property by which it can be characterized. A functional enzyme, for example, is one which exhibits the characteristic catalytic activity by which the enzyme is characterized.

As used herein, the term "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, the term "homology" is used synonymously with the term "identity". Similarly, the term "homologous" is used synonymously with the term "identical".

The determination of percent identity between two nucleotide or amino acid sequences can be accomplished using a mathematical algorithm. For example, a mathematical algorithm useful for comparing two sequences is the algorithm of Karlin & Altschul, 1990, modified as in Karlin & Altschul, 1993. This algorithm is incorporated into the NBLAST and XBLAST programs of Altschul et al., 1990a, and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997. Alternatively, PSI-Blast or PHI-Blast can be used to perform an iterated search which detects distant relationships between molecules (Altschul et al., 1997) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted. In some embodiments, a percent identity is computed over a subsequence of the nucleic acid or amino acid, and in some embodiments the percent identity relates to comparing the full length sequence of a first nucleic acid or amino acid to either a subsequence of a second nucleic acid or amino acid or the full length sequence of the second nucleic acid or amino acid.

As used herein, the term "inhaler" refers both to devices for nasal and pulmonary administration of a drug, e.g., in solution, powder, and the like. For example, the term "inhaler" is intended to encompass a propellant driven inhaler, such as is used to administer antihistamine for acute asthma attacks, and plastic spray bottles, such as are used to administer decongestants.

As used herein "injecting" or "applying" includes administration of a compound (e.g., a peptide) of the presently disclosed subject matter by any number of routes including, but not limited to, topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary, and rectal routes of administration.

A "ligand" is a molecule that specifically binds to a target molecule such as but not limited to a receptor. A "receptor" is a molecule that specifically binds to a ligand. In some embodiments, the attribution of a given molecule as being a "ligand" or a "receptor" is merely one of convenience in the event that the "receptor" can be a molecule that is not recognized as a "receptor" as that term might be understood with respect to cell biology and/or signal transduction.

As such, in some embodiments a ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow & Lane, 1988 for a description of immunoassay formats and conditions that can be used to determine specific immunoreactivity.

The phrase "nasal administration" in all its grammatical forms refers to administration of at least one compound of the presently disclosed subject matter through the nasal mucous membrane to the bloodstream for systemic delivery of at least one compound of the presently disclosed subject matter. The advantages of nasal administration for delivery are that it does not require injection using a syringe and needle, it avoids necrosis that can accompany intramuscular administration of drugs, and trans-mucosal administration of a drug is highly amenable to self-administration.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides. In some embodiments, a peptide of the presently disclosed subject matter is thus at least or about 6, 7, 8, 9, 10, 11, 12, 13, 14, or 15 amino acids long, including but not limited to at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids long. The peptides of the presently disclosed subject matter can in some embodiments also have a length that falls in the ranges of 6-8, 8-10, 9-12, 10-13, 11-14, 12-15, 15-20, 20-25, 25-30, 30-35, 35-40, and 45-50 amino acids. In some embodiments, exactly, about, or at least 1, 2, 3, 4, 5, 6, 7, 8, 9, 10, 11, 12, 13, 14, 15, 16, 17 or more of the amino acid residues within a recited sequence of a target peptide contains an O-GlcNAc moiety, a hexose-GlcNAc moiety, or any combination thereof.

The phrase "per application" as used herein refers to administration of a drug or compound to a subject.

The phrase "pharmaceutical composition" refers to a composition comprising at least one active ingredient, whereby the composition is amenable to administration for a specified, efficacious outcome to a mammal (for example, without limitation, a human). Those of ordinary skill in the art will understand and appreciate the techniques appropriate for determining whether an active ingredient has a desired efficacious outcome based upon the needs of the artisan.

As used herein, the phrase "pharmaceutically-acceptable carrier" means a chemical composition with which an appropriate compound and/or derivative can be combined and which, following the combination, can be used to administer the appropriate compound to a subject. In some embodiments, a pharmaceutically-acceptable carrier is pharmaceutically acceptable for use in a human, which means that the carrier is in some embodiments generally recognized as being safe (GRAS) for human consumption and/or administration. "Pharmaceutically acceptable" thus means physiologically tolerable, for either human or veterinary application.

As used herein, the phrase "physiologically acceptable" ester or salt means an ester or salt form of the active ingredient which is compatible with any other ingredients of the pharmaceutical composition, which is not deleterious to the subject to which the composition is to be administered.

As used herein, "pharmaceutical compositions" include formulations for human and veterinary use.

As used herein, the term "plurality" means at least two and, unless specifically limited herein, has no upper boundary.

As used herein, the term "polypeptide" refers to a polymer composed of amino acid residues, related naturally occurring structural variants, and/or synthetic non-naturally occurring analogs thereof linked via peptide bonds, related naturally occurring structural variants, and synthetic non-naturally occurring analogs thereof.

As used herein, the phrase "synthetic peptides or polypeptides" refers to non-naturally occurring peptides and polypeptides. Synthetic peptides and polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, the terms "primer" and "oligonucleotide" refer to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "recombinant polypeptide" is one which is produced upon expression of a recombinant polynucleotide.

A "sample", as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include in some embodiments mammals, which in some embodiments can be a human.

As used herein, a "subject in need thereof" is a subject, animal, mammal, or human, who will benefit from the method of the presently disclosed subject matter.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom", as used herein, refers to any morbid phenomenon or departure from the normal in structure, function, or sensation, experienced by the subject and indicative of disease. In contrast, a "sign" is objective evidence of disease. For example, in some embodiments a bloody nose is a sign. It is evident to the subject, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat", as used herein, means reducing the frequency and/or severity of at least one symptom that is experienced by a subject or subject or administering an agent or compound to reduce the frequency and/or severity of at least one symptom that is experienced.

II. Compositions

II.A. Generally

In some embodiments, the presently disclosed subject matter provides compositions for inhibiting bacterial biofilm development and/or for reducing or eliminating a bacterial biofilm present on a surface. In some embodiments, the compositions comprise an effective amount of a peptide or polypeptide comprising a peptide or polypeptide derived from and/or that is a fragment of an Adenylate Cyclase Toxin (ACT) polypeptide of *Bordetella*, such as but not limited to a catalytic domain (AC domain) thereof, a T25 peptide thereof, a T18 peptide thereof, or any combination thereof. In some embodiments, the peptide or polypeptide comprises, consists essentially of, or consists of an amino acid sequence selected from the group consisting of SEQ ID NOs: 1-5 and 44-53.

As used herein, the phrases "Adenylate Cyclase Toxin" and "ACT" refer to a bifunctional hemolysin-adenylate cyclase gene and/or gene product encoding or having an amino acid sequence emplified by, but not limited to, that set forth in GENBANK® biosequence database Accession Nos. NP_879578.1 (SEQ ID NO: 1), WP_080702041.1 (SEQ ID NO: 44), and WP_010927405.1 (SEQ ID NO: 49). This amino acid sequence is set forth in SEQ ID NO: 1. While this particular amino acid sequence represents the amino acid sequence of ACT from *Bordetella pertussis* Tohama I, it is recognized that the genomes of other isolates of *B. pertussis, B. bronchiseptica,* and/or *B. parapertussis* might encode ACT polypeptides with one or more modifications of the sequence of SEQ ID NO: 1. For example, the ACT polypeptide of certain isolates of *B. pertussis* include a serine at position 304 in place of the asparagine of SEQ ID NO: 1. The presently disclosed subject matter is understood to encompass all such ACT polypeptides, both naturally occurring and artificially produced.

As used herein, the phrases "Adenylate Cyclase domain" and "AC domain" refer to the catalytic domain of an ACT polypeptide. The AC domain of *B. pertussis* ACT includes the N-terminal approximately 400 amino acids of an ACT polypeptide. Exemplary AC domains include in some embodiments amino acids 1-398, in some embodiments amino acids 1-399, in some embodiments amino acids 1-400 of SEQ ID NO: 1 (i.e., SEQ ID NO: 2), amino acids 1-400 of SEQ ID NO; 45 (i.e., SEQ ID NO: 45), and amino acids 35-434 of SEQ ID NO: 49 (i.e., SEQ ID NO: 50). Here as well, it is recognized that the genomes of other isolates of *B. pertussis, B. bronchiseptica,* and/or *B. parapertussis* might encode AC domain polypeptides with one or more modifications of the sequence of SEQ ID NOs: 2, 45, and 50, and the presently disclosed subject matter is understood to encompass all such AC domain polypeptides, both naturally occurring and artificially produced.

As used herein, the term "T25 peptide" refers to a subsequence of the AC domain of *B. pertussis* that includes in some embodiments amino acids 1-225 of SEQ ID NO: 1 or SEQ ID NO: 2. SEQ ID NO: 3 presents an amino acid sequence of an exemplary T25 peptide. Similarly, "T25 peptide" also refers to a subsequence of the AC domain of *B. bronchiseptica* that includes in some embodiments amino acids 1-225 of SEQ ID NO: 44 or SEQ ID NO: 45. SEQ ID NO: 46 presents an amino acid sequence of an exemplary T25 peptide. Also similarly, "T25 peptide" refers to a subsequence of the AC domain of *B. parapertussis* that includes in some embodiments amino acids 35-249 of SEQ ID NO: 49 or SEQ ID NO: 50. SEQ ID NO: 51 presents an amino acid sequence of an exemplary T25 peptide.

The term "T18 peptide" refers to a subsequence of the AC domain of *B. pertussis* that includes in some embodiments amino acids 226-400 of SEQ ID NO: 1 or SEQ ID NO: 2. Similarly, "T18 peptide" also refers to a subsequence of the AC domain of *B. bronchiseptica* that includes in some embodiments amino acids 226-400 of SEQ ID NO: 44 or SEQ ID NO: 45. SEQ ID NO: 47 presents an amino acid sequence of an exemplary T18 peptide. Also similarly, "T18 peptide" refers to a subsequence of the AC domain of *B. parapertussis* that includes in some embodiments amino acids 250-434 of SEQ ID NO: 49 or SEQ ID NO: 50. SEQ ID NO: 52 presents an amino acid sequence of an exemplary T18 peptide.

Thus, in some embodiments, a peptide or polypeptide of the presently disclosed subject matter comprises, consists essentially of, or consists of an amino acid sequence selected from the group consisting of SEQ ID NOs: 1-5 and 44-53.

Variants, both naturally occurring and artificially produced, are also encompassed by the presently disclosed subject matter. In some embodiments, a variant of a peptide or polypeptide of the presently disclosed subject matter is characterized by having a substantially identical amino acid sequence to one or more of SEQ ID NOs: 1-5 and 44-53. As used herein, a "substantially identical amino acid sequences" includes those amino acid sequences which have in some embodiments at least about 80% amino acid sequence identity, in some embodiments at least about 85% amino acid sequence identity, in some embodiments at least about 90% amino acid sequence identity, in some embodiments at least about 91% amino acid sequence identity, in some embodiments at least about 92% amino acid sequence identity, in some embodiments at least about 93% amino acid sequence identity, in some embodiments at least about 94% amino acid sequence identity, in some embodiments at least about 95% amino acid sequence identity, in some embodiments at least about 96% amino acid sequence identity, in some embodiments at least about 97% amino acid sequence identity, in some embodiments at least about 98% amino acid sequence identity, and in some embodiments at least about 99% or more amino acid sequence identity to an amino acid sequence as set forth herein. Amino acid sequence amino acid sequence identity, similarity, or identity can be computed by using the BLASTP and TBLASTN programs which employ the BLAST (basic local alignment search tool) 2.0.14 algorithm (Altschul et al., 1990a; Altschul et al., 1990b). The default settings used for these programs are suitable for identifying substantially similar amino acid sequences for purposes of the presently disclosed subject matter.

II.A. Pharmaceutical Compositions

In some embodiments, a composition of the presently disclosed subject matter is intended for use as a therapeutic or preventative. As such, in some embodiments the composition is a pharmaceutical composition comprising or consisting essentially of one or more peptides and/or polypeptides in combination with one or more pharmaceutically acceptable excipients and/or carriers. In some embodiments, a peptide or polypeptide of the presently disclosed subject matter is present in the pharmaceutical composition in an inactivated form.

As used herein, the terms "inactivated" and grammatical variants thereof refer to a biomolecule that has been modified in order to reduce or eliminate a biological activity that, under certain circumstances, is undesirable. By way of example and not limitation, an ACT polypeptide or a fragment thereof (such as but not limited to an AC domain) is characterized by adenylate cyclase activity, which is known to be involved in the virulence of *B. pertussis*. This adenylate cyclase activity is in some embodiments undesirable, and thus inactivated versions of the presently disclosed peptides and polypeptides are employed in the compositions and methods of the presently disclosed subject matter. It has been determined that the adenylate cyclase activity of the peptides and polypeptides of the presently disclosed subject matter can be reduced or eliminated by making substitutions in the amino acid sequences of the peptides and polypeptides of the presently disclosed subject matter. An exemplary such modification is to substitute the aspartic acid at amino acid position 188 of SEQ ID NO: 1 or SEQ ID NO: 2 with a cysteine and to substitute the isoleucine at amino acid position 189 of SEQ ID NO: 1 or SEQ ID NO: 2 with a threonine. An inactivated ACT polypeptide or AC domain of the presently disclosed subject matter thus in some embodiments comprises, consists essentially of, or consists of SEQ ID NO: 5. Other methods of inactivation are also encompassed by the presently disclosed subject matter, including but not limited to treatment with chemical crosslinkers such as formaldehyde as is currently performed on many components of vaccines (see e.g., U.S. Pat. Nos. 4,057,626; 8,444,992).

In some embodiments, a pharmaceutical composition of the presently disclosed subject matter comprises a delivery vehicle, and in some embodiments the peptide or polypeptide is optionally associated with, conjugated to, and/or encapsulated by a delivery vehicle. In some embodiments, a he delivery vehicle comprises a liposome, a microparticle, or a nanoparticle, optionally wherein the liposome, microparticle, or nanoparticle is designed to be biodegradable in a subject. Biodegradable delivery vehicles are known in the art and can be designed to release the peptide(s) and/or polypeptide(s) of the presently disclosed subject matter under various release parameters. Exemplary delivery vehicles are described, for example, in U.S. Pat. Nos. 7,393,924; 8,404,662; 9,028,864; 9,089,677; and 9,566,247; and in U.S. Patent Application Publication No. 2010/0021391, each of which is incorporated by reference in its entirety.

In some embodiments, a composition or pharmaceutical composition of the presently disclosed subject matter further comprises one or more pharmaceutically acceptable excipients and/or carriers (discussed in more detail herein below). In some embodiments, the one or more pharmaceutically acceptable excipients and/or carriers are pharmaceutically acceptable for use in a human (i.e., are biocompatible with human administration).

The pharmaceutical compositions of the presently disclosed subject matter can be formulated for whatever route of administration that might be desirable. By way of example and not limitation, the pharmaceutical compositions of the presently disclosed subject matter can be formulated for oral administration, intravenous administration, intramuscular administration, intrathecal administration, cutaneous administration, topical administration, transdermal administration, systemic administration, subcutaneous administration, sublingual administration, buccal administration, ocular administration, otic administration, nasal administration, inhalation, nebulization, or any combination thereof.

The compositions of the presently disclosed subject matter have activity in inhibiting bacterial biofilm development and/or in reducing or eliminating a bacterial biofilm present on a surface. The compositions of the presently disclosed subject matter thus have activity in various different bacterial species that form biofilms. By way of example and not limitation, compositions of the presently disclosed subject matter have activity against bacterial biofilms comprising a strain of bacteria selected from the group consisting of *Bordetella* spp., optionally *Bordetella pertussis* or *Bordetella bronchiseptica*; *Salmonella* spp., optionally *Salmonella typhimurium*; *Pseudomonas* sp., optionally *Pseudomonas aeruginosa*; coliform bacterial including *E. coli* spp.; *Listeria* spp.; *Neisseria* spp.; *Streptococcus* spp.; *Staphylococcus* spp.; *Yersinia* spp.; *Campylobacter* spp.; *Helicobacter* spp.; *Aeromonas* spp.; atypical Mycobacteria; and *Legionella* spp. It is noted, however, that compositions of the presently disclosed subject matter also have activity against other biofilm-producing microorganisms such as, but not limited to *Candida, Giardia*, and *Cryptosporidium*.

III. Methods of Use in Prevention and/or Treatment of Disorders, Diseases, and Conditions Associated with the Formation and/or Presence of Bacterial Biofilms III.A. Generally Bacterial biofilms are surface-associated communities of bacteria embedded in a self-produced matrix of polysaccharides, extracellular DNA (eDNA), and proteins. These communities are the most widely distributed and successful modes of life on earth, found in humans, plants, animals, and surfaces in the environment. While biofilms can drive important bio-geochemical processes, such as organic matter decomposition, nitrogen fixation, nitrification, denitrification, iron reduction, and sulfate reduction, harmful types of biofilms are associated with persistent infections in humans, plants, and animals, including infections associated with the use of medical devices and implants. In humans and animals, antibiotics are a common treatment for bacterial infections caused by biofilm, but bacteria in biofilms are frequently resistant to antibiotics due to changes in metabolism and antibiotic resistance, rendering antibiotic treatment ineffective.

The presently disclosed subject matter thus provides in some embodiments methods for using the presently disclosed compositions to prevent and/or treat a disease, disorder, or condition associated with the presence and/or development of bacterial biofilm in a subject. In some embodiments, the presently disclosed methods comprise administering to a subject a composition as disclosed herein in an effective amount and via a route sufficient for preventing and/or reducing the severity of at least one symptom of the disease, disorder, or condition. Various diseases, disorders, and conditions are known to be associated with the presence of bacterial biofilms. In some embodiments, a disease, disorder, or condition associated with a bacterial biofilm is selected from the group consisting of whooping cough, cystic fibrosis, bacterial vaginosis, urinary tract infections, infections associated with catheter use, middle ear infections, formation of dental plaque, gingivitis, eye infections associated with contact lens use, endocarditis, and infections resulting from use of medical and/or dental implants such as but not limited to joint prostheses and heart valves.

As such, in some embodiments the biofilm is present on a surface or could possibly grow on the surface, and the presently disclosed methods comprise contacting the surface with a composition of the presently disclosed subject matter. In some embodiments, the contacting comprises administering a pharmaceutical composition comprising the peptide or polypeptide to the subject in an amount and via a route of administration whereby the peptide or polypeptide contacts the surface or the biofilm present thereon and inhibits bacterial biofilm development on the surface and/or reduces or eliminates the existing bacterial biofilm present thereon.

Thus, in the instant context, in some embodiments a surface is a cellular surface, a tissue surface, and/or an organ surface present within a subject, including but not limited to a surface of the respiratory system such as but not limited to a nasal surface, a tracheal surface, and a lung surface. With respect to respiratory system surfaces, in some embodiments the respiratory surface is a nasal surface, a tracheal surface, and/or a lung surface, and the pharmaceutical composition is configured for inhalation and/or insufflation by the subject. In some embodiments, the composition comprises a delivery vehicle, optionally wherein the peptide or polypeptide is associated with, conjugated to, and/or encapsulated by a delivery vehicle in the pharmaceutical composition. In some embodiments, the delivery vehicle comprises a liposome, a microparticle, or a nanoparticle, optionally wherein the liposome, microparticle, or nanoparticle is designed to be biodegradable in the subject.

In some embodiments, a peptide and/or polypeptide composition of the presently disclosed subject matter is administered as part of a combination therapy with another therapeutic composition or method, which in some embodiments can be an anti-biofilm therapeutic composition or method. Exemplary anti-biofilm therapeutic compositions and methods include, but are not limited to those described in U.S. Pat. Nos. 6,726,898; 6,830,745; 9,339,525; and 9,566,247; U.S. Patent Application Publication Nos. 2002/0037260; 2006/0105025; 2010/0322872; and references cited therein, each of which is incorporated by reference in its entirety.

III.B. Administration of Compositions

III.B.1. Routes of Administration

The compositions of the presently disclosed subject matter can be administered parenterally, systemically, topically, or any combination thereof. By way of example and not limitation, administration of a composition of the presently disclosed subject matter can be performed by intravenous (i.v.) injection, subcutaneous (s.c.) injection, intradermal (i.d.) injection, intraperitoneal (i.p.) injection, and/or intramuscular (i.m.) injection. One or more such routes can be employed. Parenteral administration can be, for example, by bolus injection or by gradual perfusion over time. Alternatively or in addition, administration can be by the oral route.

For delivery to nasal or lung surfaces, the compositions of the presently disclosed subject matter are in some embodiments suitable for administration via inhalation or insufflation.

Other acceptable routes of administration include but are not limited to oral (enteral), nasal, ophthal, and transdermal. In some embodiments, the administration is subcutaneous, and in some embodiments the subcutaneous administration is by an infusion pump.

III.B.2. Formulations

Pharmaceutical carriers, diluents, and excipients are generally added to the compositions of the presently disclosed subject matter (or kits comprising the same) that are compatible with the active ingredients and acceptable for pharmaceutical use (including but not limited to pharmaceutical use in a human). Examples of such carriers include but are not limited to water, saline solutions, dextrose, and/or glycerol. Combinations of carriers can also be used.

The compositions of the presently disclosed subject matter can further incorporate additional substances to stabilize pH and/or to function as adjuvants, wetting agents, and/or emulsifying agents, which can serve to improve the effectiveness of the pharmaceutical compositions.

In some embodiments, a composition can include one or more sugars, sugar alcohols, amino acids such but not limited to glycine, arginine, glutamic acid, and/or others as framework formers. The sugars can be mono-, di-, or trisaccharides. These sugars can be used alone and/or in combination with sugar alcohols. Exemplary sugars include glucose, mannose, galactose, fructose, or sorbose as monosaccharides; sucrose, lactose, maltose, and trehalose as disaccharides; and raffinose as a trisaccharide. A sugar alcohol can be, for example, mannitose. In some embodiments, the composition comprises sucrose, lactose, maltose, trehalose, mannitol, and/or sorbitol. In some embodiments, the composition comprises mannitol.

Furthermore, in some embodiments compositions can include physiological well-tolerated excipients (see Strickley, 2004; Rowe et al., 2006) such as antioxidants like ascorbic acid or glutathione; preserving agents such as phenol, m-cresol, methyl- or propylparabene, chlorobutanol, thiomersal/thimerosal, and/or benzalkoniumchloride; stabilizers, framework formers such as sucrose, lactose, maltose, trehalose, mannitose, mannitol, and/or sorbitol; mannitol and/or lactose and solubilizers such as polyethylene glycols (PEG; e.g., PEG 3000, 3350, 4000, or 6000), cyclodextrins (e.g., hydroxypropyl-β-cyclodextrin, sulfobutylethyl-β-cyclodextrin, or γ-cyclodextrin), dextranes, or poloxamers (e.g., poloxamer 407 or poloxamer 188); or TWEEN® 20 or TWEEN® 80. In some embodiments, one or more well-tolerated excipients can be included, optionally selected from the group consisting of antioxidants, framework formers, and stabilizers.

III.B.3. Dosages

It is understood that a suitable dosage of a composition of the presently disclosed subject matter can depend upon the age, sex, health, and/or weight of the recipient, the kind of concurrent treatment, if any, the frequency of treatment, and the nature of the effect desired. However, it is understood that dosages can be tailored to the individual subject, as determined by the researcher or clinician. The total dose required for any given treatment will in some embodiments be determined with respect to a standard reference dose based on the experience of the researcher or clinician, such dose being administered either in a single treatment or in a series of doses, the success of which will depend on the production of a desired therapeutic response.

Thus, in some embodiments the overall administration schedule is considered in determining the success of a course of treatment and not whether a single dose, given in isolation, would or would not produce the desired immunologically therapeutic result or effect. As such, a therapeutically effective amount can depend on the composition used, the nature of the disease condition, the severity of the disease condition, the extent of any need to prevent such a condition where it has not already been detected, the manner of administration dictated by the situation requiring such administration, the weight and state of health of the individual receiving such administration, and/or the sound judgment of the clinician or researcher. In some embodiments, the efficacy of administering additional doses and/or of increasing or decreasing the interval can be continually re-evaluated in view of the recipient's response.

The compositions of the present presently disclosed subject matter can in some embodiments also be contained in artificially created structures such as liposomes, which structures in some embodiments can contain additional molecules such as but not limited to proteins or polysaccharides, inserted in the outer membranes of said structures and having the effect of targeting the liposomes to particular areas of the body and/or to particular cells within a given organ or tissue. Such targeting molecules can in some embodiments comprise an immunoglobulin. Antibodies can work particularly well for targeting of liposomes and/or other scaffolds to tumor cells.

Single doses of in some embodiments about 1 to 50 µg, in some embodiments about 1 to 100 µg, in some embodiments about 1 to 500 µg, in some embodiments about 1 to 1000 µg, in some embodiments about 1 to 50 mg, in some embodiments about 1 to 100 mg, in some embodiments about 1 to 500 mg, or in some embodiments about 1 to 1000 mg of a peptide and/or polypeptide composition of the presently disclosed subject matter can be given and can depend from the respective compositions of compositions with respect to total amount for all peptides and/or polypeptides in the composition or alternatively for each individual peptide and/or polypeptide in the composition. A single dose of a peptide and/or polypeptide composition of the presently disclosed subject matter can in some embodiments have a target peptide amount (e.g., total amount for all peptides and/or polypeptides in the composition or alternatively for each individual peptide and/or polypeptide in the composition) of about or at least 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 950 µg. In some embodiments, a single dose of a peptide and/or polypeptide composition of the presently disclosed subject matter can have a total peptide and/or polypeptide amount (e.g., total amount for all peptides and/or polypeptides in the composition or alternatively for each individual peptide and/or polypeptide in the composition) of about or at least 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 950 mg. In some embodiments, the peptides and/or polypeptides of a composition of the presently disclosed subject matter are present in equal amounts of about 100 micrograms per dose.

In a single dose of a peptide and/or polypeptide composition of the presently disclosed subject matter, the amount of each peptide and/or polypeptide in the composition is in some embodiments equal or substantially equal. Alternatively, a ratio of the peptides and/or polypeptides present in the least amount relative to the peptide and/or polypeptide present in the greatest amount is about or at least 1:1.25, 1:1.5, 1:1.75, 1:2.0, 1:2.25, 1:2.5, 1:2.75, 1:3, 1:4, 1:5, 1:6, 1:7, 1:8, 1:9, 1:10, 1:20, 1:30; 1:40, 1:50, 1:100, 1:200, 1:500, 1:1000, 1:5000; 1:10,000; or 1:100,000. Alternatively, a ratio of the peptides and/or polypeptides present in the least amount relative to the peptide and/or polypeptide present in the greatest amount is about or at least 1 or 2 to 25; 1 or 2 to 20; 1 or 2 to 15; 1 or 2 to 10; 1 to 3; 1 to 4; 1 to 5; 1 to 6; 1 to 7; 1 to 10; 2 to 3; 2 to 4; 2 to 5; 2 to 6; 2 to 7; 2 to 10; 3 to 4; 3 to 5; 3 to 6; 3 to 7; 3 to 10; 5 to 10; 10 to 15; 15 to 20; 20 to 25; 1 to 40; 1 to 30; 1 to 20; 1 to 15; 10 to 40; 10 to 30; 10 to 20; 10 to 15; 20 to 40; 20 to 30; or 20 to 25; 1 to 100; 25 to 100; 50 to 100; 75 to 100; 25 to 75, 25 to 50, or 50 to 75; 25 to 40; 25 to 50; 30 to 50; 30 to 40; or 30 to 75.

Single dosages can be given to a subject about or at least 1, 2, 3, 4, or 5 times per day. Single dosages can be given to a subject about or at least 1, 2, 3, 4, 5, 6, 7, 8, 9, 10, 11, 12, 13, 14, 15, 16, 18, 19, 20, 21, 22, 23, 24, 36, 48, 60, or 72 hours subsequent to a previous dose.

Single dosages can be given to a subject about or at least 1, 2, 3, 4, 5, 6, or 7 times per week, or every other, third, fourth, or fifth day. Single doses can also be given every week, every other week, or only during 1, 2, or 3 weeks per month. A course of treatment can in some embodiments last about or at least 1, 2, 3, 4, 5, 6, 7, 8, 9, 10, 11, or 12 months.

In some embodiments, the single dosages of the compositions of the presently disclosed subject matter can be provided to a subject in at least two phases: e.g., during an initial phase and then during a subsequent phase. An initial phase can be about or at least 1, 2, 3, 4, 5, or 6 weeks in length. The subsequent phase can last at least or about 1, 2, 3, 4, 5, 6, 7, or 8 times as long as the initial phase. The initial phase can be separated from the subsequent phase by about or at least 1, 2, 3, 4, 5, 6, 7, 8, 9, 10, 11, or 12 weeks or months.

The composition dosage during the subsequent phase can be at least 1, 2, 3, 4, 5, 6, 7, 8, 9, 10, 15, 20, 30, 40, 50, 60, 70, 80, 90, 100, 200, 300, 400, 500, 600, 700, 800, 900, or 1000 times greater than during the initial phase.

The composition dosage during the subsequent phase can be at least 1, 2, 3, 4, 5, 6, 7, 8, 9, 10, 15, 20, 30, 40, 50, 60, 70, 80, 90, 100, 200, 300, 400, 500, 600, 700, 800, 900, or 1000 times less than during the initial phase.

In some embodiments, the initial phase is about three weeks and the second phase is about 9 weeks. The compositions can be administered to the subject on or about days 1, 8, 15, 36, 57, and 78.

III.C. Kits and Storage

In some embodiments, a kit is disclosed comprising (a) a container that contains at least one composition as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit can further comprise one or more of (iii) a buffer, (iv) a diluent, (v) a filter, (vi) a needle, or (v) a syringe. In some embodiments, the container is selected from the group consisting of a bottle, a vial, a syringe, a test tube, or a multi-use container. In some embodiments, the composition is lyophilized.

The kits can contain exactly, about, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, or more compositions. Each composition in the kit can be administered at the same time or at different times.

In some embodiments, the kits can comprise a lyophilized formulation of the presently disclosed compositions in a suitable container and instructions for its reconstitution and/or use. Suitable containers include, for example, bottles, vials (e.g., dual chamber vials), syringes (such as dual chamber syringes), and test tubes. The container can be formed from a variety of materials such as glass or plastic. In some embodiments, the kit and/or the container contain(s) instructions on or associated therewith that indicate(s) directions for reconstitution and/or use of a lyophilized formulation. For example, the label can indicate that the lyophilized formulation is to be reconstituted to concentrations as described herein. The label can further indicate that the formulation is useful or intended for subcutaneous administration. Lyophilized and liquid formulations are typically stored at −20° C. to −80° C.

The container holding the composition(s) can be a multi-use vial, which in some embodiments allows for repeat administrations (e.g., from 2-6 or more administrations) of the reconstituted formulation. The kit can further comprise a second container comprising a suitable diluent (e.g., sodium bicarbonate solution).

In some embodiments, upon mixing of the diluent and the lyophilized formulation, the final concentration of an active agent in the reconstituted formulation is at least or about 0.15, 0.20, 0.25, 0.5, 0.75, 1.0, 1.25, 1.5, 1.75, 2.0, 2.25, 2.5, 2.75, 3.0, 3.25, 3.50, 3.75, 4.0, 4.25, 4.5, 4.75, 5.0, 6.0, 7.0, 8.0, 9.0, or 10 mg/mL/target peptide. In some embodiments, upon mixing of the diluent and the lyophilized formulation, the concentration of an active agent in the reconstituted formulation is at least or about 0.15, 0.20, 0.25, 0.5, 0.75, 1.0, 1.25, 1.5, 1.75, 2.0, 2.25, 2.5, 2.75, 3.0, 3.25, 3.50, 3.75, 4.0, 4.25, 4.5, 4.75, 5.0, 6.0, 7.0, 8.0, 9.0, or 10 µg/mL/active agent.

The kit can further include other materials desirable from a commercial and/or user standpoint, including other buffers, diluents, filters, needles, syringes, and package inserts with or without instructions for use.

The kits can have a single container that contains the formulation of the target peptide compositions with or without other components (e.g., other compounds or compositions of these other compounds) or can have a distinct container for each component.

Additionally, the kits can include a formulation of the presently disclosed compositions packaged for use in combination with the co-administration of a second compound. One or more of the components of the kit can be pre-complexed or one or more components can be in a separate distinct container prior to administration to a subject. One or more of the components of the kit can be provided in one or more liquid solutions. In some embodiments, the liquid solution is an aqueous solution. In a further embodiment, the liquid solution is a sterile aqueous solution. One or more of the components of the kit can also be provided as solids, which in some embodiments can be converted into liquids by addition of suitable solvents, which in some embodiments can be provided in another distinct container.

The container of a therapeutic kit can be a vial, a test tube, a flask, a bottle, a syringe, or any other structure suitable for enclosing a solid or liquid. Typically, when there is more than one component, the kit contains a second vial or other container that allows for separate dosing. The kit can also contain another container for a pharmaceutically acceptable liquid. In some embodiments, a therapeutic kit contains an apparatus (e.g., one or more needles, syringes, eye droppers, pipette, etc.), which enables administration of the peptide and/or polypeptide compositions of the disclosure that are components of the kit.

IV. Methods for Inhibiting the Development and/or Reducing the Presence of Biofilm on Abiotic Surfaces The presence of biofilm on abiotic surfaces is also detrimental in the medical, dental, and industrial contexts. Thus, in some embodiments the presently disclosed subject matter provides compositions and methods for inhibiting the development and/or reducing the presence of biofilm on abiotic surfaces.

In some embodiments, the presently disclosed subject matter provides methods for inhibiting bacterial biofilm development and/or for reducing or eliminating a bacterial biofilm present on an abiotic surface that comprises contacting the abiotic surface or the biofilm present thereon with an effective amount of a peptide or polypeptide derived from Adenylate Cyclase Toxin (ACT) of *Bordetella* or a catalytic domain (AC domain) thereof, optionally wherein the peptide or polypeptide comprises an amino acid sequence selected from the group consisting of SEQ ID NOs: 1-5 and 44-53, whereby bacterial biofilm development on the abiotic surface is inhibited and/or existing bacterial biofilm on the on the abiotic surface is reduced or eliminated. In some embodiments, the bacterial biofilm comprises a strain of bacteria selected from the group consisting of *Bordetella* spp., optionally *Bordetella pertussis* or *Bordetella bronchiseptica; Salmonella* spp., optionally *Salmonella typhimurium*; and *Pseudomonas* spp., optionally *Pseudomonas aeruginosa*. Other exemplary microorganisms associated with biofilm formation for which the presently disclosed methods is applicable include coliform bacterias, *Yersinia, Campylobacter, Helicobacter, Aeromonas*, atypical Mycobacteria, Giardia cysts, *Cryptosporidium* oocysts, *Klebsiella pneumoniae, Staphylococcus epidermidis, Staphylococcus aureus, Porphyromonas gingivalis*, and *Legionella*.

IV.A. Methods for Reducing the Incidence of Nosocomial Infection

Biofilms are also associated with nosocomial (i.e., hospital-acquired) infections, and thus use the presently disclosed subject matter provides methods for reducing the incidence of nosocomial infection associated with the presence of or the development of biofilm. Exemplary biofilm-forming organisms associated with nosocomial infections include *Klebsiella pneumoniae, Staphylococcus epidermidis, Staphylococcus aureus, Porphyromonas gingivalis, Pseudomonas aeruginosa*, and others. Whereas antibiotics are typically employed to combat these bacteria, antibiotic resistance in these species is increasing such that the front-line strategies are becoming less effective and in fact could be contributing to the problems associated with the presenece of biofilms inn medical and/or dental facilities.

In some embodiments, the presently disclosed subject matter relates to methods for reducing the incidence of nosocomial infection, wherein the method comprises contacting a surface present in a medical and/or dental facility with a composition as described herein in an amount sufficient to inhibit bacterial biofilm development and/or reduce or eliminate bacterial biofilm present on the surface, thereby reducing the incidence of a nosocomial infection associated with the incidence of nosocomial infection is a subject. In some embodiments, the surface is a door surface, a door handle surface, a sink surface, a toilet surface, a faucet surface, a furniture surface, optionally a bed surface, and a window surface.

IV.B. Methods for Reducing Biofilms on Medical and Dental Devices

In some embodiments, an abiotic surface is a part of a device selected from the group consisting of a medical device, a dental device, and an industrial device.

In some embodiments, the medical/dental device is selected from the group consisting of a surgical tool, an implant, a catheter, a stent, a replacement for a bone or joint (e.g., a hip, knee, ankle, elbow, or shoulder replacement device), and ventilator tubing. In some embodiments, the medical device is a cardiac implant. Reducing or eliminating biofilm on any such device can reduce infections associated with the use of the devices.

IV.C. Methods for Reducing Biofilms on Industrial Devices

Biofilms present on industrial devices are also associated with various deleterious effects. This is particularly common with respect to devices employed in water treatment, sewage treatment, petroleum manufacturing and/or storage, and recycling. As such, in some embodiments the industrial device is selected from the group consisting of a pipe, a tube, a valve, an air-cooled tower, a warm water system, a coolant circuit, a silo, a fermenter, a colander, a piece of furniture, and a sink.

Irrespective of the location and/or type of surface, in some embodiments the presently disclosed methods further comprise contacting the surface with one or more additional compositions that inhibit bacterial biofilm development and/or reduces or eliminates bacterial biofilm present on the surface.

EXAMPLES

The following Examples provide further illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the EXAMPLES

Bacterial Strains and Growth Conditions.

*Bordetella pertussis* wild-type BP338 (Tohama I); Bvg(2) BP347 (TN5::bvgS mutant derived from BP338); wild-type BPSM (Tohama I); BPSM JS20 (fhaB ΔMCD and C-terminal prodomain derivative of BPSM); and BPSM T-N (fhaB with transposon insertion in C-terminal prodomain derivative of BPSM) were grown on Bordet-Gengou (BG) agar (GIBCO™ brand, available from Thermo Fisher Scientific Inc., Waltham, Mass., United States of America) supplemented with 15% defibrinated sheep blood (Cocalico Biologicals Inc., Reamstown, Pa., United States of America) for 48 hours at 37° C. The same growth conditions were used for *B. bronchiseptica* strains, wild-type RB50; Bvg(−) RB54; RBX11-JS20 (fhaB ΔMCD and C-terminal prodomain); and RBX11 T-N (fhaB with transposon insertion in C-terminal domain). These *B. pertussis* strains have been previously reported (Weiss et al., 1983; Mazar & Cotter, 2006), as have *B. bronchiseptica* strains (Mazar & Cotter, 2006). Bacteria were then transferred to liquid culture in modified synthetic Stainer-Scholte liquid medium (SSM) and grown for 24 hours at 37° C., shaking at 150 RPM. Bacteria were pelleted and washed in SSM, and then resuspended to an $OD_{600}$ of 0.1 for biofilm experiments.

Strain Construction (ΔAC Domain).

Two DNA fragments (517 and 513 bps), corresponding to the 5' and the 3' flanking region of the in-frame deletion, were amplified from *B. pertussis* genomic DNA as a template by PCR using the following two pairs of primers:

```
F1:
                                  (SEQ ID NO: 6)
5'-TTTACTAGTGGGATTGAGGAGGGAGGGC-3';

R1:
                                  (SEQ ID NO: 7)
5'-TTTATGCATGTGGATCTGTCGATAAGTAGTC-3';

F2:
                                  (SEQ ID NO: 8)
5'-TTTATGCATAAGTTCTCGCCGGATGTACTG-3';

R2:
                                  (SEQ ID NO: 9)
5'-TTTGAATTCGCCGCCTCCCAGCGCCAT-3'.
```

The primers were cut with the SpeI/NsiI and NsiI/EcoRI respectively, and ligated with the SpeI/EcoRI-cleaved pSS4245 vector (see Inatusuka et al., 2010; U.S. Pat. No. 9,187,754). Bacteria were mated following the previously described methods for *B. pertussis*. Briefly, *B. pertussis* BP338 was passaged 2-3 days on BG and grown over night in SSM. The $OD_{600}$ was between 0.7 and 0.8. RHO3 *E. coli* were grown in antibiotic selection media, LB+150 μg/ml ampicillin (AMP) supplemented with 400 μg/ml DAP to mid-log phase. A 2:1 donor to recipient ratio was used. After washing, the bacteria were resuspended in 100 ml SSM and plated on BG+ $MgSO_4$+ DAP plates. After an overnight incubation (approximately 15 hours), the plates were swabbed, the material was washed to remove residual DAP and resuspended in 100 ml SSM. Bacteria were plated on BG+ $MgSO_4$+ AMP. Colonies were isolated and confirmed to lack the AC domain via western blot and PCR.

ACT and ACT Mutant Protein Purification.

As previously described, calmodulin columns were used to isolate holotoxin ACT from whole-cell urea extracts of XL1-Blue *E. coli* (Agilent Technologies, Santa Clara, Calif., United States of America) transformed with plasmid pT7cACT1 (Osička et al., 2000) Delivery of CD8+ T-Cell Epitopes into Major Histocompatibility Complex Class I Antigen Presentation Pathway by *Bordetella pertussis* Adenylate Cyclase: Delineation of Cell Invasive Structures and Permissive Insertion Sites. Infect Immun. 68:247-256). Similar methods were used to purify the ACT deletion mutants expressed from the previously described plasmid constructs with similar backbone, whole-cell urea extracts of XL1-Blue *E. coli* transformed with the following plasmids and urea-extracted material was used in assays described below; $ACT_{\Delta AC}$ (pCACT Δ-373), $ACT_{\Delta HR}$ (pCACT Δ385-1489), $ACT_{\Delta H}$ (pCACT Δ385-1006), $ACT_{\Delta R}$ (pCACT ΔC217), and iACT (pGW44/188; Lee et al., 1999). The AC domain was purified from the *E. coli* BL21 (kDE3) strain expressing the AC-int-CBD fusion protein (Sadilkova et al., 2008). Briefly, bacteria were grown at 30° C. in MDO medium supplemented with 150 mg/ml of ampicillin. Cultures were induced with IPTG (1 mM), the cells were washed and resuspended in 50 mM Tris-HCl (pH 7.4), 150 mM NaCl (TN buffer) containing 1 mM EDTA (EDTA buffer), and disrupted by sonication. For protein purification by chitin affinity chromatography, the cell extract was cleared at 20,000×g and loaded on a chitin bead column. After washing, EDTA buffer containing 50 mM dithiothreitol was loaded on the column to promote self-excision of the intein-CBD from the AC-intein-CBD fusion protein during overnight incubation at 4° C. The AC domain was then eluted with EDTA buffer and dithiothreitol was removed by dialysis against TN buffer. Purified proteins were stored at −70° C. until use.

FHA and FHA44 Purification.

FHA was produced using *B. pertussis* Tohama I, while *B. pertussis* Fha44-stop was used to produce the ~80 kDa N-terminal fragment of FHA that comprises residues 72-862 of FhaB (the fhaB allele having a stop codon inserted at position 863 was constructed according to Renaud-Mongenie). Bacteria were grown in 1 liter (I) shaking liquid cultures in SSM supplemented with 1 g/1 of (2,6-O-dimethyl)-b-cyclodextrin (Sigma-Aldrich Corp., St. Louis, Mo., United States of America). At $OD_{600}$≥4.0, culture supernatants were collected by centrifugation at 10,000×g for 20 minutes at 4° C. and were sterilized by passage through filters with 0.22 μm pore diameter before loading onto 5 ml CELLUFINE™ brand sulfate columns (JNC Corporation, Tokyo, Japan) equilibrated with 10 mM sodium phosphate buffer at pH 7.6 (buffer A). After sample application, both matrices containing adsorbed FHA or FHA44 were washed with 80 column volumes (cv) of buffer A, after which a second wash of 20 cv was performed with buffer A containing 300 mM NaCl. The purified FHA and FHA44 proteins were eluted with 700 mM NaCl in buffer A and were stored frozen at −70° C. until use. The entire purification procedure on chromatography column was performed at 4° C.

Microtiter Crystal Violet Assay.

*Bordetella* biofilm was measured using the microtiter plate assay, coupled with crystal violet staining, as previously described (O'Toole, 2011). Briefly, *Bordetella* bacteria were grown in a total volume of 100 μl of Stainer-Scholte medium at 37° C. in 96-well polyvinylchloride (PVC), round bottom, non-tissue-culture treated microtiter plates (NUNC™ brand, available from Thermo Fisher Scientific Inc., Waltham, Mass., United States of America). *B. pertussis* biofilm was measured at 96 hours and *B. bronchiseptica* biofilm was measured at 72 hours. Wells were washed at the final time point to remove planktonic bacteria. Bacterial cells that remained attached to the wells were stained with a 0.1% solution of crystal violet (CV) and were incubated at room temperature for 30 minutes. The washing process was repeated, and the CV stain was solubilized from bacterial cells with 200 μl of 95% ethanol. Biofilm formation was quantitated by measuring $OD_{595}$.

Scanning Electron Microscopy.

Biofilms were grown statically in 24-well non-tissue culture treated polypropylene plates (0.5 ml cultures per well), and a circular microscope cover glass (12CIR.-1.5) was inserted into each well. Bacteria successfully adhered to the coverslip, as initially confirmed by Gram stain, and matrix was present as determined by Calcofluor White staining. Coverslips were placed in 4% paraformaldehyde to fix samples. *B. pertussis* biofilm was observed on the surfaces of the coverslips at 96 hours under various conditions.

Aggregation Assay.

Bacterial aggregation was measured using previously described methods for *B. pertussis* (Arnal et al., 2015). Briefly, BP338 was grown in the presence and absence of AC domain for 24 hours at 37° C. shaking. At 24 hours, six 1 ml samples were collected. Three were homogenized by vigorous vortexing and three were not homogenized before centrifugation at 650×g for 2 minutes. The $OD_{600}$ was then measured from the supernatant, and the aggregation index (AI) was calculated based on the following equation:

$$(OD_{homogenized}-OD_{nonhomogenized})/OD_{homogenized}$$

Three independent experiments were performed in triplicate.

Surface Plasmon Resonance (SPR).

SPR measurements were performed at 25° C. using a ProteOn XPR36 Protein Interaction Array System (Bio-Rad, Hercules, Calif., United States of America). FHA and FHA44 were diluted to a final concentration of 1 mg/ml in PBS containing 0.005% TWEEN® 20 brand non-ionic detergent and immobilized as ligands to a GLC sensor chip (Bio-Rad Laboratories, Hercules, Calif., United States of America) at flow rate of 30 μl/min. SPR measurements were carried out in the running buffer containing PBS supplemented with 0.005% TWEEN® 20 brand non-ionic detergent at the flow rate of 30 μl/min for association and dissociation phase of sensograms. The purified AC domain was diluted in the running buffer to the indicated concentrations and injected in parallel ("one-shot kinetics") over the chip surface. The sensograms were corrected for sensor background by interspot referencing (the sites within the 6×6 array which are not exposed to ligand immobilization but are exposed to analyte flow), and double referenced by subtraction of analyte (channels 1-5) using a 'blank' injection (channel 6). The data were analyzed globally by fitting both the association and the dissociation phases simultaneously for five different AC domain concentrations using a 1:1 Langmuir-type binding model. An apparent equilibrium dissociation constant ($K_D$) was determined as KD=$k_d/k_a$.

ELISA-Based Binding Assay.

ELISA-specific MaxiSorp 96-well immunoplates (Thermo Fisher Scientific Inc., Waltham, Mass., United States of America) were coated with 0.5 μg/ml FHA overnight in 100 μl bicarbonate solution. Before beginning the assay, the wells were washed and then blocked in 5% milk 1×PBS 0.05% Tween for 1 hour. Wells were washed and control (no protein), ACT, AC domain, or ACT$_{\Delta AC}$ (50 μl) was added for 30 minutes. Anti-MCD antibodies described previously (Noel et al., 2012; 50 μl of 1:100,000 dilution) were added to wells for 30 minutes after the addition of the first 50 μl solution. Wells were washed and a secondary anti-rabbit-HRP linked antibody was added to wells for 1 hour. Wells were washed again and the detection solution (SUREBLUE™ TMB Microwell Peroxidase Substrate; VWR, Radnor, Pa., United States of America) was added for 15 minutes. HCl 1N was added to stop the detection solution reaction and the absorbance at OD$_{450}$ was read using an μQUANT™ brand ELISA reader (BIOTEK® Instruments, Inc., Winooski, Vt., United States of America).

Statistics.

Statistical analysis was performed using Student's unpaired t test with Welch's correction, assuming Gaussian distribution (parametric test), these tests were performed on data sets to compare conditions within experiments.

Example 1

Exogenous ACT Inhibits Biofilm in a Concentration-Dependent Manner

Whether ACT had an inhibitory effect on *B. pertussis* biofilm was tested. The *B. pertussis* mutant, BP348, lacking ACT by virtue of a transposon insertion in cyaA, and the parental wild-type strain, BP338, were compared for their abilities to form biofilm. BP338, BP348, and BP347 were grown in 96-well plates and biofilm formation was measured by bacterial accumulation on wells using the crystal violet assay. As shown in FIG. 1, BP348 made more biofilm than BP338. Bvg(−) BP347, a negative control, formed no biofilm; the low, but measurable, $OD_{595}$ reflected basal levels of bacterial adherence, and was previously observed for Bvg (−) *B. pertussis* (Mishra et al., 2005). These differences in biofilm formation were not due to differences in bacteria growth, in 10 ml SSM shaking cultures all strains grew at the same rate, while under 100 μl static culture conditions in 96-well plates, BP338 and BP348 grew at similar rates. BP347, which does not make biofilm, reached a higher $OD_{600}$ more quickly (FIGS. 2A and 2B), excluding impaired bacterial growth as the cause of differences in biofilm formation.

Exogenous, purified, recombinant ACT was then tested for its ability to inhibit biofilm formation by *B. pertussis* and *B. bronchiseptica*. Exogenous ACT was added at concentrations of 10, 100, or 1000 ng/ml (56 μM, 565 μM, and 5650 pM respectively) to BP338 cultures. The concentration-dependent inhibition of biofilm is shown in FIG. 3 ($IC_{50}$ 17.32 ng/ml to reduce biofilm to negative control $OD_{595}$). *B. pertussis* grown in the presence of ACT or urea, a major component of the solution in which ACT was stored, grew at the same rate as in media alone, further showing that differences in growth rate did not account for reduced biofilm formation (FIG. 4). The same concentration-dependent inhibition of biofilm by ACT occurred with *B. bronchiseptica* (FIG. 5). Importantly, the concentrations of ACT (approximately 100 ng/ml) employed were comparable to calculated concentrations found in nasopharyngeal washes from baboons and infants infected with *B. pertussis* (Eby et al., 2013).

Example 2

The AC Domain is Necessary and Sufficient for Inhibition of Biofilm

ACT is a 177 kDa, multi-domain protein, and to determine which part(s) of the ACT molecule were involved in the inhibitory effect, truncated ACT variants and an ACT protein mutant lacking AC enzymatic activity (iACT) were tested for their abilities to inhibit biofilm formation (FIG. 6 is a schematic representation of modifications). These variants, which were partial deletions from full-length ΔcyaA (Sebo & Ladant, 1993; Sadilkova et al., 2008), were previously used to characterize monoclonal antibodies (Lee et al., 1999) and have been used previously in functional assays (Sakamoto et al., 1992; Iwaki et al., 1995; Macdonald-Fyall et al., 2004; Eby et al., 2014). All ACT variants, with one exception, inhibited biofilm formation to the same extent as full-length ACT (FIG. 6). $ACT_{\Delta Ac}$, ACT lacking the catalytic domain, was without an inhibitory effect at 100 ng/ml, while the 43 kDa AC domain was comparable to native ACT in inhibiting biofilm formation at just 10 ng/ml (comparable molar concentrations), and did so in a concentration-dependent manner (FIG. 7). iACT, the enzymatically inactive form of the toxin (1000-fold reduction in enzymatic activity in comparison to ACT holotoxin), inhibited biofilm comparably to ACT at 100 ng/ml (FIG. 8), establishing that the enzymatic activity of the toxin was not required for the inhibitory effect. Thus the AC domain was both necessary and sufficient for biofilm inhibition, yet its catalytic activity contained in the AC domain was not required.

The AC domain is the most conserved portion of ACT among *Bordetella* species that encode the toxin (Park et al., 2012), indicating the possibility of a comparable inhibitory role for the AC domain in biofilm regulation among the Bordetellae. The AC domain is also necessary and sufficient to inhibit *B. bronchiseptica* RB50 biofilm (FIG. 9). To confirm the role of endogenous ACT and its catalytic domain, BP338 ΔAC was constructed. The portion of cyaA encoding the AC domain (Δ1-373) was deleted and the resultant strain, BP338 ΔAC, was tested for biofilm formation as in in vitro assays described above. A Western blot was completed to show that the BP338 ΔAC mutant expressed truncated ACT peptide (FIG. 10). As expected, BP338 ΔAC made more biofilm than the parental wild-type BP338 (FIG. 11), confirming the necessity for and specificity of the AC domain to inhibit biofilm in *B. pertussis.*

In that the crystal violet assay is an indirect quantification of biofilm, scanning electron microscopy was employed to determine the effects of AC domain on BP338 biofilm, using BP347 as a biofilm-negative control. *B. pertussis* was allowed to form biofilm on glass coverslips in the absence and presence of exogenous AC domain to complement data from the crystal violet assay. Samples obtained under these conditions were imaged using a Zeiss Sigma VP HD field emission scanning electron microscope (SEM). FIGS. 12A-

Figure 12A:
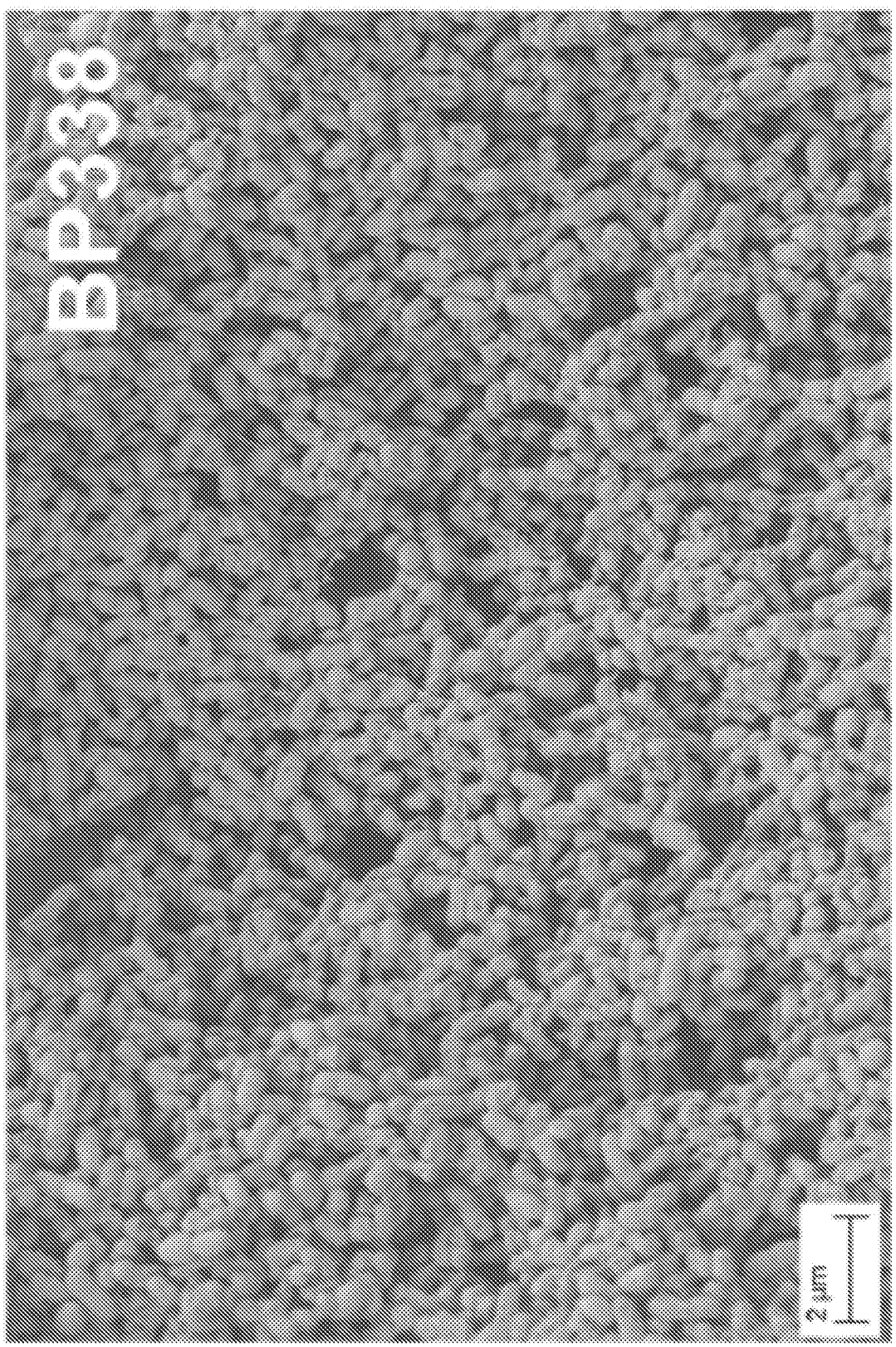
FIGS. 12A-12C show SEM images showing that AC domain inhibits biofilm formation on glass coverslips. *B. pertussis* was grown in 24-well plates with inverted glass coverslips so that biofilm formation could occur at the air liquid interface. At 96 hours, the coverslips were fixed in 4% paraformaldehyde and prepared for SEM imaging using a Zeiss Sigma VP HD field emission scanning electron microscope at the University of Virginia Microscopy Core. Representative images were chosen from four experimental replicates.
Figure 12B:
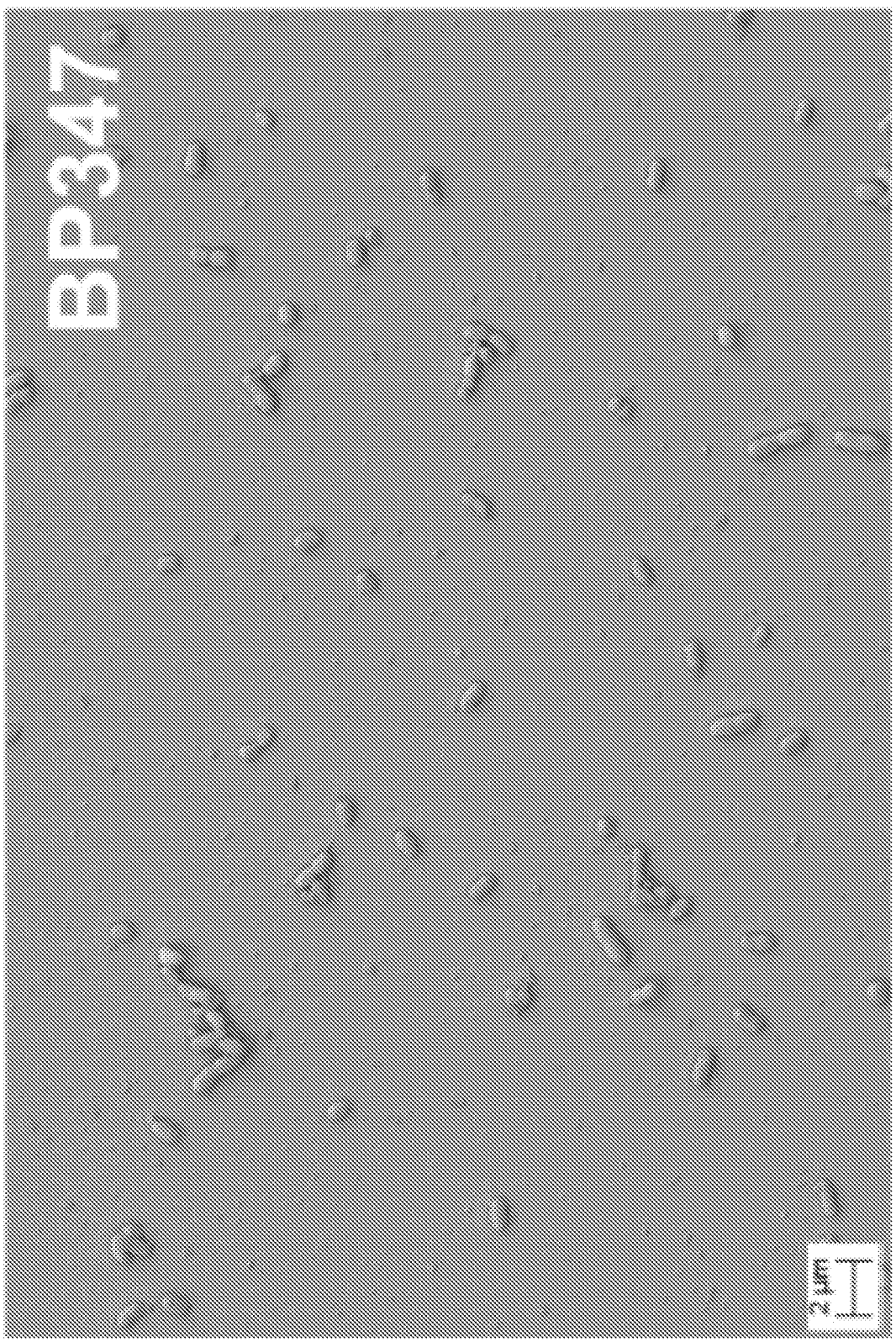
Figure 12C:
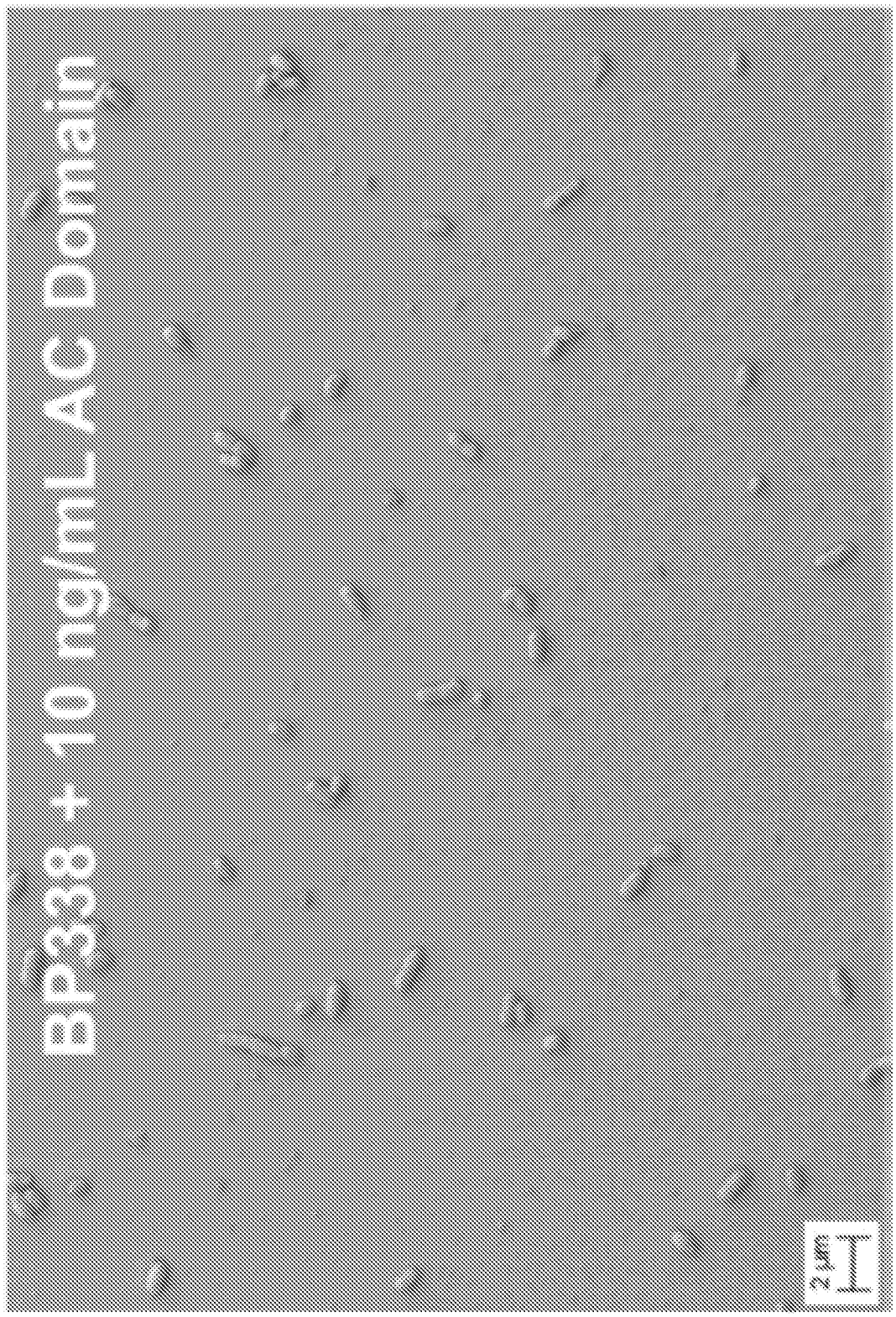

12C illustrate the dramatic effects of AC domain under these conditions. Wild-type BP338 (FIG. 12A) and Bvg(-) BP347 (FIG. 12B) biofilm were compared to BP338 grown in the presence of 10 ng/ml AC domain (FIG. 12C). The exogenous AC domain precluded biofilm accumulation on glass coverslips, such that BP338 plus AC domain was equivalent to the negative control, BP347. In the images of BP347 and BP338 plus AC domain, there were few bacteria adherent to the coverslip. The lack of bacterial accumulation under these conditions suggested a defect in the initial binding of bacteria, which then impairs subsequent biofilm accumulation. Thus, the initial step of binding to the abiotic surface would be one determinant of the ability of B. pertussis to produce robust biofilm.

Example 3

Figure 13A:
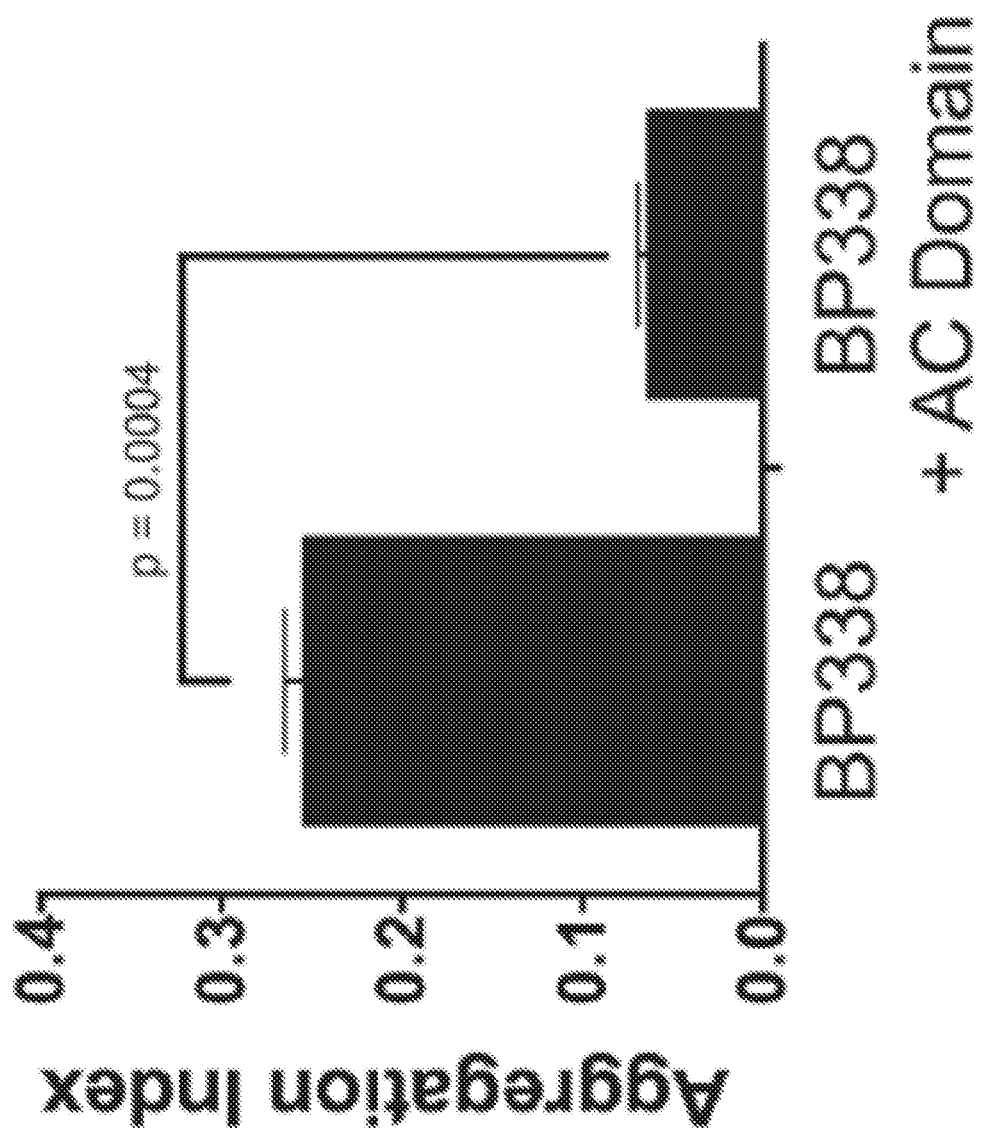
FIGS. 13A and 13B are graphs showing that exogenous AC domain inhibited bacterial aggregation and disrupted preformed biofilm, respectively.

AC Domain Inhibits Bacterial Aggregation and Disrupts Preformed B. pertussis Biofilm To address the underlying mechanisms of ACT inhibition of biofilm, other steps in the biofilm life cycle were tested for susceptibility to ACT inhibition. Bacterial aggregates form in shaking culture and positively correlate with biofilm formation in many bacterial species (Sorroche et al., 2012; Kragh et al., 2016). Exogenous AC domain was added to growing cultures of B. pertussis and the aggregation index was determined at 24 hours, as previously described for B. pertussis (Arnal et al., 2015). Exogenous AC domain decreased bacteria aggregation by 75% (FIG. 13A).

Figure 13B:
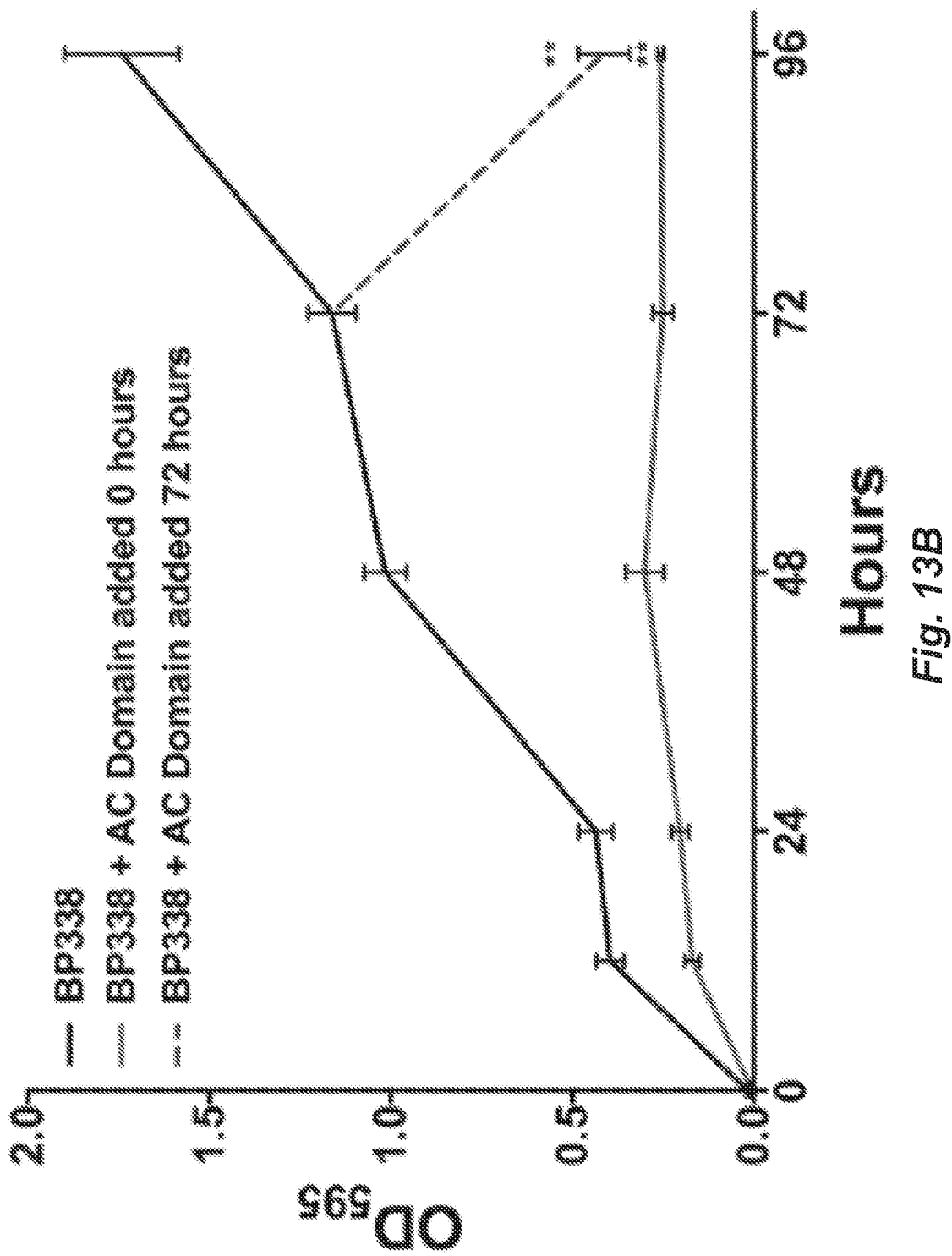

The final stages of the biofilm lifecycle involve dispersal of the bacteria from the biofilm structure. In order to investigate further the regulatory effect of ACT on biofilm, the effect of AC domain when added to existing biofilm was tested. FIG. 13B shows the time course of biofilm formation in the presence (gray line) and absence of AC domain (black line). When AC domain was added to BP338 biofilm at 72 hours post-inoculation and measured 24 hours later (96 hours), biofilm formation was reduced 76% (dotted line) compared to BP338 alone at 96 hours, resulting in quantities comparable to biofilm formed in the continuous presence of AC domain (gray line). This disruption of existing biofilm did not occur when full-length ACT was added at 72 hours. Although the mechanism of disruption is unknown, it appeared that the lack of effect of ACT was due to limitations in the ability of the large hydrophobic protein to access the necessary site(s) within the biofilm. Collectively, these data suggested that ACT played several roles in regulation of Bordetella biofilm, not only during the initial steps, but also during later stages.

Example 4

The Inhibition of Biofilm Formation by ACT was Specific

Figure 14:
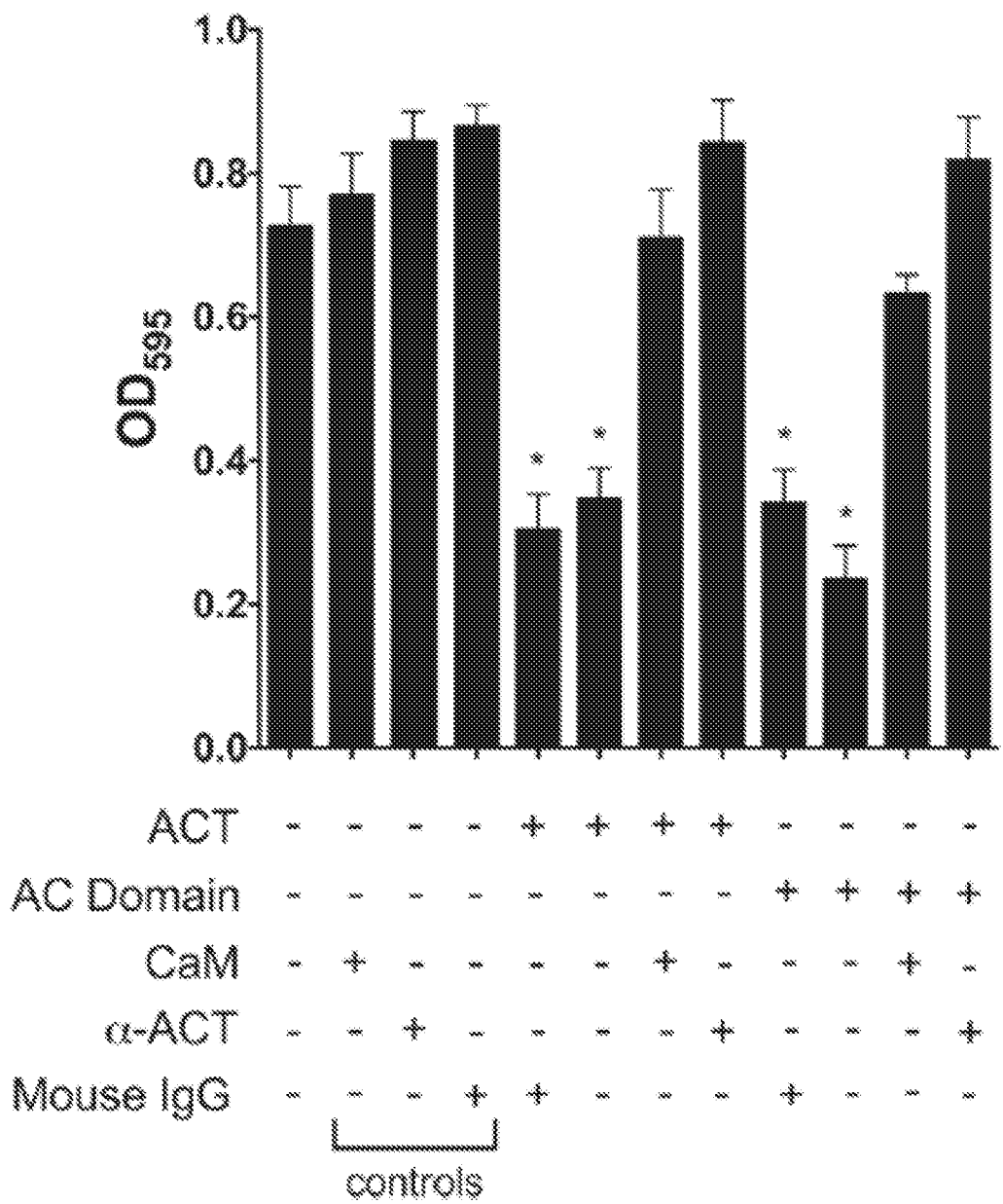
FIG. 14 is a bar graph showing that CaM and anti-ACT antibodies blocked ACT inhibitory effects. Calmodulin (1 μM) was incubated with ACT (100 ng/ml, 565 μM) or AC domain (10 ng/ml, 0.233 μM) for 15 minutes before adding the combination to BP338 cultures. ACT and AC domain alone were also incubated for 15 minutes prior to addition to bacterial cultures. Monoclonal antibody 7CE4B1 directed against the AC domain (described in Lee et al., 1999 but produced by the instant co-inventors; 2.4 mg/ml) was incubated with ACT or AC domain for 15 minutes before adding the combination to cultures in 96 well microtiter plates. Mixtures as indicated were added to bacterial cultures and biofilm formation was measured at 96 hours by crystal violet assay. Data are expressed as the mean±two (2) standard deviations, compiled from 3 experiments run in triplicate. *p<0.05 compared to wild-type. +: component added; −: component not added.

To characterize the inhibitory effects of exogenous ACT and AC domain on B. pertussis biofilm formation, molecules that interact with ACT were tested for their abilities to affect ACT-mediated inhibition. Calmodulin (CaM) binds the AC domain of ACT with high affinity ($K_d$~2 nM) and activates its enzymatic activity (Guo et al., 2005). It has been previously demonstrated that addition of CaM to ACT, prior to incubation with cells, blocks translocation of the AC domain into the cell cytosol, thereby precluding cAMP production (Mouallem et al., 1990; Gray et al., 2001). In the present studies, purified ACT or AC domain and CaM were combined before addition to bacteria. Under these conditions, a molar excess of CaM prevented the inhibitory effect of ACT or AC domain on biofilm formation (FIG. 14). Similarly, an antibody directed against the catalytic domain of ACT blocked the inhibitory effects of ACT and AC domain on biofilm (FIG. 14). The fact that CaM or an antibody blocked the inhibitory effect of ACT suggested the possibility that CaM caused a disruption of a physical interaction between ACT and another bacterial factor, such as filamentous haemagglutinin (FHA), which is involved in biofilm formation.

Example 5

The AC Domain Interacted with FHA

In a B. pertussis mutant lacking FHA, ACT is present in the media as opposed to remaining surface-associated (Weiss et al., 1983) and ACT interacts with FHA on the surface of bacteria (Zaretzky et al., 2002). These data suggested the possibility that ACT directly interacts with FHA to inhibit biofilm formation. In light of this collection of observations and the fact that AC domain was necessary and sufficient for inhibition of biofilm, the interaction of the AC domain with FHA was examined by surface plasmon resonance (SPR).

Figure 15:
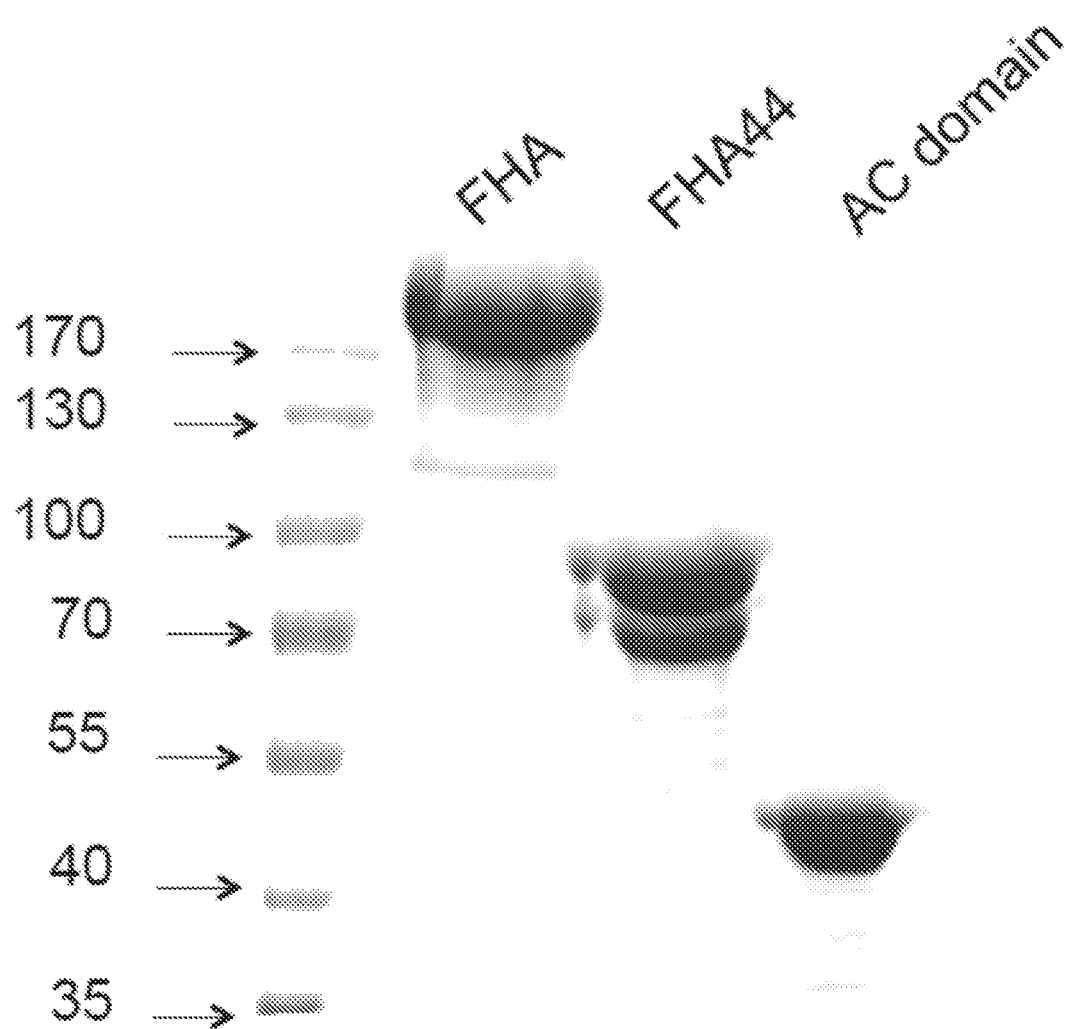
FIG. 15 is an image of a western blot of purified proteins used in SPR experiments. 10 μg of each protein were separated by 7.5% SDS-PAGE gel. Coomassie staining was used to visualize the purities of the proteins used in SPR experiments.
Figure 16A:
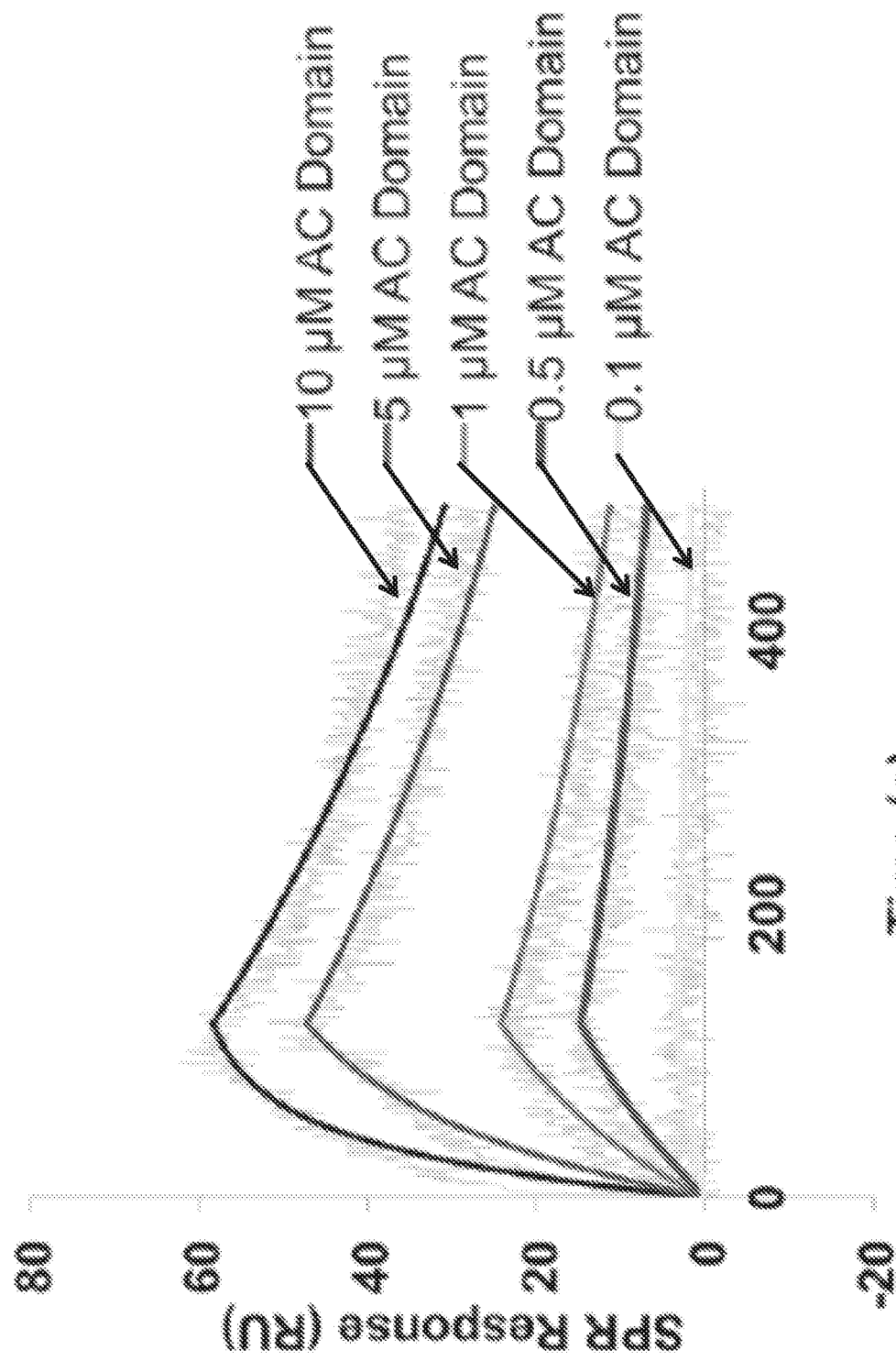
FIGS. 16A-16C are plots showing SPR kinetic binding analysis of the interaction between FHA and the AC domain of ACT. The recombinant AC domain at indicated concentrations was injected in parallel ("one-shot kinetics") over the sensor chip coated with purified FHA (FIG. 16A) or FHA44 (FIG. 16B) proteins at a flow rate of 30 μL/min for both association and dissociation phases of the sensogram. The kinetic data were fitted globally by using a 1:1 Langmuir model to obtain association [$k_a$=2.9±0.4×10$^3$ M$^{-1}$ s$^{-1}$] and dissociation [$k_d$=1.9±0.2×10$^{-2}$ s$^{-1}$] rate constants of the interaction. The equilibrium dissociation constant, $K_D$, was determined as $k_d/k_a$ and found to be 650 nM between AC domain and FHA. No binding was observed between AC domain and FHA44. The fitted curves are superimposed as lines on top of the binding curves. Representative data from a single experiment are shown.
Figure 16B:
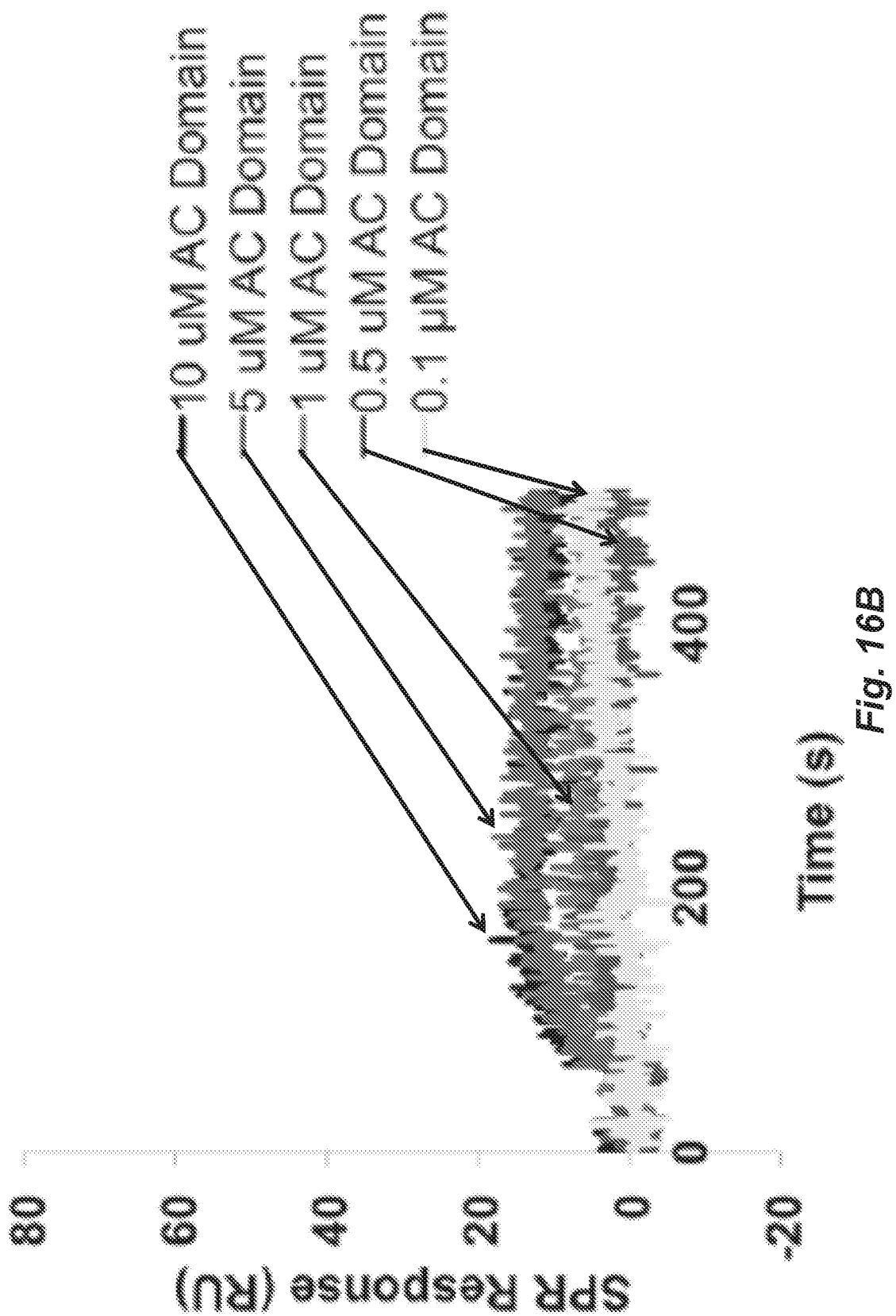

The FHA (~220 kDa) protein, purified from B. pertussis culture supernatant (FIG. 15), was immobilized on GLC sensor chip and real-time kinetics of the interaction of the recombinant AC domain with FHA was analyzed by parallel injection of diluted AC protein over the sensor chip surface at a constant flow rate of 30 µl/min (FIG. 16A). Interaction of the AC domain with FHA was specific, since negligible binding of the AC domain was observed to the chip coated with FHA44, a truncated FHA protein corresponding to residues 72-862 of FHA, which did not contain the c-terminal domain (FIG. 16B). Kinetic parameters of the AC-FHA interaction were calculated from global fitting of concentration-dependent binding curves. As shown in FIG. 16A, the binding curves fit well to a Langmuir-type binding model indicating a simple 1:1 interaction between the AC domain and FHA with equilibrium dissociation constant ($K_D$) of approximately 650 nM. These data suggested that the AC domain only interacted with FHA when the C-terminal segment was present.

Figure 16C:
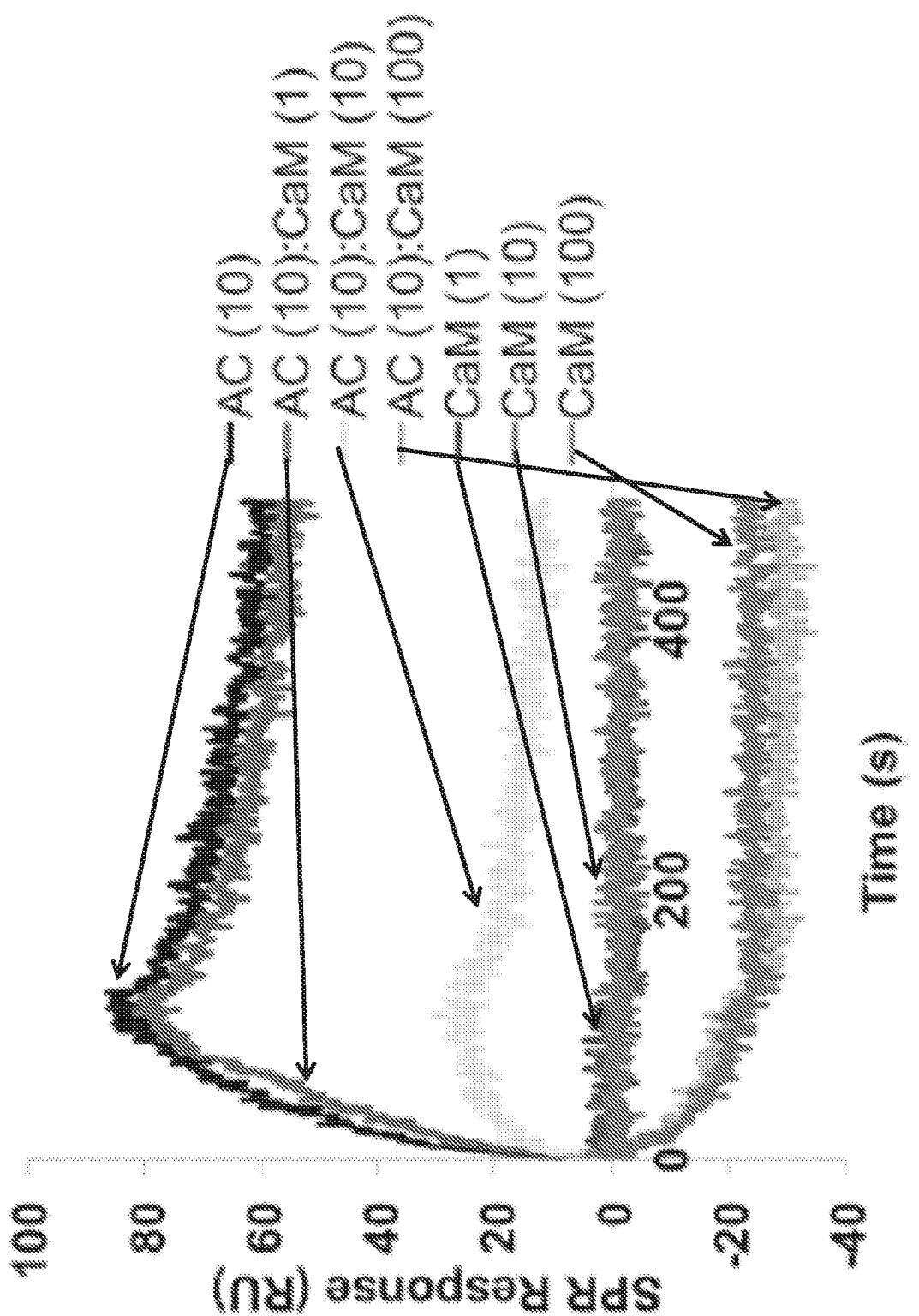

To complement the functional data which showed CaM blocked the inhibitory effects of AC domain on biofilm formation, AC domain was mixed with CaM in molar ratios of 10:1, 1:1 or 1:10 and the capacity of AC domain-CaM complex to interact with FHA was probed by SPR. As shown in FIG. 16C, binding of the AC domain to FHA in the presence of CaM (10:10) was reduced approximately 75% as compared to AC domain alone, suggesting that CaM and FHA competed for the same site on AC domain, or that CaM binding altered conformation of the AC domain thereby interfering with the ACT-FHA interaction. The data presented in FIG. 14 showed that an excess of CaM blocked AC domain inhibition of biofilm, and the data in FIG. 16C showed that equal molar ratios of AC domain:CaM reduced binding to FHA by 75%. Based on these data, it was hypothesized that the molar excess of CaM used in the biofilm assay blocked the inhibitory effects of ACT on biofilm formation by blocking the physical interaction between ACT and FHA.

In that the C-terminal portion of FHA was required for AC domain binding to FHA (FIG. 16B, FHA44), it was hypothesized that ACT and the AC domain would block specific antibody interactions with FHA. To test this hypothesis, an ELISA-based assay to characterize the interaction between ACT and the C-terminal segment of FHA was developed. Plates were coated with full length FHA and incubated with buffer, ACT, or AC domain over a range of concentrations (0.1-10 µg/ml), or $ACT_{\Delta AC}$ at 10 µg/ml. Monoclonal antibodies directed against the mature C-terminal domain (MCD) of FHA (residues 1870-2362) were used to determine the accessibility of the C-terminal segment of FHA. This anti-MCD antibody has been used previously to detect FHA and study FHA processing (Mazar & Cotter, 2006; Noel et al., 2012), and was used in the experiments disclosed herein because it recognizes a large portion of FHA that was deleted from the truncated FHA44 mutant protein.

Figure 17:
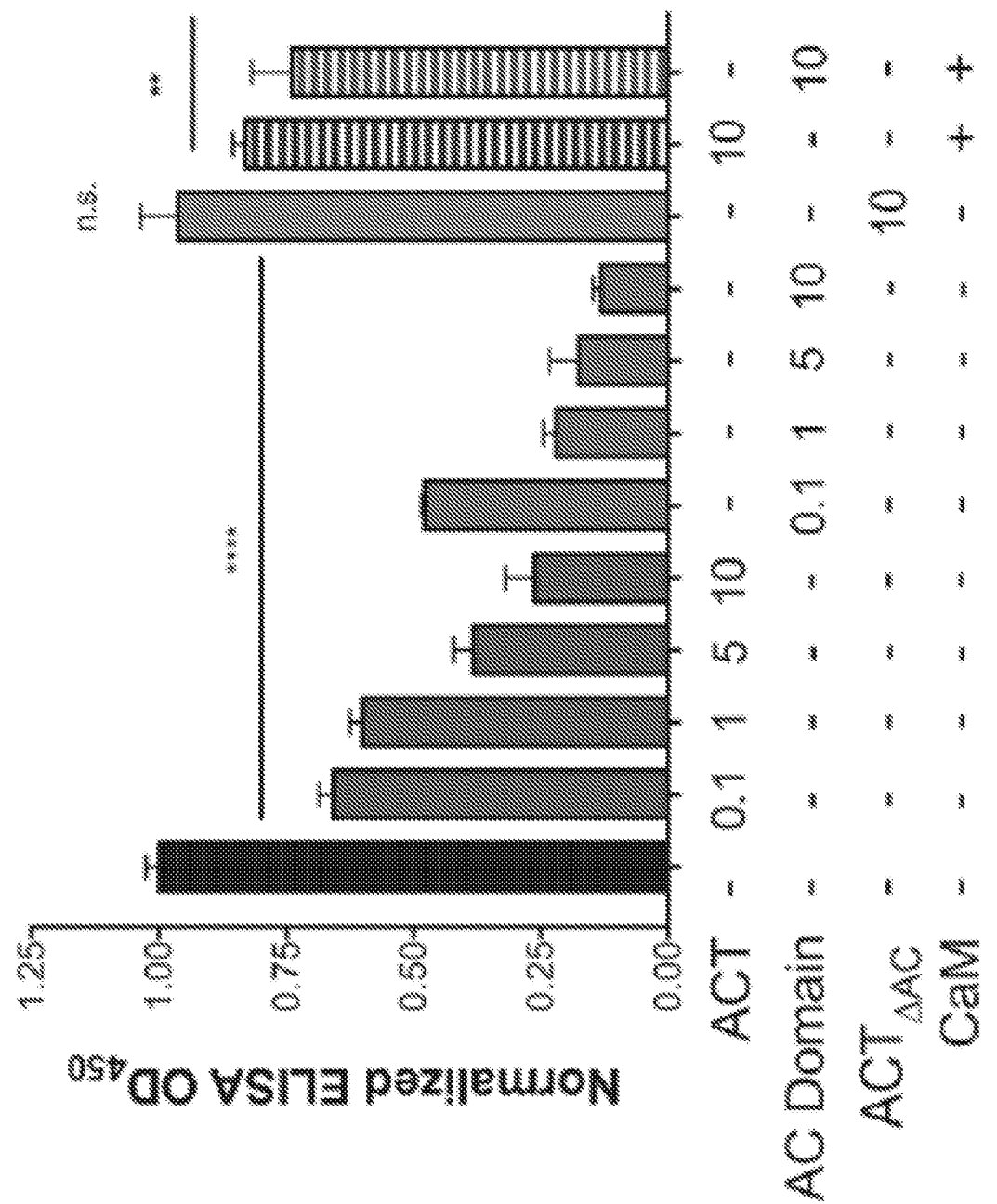
FIG. 17 is a bar graph showing that the AC domain and ACT inhibited MCD antibody binding to FHA. In an ELISA binding assay, plates were coated with FHA and an anti-MCD antibody was used as a detection reagent. ACT, AC domain, and $ACT_{\Delta AC}$, added at a range of mg/ml concentrations, were added prior to the addition of the anti-MCD antibody to determine if AC domain binding interfered with MCD antibody detection. In addition to these conditions, 10 μM CaM was incubated with the various concentrations of ACT or AC domain for 15 minutes prior to addition of ACT to the wells. All values were normalized to the control ($OD_{450}$ 0.284) using GraphPad Prism 6 software (GraphPad Software, Inc., La Jolla, Calif., United States of America). Data expressed as the mean±two (2) standard deviations, compiled from three experiments run in triplicate p<0.01 and **p<0.0001 compared to control.

The presence of ACT or AC domain blocked anti-MCD antibodies from binding to FHA (FIG. 17). Both ACT and the AC domain produced a concentration-dependent inhibition of anti-MCD antibody binding to FHA, but, in accordance with the earlier functional data on inhibition of biofilm, $ACT_{\Delta AC}$ had no effect (FIG. 17). Furthermore, incubation of ACT or the AC domain with CaM prior to addition to FHA-coated plates precluded them from blocking the binding of MCD antibody to FHA (striped bars; FIG. 17). Because the data regarding ACT inhibition of biofilm correlated with the physical binding of the AC domain and FHA, the consequences of their physical interaction were investigated to better understand the molecular mechanisms involved in biofilm inhibition.

In summary, the data presented in FIGS. 16A-16C demonstrated that with higher concentrations of the the AC domain, there was more of an SPR response recorded because more of the AC domain was binding the FHA-coated sensor chip.

Example 6

The MCD of FHA was Required for ACT Inhibition of Biofilm

FHA is delivered to the bacterial surface via a two-partner secretion pathway. This process involves translocation of FhaB, the FHA precursor, through FhaC, an FhaB-specific outer-membrane transporter (Fan et al., 2012). FhaB enters the FhaC channel as a hairpin and then begins folding in an N-to-C-terminal manner on the cell surface, creating a β-helical shaft (Mazar & Cotter, 2006; Mazar & Cotter, 2007). After the region distal to the β-helical shaft reaches the cell surface, the C-terminal prodomain is proteolyzed in the periplasm, creating the "mature C-terminal domain" (MCD), which is located on the distal portion of FHA (Noel et al., 2012).

To better understand the functional domains involved in ACT binding and inhibition of biofilm, B. pertussis and B. bronchiseptica mutants with altered secretion and processing of FHA were examined.

Figure 18B:
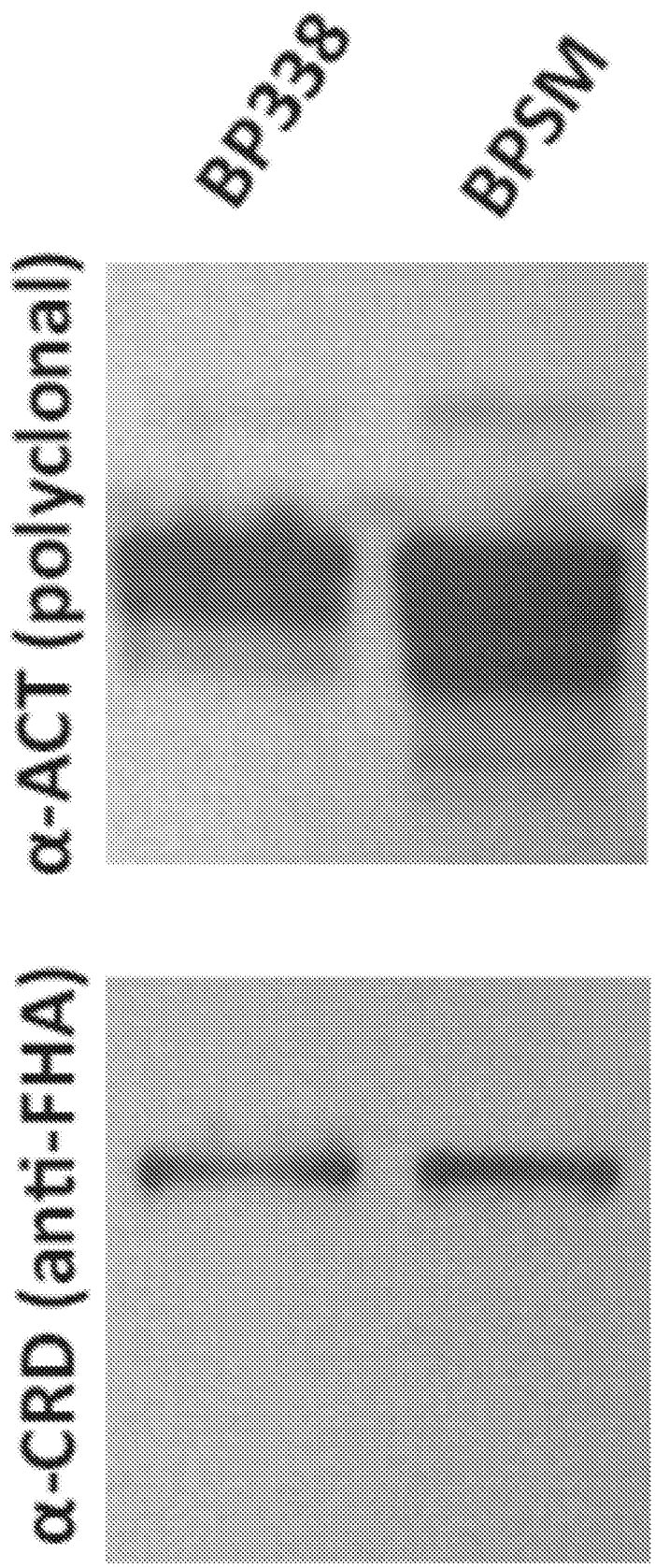
Figure 19A:
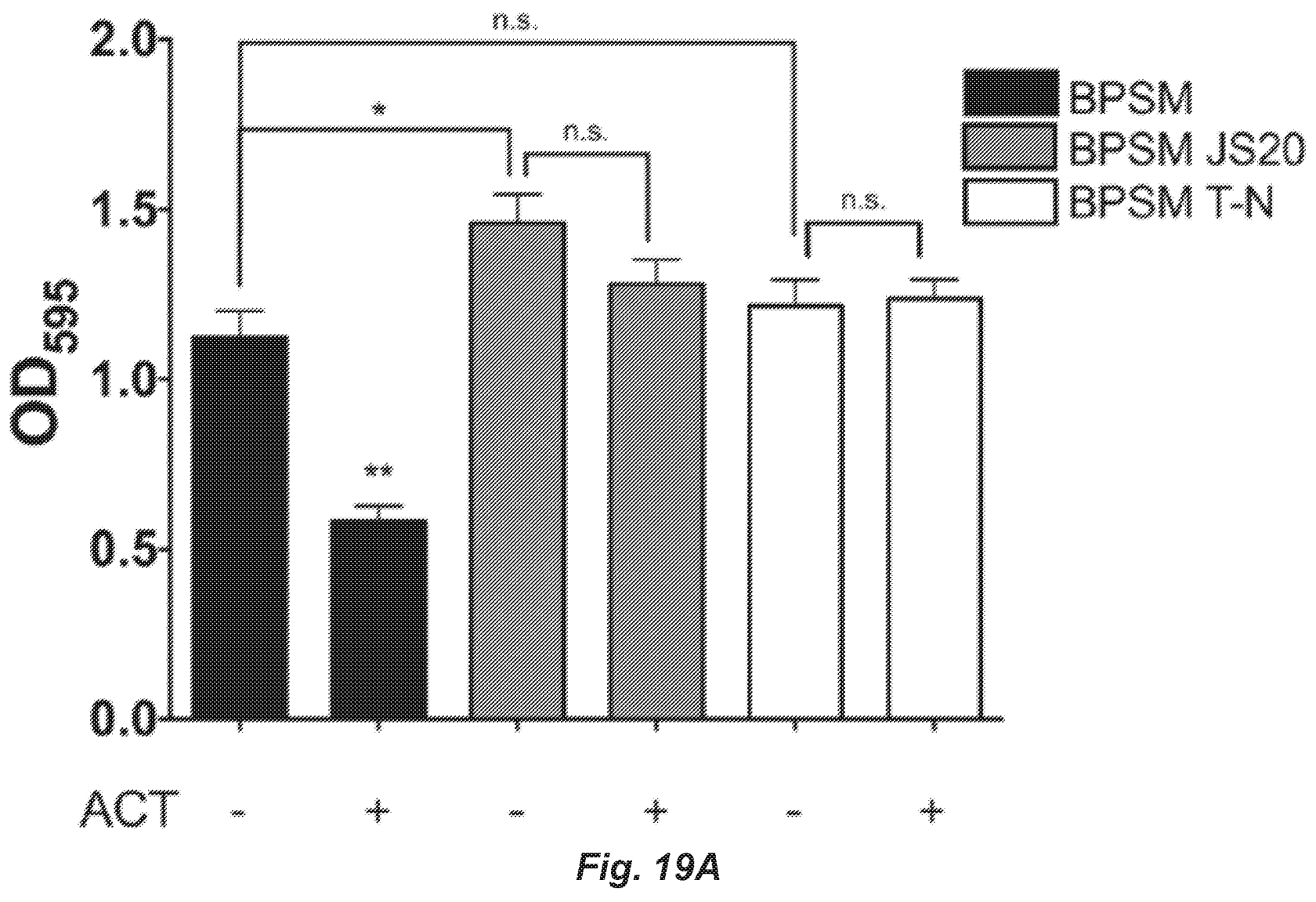
Figure 19B:
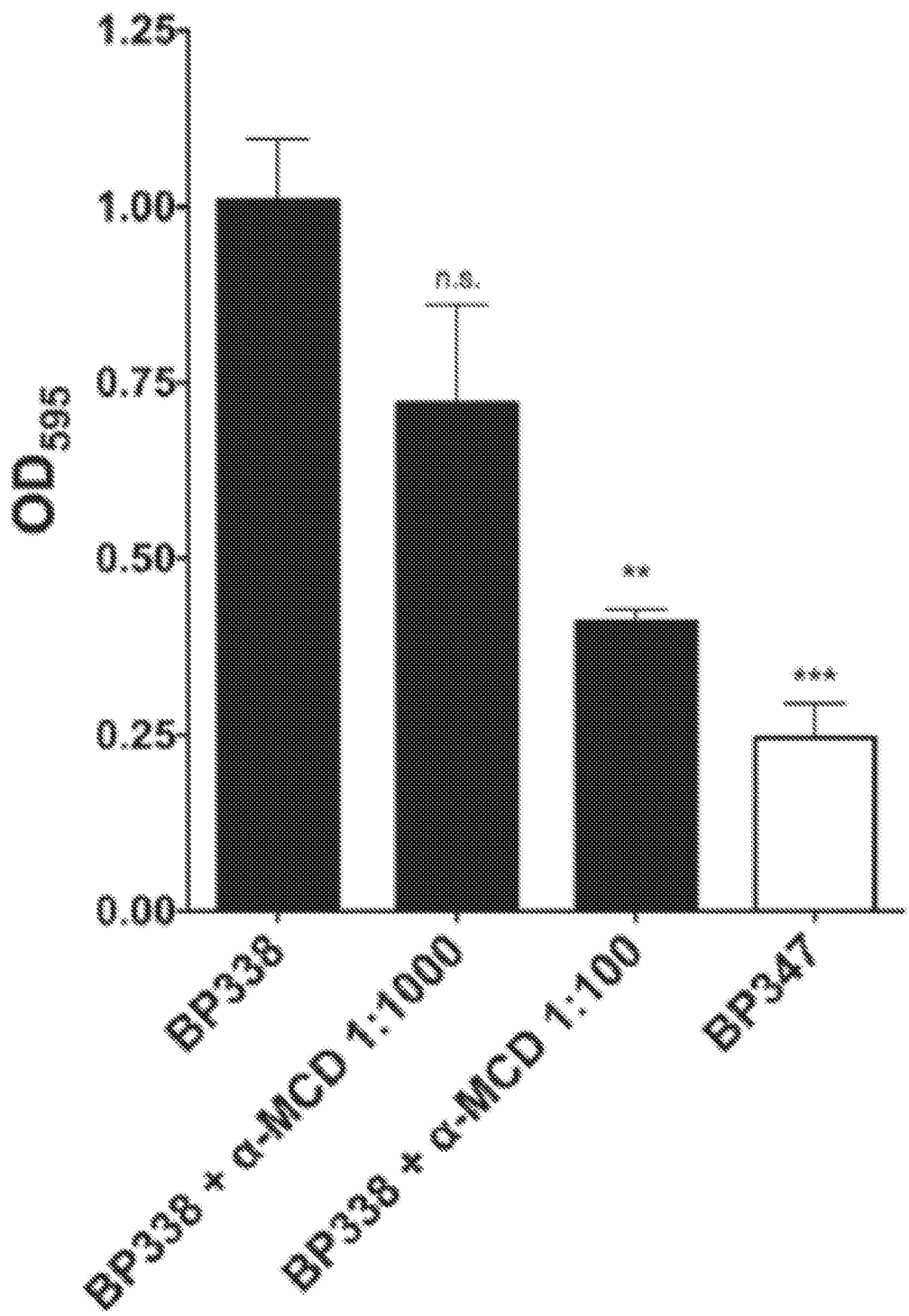
Figure 20:
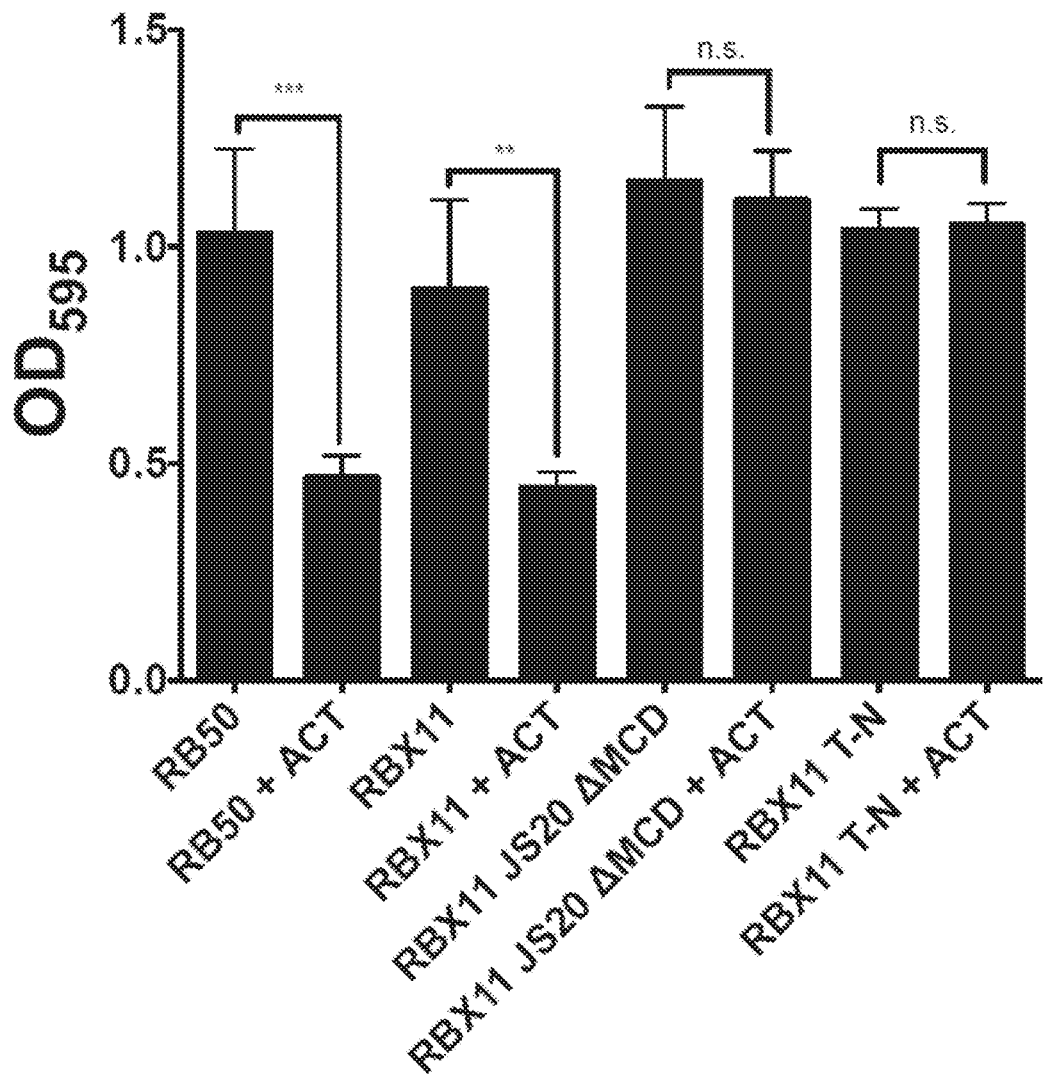
FIG. 20 is a bar graph showing that the MCD of FHA must be present and properly folded for ACT inhibition of *B. bronchiseptica* biofilm. FHA mutants were generated in the *B. bronchiseptica* RBX11 parent strain. RBX11 was derived from RB50; it is a ΔfhaS mutant. RBX11 JS20 (ΔMCD) had the entire MCD sequence deleted. RBX11 T-N had a transposon inserted into the prodomain sequence, precluding prodomain cleavage and processing of the MCD, leaving the MCD unfolded in the final FHA molecule. *B. bronchiseptica* strains were allowed to form biofilm for 96 hours in the presence or absence of ACT. Biofilm was measured by crystal violet assay. Data expressed as the mean±two (2) standard deviations, compiled from three (3) experiments run in triplicate. p<0.01 and *p<0.001 compared to wild-type (RB50). n.s.: not significant.

Since the MCD of FHA is required for AC domain binding (FIG. 16B), it was hypothesized that the MCD must be present in order for ACT inhibition to occur. A B. pertussis mutant lacking the MCD was assessed for biofilm formation in the presence and absence of ACT to determine the role of the MCD in the inhibitory process. BPSM JS20, a derivative of parental strain BPSM, produces a truncated FHA by virtue of deletion of the MCD and C-terminal prodomain and, is therefore, composed only of the β-helical shaft. BPSM and BPSM JS20 were grown in the presence and absence of ACT and biofilm formation was measured at 96 hours. wild-type BPSM formed biofilm that was susceptible to inhibition by ACT. Importantly, the BPSM isogenic strain and the BP338 isogenic strain, both of which are Tohama I derivatives, were compared for biofilm formation, ACT expression, and FHA expression. No significant differences were observed in biofilm formation between the parental wild-type strains (FIG. 18A). FHA protein expression was similar between the two strains, although there was slightly more ACT protein expression in BPSM (FIG. 18B). BPSM JS20 formed equivalent amounts of biofilm in the presence and absence of exogenous ACT (FIG. 19A) and made more biofilm than the parental BPSM strain in the absence of exogenous ACT. Without wishing to be bound by any theory, this might have been due to the inability of endogenous ACT to have an effect on BPSM JS20 biofilm. The equivalent BPSM JS20 mutant strain in B. bronchiseptica, which was derived from RBX11 and lacked the MCD and C-terminal prodomain, produced biofilm that was not inhibited by ACT (FIG. 20). Although the MCD was not required for biofilm formation, it appeared to be necessary for ACT-mediated inhibition of biofilm to occur. These data were consistent with the SPR results showing ACT did not bind FHA44, which lacks the MCD (FIG. 16B).

To validate the role of the MCD in ACT inhibition of biofilm, a mutant in which the MCD is improperly folded was tested. BPSM T-N, also derived from BPSM parental wild-type strain, contained a mutation in fhaB such that a stop codon was introduced in the region encoding the N-terminus of the prodomain. As a result, the MCD was present and located distally from the cell surface, but was not folded in its native conformation (Mazar & Cotter, 2006; Noel et al., 2012). BPSM T-N formed similar amounts of biofilm compared to BPSM, yet like BPSM JS20, ACT did not inhibit biofilm formation of this strain (FIG. 19A). The same was true for RBX11 T-N, the equivalent B. bronchiseptica strain with a misfolded MCD (FIG. 20). Although the MCD itself was not required for biofilm formation, the MCD of FHA had to be present and in the proper conformation for the inhibition of biofilm by ACT to occur. These data directly linked the ACT-FHA interaction to inhibition of biofilm by ACT in B. pertussis and B. bronchiseptica.

In light of the inhibitory effects of ACT and the fact that ACT and anti-MCD antibody both bound to the MCD, the ability of the anti-MCD antibody to block biofilm was tested. Indeed, when BP338 was grown in the presence of anti-MCD antibodies, there was a reduction in biofilm (FIG. 19B). These data suggested that the anti-MCD antibody might block biofilm formation in a similar manner to ACT, support the competition between the ACT and the anti-MCD antibodies for FHA binding, and corroborated previous studies showing that polyclonal antibodies directed against FHA blocked biofilm formation (Serra et al., 2011). It is thus clear that the MCD of FHA played a part in inhibition of biofilm. When binding partners, either anti-MCD antibodies or the AC domain, were present, biofilm formation was inhibited.

Example 7

ACT and the AC Domain Inhibit Pseudomonas aeruginosa Biofilm Formation

Figure 4A:
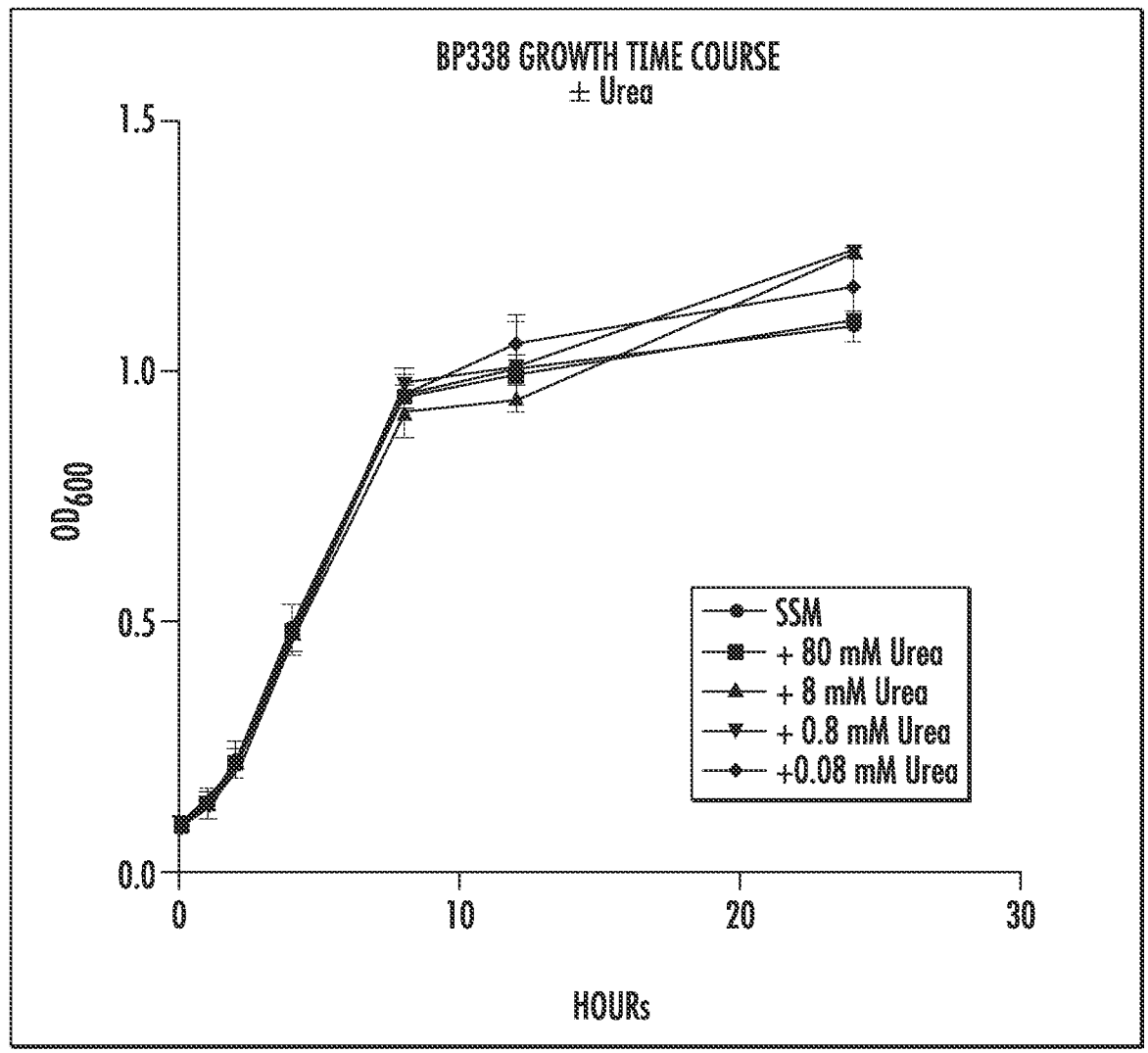
FIGS. 4A and 4B are growth time course plots for B. pertussis strains.
Figure 4B:
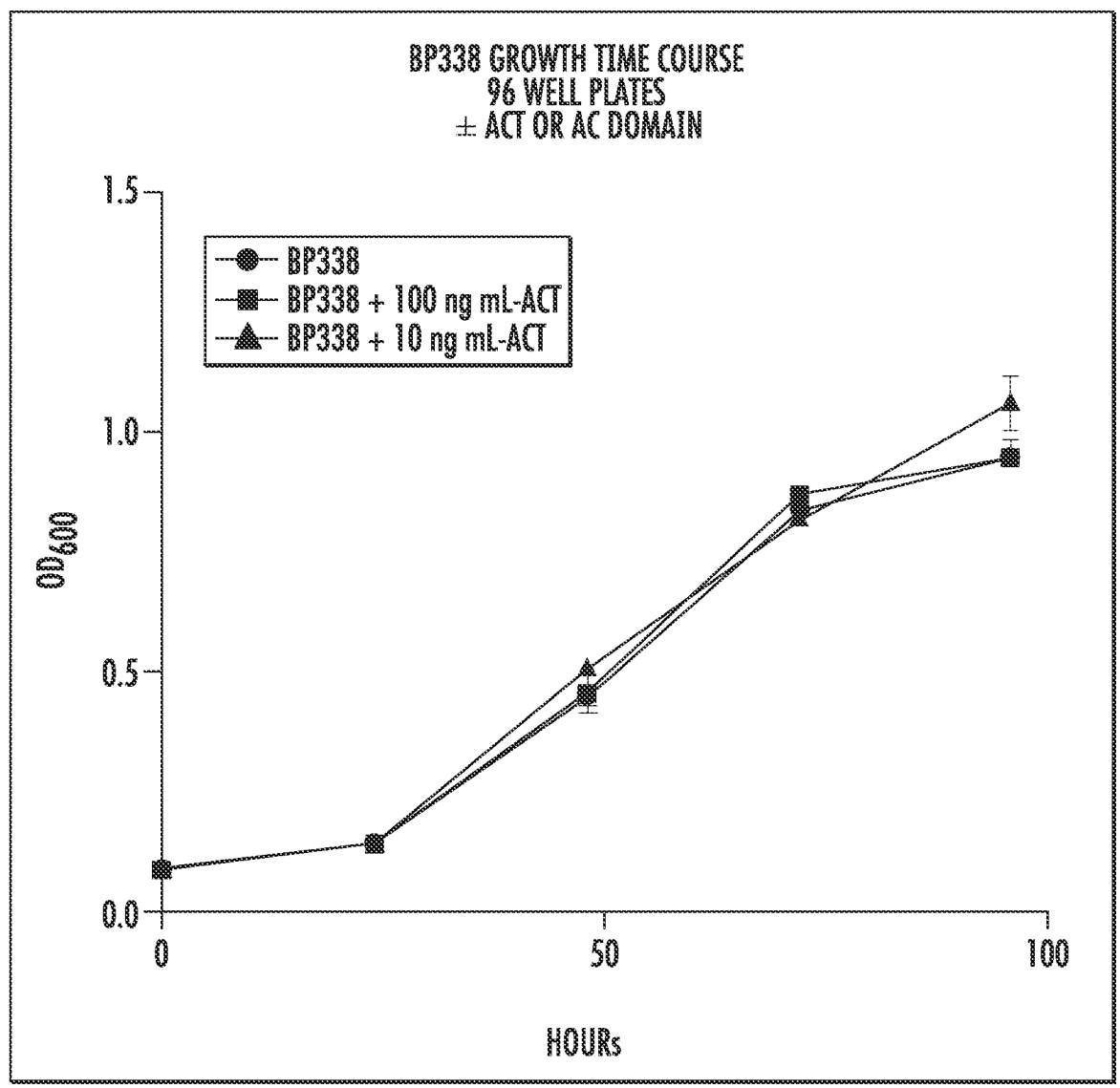
Figure 5:
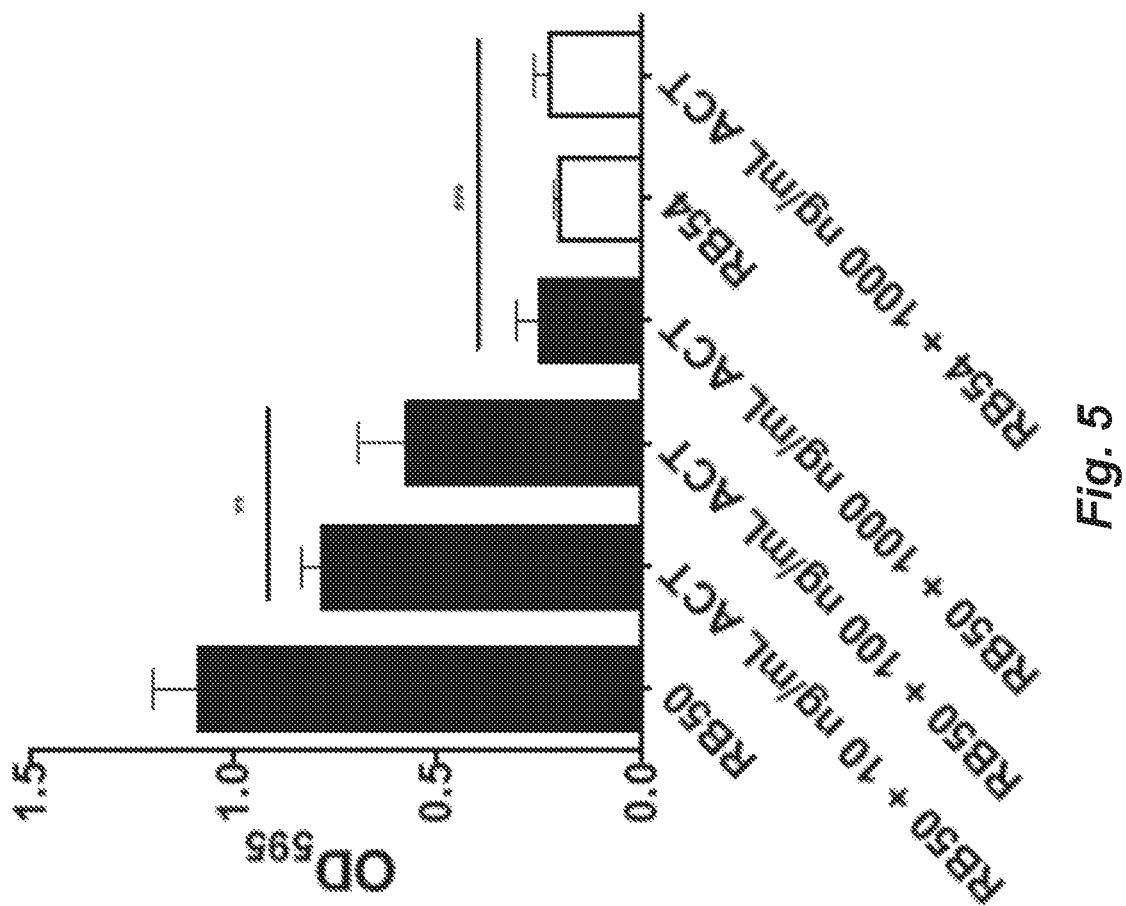
FIG. 5 is a bar graph showing that ACT inhibited B. bronchiseptica biofilm in a concentration-dependent manner. wild-type RB50 biofilm formation in the presence of increasing concentrations of recombinant purified ACT (10, 100, or 1000 ng/ml) for 96 hours. Biofilm formation was measured by crystal violet assay. Bvg(−) RB54 strain served as negative control. Data expressed as the mean±two (2) standard deviations, compiled from 3 experiments run in triplicate. $p<0.01$ and *$p<0.001$ compared to wild-type without ACT.
Figure 6:
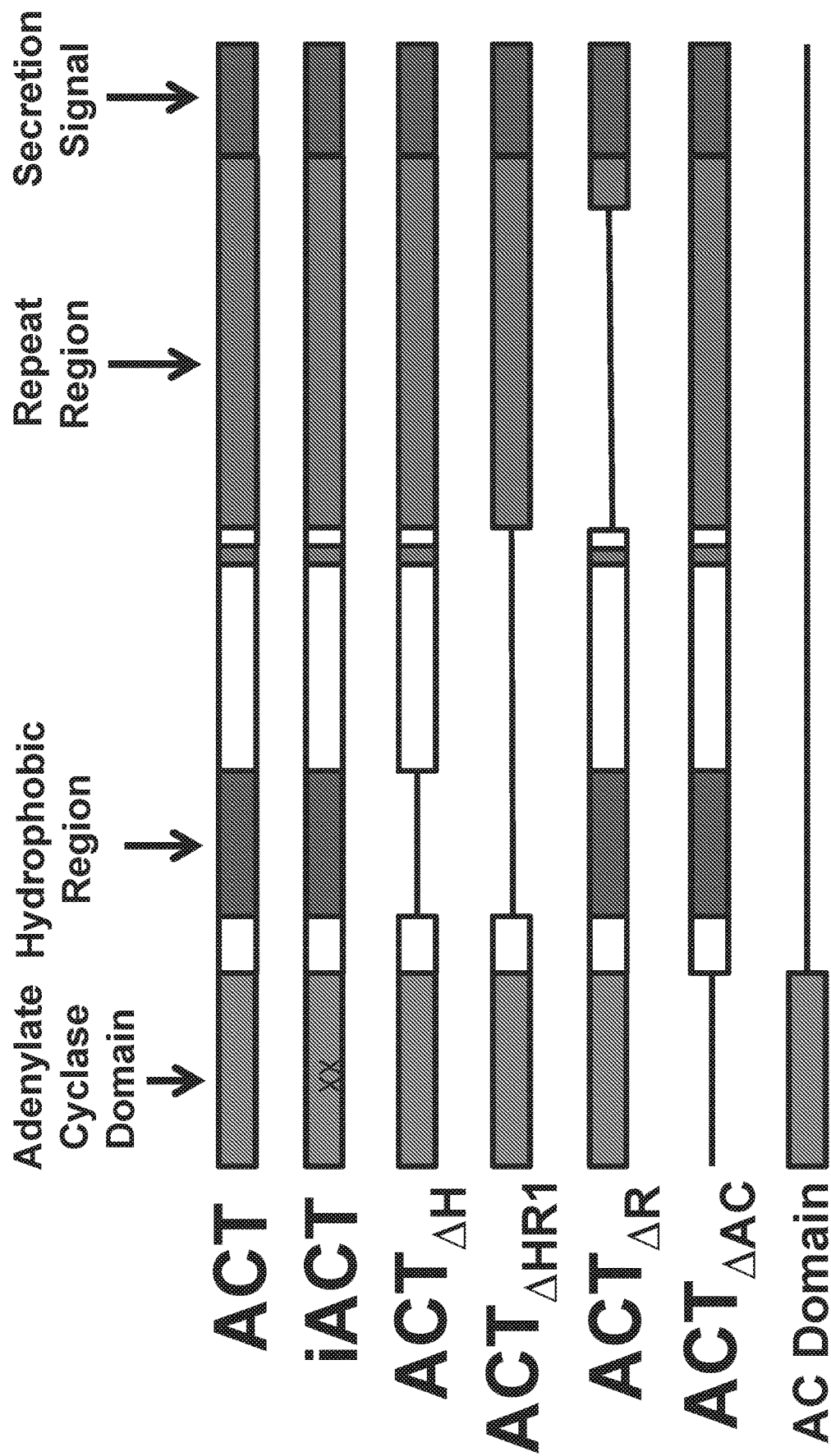
FIG. 6 is a series of schema of ACT truncated and enzymatically inactive mutant proteins.
Figure 7:
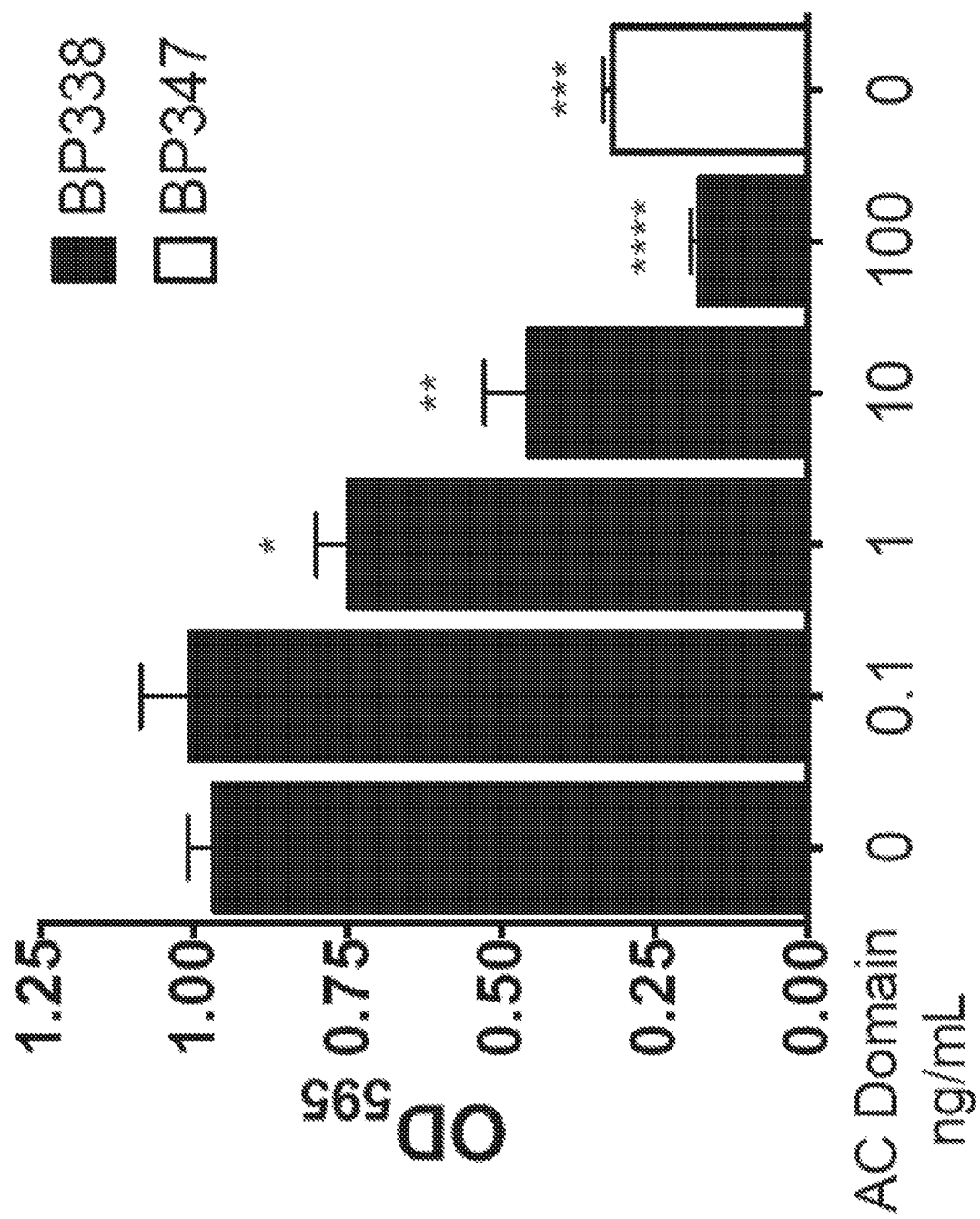
FIG. 7 is a bar graph showing that the AC domain inhibited biofilm in a concentration-dependent manner. BP338 biofilm formation in the presence of increasing concentrations of recombinant purified ACT (10, 100, or 1000 ng/ml) for 96 hours. Biofilm formation was measured by crystal violet assay. Bvg(−) strain served as negative control. Data expressed as the mean±two (2) standard deviations, compiled from 3 experiments run in triplicate. *p<0.05; p<0.01; *p<0.001; ****p<0.0001 compared to wild-type without ACT.
Figure 8:
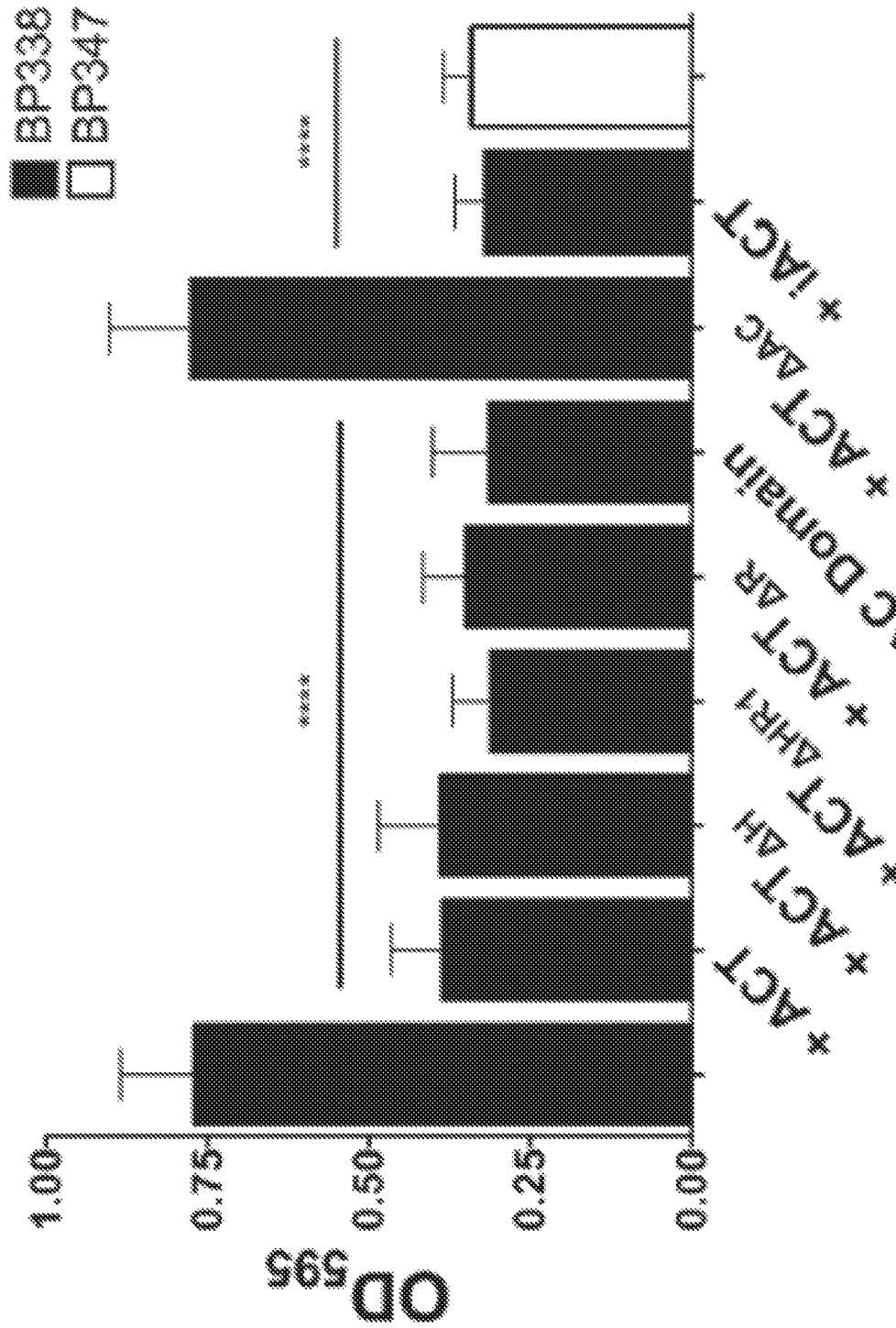
FIG. 8 is a bar graph showing that the AC domain was necessary and sufficient for biofilm inhibition, although the catalytic activity of ACT was not required. ACT, iACT or other ACT mutant proteins were added to wild-type BP338 and biofilm formation was measured by crystal violet assay at 96 hours. AC domain was added at 10 ng/ml and additional ACT proteins including ΔH, ΔHR1, ΔR, and ΔAC (see FIG. 6) were all added to a final concentration of 100 ng/ml. Data are expressed as the mean±two (2) standard deviations, compiled from 3 experiments run in triplicate. ***P<0.0005 compared to wild-type BP338 without ACT.
Figure 9:
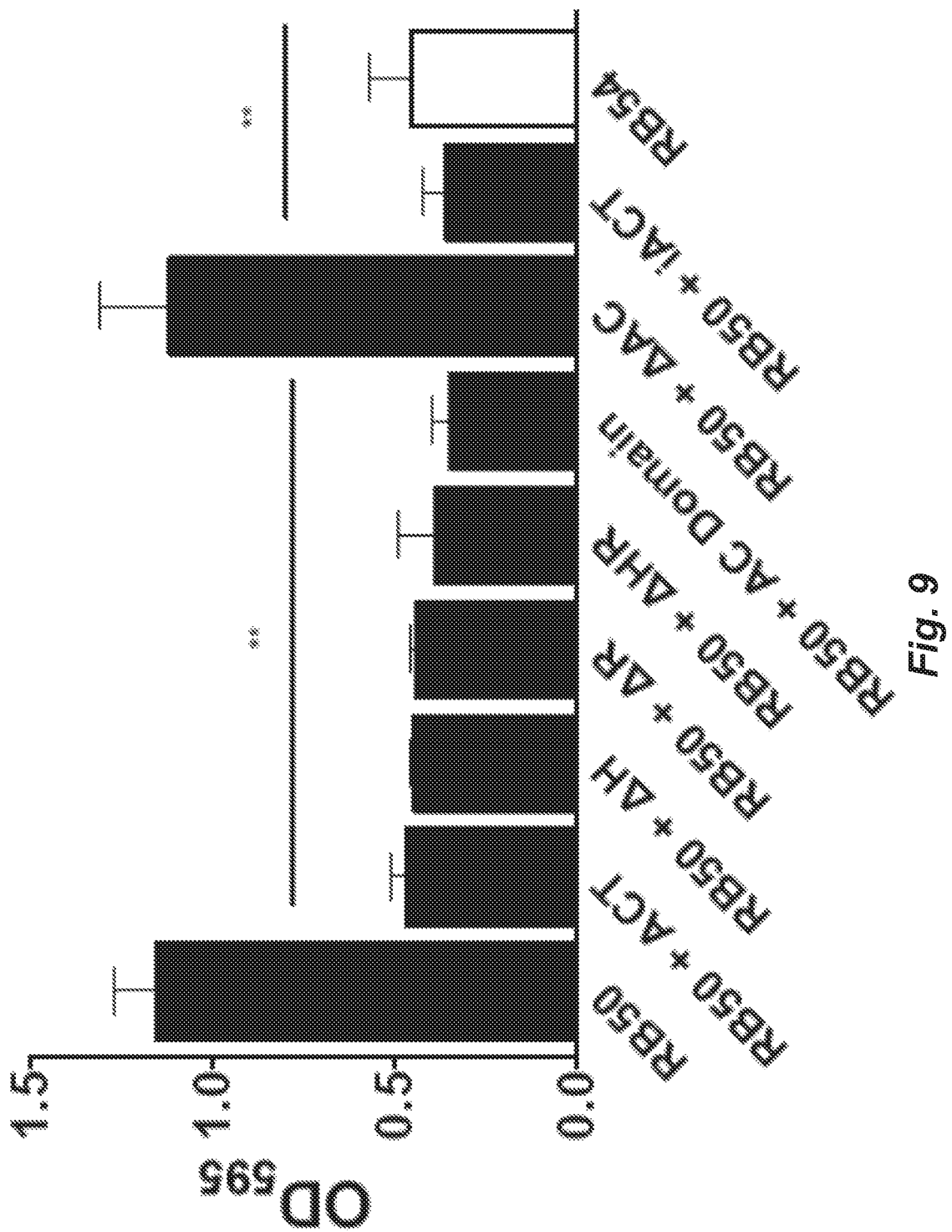
FIG. 9 is is a bar graph showing that the the AC domain was necessary and sufficient for *B. bronchiseptica* biofilm inhibition, although the catalytic activity of ACT was not required. ACT, iACT, or other ACT-truncated mutant proteins were added to RB50 and biofilm formation was measured by crystal violet assay at 96 hours. AC domain was added at 10 ng/ml and additional ACT proteins including ΔH, ΔHR1, ΔR, and ΔAC were all added to a final concentration of 100 ng/ml. Bvg(−) RB54 strain served as negative control. Data are expressed as the mean±two (2) standard deviations, compiled from 3 experiments run in triplicate. **p<0.01 compared to wild-type RB50.
Figure 10:
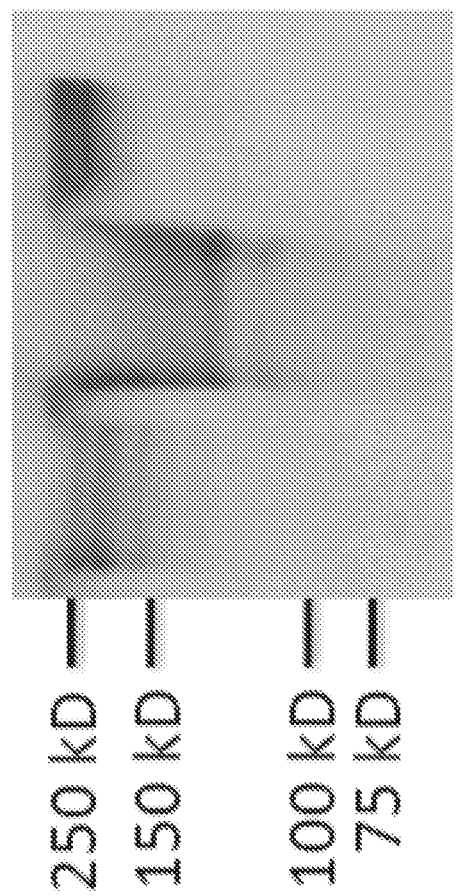
FIG. 10 shows an image of a western blot of BP338 ΔAC, which provided confirmation of deletion of AC domain and presence of truncated ACT peptide. Bacterial strains were grown 48 hours on BG plates at 37° C., transferred to 10 mL shaking SSM cultures, and grown for 24 hours. At 24 hours samples were taken and the $OD_{600}$ of each sample was matched. Samples were boiled 5 minutes and 30 μl of the sample was loaded per well. 1 μg of ACT was loaded. A western blot was performed using a polyclonal ACT antibody (see Lee et al., 1999).
Figure 11:
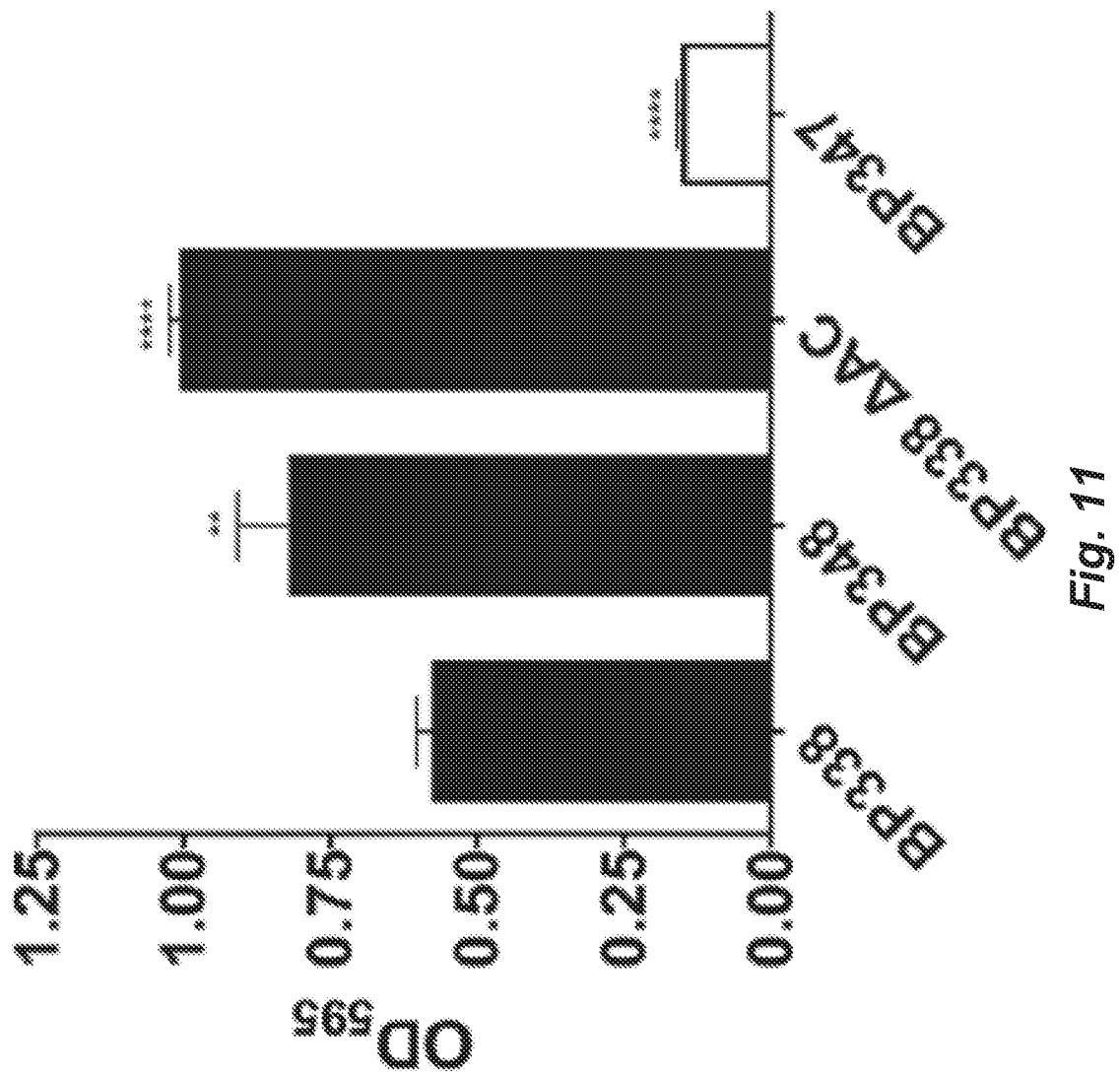
FIG. 11 is a bar graph showing that BP338 lacking the AC domain (BP338 ΔAC) made more biofilm than the parental wild-type strain. Strains were grown in 96 well microtiter plates and biofilm formation was assessed using the crystal violet assay at 96 hours. Mean values represented by bars, error bars represent standard deviations. A Bvg(−) strain served as a negative control. Data are expressed as the mean±two (2) standard deviations, compiled from 3 experiments run in triplicate. p<0.01 and **p<0.0001 compared to wild-type.

Although there are multiple bacterial species that express FHA-like proteins, P. aeruginosa is one of the best-studied biofilm forming bacteria due to its prevalence in Cystic Fibrosis and wound infections. P. aeruginosa biofilm was selected for testing because the FHA-like protein, CdrA, is involved in biofilm formation, and because of the striking structural homology between P. aeruginosa CdrA and Bordetella FHA (compare FIG. 1 of Borlee et al., 2010 with FIG. 4 of Kajava et al., 2001).

Figure 22A:
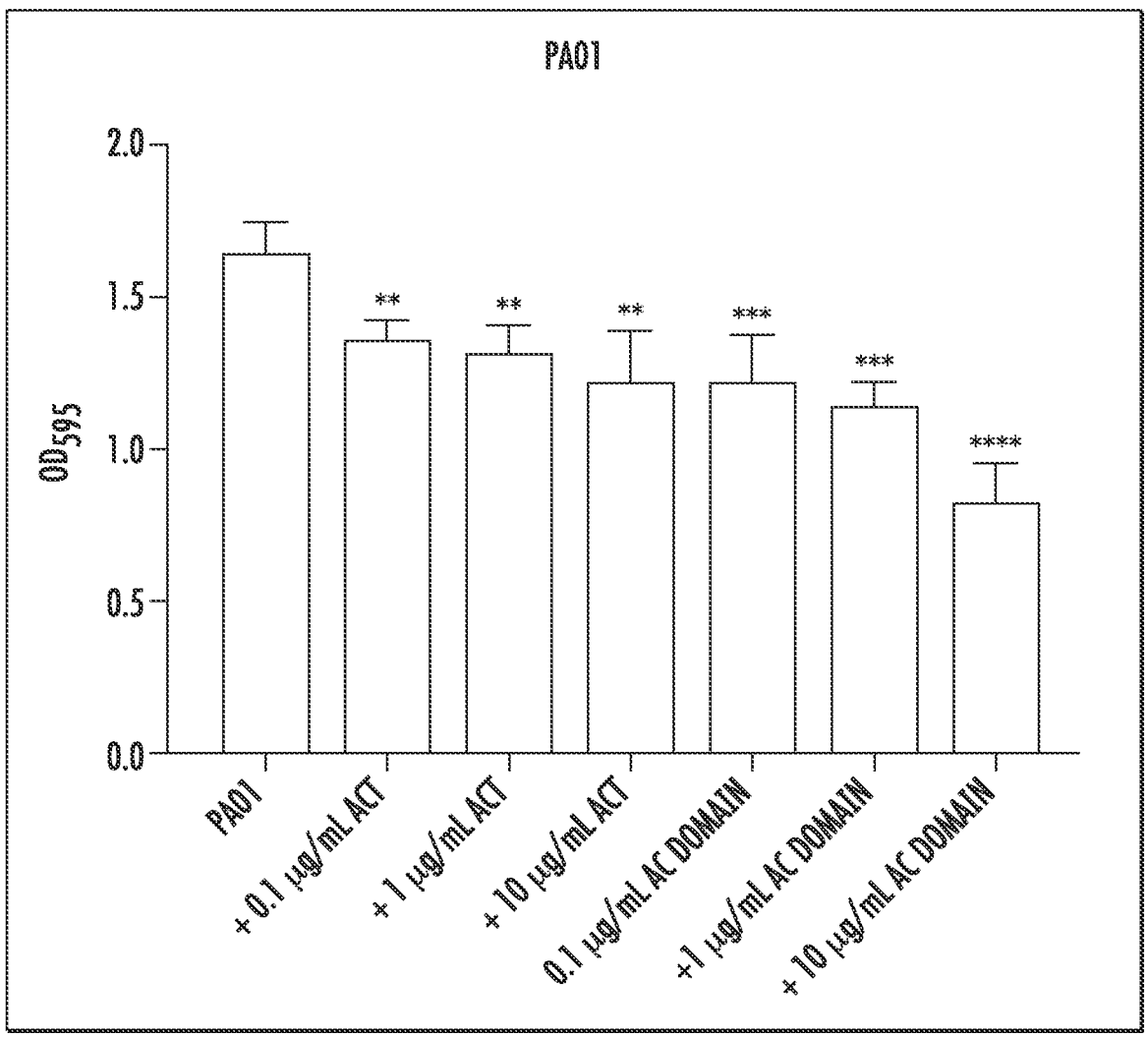
FIGS. 22A-22C are a series of graphs showing that ACT and AC Domain inhibited *P. aeruginosa* biofilm in a concentration-dependent manner.
Figure 22B:
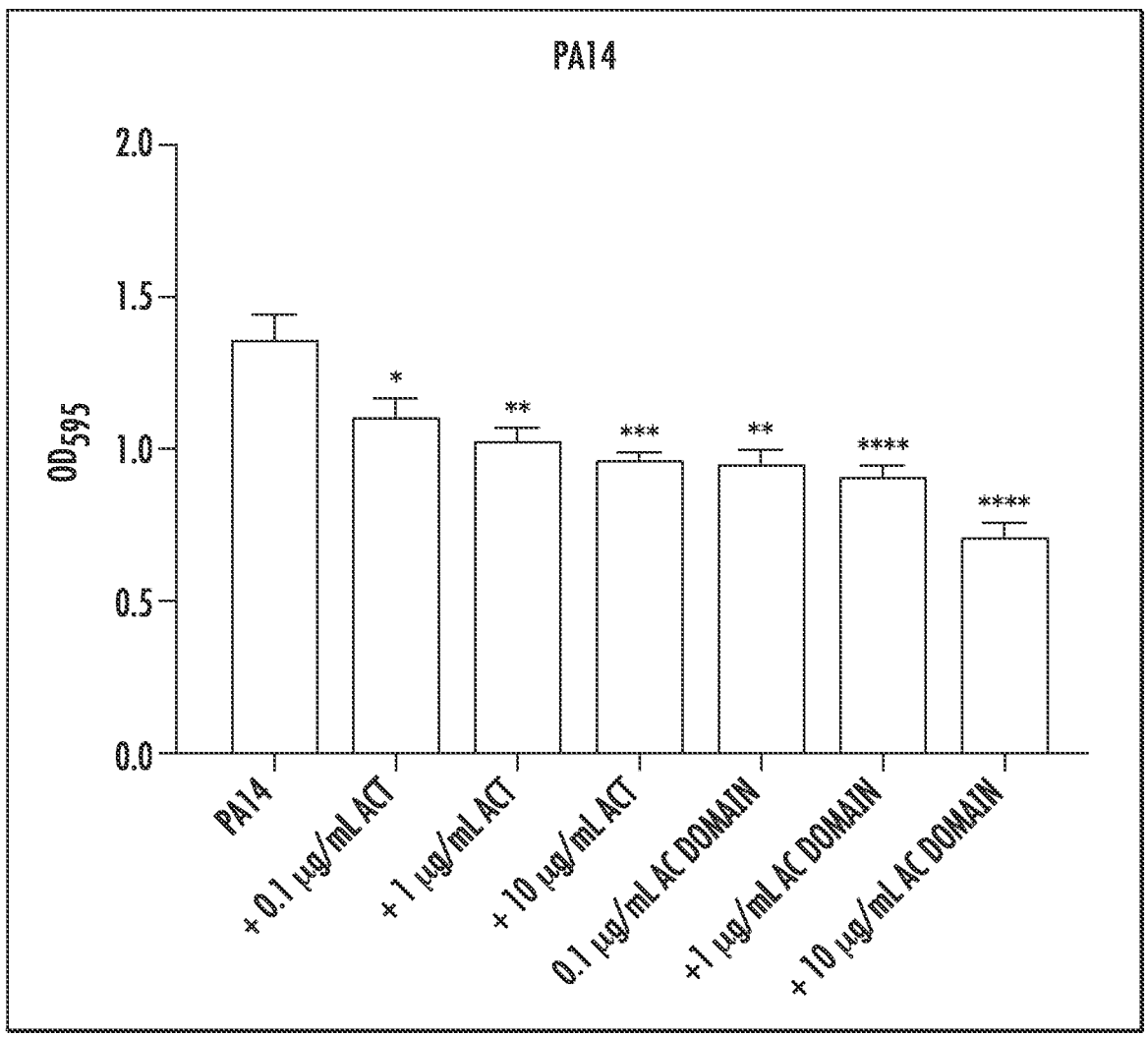

First, the ability of full-length holotoxin ACT to inhibit biofilm formation of *P. aeruginosa* was tested. Two lab-adapted parental strains were used: PA14 and PA01. Bacteria were grown over night as shaking cultures, and following procedures described for measuring biofilm in the microtiter assay for *P. aeruginosa*, bacteria were diluted to an $OD_{600}$ of 0.05 before inoculating 100 μL Luria Broth (LB) cultures in 96 well plates. Recombinant purified *B. pertussis* ACT was added exogenously to *P. aeruginosa* cultures at concentrations of 0.1, 1, and 10 μg/ml. Biofilm formation, or bacterial accumulation in wells, was determined at 12 hours by crystal violet assay as described herein above. A concentration-dependent inhibition of biofilm by ACT was observed in both PA01 and PA14 (FIGS. 22A and 22B; bars 5-7).

Figure 22C:
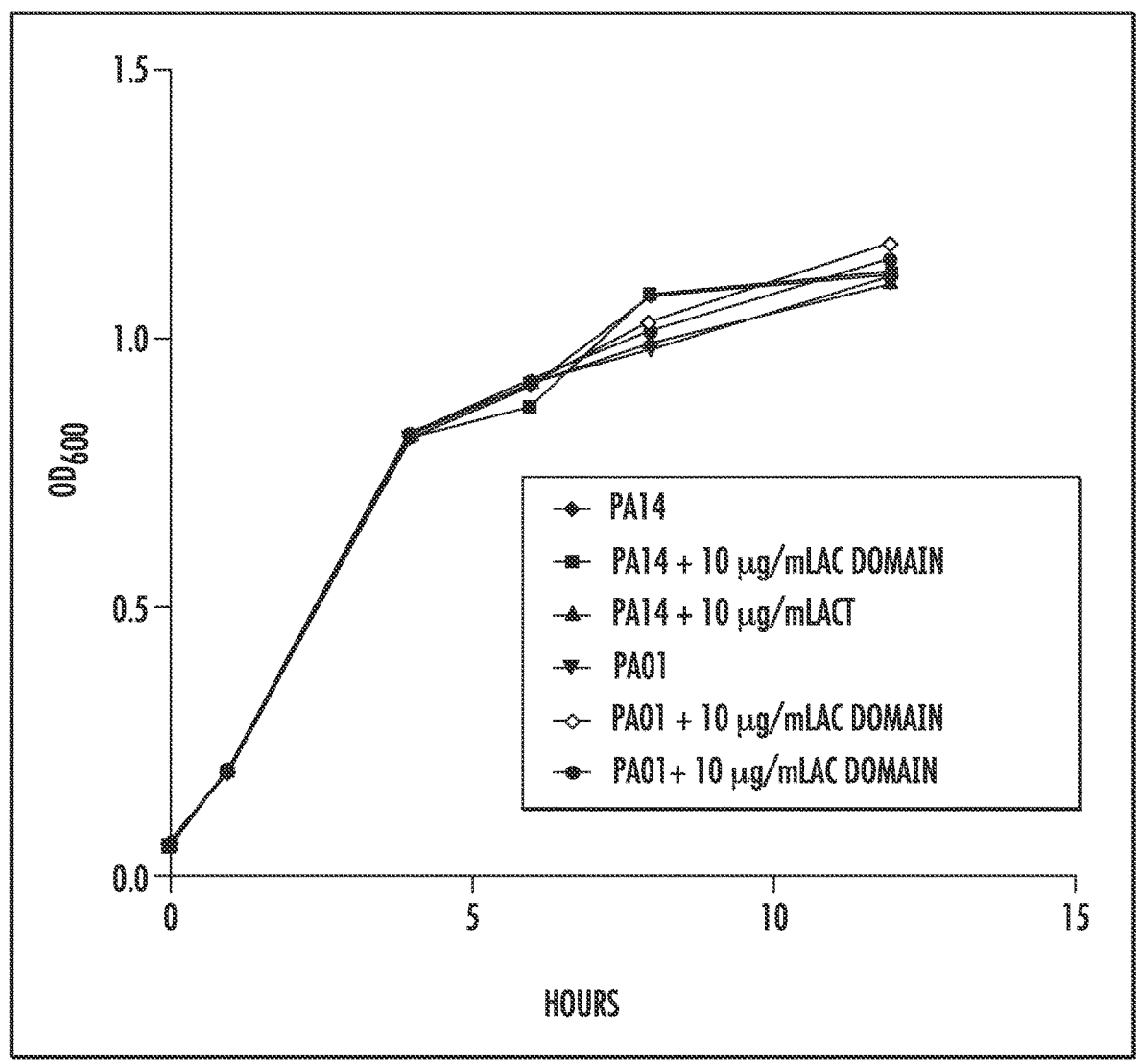

The ability of AC domain to inhibit biofilm was also tested, as the AC domain is necessary and sufficient for biofilm inhibition in Bordetellae. AC domain was added at 0.1, 1, and 10 μg/ml to PA01 and PA14 cultures in 96 well plates and biofilm formation was assessed at 12 hours using the crystal violet assay (FIGS. 22A and 22B; bars 2-4). The AC domain inhibited biofilm formation of both *P. aeruginosa* strains in a concentration-dependent manner. There were no observed differences in growth between PA14 or PA01 grown in the presence or absence of the highest concentration of ACT or AC domain (10 μg/ml), as measured by $OD_{600}$; ACT and the AC domain did not inhibit biofilm by altering growth rates under these conditions (FIG. 22C).

Figure 23:
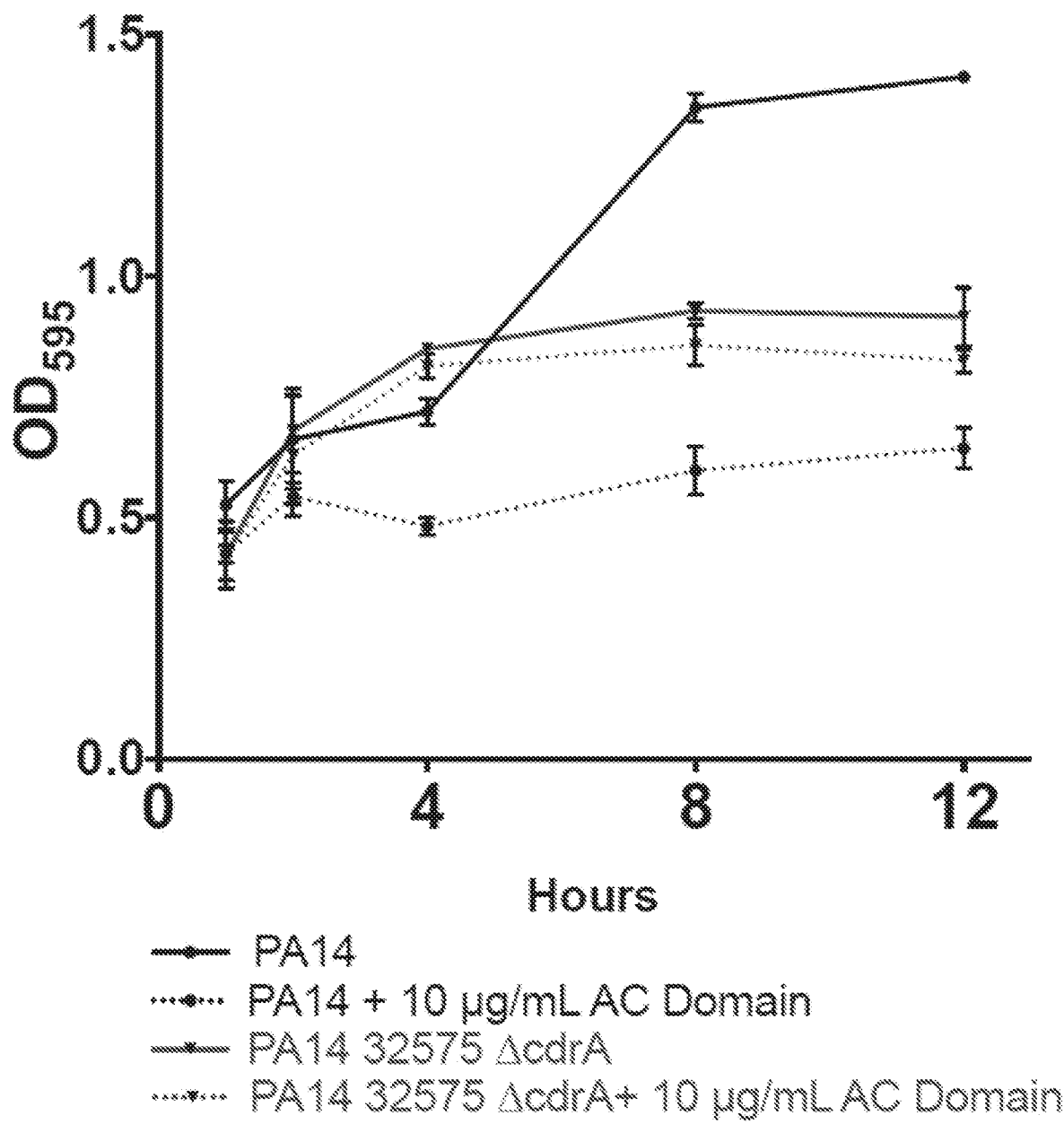
FIG. 23 is a graph showing that exogenous AC domain inhibited *P. aeruginosa* PA14 biofilm, but not biofilm of the CdrA transposon mutant, PA14 32575 (tn::cdrA). The graph is a time course of biofilm formation of the wild-type PA14 (solid black line with solid circles) and CdrA transposon mutant, PA14 32575 (solid gray line with inverted triangles) measured over 12 hours via the crystal violet assay. Concurrently, 10 μg/m AC domain was added at time zero to PA14 (dotted black line with solid circles) and the PA14 32575 mutant (dotted gray line with inverted triangles) and biofilm was measured at the same time points. Mean values represented by circles and error bars represent standard deviations. Data compiled from three (3) experiments run in triplicate. Statistics are not included on graph for clarity were as follows: at 12 hours, PA14 vs. PA14+AC domain: p<0.0001; PA14 vs. PA14 32575: p<0.001; and PA14 32575 vs. PA14 32575+AC domain: not significant.

In order to test the hypothesis that ACT and AC domain inhibited biofilm formation by bacteria that expressed FHA-like proteins via a conserved mechanism, a transposon mutant from the PA14 transposon library, PA14 32575 (tn::cdrA, transposon insertion at 249 codons from start) which lacks CdrA, the *Pseudomonas* FHA-like protein, was obtained. Biofilm formation of PA14 and the CdrA transposon mutant was determined over a 12-hour time course in the presence and absence of 10 μg/ml AC domain (FIG. 23). PA14 32575 (gray solid line) made less biofilm than the parental wild type strain PA14 (black solid line), which is consistent with previous observation that a ΔcdrA mutant made less biofilm than the parental wild type strain. The AC domain inhibited PA14 biofilm throughout the experiment (black dotted line), but did not significantly decrease biofilm formation of PA14 32575 (gray dotted line) at anytime point during the experiment (FIG. 23). These data suggested that the AC domain inhibited biofilm by targeting (and possibly binding) the FHA-like protein, CdrA, in *P. aeruginosa*.

Because the AC domain was able to disrupt preformed *Bordetella* biofilm, the AC domain was also tested to determine its ability to disrupt preformed *P. aeruginosa* biofilm. PA14 was allowed to form biofilm for 6, 8, and 10 hours before the AC domain was added to cultures. Biofilm formation was measured at 12 hours by the crystal violet assay. No differences in biofilm formation were observed; the AC domain does not disrupt biofilm of *Pseudomonas*. While not wishing to be bound by any theory of operation, it is possible that the AC domain is too large to access the correct sites once biofilm formation has already occurred in *P. aeruginosa*, as the matrix material is denser than that of *B. pertussis*, or because once mature biofilm has formed, *P. aeruginosa* has other matrix components and proteins that reinforce the biofilm independent of CdrA. It is possible that a smaller peptide might be able to disrupt biofilm.

Example 8

Anti-MCD Antibodies Inhibit *P. aeruginosa* Biofilm

Figure 24:
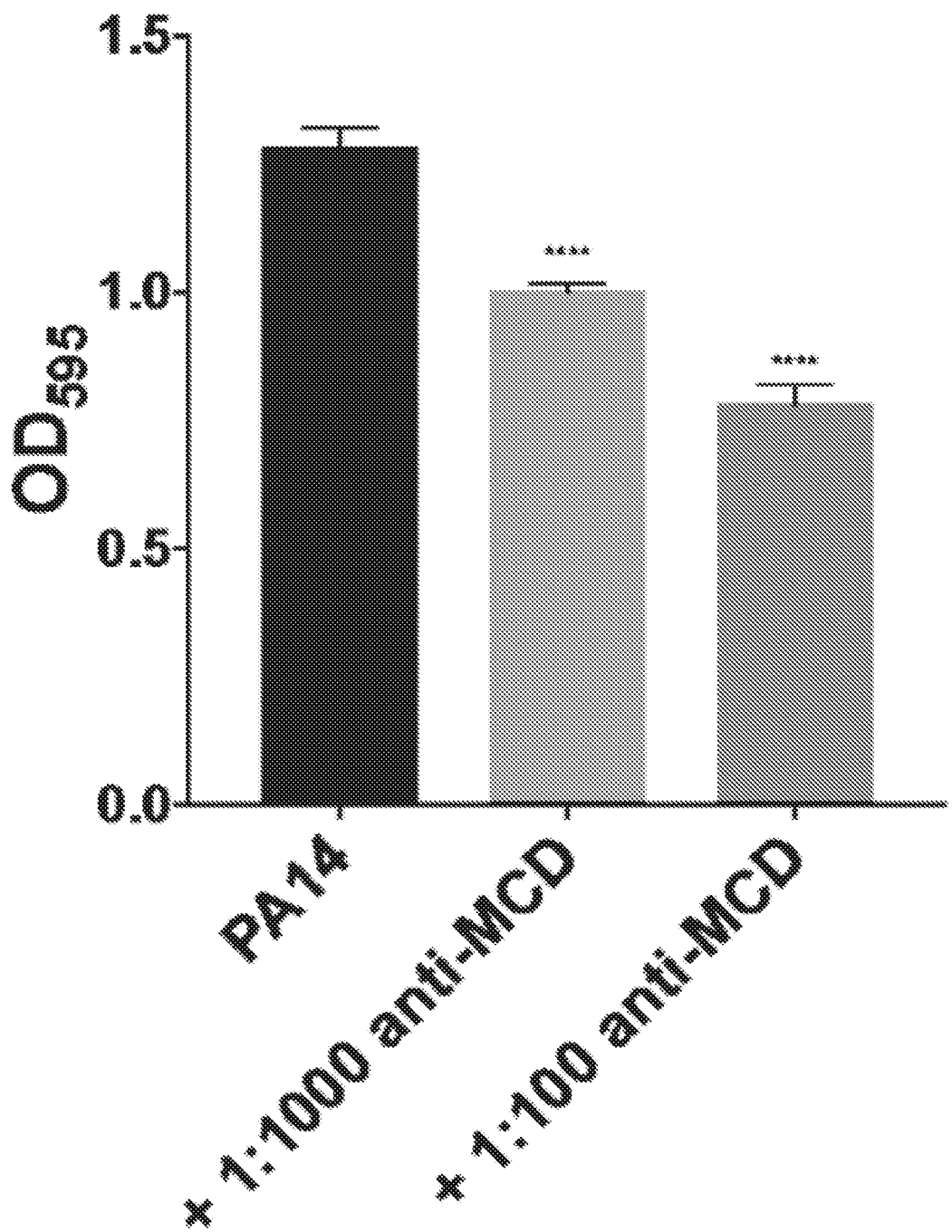
FIG. 24 is a bar graph showing that anti-MCD antibodies inhibited *P. aeruginosa* PA14 biofilm. Anti-MCD antibodies were added at 1:1000 and 1:100 dilutions to wild-type *P. aeruginosa* PA14 cultures in 96 well microtiter plates to observe their effects on biofilm formation. Biofilm formation was measured at 12 hours using the crystal violet assay. Data expressed as the mean±two (2) standard deviations, compiled from three (3) experiments run in triplicate. **** p<0.0001 compared to wild-type PA14 alone.

As demonstrated in *B. pertussis*, anti-FHA antibodies prevent biofilm formation and more specifically, anti-MCD monoclonal antibodies prevent biofilm formation. Because the AC domain and anti-MCD antibodies both bind the MCD, the two binding events might prevent biofilm in a similar manner. The anti-MCD antibody was tested for its ability to inhibit *P. aeruginosa* PA14 biofilm, and was added at dilutions of 1:100 and 1:1000 to PA14 cultures in 96 well plates, similar to concentrations used in *B. pertussis* biofilm experiments. Biofilm formation was assessed at 12 hours using the crystal violet assay (FIG. 24). Anti-MCD antibodies inhibited PA14 biofilm formation in a concentration-dependent manner, suggesting that a direct binding event to the distal globular tip of CdrA, or some other MCD-like epitope, prevented biofilm formation.

Example 9

The AC Domain Inhibits Biofilm Formation of Other Bacterial Species

In addition to testing the inhibitory ability of the AC domain on *P. aeruginosa*, the ability of AC domain to decrease or inhibit biofilm was tested on other bacterial species, including *Escherichia coli* and *Salmonella typhimurium*. Species were selected based upon availability and presence of FHA-like proteins found in their genomes. *Escherichia coli* expresses Filamentous Hemagglutinin (hypothetical protein, member of the ShlA/HecNFha exoprotein family) that shares sequence and structural homology to *Bordetella* FHA (including the portion of the protein which maps to the MCD of *Bordetella* FHA). *E. coli* also expressed amyloid proteins that are involved in biofilm formation. These amyloid proteins react with congo red dye, as does *Bordetella* FHA. *Salmonella enterica* serovars express BapA, which shares structural homology to *Bordetella* FHA and is involved in biofilm development (biofilm associated protein, BapA).

Figure 25A:
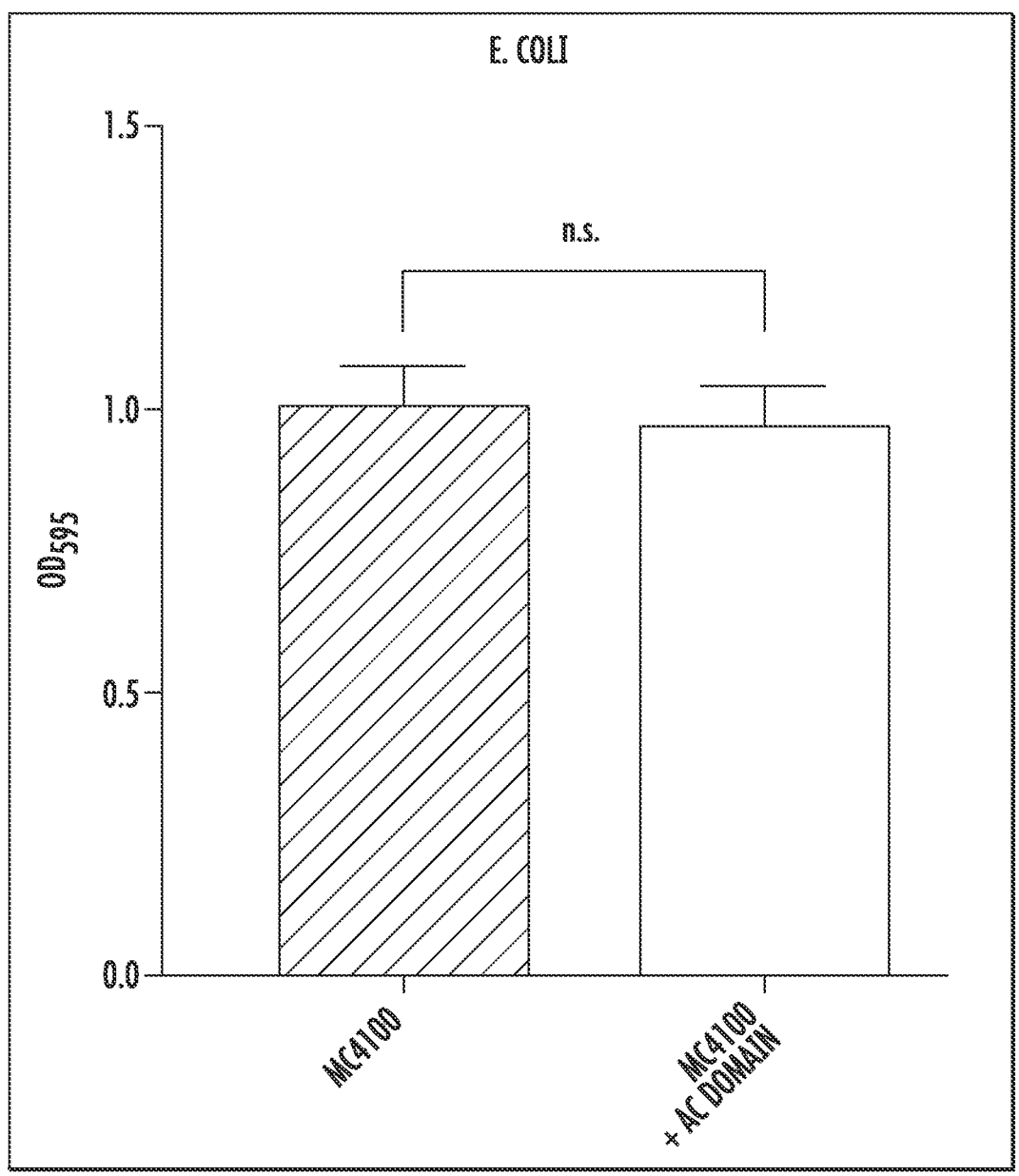
FIGS. 25A-25C are a series of bar graphs showing that the AC Domain inhibited *E. coli* and *S. typhimurium* biofilm.

Biofilm formation of *E. coli* and *S. typhimurium* was assessed in the presence or absence of 10 μg/ml AC domain using the crystal violet assay. Bacteria were grown overnight in liquid LB culture and diluted to an $OD_{600}$ of 0.05 in the morning. 100 μL cultures of bacteria were added to wells in 96 well plates and biofilm was measured at 12 hours for both *E. coli* and *S. typhimurium*. Two strains of *E. coli* were tested: *E. coli* MC4100, which has been studied in the context of curli proteins and biofilm, and *E. coli* 87-23, which is a shigatoxin negative 0157:H7 *E. coli* strain. The results are shown in FIGS. 25A-25C.

Figure 25B:
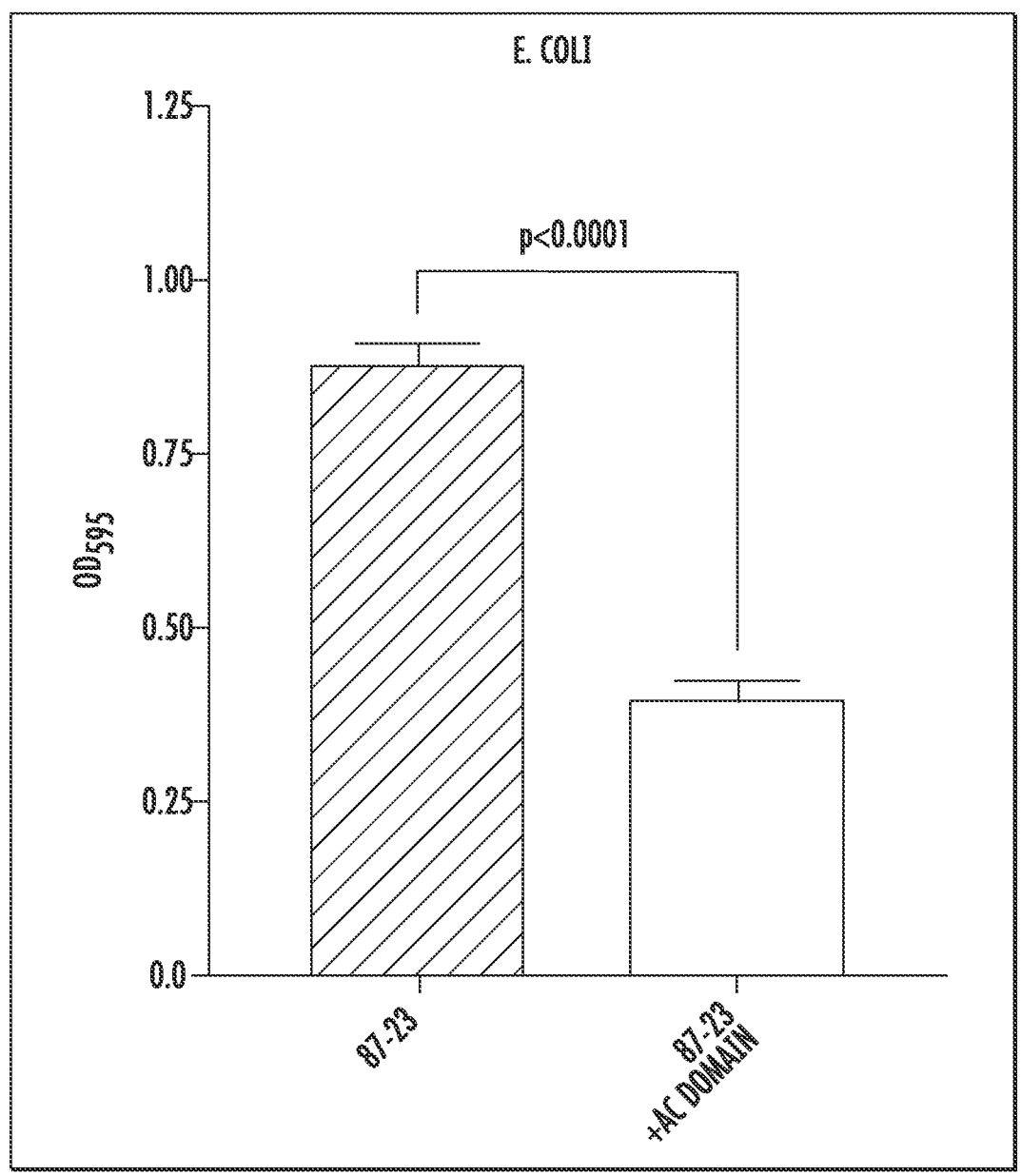

The AC domain was able to inhibit biofilm of one strain of *E. coli*, 87-23 (FIG. 25A), but was ineffective against biofilm formation of the other *E. coli* strain tested, MC4100 (FIG. 25B).

It is unclear why AC domain only inhibited one of the *E. coli* strains tested, but in some bacteria, such as *Salmonella*, curli proteins can compensate for biofilm defects. To analyze this, the presence of FHA-like proteins in both of the *E. coli* strains are tested using polyclonal anti-*B. pertussis* FHA antibodies (and the anti-MCD antibody). The requirement of these predicted FHA-like proteins in biofilm formation and inhibition by AC domain is determined as well.

Figure 25C:
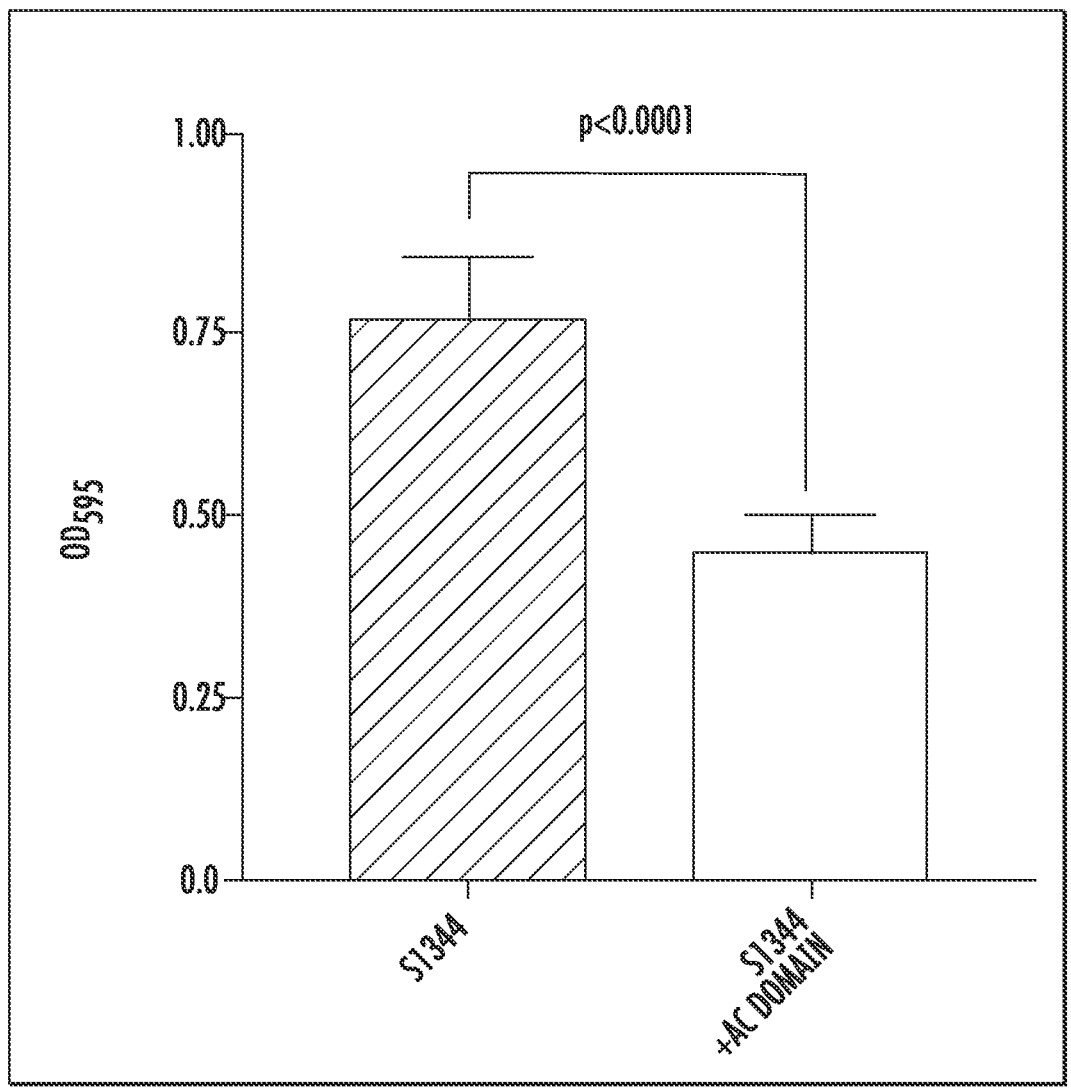

The AC domain did inhibit biofilm formation of *S. typhimurium* at 10 µg/ml at 12 hours, as measured by the crystal violet assay (FIG. 25C).

Example 10

A Fragment of the AC Domain Inhibited Biofilm

Figure 26A:
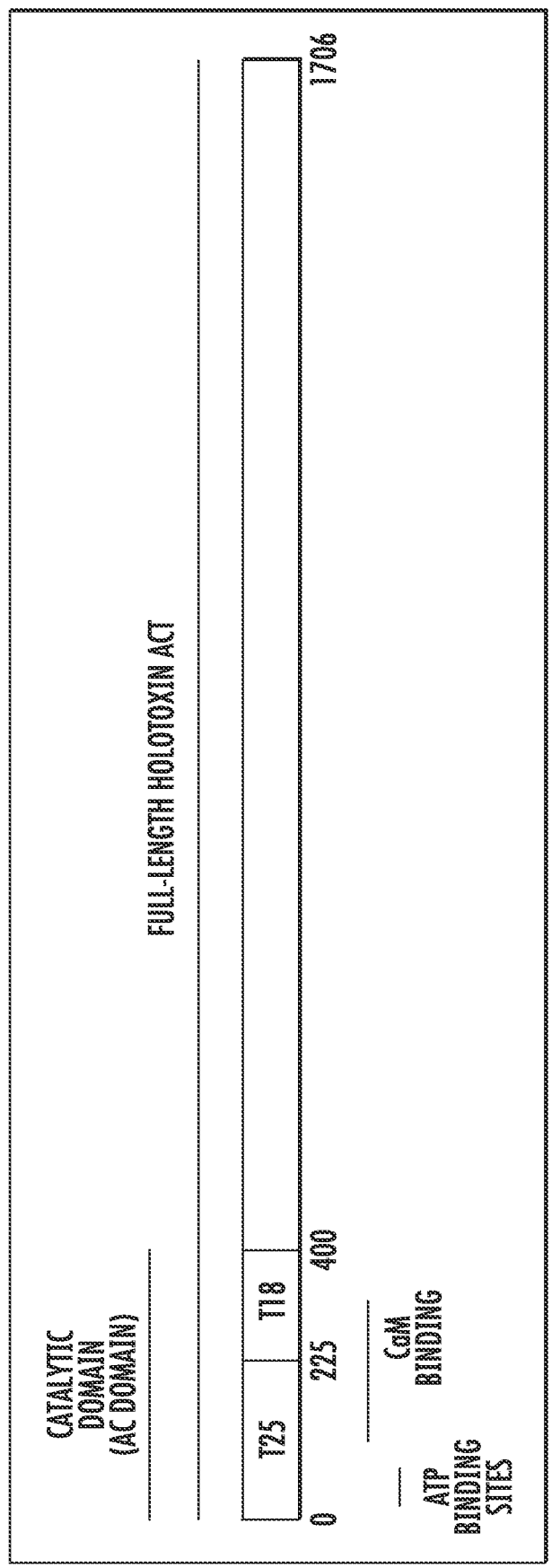
FIGS. 26A and 26B relate to experiments showing that the T18 and the T25 peptides inhibited *B. pertussis* biofilm in a concentration-dependent manner.

Because the AC domain is a smaller, more potent biofilm inhibitory peptide than full length holotoxin ACT, whether an even smaller peptide that retained the inhibitory properties would be more potent than the AC domain was tested. The AC domain has a natural trypsin cleavage site, which cleaves the AC domain into two pieces referred to herein as T25 and T18 (see FIG. 26A).

The ability of trypsin-treated AC domain to inhibit biofilm was first examined. The smaller peptides, T18 and T25, although still mixed together, were able to inhibit biofilm. To resolve which of these peptides retained the inhibitory activity, plasmids encoding the genes for the T18 and T25 peptides were utilized. The commercially available BACTH plasmids (bacterial adenylate cyclase two-hybrid; Euromedex, Strasbourg, France), containing the T18 and T25 peptides, were obtained from collaborators at the University of Virginia. The plasmids were transformed into and expressed in *E. coli* BL21 (DE3) and methods similar to those that were used to purify full-length holotoxin and the AC domain were used to purify the T18 and T25 plasmids. Briefly, plasmids contained an IPTG inducible promoter and peptide expression was induced in early log phase. During mid log phase, bacteria were pelleted and sonicated to release cellular contents. Bacterial membranes and cell debris were spun down and the supernatent fraction was removed. Preliminary data demonstratd that the plasmids were functional and the T18 and T25 peptides remained membrane-associated. Urea extraction of bacterial membranes resulted in enrichment for the T18 and T25 peptides, but did not remove all other *E. coli* membrane proteins (similar to urea extracts from BL21 (DE3) *E. coli* expressing the plasmid encoding holotoxin ACT (pT7cACT1)).

Figure 26B:
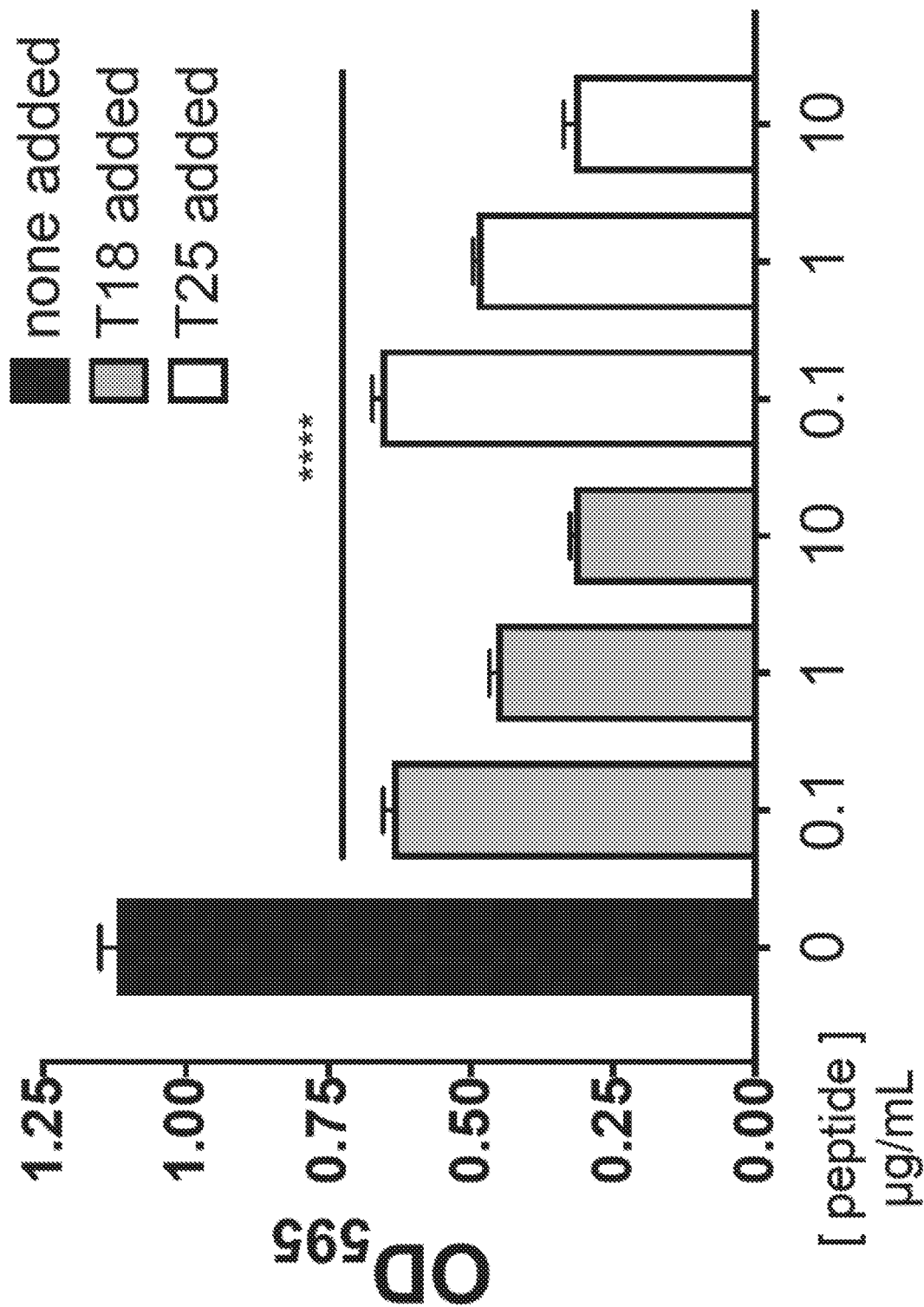

The T18 and T25 peptides were added separately to *B. pertussis* BP338 (wild-type) cultures during biofilm growth in 96 well plates. Both of these peptides retained inhibitory activity on *B. pertussis* biofilm formation, which was concentration dependent (FIG. 26B).

Discussion of the Examples

In addition to biofilms which form on surfaces associated with living organisms, biofilm can also occur on man-made structures in the environment, such as but not limited to water and sewage pipelines, bathroom drains and faucets, water holding tanks, etc. These biofilms can lead to complications with the efficiency of processes that involve these structures and materials. Thus, eradication of these unwanted communities of bacteria, either by disrupting preformed biofilm or preventing biofilm from occurring in the first place, would be desirable.

Virtually all surfaces, both man-made and naturally occurring, are susceptible to bacterial deposition and subsequent biofilm formation and thus prevention has been difficult. Disruption of biofilm typically consists of abrasive mechanical treatment and the application of harsh chemicals, which kills all living cells. While this is an option for abiotic sites such as sewage pipelines and sinks, these types of treatments are not suited for use in humans, animals, or plants.

Disclosed herein is the discovery that the 177 kD *Bordetella* adenylate cyclase toxin (ACT) and several fragments thereof including, but not limited to the 40 kDa AC domain (which comprises the catalytic domain of the toxin) as well as the T18 and T25 peptides were able to inhibit biofilm formation. ACT is a bacterial adenylate cyclase expressed by some *Bordetella* species (*B. pertussis, B. bronchiseptica, B. parapertussis, B. hinzii*, and *B. ansorpii*). The holotoxin is a major virulence factor of Bordetellae, which kills macrophages, blocks neutrophil function, and helps *B. pertussis* and *B. bronchiseptica* establish infection in hosts (mice and humans). The inhibitory effect on biofilm was mediated by a direct binding event between ACT and the 220 kD surface displayed adhesin, Filamentous Hemagglutinin (FHA). *Bordetella* FHA is involved in a variety of processes, such as binding to epithelial cells in the nares, trachea and lungs, and altering the host immune response, but is also described as one of the major protein components of *Bordetella* biofilm. *B. pertussis* and *B. bronchiseptica* lacking FHA do not form biofilm compared to their parental wild type strains in vitro or in vivo. The ACT-FHA interaction occurs between the 40 kDa catalytic domain of ACT (amino acids 1-400) (AC domain) and the distal tip of FHA, the mature C-terminal domain (MCD amino acids 1870-2362). The AC domain is sufficient for FHA-binding, and necessary and sufficient for biofilm inhibition. The c-terminal portion of FHA is required for AC domain-FHA binding, and the MCD must be present and properly folded for biofilm inhibition. We hypothesize that the ACT-FHA interaction results in some hindrance of FHA for biofilm formation, either through a conformational change of FHA or through spatial hindrance of FHA, as opposed to sending a signal via the binding event. In addition to inhibitory properties of the AC domain, the peptide is able to disrupt preformed *B. pertussis* biofilm. The full-length holotoxin lacks this biofilm disruptive activity, which may be due to the size difference between ACT and AC domain and inability of full-length ACT to access FHA within mature biofilm structures.

The MCD is just one of many domains within the FHA protein. Several of the proteins domains, such as the carbohydrate recognition domain, confer binding to substrates, such as epithelial cells, macrophages, leukocytes, and monocytes. These domains and the overall structure of FHA are highly conserved amongst Bordetellae (*B. ansorpii* do not express FHA) and bacterial species outside of the *Bordetella* genus. Many of these FHA-like proteins act as adhesins, similar to FHA of *B. pertussis*, and some have been implicated in biofilm or aggregative growth, a precursor to biofilm.

In other bacterial species, specifically *Pseudomonas fluorescens* and *Pseudomonas aeruginosa*, the FHA-like protein, CdrA, is major components of the biofilm matrices. CdrA directly binds the polysaccharide component of *Pseudomonas* matrix, Psi, to reinforce biofilm structure. Strains that lack CdrA form less complex biofilm structures than the parental wild type strains. Biofilm of the ΔcdrA strain grows as a thin field, as opposed to growing into a complex three-dimensional structure. Biofilm of the CdrA deficient mutant accumulates at low levels, likely because Pseudomonads have other mechanisms to partially compensate for this defect. *P. aeruginosa* CdrA shows high structural similarity to *Bordetella* FHA, although the homology between the two genes encoding the proteins is low. Both the predicted structures for FHA and CdrA contain β-helical shafts, a globular c-terminal domain located at the distal tip of the protein, and CRD binding domains. The peptides are both inserted into a specific transporter in a hairpin structure, begin folding into β-helical sheets, and via proteolytic processing, the protein reaches its final structure and is displayed on the surface of the bacterial outer membrane. FHA requires a two-partner secretion system, while CdrA is an RTX toxin secreted via the Type 1 Secretion System. Both FHA and CdrA can be released into the extracellular milieu, albeit via different mechanisms. CdrA is cleaved by the LapG protease, located in the periplasm, and is dependent on c-di-GMP levels within the cell. The mechanism by which FHA is released into the media is unknown, but does not require a proteolytic cleavage event. Because of the similarities between FHA and CdrA, we hypothesized that Pseudomonas, and possibly other bacteria that express FHA-like proteins, may be susceptible to biofilm inhibition by AC domain.

Thus, disclosed herein are experiments linking the ACT-FHA interaction to inhibition of biofilm formation by Bordetella pertussis and Bordetella bronchiseptica. The AC domain was necessary and sufficient, yet the catalytic activity of the toxin was not required for this inhibitory phenomenon. These effects of ACT could be blocked by CaM or by a catalytic domain-specific antibody. Thus, the AC domain was been identified as a sufficient binding partner for FHA, and the MCD as necessary for this binding and the inhibitory effect on biofilm to occur. The inhibitory effect could result from the AC domain—MCD interaction simply blocking the FHA molecule in its yet-to-be-identified role in Bordetella biofilm production, or by inducing a conformational change in FHA that has this and other effects.

Figure 21:
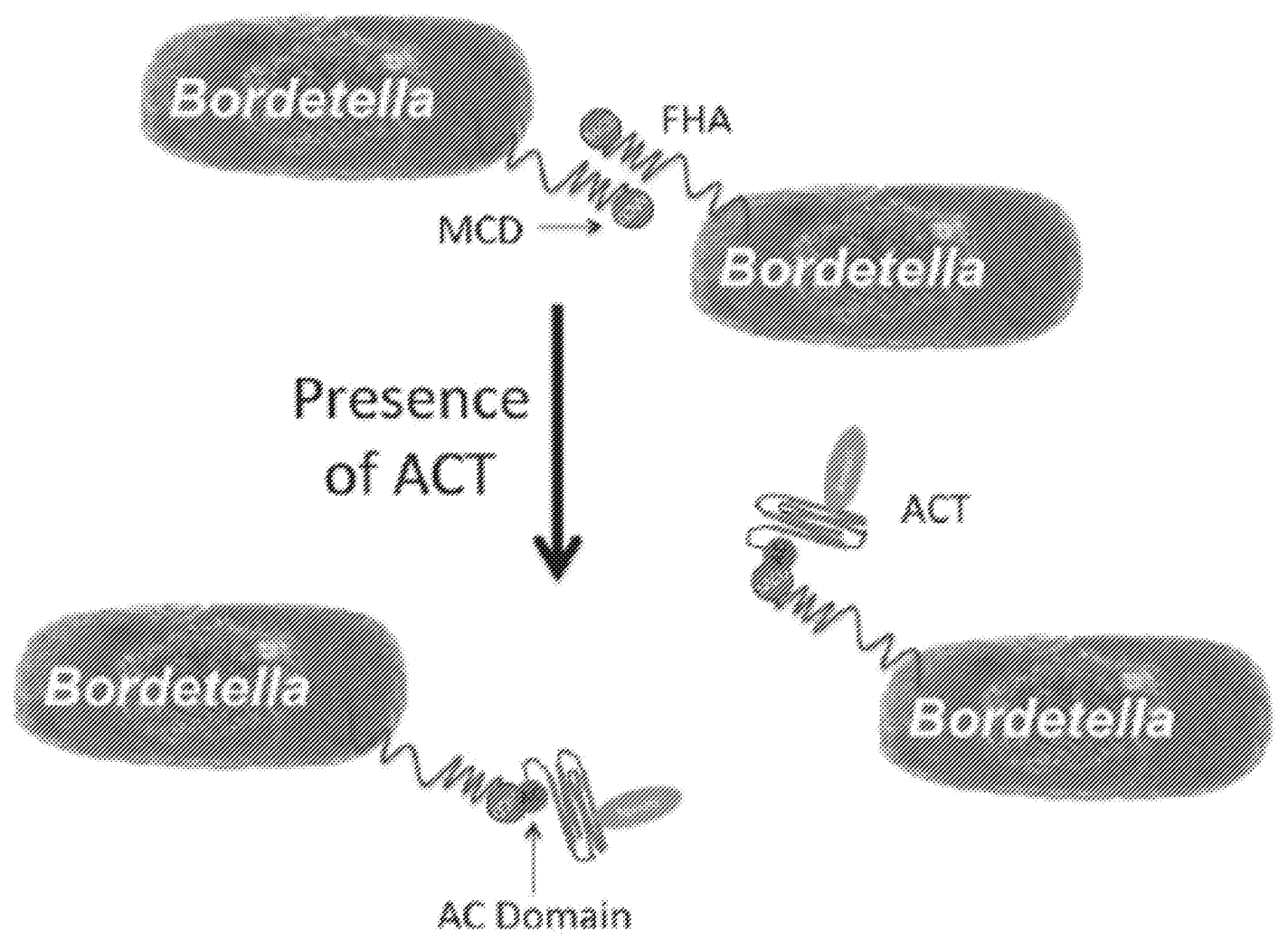

An exemplary working model for the inhibition of B. pertussis biofilm by ACT is diagrammed in FIG. 21, in which the AC domain of ACT binds the MCD of FHA to interfere with inter-bacterial FHA-FHA interactions, which have been previously described as important for biofilm formation. The inhibition by ACT might start in the early steps of biofilm formation, by ACT blocking initial bacteria-substrate, as well as bacteria-bacteria interactions and thus limiting subsequent biofilm accumulation. These observations are, however, in contrast to the observations by Perez Vidakovics et al. showing that the absence of ACT reduces B. pertussis binding to alveolar epithelial cells (Perez Vidakovics et al., 2006).

The data illustrating inhibition of Bordetella biofilm by ACT through its interaction with FHA presented herein raise the important question of how this phenomenon fits with the current concepts of Bordetella pathogenesis and biofilm production. Others have shown that multiple factors, ranging from (p)ppGpp and c-di-GMP to transcriptional regulators of Bps polysaccharide production, control biofilm production by Bordetellae (see e.g., Conover et al., 2012; Sugisaki et al., 2013; Sisti et al., 2013). Specifically, Irie et al. and Mishra et al. demonstrated that BvgAS modulates the formation of biofilm and that there is an increase in B. bronchiseptica biofilm under Bvg(i) conditions (Irie et al., 2004). This scenario can now be explained, at least in part, by a reduction in the amount of inhibitory ACT in the presence of a constant level of FHA in the Bvg(i) phase (Cotter & Miller, 1997; Mattoo & Cherry, 2005; Vergara-Irigaray et al., 2005). Thus, during active phase of infection in which conditions are optimal for the bacteria, ACT is actively produced for its inhibitory effects on the host immune response and biofilm production is suppressed (FIG. 21). Under less favorable conditions, during which a defensive posture might be beneficial, a reduction in ACT production could be one of several mechanisms by which production of biofilm is initiated.

Given the active production of ACT during the Bvg(+) phase, it is appropriate to ask why there was any biofilm produced during these in vitro assays. It is now apparent that the quantity and distribution of ACT was different than what occurs in vivo. Previously, it has been demonstrated that in ex vivo samples obtained during active infection, concentrations of ACT can reach approximately 100 ng/ml and all of the ACT is in the supernatant fraction, as opposed to being surface associated (Eby et al., 2013). This is in contrast to B. pertussis cultured in vitro in SSM, in which >90% of the ACT remained surface-associated and concentrations rarely got as high as seen in the ex vivo samples (Eby et al., 2013). It has also been demonstrated that the functional form of the toxin is that which is released into the media (Gray et al., 2004), while the surface-associated toxin is likely an improperly folded, inert pool.

Finally, Dr. Constance Jeffery has described and catalogued (see the Moonlight Proteins (MoonProt) Database, accessible through the World Wide Web at <<moonlightingproteins>>.<<org>>; see also Mani et al., 2015) a number of dual function protein molecules, in which a single protein performs multiple physiologically relevant biochemical or biophysical roles (Jeffery, 1999; Jeffery, 2003; Jeffery, 2009; Jeffery, 2014; and Jeffery, 2015). On the basis of recognizing additional functions for known proteins, these fascinating molecules, which are from both prokaryotic and eukaryotic sources, have been designated "moonlighting proteins". Their study has facilitated identification of novel biochemical pathways and protein functions, and allowed systems biologists to better understand cellular processes.

Prior to the present disclosure, ACT had been studied and characterized solely as a host-directed protein bacterial toxin that modulates function and is cytotoxic for some target cells by increasing cAMP levels and, depending on concentration, depleting ATP levels. ACT is also a hemolysin and member of the RTX family of pore-forming toxins, which includes E. coli hemolysin, HlyA (Menestrina et al., 1994). The pore-forming function, which for ACT is involved in delivery of its catalytic domain to the target cell interior, has an additional effect of compromising membrane integrity and polarization and contributes to cytotoxicity. The additional role for this protein bacterial toxin, contained within its catalytic domain, namely interaction with a surface adhesion to impair formation of biofilm makes it unlike any other moonlighting protein that has been described in the MoonProt Database (Mani et al., 2015). This information can now be used to study Bordetella biofilm and to hypothesize when formation may occur in vivo.

Summarily, disclosed herein are experiments that tested the hypothesis that the ACT-FHA interaction inhibits biofilm by adding purified ACT to cultures of B. pertussis and B. bronchiseptica in vitro. Indeed, exogenous ACT inhibited biofilm formation, adding to the effect of endogenously produced and secreted ACT. This effect of added ACT occurred through binding of the catalytic AC domain, independently of its enzyme activity, to the mature C-terminal domain (MCD) of FHA, which must be properly folded for the inhibitory effect of ACT to occur. An exemplary relationship of this novel regulatory role for a bacterial toxin to the hypothetical "life cycle" of B. pertussis, controlled by BvgAS, is also provided.

As such, the present disclosure demonstrates that Bordetella pertussis, the causative agent of whooping cough, secretes and releases adenylate cyclase toxin (ACT), a protein bacterial toxin that targets host cells and disarms immune defenses. ACT binds filamentous haemagglutinin (FHA), a surface-displayed adhesin, and until now, the consequences of this interaction were unknown. Disclosed herein are characterizations of the physical interaction of ACT with FHA as well as evidence linking that interaction to inhibition of biofilm in vitro. Exogenous ACT inhibited biofilm formation in a concentration-dependent manner and the N-terminal catalytic domain of ACT (AC domain) was necessary and sufficient for this inhibitory effect. AC Domain interacted with the C-terminal segment of FHA with ~650 nM affinity. ACT did not inhibit biofilm formation by *Bordetella* lacking the mature C-terminal domain (MCD), suggesting the direct interaction between AC domain and the MCD was required for the inhibitory effect. Additionally, AC domain disrupted preformed biofilm on abiotic surfaces. The demonstrated inhibition of biofilm formation by a host-directed protein bacterial toxin represents a novel regulatory mechanism and provides an unprecedented role for ACT.

REFERENCES

All references listed in the instant disclosure, including but not limited to all patents, patent applications and publications thereof, scientific journal articles, and database entries (including but not limited to GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Altschul et al. (1990a) Basic local alignment search tool. *J Mol Biol* 215:403-410.

Altschul et al. (1990b) Protein database searches for multiple alignments. *Proc Natl Acad Sci USA* 87(14):5509-5513.

Altschul et al. (1997) Gapped BLAST and PSI-BLAST: a new generation of protein database search programs. *Nucleic Acids Res* 25:3389-3402.

Arnal et al. (2015) *Bordetella pertussis* isolates from argentinean whooping cough patients display enhanced biofilm formation capacity compared to Tohama I reference strain. *Front Microbiol* 6:1352.

Basler et al. (2006) Pore-forming and enzymatic activities of *Bordetella pertussis* adenylate cyclase toxin synergize in promoting lysis of monocytes. *Infect Immun* 74:2207-2214.

Birkebaek et al. (1999) *Bordetella pertussis* and chronic cough in adults. *Clin Infect Dis* 29:1239-1242.

Bisgard et al. (2004) Infant pertussis: who was the source? *Pediatr Infect Dis J* 23:985-989.

Borlee et al. (2010) *Pseudomonas aeruginosa* uses a cyclic-di-GMP-regulated adhesin to reinforce the biofilm extracellular matrix. *Mol Microbiol* 75:827-842.

Bumba et al. (2010) *Bordetella* adenylate cyclase toxin mobilizes its beta2 integrin receptor into lipid rafts to accomplish translocation across target cell membrane in two steps. *PLoS Pathog* 6:e1000901.

Bumba et al. (2016) Calcium-Driven folding of RTX domain beta-rolls ratchets translocation of RTX proteins through type I secretion ducts. *Mol Cell* 62:47-62.

Cherry & Heinninger (2004) Pertussis and other *Bordetella* infections. *In Textbook of Pediatric Diseases*. Cherry et al. (eds). Philadelphia: W.B. Saunders, pp. 1616-1639.

Cherry & Olin (1999) The science and fiction of pertussis vaccines. *Pediatrics* 104:1381-1383.

Confer & Eaton (1982) Phagocyte impotence caused by an invasive bacterial adenylate cyclase. *Science* 217:948-950.

Conover et al. (2010) The Bps polysaccharide of *Bordetella pertussis* promotes colonization and biofilm formation in the nose by functioning as an adhesin. *Mol Microbiol* 77:1439-1455.

Conover et al. (2011) Extracellular DNA is essential for maintaining *Bordetella* biofilm integrity on abiotic surfaces and in the upper respiratory tract of mice. *PLoS One* 6:e16861.

Conover et al. (2012) BpsR modulates *Bordetella* biofilm formation by negatively regulating the expression of the Bps polysaccharide. *J Bacteriol* 194:233-242.

Costache et al. (2013) Adenylate cyclases involvement in pathogenicity, a minireview. *Roum Arch Microbiol Immunol* 72:63-86.

Cotter & Miller (1997) A mutation in the *Bordetella bronchiseptica* bvgS gene results in reduced virulence and increased resistance to starvation, and identifies a new class of Bvg-regulated antigens. *Mol Microbiol* 24:671-685.

de Gouw et al. (2014) The vaccine potential of *Bordetella pertussis* biofilm-derived membrane proteins. *Emerg Microbes Infect* 3:e58.

Eby et al. (2010) Selective translocation of the *Bordetella pertussis* adenylate cyclase toxin across the basolateral membranes of polarized epithelial cells. *J Biol Chem* 285:10662-10670.

Eby et al. (2012) Role of CD11b/CD18 in the process of intoxication by the adenylate cyclase toxin of *Bordetella pertussis*. *Infect Immun* 80:850-859.

Eby et al. (2013) Quantification of the adenylate cyclase toxin of *Bordetella pertussis* in vitro and during respiratory infection. *Infect Immun* 81:1390-1398.

Eby et al. (2014) Cyclic AMPmediated suppression of neutrophil extracellular trap formation and apoptosis by the *Bordetella pertussis* adenylate cyclase toxin. *Infect Immun* 82:5256-5269.

El-Azami-El-Idrissi et al. (2003) Interaction of *Bordetella pertussis* adenylate cyclase with CD11b/CD18: Role of toxin acylation and identification of the main integrin interaction domain. *J Biol Chem* 278:38514-38521.

Fan et al. (2012) Two-partner secretion of gram-negative bacteria: a single beta-barrel protein enables transport across the outer membrane. *J Biol Chem* 287:2591-2599.

Fedele et al. (2013) The virulence factors of *Bordetella pertussis*: talented modulators of host immune response. *Arch Immunol Ther Exp* (Warsz) 61:445-457.

Fenwick (2013) *Bordetella*. *In Veterinary Microbiology*. McVey et al. (eds). Hoboken: Wiley Blackwell, Section 14.

Fiser et al. (2012) Calcium influx rescues adenylate cyclase-hemolysin from rapid cell membrane removal and enables phagocyte permeabilization by toxin pores. *PLoS Pathog* 8:e1002580.

Gray et al. (2001) Translocation-specific conformation of adenylate cyclase toxin from *Bordetella pertussis* inhibits toxin-mediated hemolysis. *J Bacteriol* 183:5904-5910.

Gray et al. (2004) Newly secreted adenylate cyclase toxin is responsible for intoxication of target cells by *Bordetella pertussis*. *Mol Microbiol* 53:1709-1719.

Guermonprez et al. (2001) The adenylate cyclase toxin of *Bordetella pertussis* binds to target cells via the alpha(M) beta(2) integrin (CD11b/CD18). *J Exp Med* 193:1035-1044.

Guo et al. (2005) Structural basis for the interaction of *Bordetella pertussis* adenylyl cyclase toxin with calmodulin. *EMBO J* 24:3190-3201.

Harlow & Lane (1988) *Antibodies: A Laboratory Manual*, Cold Spring Harbor Laboratory Press, Cold Spring Harbor, N.Y., United States of America.

Hewlett et al. (2006) Macrophage cytotoxicity produced by adenylate cyclase toxin from *Bordetella pertussis*: more than just making cyclic AMP!. *Mol Microbiol* 59:447-459.

Inatsuka et al. (2010) Pertactin Is Required for *Bordetella* Species To Resist Neutrophil-Mediated Clearance. *Infect Immun* 7:2901-2909.

Irie et al. (2004) The Bvg virulence control system regulates biofilm formation in *Bordetella bronchiseptica*. *J Bacteriol* 186:5692-5698.

Iwaki et al. (1995) Identification by in vitro complementation of regions required for cell-invasive activity of *Bordetella pertussis* adenylate cyclase toxin. *Mol Microbiol* 17:1015-1024.

Jeffery (1999) Moonlighting proteins. *Trends Biochem Sci* 24:8-11.

Jeffery (2003) Moonlighting proteins: old proteins learning new tricks. *Trends Genet* 19:415-417.

Jeffery (2009) Moonlighting proteins—an update. *Mol Biosyst* 5:345-350.

Jeffery (2014) An introduction to protein moonlighting. *Biochem Soc Trans* 42:1679-1683.

Jeffery (2015) Why study moonlighting proteins? *Front Genet* 6:211.

Kajava et al. (2001) Beta-helix model for the filamentous haemagglutinin adhesin of *Bordetella pertussis* and related bacterial secretory proteins. *Mol Microbiol* 42:279-292.

Karlin & Altschul (1990) Methods for assessing the statistical significance of molecular sequence features by using general scoring schemes. *Proc Natl Acad Sci USA* 87:2264-2268.

Karlin & Altschul (1993) Applications and statistics for multiple high-scoring segments in molecular sequences. *Proc Natl Acad Sci USA* 90:5873-5877.

Kragh et al. (2016) Role of Multicellular Aggregates in Biofilm Formation. *MBio* 7:e00237-e00216.

Lee et al. (1999) Epitope mapping of monoclonal antibodies against *Bordetella pertussis* adenylate cyclase toxin. *Infect Immun* 67:2090-2095.

Lim et al. (2014) Protective role of adenylate cyclase in the context of a live pertussis vaccine candidate. *Microbes Infect* 16:51-60.

Macdonald-Fyall et al. (2004) Adjuvanticity of native and detoxified adenylate cyclase toxin of *Bordetella pertussis* towards co-administered antigens. *Vaccine* 22:4270-4281.

Mani et al. (2015) MoonProt: a database for proteins that are known to moonlight. *Nucleic Acids Res* 43: D277-D282.

Martin et al. (2010) *Bordetella* adenylate cyclase toxin promotes calcium entry into both CD11b1 and CD11b- cells through cAMPdependent L-type-like calcium channels. *J Biol Chem* 285:357-364.

Mattoo & Cherry (2005) Molecular pathogenesis, epidemiology, and clinical manifestations of respiratory infections due to *Bordetella pertussis* and other *Bordetella* subspecies. *Clin Microbiol Rev* 18:326-382.

Mazar & Cotter (2006) Topology and maturation of filamentous haemagglutinin suggest a new model for two-partner secretion. *Mol Microbiol* 62:641-654.

Mazar & Cotter (2007) New insight into the molecular mechanisms of two-partner secretion. *Trends Microbiol* 15:508-515.

Menestrina et al. (1994) Pore-formation by *Escherichia coli* hemolysin (HlyA) and other members of the RTX toxins family. *Toxicology* 87:249-267.

Mishra et al. (2005) The BvgAS signal transduction system regulates biofilm development in *Bordetella*. *J Bacteriol* 187:1474-1484.

Mouallem et al. (1990) *Bordetella pertussis* adenylate cyclase toxin: intoxication of host cells by bacterial invasion. *Infect Immun* 58:3759-3764.

Nelson (1978) The changing epidemiology of pertussis in young infants. The role of adults as reservoirs of infection. *Am J Dis Child* 132:371-373.

Noel et al. (2012) The prodomain of the *Bordetella* two-partner secretion pathway protein FhaB remains intracellular yet affects the conformation of the mature C-terminal domain. *Mol Microbiol* 86:988-1006.

O'Toole (2011) Microtiter dish biofilm formation assay. *J Vis Exp* pii:2437.

Osička et al. (2000) Delivery of CD8+ T-Cell Epitopes into Major Histocompatibility Complex Class I Antigen Presentation Pathway by *Bordetella pertussis* Adenylate Cyclase: Delineation of Cell Invasive Structures and Permissive Insertion Sites. *Infect Immun* 68:247-256.

Osička et al. (2015) *Bordetella* adenylate cyclase toxin is a unique ligand of the integrin complement receptor 3. *eLife* 4:e10766.

Osickova et al. (2010) Adenylate cyclase toxin translocates across target cell membrane without forming a pore. *Mol Microbiol* 75:1550-1562.

Park et al. (2012) Comparative genomics of the classical *Bordetella* subspecies: the evolution and exchange of virulence-associated diversity amongst closely related pathogens. *BMC Genomics* 13:545.

Pearson et al. (1987) Inhibition of monocyte oxidative responses by *Bordetella pertussis* adenylate cyclase toxin. *J Immunol* 139:2749-2754.

Perez Vidakovics et al. (2006) Adenylate cyclase influences filamentous haemagglutinin-mediated attachment of *Bordetella pertussis* to epithelial alveolar cells. *FEMS Immunol Med Microbiol* 48:140-147.

Perkins et al. (2007) *Bordetella pertussis* adenylate cyclase toxin (ACT) induces cyclooxygenase-2 (COX-2) in murine macrophages and is facilitated by ACT interaction with CD11b/CD18 (Mac-1). *Mol Microbiol* 66:1003-1015.

Quinn & McIntyre (2011) The impact of adolescent pertussis immunization, 2004-2009: lessons from Australia. *Bull World Health Organ* 89:666-674.

Rowe et al. (eds.) (2006) *Handbook of Pharmaceutical Excipients*, 5th Ed., Pharmaceutical Press, London, United Kingdom.

Sadilkova et al. (2008) Single-step affinity purification of recombinant proteins using a self-excising module from *Neisseria meningitidis* FrpC. *Protein Sci* 17:1834-1843.

Sakamoto et al. (1992) *Bordetella pertussis* adenylate cyclase toxin. Structural and functional independence of the catalytic and hemolytic activities. *J Biol Chem* 267: 13598-13602.

Sebo & Ladant (1993) Repeat sequences in the *Bordetella pertussis* adenylate cyclase toxin can be recognized as alternative carboxy-proximal secretion signals by the *Escherichia coli* alpha-haemolysin translocator. *Mol Microbiol* 9:999-1009.

Serra et al. (2007) Continuous nondestructive monitoring of *Bordetella pertussis* biofilms by Fourier transform infrared spectroscopy and other corroborative techniques. *Anal Bioanal Chem* 387:1759-1767.

Serra et al. (2011) FHA-mediated cell-substrate and cell-cell adhesions are critical for *Bordetella pertussis* biofilm formation on abiotic surfaces and in the mouse nose and the trachea. *PLoS One* 6:e28811.

Sisti et al. (2013) Cyclic-di-GMP signalling regulates motility and biofilm formation in *Bordetella bronchiseptica*. *Microbiology* 159:869-879.

Sloan et al. (2007) The *Bordetella* Bps polysaccharide is critical for biofilm development in the mouse respiratory tract. *J Bacteriol* 189:8270-8276.

Sorroche et al. (2012) A positive correlation between bacterial autoaggregation and biofilm formation in native *Sinorhizobium meliloti* isolates from Argentina. *Appl Environ Microbiol* 78:4092-4101.

Strebel et al. (2001) Population-based incidence of pertussis among adolescents and adults, Minnesota, 1995-1996. *J Infect Dis* 183:1353-1359.

Strickley (2004) Solubilizing excipients in oral and injectable formulations. *Pharm Res* 21:201-230.

Sugisaki et al. (2013) Role of (p)ppGpp in biofilm formation and expression of filamentous structures in *Bordetella pertussis*. *Microbiology* 159:1379-1389.

Thorstensson et al. (2014) A phase I clinical study of a live attenuated *Bordetella pertussis* vaccine-BPZE1; a single centre, double-blind, placebocontrolled, dose-escalating study of BPZE1 given intranasally to healthy adult male volunteers. *PLoS One* 9:e83449.

U.S. Patent Application Publication Nos. 2002/0037260; 2006/0105025; 2010/0021391; 2010/0322872.

U.S. Pat. Nos. 4,057,626; 6,726,898; 6,830,745; 7,393,924; 8,404,662; 8,444,992; 9,028,864; 9,089,677; 9,187,754; 9,339,525; 9,566,247; 9,566,247.

Uribe et al. (2013) Ca21 influx and tyrosine kinases trigger *Bordetella* adenylate cyclase toxin (ACT) endocytosis. Cell physiology and expression of the CD11b/CD18 integrin major determinants of the entry route. *PLoS One* 8: e74248.

Vergara-Irigaray et al. (2005) Evaluation of the role of the Bvg intermediate phase in *Bordetella pertussis* during experimental respiratory infection. *Infect Immun* 73:748-760.

Vojtova et al. (2006) *Bordetella* adenylate cyclase toxin induces a cascade of morphological changes of sheep erythrocytes and localizes into clusters in erythrocyte membranes. *Microsc Res Tech* 69:119-129.

Weiss et al. (1983) Tn5-induced mutations affecting virulence factors of *Bordetella pertussis*. *Infect Immun* 42:33-41.

Wendelboe et al. (2007) Transmission of *Bordetella pertussis* to young infants. *Pediatr Infect Dis J* 26:293-299.

Zaretzky et al. (2002) Mechanism of association of adenylate cyclase toxin with the surface of *Bordetella pertussis*: a role for toxinfilamentous haemagglutinin interaction. *Mol Microbiol* 45:1589-1598.

Headings are included herein for reference and to aid in locating certain sections. These headings are not intended to limit the scope of the concepts described therein under, and these concepts can have applicability in other sections throughout the entire specification.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for inhibiting bacterial biofilm development and/or for reducing or eliminating a bacterial biofilm present on a surface, the method comprising contacting the surface or the biofilm present thereon with an effective amount of a composition comprising an effective amount of a peptide or polypeptide derived from Adenylate Cyclase Toxin (ACT) of *Bordetella* or a catalytic domain (AC domain) thereof, wherein the peptide or polypeptide comprises an amino acid sequence that is at least 95% identical to an amino acid sequence selected from the group consisting of SEQ ID NOs: 1-5 and 44-53, whereby bacterial biofilm development on the surface is inhibited and/or existing bacterial biofilm on the on the surface is reduced or eliminated.

2. The method of claim 1, wherein the bacterial biofilm comprises a strain of bacteria selected from the group consisting of *Bordetella* spp.; *Salmonella* spp.; *Pseudomonas* sp.; *E. coli* spp.; *Listeria* spp.; *Neisseria* spp.; *Streptococcus* spp.; *Staphylococcus* spp.; *Yersinia* spp.; *Campylobacter* spp.; *Helicobacter* spp.; *Aeromonas* spp.; atypical Mycobacteria; and *Legionella* spp.

3. The method of claim 1, wherein the surface is a part of a device selected from the group consisting of a medical device, a dental device, and an industrial device.

4. The method of claim 3, wherein the medical device is selected from the group consisting of a surgical tool, an implant, a catheter, a stent, a ventilator tubing, and a bone or joint implant.

5. The method of claim 4, wherein the implant is a cardiac implant.

6. The method of claim 3, wherein the industrial device is selected from the group consisting of a pipe, a tube, a valve, an air-cooled tower, a warm water system, a coolant circuit, a silo, a fermenter, a colander, a piece of furniture, and a sink.

7. The method of claim 3, wherein the industrial device is part of device used for water treatment, sewage treatment, petroleum manufacturing and/or storage, or recycling.

8. The method of claim 1, wherein the surface is a cellular surface, a tissue surface, and/or an organ surface present within a subject.

9. The method of claim 8, wherein the contacting comprises administering a pharmaceutical composition comprising the peptide or polypeptide to the subject in an amount and via a route of administration whereby the peptide or polypeptide contacts the surface or the biofilm present thereon and inhibits bacterial biofilm development on the surface and/or reduces or eliminates the existing bacterial biofilm present thereon.

10. The method of claim 9, wherein the surface is a nasal surface and/or a lung surface and the pharmaceutical composition is configured for inhalation and/or insufflation by the subject.

11. The method of claim 9, wherein the composition comprises a delivery vehicle.

12. The method of claim 11, wherein the delivery vehicle comprises a liposome.

13. The method of claim 1, further comprising contacting the surface with one or more additional compositions that inhibit bacterial biofilm development and/or reduces or eliminates bacterial biofilm present on the surface.

14. The method of claim 1, wherein the percent identity exists over the full length of one of SEQ ID NOs: 1-5 and 44-53.

15. The method of claim 2, wherein the bacterial biofilm comprises a strain of bacteria selected from the group consisting of *Bordetella pertussis*; *Bordetella bronchiseptica*; *Salmonella typhimurium*; and *Pseudomonas aeruginosa*.

16. The method of claim 4, wherein the medical device is a hip, knee, ankle, wrist, elbow, or shoulder prosthesis.

17. The method of claim 11, wherein the peptide or polypeptide is associated with, conjugated to, and/or encapsulated by a delivery vehicle in the pharmaceutical composition.

18. The method of claim 12, wherein the liposome, microparticle, or nanoparticle is designed to be biodegradable in the subject.

19. The method of claim 1, wherein the peptide or polypeptide comprises an amino acid sequence selected from the group consisting of SEQ ID NOs: 1-5 and 44-53.

\* \* \* \* \*